United States Patent
Romano

(10) Patent No.: US 7,408,096 B2
(45) Date of Patent: *Aug. 5, 2008

(54) EXPRESSION OF CRY3B INSECTICIDAL PROTEIN IN PLANTS

(75) Inventor: Charles P. Romano, Medfield, MA (US)

(73) Assignee: Monsanto Technology LLC, St. Louis, MO (US)

( * ) Notice: Subject to any disclaimer, the term of this patent is extended or adjusted under 35 U.S.C. 154(b) by 121 days.

This patent is subject to a terminal disclaimer.

(21) Appl. No.: 11/192,801

(22) Filed: Jul. 29, 2005

(65) Prior Publication Data

US 2005/0273882 A1     Dec. 8, 2005

Related U.S. Application Data

(62) Division of application No. 10/232,665, filed on Aug. 29, 2002, now Pat. No. 6,943,281, which is a division of application No. 09/377,466, filed on Aug. 19, 1999, now Pat. No. 6,501,009.

(51) Int. Cl.
*A01H 5/00* (2006.01)
*A01H 5/10* (2006.01)
*C12N 15/82* (2006.01)
*C12N 15/32* (2006.01)

(52) U.S. Cl. .................. 800/302; 536/23.71; 424/93.2; 424/405; 435/419; 435/412; 435/440; 435/468; 435/320.1; 800/279

(58) Field of Classification Search ........................ None
See application file for complete search history.

(56) References Cited

U.S. PATENT DOCUMENTS

| | | | |
|---|---|---|---|
| 5,024,837 A | 6/1991 | Donovan et al. | |
| 5,378,625 A | 1/1995 | Donovan et al. | |
| 5,424,412 A | 6/1995 | Brown et al. | |
| 5,500,365 A | 3/1996 | Fischhoff et al. | |
| 5,659,123 A | 8/1997 | VanRie et al. | |
| 5,689,052 A | 11/1997 | Brown et al. | |
| 6,023,013 A * | 2/2000 | English et al. | 800/302 |
| 6,501,009 B1 * | 12/2002 | Romano | 800/302 |
| 6,943,281 B2 * | 9/2005 | Romano | 800/302 |

FOREIGN PATENT DOCUMENTS

| | | |
|---|---|---|
| WO | WO 91/14778 | 10/1991 |
| WO | WO 97/13402 | 4/1997 |
| WO | WO 98/23641 | 6/1998 |
| WO | WO 99/31248 | 6/1999 |

OTHER PUBLICATIONS

Arpaia et al., Production of transgenic eggplant (*Solanum melongena* L.) resistant to Colorado Potato Beetle (*Leptinotarsa decemlineata* Say), *Theor. Appl. Genet.* 95:329-334 (1997).
Chen et al., Transfer and Transcriptional Expression of Coleopteran *cryIIIB* Endotoxin Gene of *Bacillus thuringiensis* in Eggplant, *J. Amer. Soc. Hort. Sci.* 120:921-927 (1995).
Crickmore et al., *Microbiol. Mol. Biol. Rev.* 62:807-813 (1998).
Diehn et al, Problems that can limit the expression of foreign genes in plants: Lessons to be learned from B.t. toxin genes, *Genetic Engineering* 18:83-99 (1996).
Hill et al., *Biochem. Biophys. Res. Comm.* 244:573-577 (1998).
Iannacone et al., *Plant Mol. Biol.* 34:484-496 (1997).
Lamppa et al., Structure and Developmental Regulation of a Wheat Gene Encoding the Major Chlorophyll a/b-Binding Polypeptide, *Molecular and Cellular Biology* 5:1370-1378 (1985).
Lazar et al., *Mol. Cell. Biol.* 8:1247-1252 (1988).
McGaughey et al., Managing insect resistance to *Bacillus thuringiensis* toxins, *Science* 258:1451-1455 (1992).
Murray et al., Codon usage in plant genes, *Nucleic Acids Research* 17:477-498 (1989).
Roush, Managing pests and their resistance to *Bacillus thuringiensis*: Can Transgenic crops be better than sprays?, *Biocontrol Science and Technology* 4:501-516 (1994).
Sutton et al., Synthetic *cryIIIA* gene from *Bacillus thuringiensis* improved for high expression in plants, *Transgenic Research* 1:228-236 (1992).

* cited by examiner

*Primary Examiner*—Anne Kubelik
(74) *Attorney, Agent, or Firm*—Timothy K. Ball

(57) ABSTRACT

The present invention discloses methods and compositions comprising a novel expression cassette providing significantly improved levels of accumulation of *Coleopteran* inhibitory Cry3B variant protein when expressed in maize plants. The preferred embodiments of the invention provide at least up to ten fold higher levels of insect controlling protein relative to the highest levels obtained using prior compositions. In particular, transgenic maize expressing higher levels of a protein designed to exhibit increased toxicity toward *Coleopteran* pests deliver superior levels of insect protection and are less likely to sponsor development of populations of target insects that are resistant to the insecticidally active protein.

15 Claims, 10 Drawing Sheets

Figure 1:
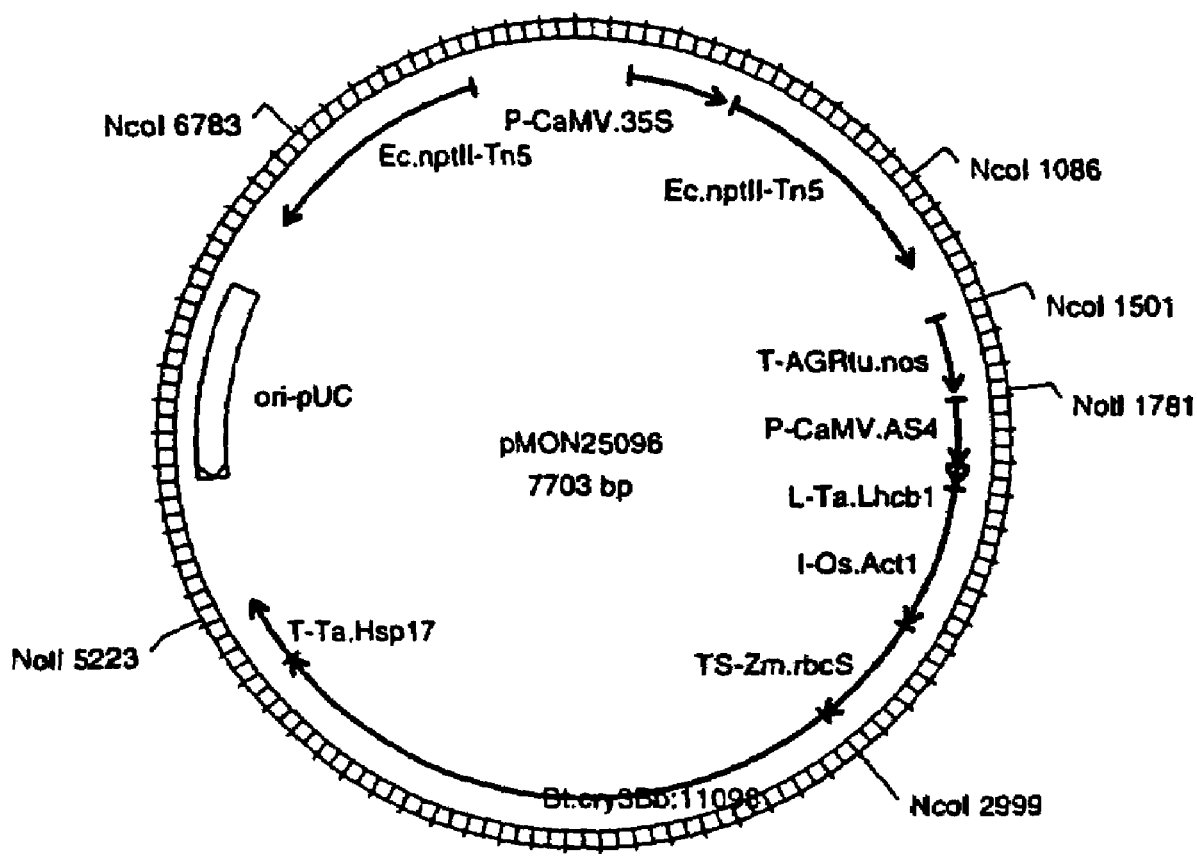

```
atg gcc aac ccc aac aat cgc tcc gag cac gac acg atc aag gtc     47
Met Ala Asn Pro Asn Asn Arg Ser Glu His Asp Thr Ile Lys Val
 1               5                  10                  15 acc ccc aac tcc gag ctc cag acc aac cac aac cag tac ccg ctg gcc  95
Thr Pro Asn Ser Glu Leu Gln Thr Asn His Asn Gln Tyr Pro Leu Ala
                 20                  25                  30 gac aac ccc aac tcc acc ctg gaa gag ctg aac tac aag gag ttc ctg 143
Asp Asn Pro Asn Ser Thr Leu Glu Glu Leu Asn Tyr Lys Glu Phe Leu
                 35                  40                  45 cgc atg acc gag gac tcc tcc acg gag gtc ctg gac aac tcc acc gtc 191
Arg Met Thr Glu Asp Ser Ser Thr Glu Val Leu Asp Asn Ser Thr Val
         50                  55                  60 aag gac gcc gtc ggg acc ggc atc tcc gtc gtt ggg cag atc ctg ggc 239
Lys Asp Ala Val Gly Thr Gly Ile Ser Val Val Gly Gln Ile Leu Gly
 65                  70                  75 gtc gtt ggc gtc ccc ttc gca ggt gct ctc acc tcc ttc tac cag tcc 287
Val Val Gly Val Pro Phe Ala Gly Ala Leu Thr Ser Phe Tyr Gln Ser
 80                  85                  90                  95 ttc ctg aac acc atc tgg ccc tcc gac gcc gac ccc tgg aag gcc ttc 335
Phe Leu Asn Thr Ile Trp Pro Ser Asp Ala Asp Pro Trp Lys Ala Phe
                100                 105                 110 atg gcc caa gtc gaa gtc ctg atc gac aag aag atc gag gag tac gcc 383
Met Ala Gln Val Glu Val Leu Ile Asp Lys Lys Ile Glu Glu Tyr Ala
                115                 120                 125 aag tcc aag gcc ctg gcc gag ctg caa ggc ctg caa aac aac ttc gag 431
Lys Ser Lys Ala Leu Ala Glu Leu Gln Gly Leu Gln Asn Asn Phe Glu
        130                 135                 140 gac tac gtc aac gcg ctg aac tcc tgg aag aag acg cct ctg tcc ctg 479
Asp Tyr Val Asn Ala Leu Asn Ser Trp Lys Lys Thr Pro Leu Ser Leu
        145                 150                 155 cgc tcc aag cgc tcc cag ggc cgc atc cgc gag ctg ttc tcc cag gcc 527
Arg Ser Lys Arg Ser Gln Gly Arg Ile Arg Glu Leu Phe Ser Gln Ala
160                 165                 170                 175 gag tcc cac ttc cgc aac tcc atg ccg tcc ttc gcc gtc tcc aag ttc 575
Glu Ser His Phe Arg Asn Ser Met Pro Ser Phe Ala Val Ser Lys Phe
                180                 185                 190 gag gtc ctg ttc ctg ccc acc tac gcc cag gct gcc aac acc cac ctc 623
Glu Val Leu Phe Leu Pro Thr Tyr Ala Gln Ala Ala Asn Thr His Leu
                195                 200                 205 ctg ttg ctg aag gac gcc cag gtc ttc ggc gag gaa tgg ggc tac tcc 671
Leu Leu Leu Lys Asp Ala Gln Val Phe Gly Glu Glu Trp Gly Tyr Ser
        210                 215                 220 tcg gag gac gtc gcc gag ttc tac cgt cgc cag ctg aag ctg acc caa 719
Ser Glu Asp Val Ala Glu Phe Tyr Arg Arg Gln Leu Lys Leu Thr Gln
225                 230                 235 cag tac acc gac cac tgc gtc aac tgg tac aac gtc ggc ctg aac ggc 767
Gln Tyr Thr Asp His Cys Val Asn Trp Tyr Asn Val Gly Leu Asn Gly
240                 245                 250                 255 ctg agg ggc tcc acc tac gac gca tgg gtc aag ttc aac cgc ttc cgc 815
Leu Arg Gly Ser Thr Tyr Asp Ala Trp Val Lys Phe Asn Arg Phe Arg
        260                 265                 270
```

Figure 5A

```
agg gag atg acc ctg acc gtc ctg gac ctg atc gtc ctg ttc ccc ttc    863
Arg Glu Met Thr Leu Thr Val Leu Asp Leu Ile Val Leu Phe Pro Phe
            275             280             285 tac gac atc cgc ctg tac tcc aag ggc gtc aag acc gag ctg acc cgc    911
Tyr Asp Ile Arg Leu Tyr Ser Lys Gly Val Lys Thr Glu Leu Thr Arg
            290             295             300 gac atc ttc acg gac ccc atc ttc ctg ctc acg acc ctc cag aag tac    959
Asp Ile Phe Thr Asp Pro Ile Phe Leu Leu Thr Thr Leu Gln Lys Tyr
            305             310             315 ggt ccc acc ttc ctg tcc atc gag aac tcc atc cgc aag ccc cac ctg   1007
Gly Pro Thr Phe Leu Ser Ile Glu Asn Ser Ile Arg Lys Pro His Leu
320             325             330             335 ttc gac tac ctc cag ggc atc gag ttc cac acg cgc ctg agg cca ggc   1055
Phe Asp Tyr Leu Gln Gly Ile Glu Phe His Thr Arg Leu Arg Pro Gly
            340             345             350 tac ttc ggc aag gac tcc ttc aac tac tgg tcc ggc aac tac gtc gag   1103
Tyr Phe Gly Lys Asp Ser Phe Asn Tyr Trp Ser Gly Asn Tyr Val Glu
            355             360             365 acc agg ccc tcc atc ggc tcc tcg aag acg atc acc tcc cct ttc tac   1151
Thr Arg Pro Ser Ile Gly Ser Ser Lys Thr Ile Thr Ser Pro Phe Tyr
            370             375             380 ggc gac aag tcc acc gag ccc gtc cag aag ctg tcc ttc gac ggc cag   1199
Gly Asp Lys Ser Thr Glu Pro Val Gln Lys Leu Ser Phe Asp Gly Gln
385             390             395 aag gtc tac cgc acc atc gcc aac acc gac gtc gcg gct tgg ccg aac   1247
Lys Val Tyr Arg Thr Ile Ala Asn Thr Asp Val Ala Ala Trp Pro Asn
400             405             410             415 ggc aag gtc tac ctg ggc gtc acg aag gtc gac ttc tcc cag tac gat   1295
Gly Lys Val Tyr Leu Gly Val Thr Lys Val Asp Phe Ser Gln Tyr Asp
            420             425             430 gac cag aag aat gaa acc tcc acc cag acc tac gac tcc aag cgc aac   1343
Asp Gln Lys Asn Glu Thr Ser Thr Gln Thr Tyr Asp Ser Lys Arg Asn
            435             440             445 aat ggc cac gtc tcc gcc cag gac tcc atc gac cag ctg ccg cct gag   1391
Asn Gly His Val Ser Ala Gln Asp Ser Ile Asp Gln Leu Pro Pro Glu
            450             455             460 acc act gac gag ccc ctg gag aag gcc tac tcc cac cag ctg aac tac   1439
Thr Thr Asp Glu Pro Leu Glu Lys Ala Tyr Ser His Gln Leu Asn Tyr
            465             470             475 gcg gag tgc ttc ctg atg caa gac cgc agg ggc acc atc ccc ttc ttc   1487
Ala Glu Cys Phe Leu Met Gln Asp Arg Arg Gly Thr Ile Pro Phe Phe
480             485             490             495 acc tgg acc cac cgc tcc gtc gac ttc ttc aac acc atc gac gcc gag   1535
Thr Trp Thr His Arg Ser Val Asp Phe Phe Asn Thr Ile Asp Ala Glu
            500             505             510 aag atc acc cag ctg ccc gtg gtc aag gcc tac gcc ctg tcc tcg ggt   1583
Lys Ile Thr Gln Leu Pro Val Val Lys Ala Tyr Ala Leu Ser Ser Gly
            515             520             525 gcc tcc atc att gag ggt cca ggc ttc acc ggt ggc aac ctg ctg ttc   1631
Ala Ser Ile Ile Glu Gly Pro Gly Phe Thr Gly Gly Asn Leu Leu Phe
            530             535             540
```

Figure 5B

```
ctg aag gag tcc tcg aac tcc atc gcc aag ttc aag gtc acc ctg aac    1679
Leu Lys Glu Ser Ser Asn Ser Ile Ala Lys Phe Lys Val Thr Leu Asn
    545             550             555 tcc gct gcc ttg ctg caa cgc tac cgc gtc cgc atc cgc tac gcc tcc    1727
Ser Ala Ala Leu Leu Gln Arg Tyr Arg Val Arg Ile Arg Tyr Ala Ser
560             565             570             575 acc acg aac ctg cgc ctg ttc gtc cag aac tcc aac aat gac ttc ctg    1775
Thr Thr Asn Leu Arg Leu Phe Val Gln Asn Ser Asn Asn Asp Phe Leu
                580             585             590 gtc atc tac atc aac aag acc atg aac aag gac gat gac ctg acc tac    1823
Val Ile Tyr Ile Asn Lys Thr Met Asn Lys Asp Asp Asp Leu Thr Tyr
            595             600             605 cag acc ttc gac ctc gcc acc acg aac tcc aac atg ggc ttc tcg ggc    1871
Gln Thr Phe Asp Leu Ala Thr Thr Asn Ser Asn Met Gly Phe Ser Gly
        610             615             620 gac aag aat gaa ctg atc att ggt gct gag tcc ttc gtc tcc aat gaa    1919
Asp Lys Asn Glu Leu Ile Ile Gly Ala Glu Ser Phe Val Ser Asn Glu
    625             630             635 aag atc tac atc gac aag atc gag ttc atc ccc gtc cag ctg            1961
Lys Ile Tyr Ile Asp Lys Ile Glu Phe Ile Pro Val Gln Leu
640             645             650
```

Figure 5C

```
atg gcc aac ccc aac aat cgc tcc gag cac gac acg atc aag gtc      47
Met Ala Asn Pro Asn Asn Arg Ser Glu His Asp Thr Ile Lys Val
 1               5                  10                  15 acc ccc aac tcc gag ctc cag acc aac cac aac cag tac ccg ctg gcc   95
Thr Pro Asn Ser Glu Leu Gln Thr Asn His Asn Gln Tyr Pro Leu Ala
                 20                  25                  30 gac aac ccc aac tcc acc ctg gaa gag ctg aac tac aag gag ttc ctg  143
Asp Asn Pro Asn Ser Thr Leu Glu Glu Leu Asn Tyr Lys Glu Phe Leu
             35                  40                  45 cgc atg acc gag gac tcc tcc acg gag gtc ctg gac aac tcc acc gtc  191
Arg Met Thr Glu Asp Ser Ser Thr Glu Val Leu Asp Asn Ser Thr Val
         50                  55                  60 aag gac gcc gtc ggg acc ggc atc tcc gtc gtt ggg cag atc ctg ggc  239
Lys Asp Ala Val Gly Thr Gly Ile Ser Val Val Gly Gln Ile Leu Gly
     65                  70                  75 gtc gtt ggc gtc ccc ttc gca ggt gct ctc acc tcc ttc tac cag tcc  287
Val Val Gly Val Pro Phe Ala Gly Ala Leu Thr Ser Phe Tyr Gln Ser
 80                  85                  90                  95 ttc ctg aac acc atc tgg ccc tcc gac gcc gac ccc tgg aag gcc ttc  335
Phe Leu Asn Thr Ile Trp Pro Ser Asp Ala Asp Pro Trp Lys Ala Phe
                100                 105                 110 atg gcc caa gtc gaa gtc ctg atc gac aag aag atc gag gag tac gcc  383
Met Ala Gln Val Glu Val Leu Ile Asp Lys Lys Ile Glu Glu Tyr Ala
            115                 120                 125 aag tcc aag gcc ctg gcc gag ctg caa ggc ctg caa aac aac ttc gag  431
Lys Ser Lys Ala Leu Ala Glu Leu Gln Gly Leu Gln Asn Asn Phe Glu
        130                 135                 140 gac tac gtc aac gcg ctg aac tcc tgg aag aag acg cct ctg tcc ctg  479
Asp Tyr Val Asn Ala Leu Asn Ser Trp Lys Lys Thr Pro Leu Ser Leu
    145                 150                 155 cgc tcc aag cgc tcc cag gac cgc atc cgc gag ctg ttc tcc cag gcc  527
Arg Ser Lys Arg Ser Gln Asp Arg Ile Arg Glu Leu Phe Ser Gln Ala
160                 165                 170                 175 gag tcc cac ttc cgc aac tcc atg ccg tcc ttc gcc gtc tcc aag ttc  575
Glu Ser His Phe Arg Asn Ser Met Pro Ser Phe Ala Val Ser Lys Phe
                180                 185                 190 gag gtc ctg ttc ctg ccc acc tac gcc cag gct gcc aac acc cac ctc  623
Glu Val Leu Phe Leu Pro Thr Tyr Ala Gln Ala Ala Asn Thr His Leu
            195                 200                 205 ctg ttg ctg aag gac gcc cag gtc ttc ggc gag gaa tgg ggc tac tcc  671
Leu Leu Leu Lys Asp Ala Gln Val Phe Gly Glu Glu Trp Gly Tyr Ser
        210                 215                 220 tcg gag gac gtc gcc gag ttc tac cgt cgc cag ctg aag ctg acc caa  719
Ser Glu Asp Val Ala Glu Phe Tyr Arg Arg Gln Leu Lys Leu Thr Gln
    225                 230                 235 cag tac acc gac cac tgc gtc aac tgg tac aac gtc ggc ctg aac ggc  767
Gln Tyr Thr Asp His Cys Val Asn Trp Tyr Asn Val Gly Leu Asn Gly
240                 245                 250                 255 ctg agg ggc tcc acc tac gac gca tgg gtc aag ttc aac cgc ttc cgc  815
Leu Arg Gly Ser Thr Tyr Asp Ala Trp Val Lys Phe Asn Arg Phe Arg
                260                 265                 270
```

Figure 6A

```
agg gag atg acc ctg acc gtc ctg gac ctg atc gtc ctg ttc ccc ttc    863
Arg Glu Met Thr Leu Thr Val Leu Asp Leu Ile Val Leu Phe Pro Phe
            275             280             285 tac gac atc cgc ctg tac tcc aag ggc gtc aag acc gag ctg acc cgc    911
Tyr Asp Ile Arg Leu Tyr Ser Lys Gly Val Lys Thr Glu Leu Thr Arg
            290             295             300 gac atc ttc acg gac ccc atc ttc ctc acg acc ctc cag aag tac        959
Asp Ile Phe Thr Asp Pro Ile Phe Leu Leu Thr Thr Leu Gln Lys Tyr
            305             310             315 ggt ccc acc ttc ctg tcc atc gag aac tcc atc cgc aag ccc cac ctg    1007
Gly Pro Thr Phe Leu Ser Ile Glu Asn Ser Ile Arg Lys Pro His Leu
320             325             330             335 ttc gac tac ctc cag ggc atc gag ttc cac acg cgc ctg agg cca ggc    1055
Phe Asp Tyr Leu Gln Gly Ile Glu Phe His Thr Arg Leu Arg Pro Gly
            340             345             350 tac ttc ggc aag gac tcc ttc aac tac tgg tcc ggc aac tac gtc gag    1103
Tyr Phe Gly Lys Asp Ser Phe Asn Tyr Trp Ser Gly Asn Tyr Val Glu
            355             360             365 acc agg ccc tcc atc ggc tcc tcg aag acg atc acc tcc cct ttc tac    1151
Thr Arg Pro Ser Ile Gly Ser Ser Lys Thr Ile Thr Ser Pro Phe Tyr
            370             375             380 ggc gac aag tcc acc gag ccc gtc cag aag ctg tcc ttc gac ggc cag    1199
Gly Asp Lys Ser Thr Glu Pro Val Gln Lys Leu Ser Phe Asp Gly Gln
385             390             395 aag gtc tac cgc acc atc gcc aac acc gac gtc gcg gct tgg ccg aac    1247
Lys Val Tyr Arg Thr Ile Ala Asn Thr Asp Val Ala Ala Trp Pro Asn
400             405             410             415 ggc aag gtc tac ctg ggc gtc acg aag gtc gac ttc tcc cag tac gat    1295
Gly Lys Val Tyr Leu Gly Val Thr Lys Val Asp Phe Ser Gln Tyr Asp
            420             425             430 gac cag aag aat gaa acc tcc acc cag acc tac gac tcc aag cgc aac    1343
Asp Gln Lys Asn Glu Thr Ser Thr Gln Thr Tyr Asp Ser Lys Arg Asn
            435             440             445 aat ggc cac gtc tcc gcc cag gac tcc atc gac cag ctg ccg cct gag    1391
Asn Gly His Val Ser Ala Gln Asp Ser Ile Asp Gln Leu Pro Pro Glu
            450             455             460 acc act gac gag ccc ctg gag aag gcc tac tcc cac cag ctg aac tac    1439
Thr Thr Asp Glu Pro Leu Glu Lys Ala Tyr Ser His Gln Leu Asn Tyr
465             470             475 gcg gag tgc ttc ctg atg caa gac cgc agg ggc acc atc ccc ttc ttc    1487
Ala Glu Cys Phe Leu Met Gln Asp Arg Arg Gly Thr Ile Pro Phe Phe
480             485             490             495 acc tgg acc cac cgc tcc gtc gac ttc ttc aac acc atc gac gcc gag    1535
Thr Trp Thr His Arg Ser Val Asp Phe Phe Asn Thr Ile Asp Ala Glu
            500             505             510 aag atc acc cag ctg ccc gtg gtc aag gcc tac gcc ctg tcc tcg ggt    1583
Lys Ile Thr Gln Leu Pro Val Val Lys Ala Tyr Ala Leu Ser Ser Gly
            515             520             525 gcc tcc atc att gag ggt cca ggc ttc acc ggt ggc aac ctg ctg ttc    1631
Ala Ser Ile Ile Glu Gly Pro Gly Phe Thr Gly Gly Asn Leu Leu Phe
            530             535             540
```

Figure 6B

```
ctg aag gag tcc tcg aac tcc atc gcc aag ttc aag gtc acc ctg aac    1679
Leu Lys Glu Ser Ser Asn Ser Ile Ala Lys Phe Lys Val Thr Leu Asn
    545             550             555 tcc gct gcc ctg ctg caa cgc tac cgc gtc cgc atc cgc tac gcc tcc    1727
Ser Ala Ala Leu Leu Gln Arg Tyr Arg Val Arg Ile Arg Tyr Ala Ser
560             565             570             575 acc acg aac ctg cgc ctg ttc gtc cag aac tcc aac aat gac ttc ctg    1775
Thr Thr Asn Leu Arg Leu Phe Val Gln Asn Ser Asn Asn Asp Phe Leu
                580             585             590 gtc atc tac atc aac aag acc atg aac aag gac gat gac ctg acc tac    1823
Val Ile Tyr Ile Asn Lys Thr Met Asn Lys Asp Asp Asp Leu Thr Tyr
            595             600             605 cag acc ttc gac ctc gcc acc acg aac tcc aac atg ggc ttc tcg ggc    1871
Gln Thr Phe Asp Leu Ala Thr Thr Asn Ser Asn Met Gly Phe Ser Gly
        610             615             620 gac aag aat gaa ctg atc att ggt gct gag tcc ttc gtc tcc aat gaa    1919
Asp Lys Asn Glu Leu Ile Ile Gly Ala Glu Ser Phe Val Ser Asn Glu
    625             630             635 aag atc tac atc gac aag atc gag ttc atc ccc gtc cag ctg            1961
Lys Ile Tyr Ile Asp Lys Ile Glu Phe Ile Pro Val Gln Leu
640             645             650
```

Figure 6C

SEQUENCE LISTING

<160> NUMBER OF SEQ ID NOS: 43

<210> SEQ ID NO 1
<211> LENGTH: 1959
<212> TYPE: DNA
<213> ORGANISM: Bacillus thuringiensis
<220> FEATURE:
<221> NAME/KEY: CDS
<222> LOCATION: (1)..(1956)
<223> OTHER INFORMATION: Description of Artificial Sequence: naturally
      occurring nucleotide sequence encoding a  Cry3Bb1 amino acid
      sequence

<400> SEQUENCE: 1

```
atg aat cca aac aat cga agt gaa cat gat acg ata aag gtt aca cct      48
Met Asn Pro Asn Asn Arg Ser Glu His Asp Thr Ile Lys Val Thr Pro
 1               5                  10                  15 aac agt gaa ttg caa act aac cat aat caa tat cct tta gct gac aat      96
Asn Ser Glu Leu Gln Thr Asn His Asn Gln Tyr Pro Leu Ala Asp Asn
             20                  25                  30 cca aat tca aca cta gaa gaa tta aat tat aaa gaa ttt tta aga atg     144
Pro Asn Ser Thr Leu Glu Glu Leu Asn Tyr Lys Glu Phe Leu Arg Met
         35                  40                  45 act gaa gac agt tct acg gaa gtg cta gac aac tct aca gta aaa gat     192
Thr Glu Asp Ser Ser Thr Glu Val Leu Asp Asn Ser Thr Val Lys Asp
```

-continued

```
                 50                      55                      60
gca gtt ggg aca gga att tct gtt gta ggg cag att tta ggt gtt gta      240
Ala Val Gly Thr Gly Ile Ser Val Val Gly Gln Ile Leu Gly Val Val
 65                  70                      75                  80 gga gtt cca ttt gct ggg gca ctc act tca ttt tat caa tca ttt ctt      288
Gly Val Pro Phe Ala Gly Ala Leu Thr Ser Phe Tyr Gln Ser Phe Leu
                     85                      90                  95 aac act ata tgg cca agt gat gct gac cca tgg aag gct ttt atg gca      336
Asn Thr Ile Trp Pro Ser Asp Ala Asp Pro Trp Lys Ala Phe Met Ala
                 100                     105                     110 caa gtt gaa gta ctg ata gat aag aaa ata gag gag tat gct aaa agt      384
Gln Val Glu Val Leu Ile Asp Lys Lys Ile Glu Glu Tyr Ala Lys Ser
             115                     120                     125 aaa gct ctt gca gag tta cag ggt ctt caa aat aat ttc gaa gat tat      432
Lys Ala Leu Ala Glu Leu Gln Gly Leu Gln Asn Asn Phe Glu Asp Tyr
         130                     135                     140 gtt aat gcg tta aat tcc tgg aag aaa aca cct tta agt ttg cga agt      480
Val Asn Ala Leu Asn Ser Trp Lys Lys Thr Pro Leu Ser Leu Arg Ser
145                     150                     155                 160 aaa aga agc caa gat cga ata agg gaa ctt ttt tct caa gca gaa agt      528
Lys Arg Ser Gln Asp Arg Ile Arg Glu Leu Phe Ser Gln Ala Glu Ser
                 165                     170                     175 cat ttt cgt aat tcc atg ccg tca ttt gca gtt tcc aaa ttc gaa gtg      576
His Phe Arg Asn Ser Met Pro Ser Phe Ala Val Ser Lys Phe Glu Val
                 180                     185                     190 ctg ttt cta cca aca tat gca caa gct gca aat aca cat tta ttg cta      624
Leu Phe Leu Pro Thr Tyr Ala Gln Ala Ala Asn Thr His Leu Leu Leu
             195                     200                     205 tta aaa gat gct caa gtt ttt gga gaa gaa tgg gga tat tct tca gaa      672
Leu Lys Asp Ala Gln Val Phe Gly Glu Glu Trp Gly Tyr Ser Ser Glu
 210                     215                     220 gat gtt gct gaa ttt tat cat aga caa tta aaa ctt aca caa caa tac      720
Asp Val Ala Glu Phe Tyr His Arg Gln Leu Lys Leu Thr Gln Gln Tyr
225                     230                     235                 240 act gac cat tgt gtt aat tgg tat aat gtt gga tta aat ggt tta aga      768
Thr Asp His Cys Val Asn Trp Tyr Asn Val Gly Leu Asn Gly Leu Arg
                 245                     250                     255 ggt tca act tat gat gca tgg gtc aaa ttt aac cgt ttt cgc aga gaa      816
Gly Ser Thr Tyr Asp Ala Trp Val Lys Phe Asn Arg Phe Arg Arg Glu
             260                     265                     270 atg act tta act gta tta gat cta att gta ctt ttc cca ttt tat gat      864
Met Thr Leu Thr Val Leu Asp Leu Ile Val Leu Phe Pro Phe Tyr Asp
         275                     280                     285 att cgg tta tac tca aaa ggg gtt aaa aca gaa cta aca aga gac att      912
Ile Arg Leu Tyr Ser Lys Gly Val Lys Thr Glu Leu Thr Arg Asp Ile
     290                     295                     300 ttt acg gat cca att ttt tca ctt aat act ctt cag gag tat gga cca      960
Phe Thr Asp Pro Ile Phe Ser Leu Asn Thr Leu Gln Glu Tyr Gly Pro
305                     310                     315                 320 act ttt ttg agt ata gaa aac tct att cga aaa cct cat tta ttt gat     1008
Thr Phe Leu Ser Ile Glu Asn Ser Ile Arg Lys Pro His Leu Phe Asp
                 325                     330                     335 tat tta cag ggg att gaa ttt cat acg cgt ctt caa cct ggt tac ttt     1056
Tyr Leu Gln Gly Ile Glu Phe His Thr Arg Leu Gln Pro Gly Tyr Phe
             340                     345                     350 ggg aaa gat tct ttc aat tat tgg tct ggt aat tat gta gaa act aga     1104
Gly Lys Asp Ser Phe Asn Tyr Trp Ser Gly Asn Tyr Val Glu Thr Arg
         355                     360                     365 cct agt ata gga tct agt aag aca att act tcc cca ttt tat gga gat     1152
```

```
                Pro Ser Ile Gly Ser Ser Lys Thr Ile Thr Ser Pro Phe Tyr Gly Asp
                    370                 375                 380 aaa tct act gaa cct gta caa aag cta agc ttt gat gga caa aaa gtt        1200
Lys Ser Thr Glu Pro Val Gln Lys Leu Ser Phe Asp Gly Gln Lys Val
385                 390                 395                 400 tat cga act ata gct aat aca gac gta gcg gct tgg ccg aat ggt aag        1248
Tyr Arg Thr Ile Ala Asn Thr Asp Val Ala Ala Trp Pro Asn Gly Lys
                405                 410                 415 gta tat tta ggt gtt acg aaa gtt gat ttt agt caa tat gat gat caa        1296
Val Tyr Leu Gly Val Thr Lys Val Asp Phe Ser Gln Tyr Asp Asp Gln
            420                 425                 430 aaa aat gaa act agt aca caa aca tat gat tca aaa aga aac aat ggc        1344
Lys Asn Glu Thr Ser Thr Gln Thr Tyr Asp Ser Lys Arg Asn Asn Gly
        435                 440                 445 cat gta agt gca cag gat tct att gac caa tta ccg cca gaa aca aca        1392
His Val Ser Ala Gln Asp Ser Ile Asp Gln Leu Pro Pro Glu Thr Thr
    450                 455                 460 gat gaa cca ctt gaa aaa gca tat agt cat cag ctt aat tac gcg gaa        1440
Asp Glu Pro Leu Glu Lys Ala Tyr Ser His Gln Leu Asn Tyr Ala Glu
465                 470                 475                 480 tgt ttc tta atg cag gac cgt cgt gga aca att cca ttt ttt act tgg        1488
Cys Phe Leu Met Gln Asp Arg Arg Gly Thr Ile Pro Phe Phe Thr Trp
                485                 490                 495 aca cat aga agt gta gac ttt ttt aat aca att gat gct gaa aag att        1536
Thr His Arg Ser Val Asp Phe Phe Asn Thr Ile Asp Ala Glu Lys Ile
                500                 505                 510 act caa ctt cca gta gtg aaa gca tat gcc ttg tct tca ggt gct tcc        1584
Thr Gln Leu Pro Val Val Lys Ala Tyr Ala Leu Ser Ser Gly Ala Ser
            515                 520                 525 att att gaa ggt cca gga ttc aca gga gga aat tta cta ttc cta aaa        1632
Ile Ile Glu Gly Pro Gly Phe Thr Gly Gly Asn Leu Leu Phe Leu Lys
        530                 535                 540 gaa tct agt aat tca att gct aaa ttt aaa gtt aca tta aat tca gca        1680
Glu Ser Ser Asn Ser Ile Ala Lys Phe Lys Val Thr Leu Asn Ser Ala
545                 550                 555                 560 gcc ttg tta caa cga tat cgt gta aga ata cgc tat gct tct acc act        1728
Ala Leu Leu Gln Arg Tyr Arg Val Arg Ile Arg Tyr Ala Ser Thr Thr
                565                 570                 575 aac tta cga ctt ttt gtg caa aat tca aac aat gat ttt ctt gtc atc        1776
Asn Leu Arg Leu Phe Val Gln Asn Ser Asn Asn Asp Phe Leu Val Ile
                580                 585                 590 tac att aat aaa act atg aat aaa gat gat gat tta aca tat caa aca        1824
Tyr Ile Asn Lys Thr Met Asn Lys Asp Asp Asp Leu Thr Tyr Gln Thr
            595                 600                 605 ttt gat ctc gca act act aat tct aat atg ggg ttc tcg ggt gat aag        1872
Phe Asp Leu Ala Thr Thr Asn Ser Asn Met Gly Phe Ser Gly Asp Lys
        610                 615                 620 aat gaa ctt ata ata gga gca gaa tct ttc gtt tct aat gaa aaa atc        1920
Asn Glu Leu Ile Ile Gly Ala Glu Ser Phe Val Ser Asn Glu Lys Ile
625                 630                 635                 640 tat ata gat aag ata gaa ttt atc cca gta caa ttg taa                    1959
Tyr Ile Asp Lys Ile Glu Phe Ile Pro Val Gln Leu
                645                 650

<210> SEQ ID NO 2
<211> LENGTH: 652
<212> TYPE: PRT
<213> ORGANISM: Bacillus thuringiensis

<400> SEQUENCE: 2
```

-continued

```
Met Asn Pro Asn Asn Arg Ser Glu His Asp Thr Ile Lys Val Thr Pro
 1               5                  10                  15

Asn Ser Glu Leu Gln Thr Asn His Asn Gln Tyr Pro Leu Ala Asp Asn
             20                  25                  30

Pro Asn Ser Thr Leu Glu Glu Leu Asn Tyr Lys Glu Phe Leu Arg Met
         35                  40                  45

Thr Glu Asp Ser Ser Thr Glu Val Leu Asp Asn Ser Thr Val Lys Asp
     50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                 85                  90                  95

Asn Thr Ile Trp Pro Ser Asp Ala Asp Pro Trp Lys Ala Phe Met Ala
             100                 105                 110

Gln Val Glu Val Leu Ile Asp Lys Lys Ile Glu Glu Tyr Ala Lys Ser
         115                 120                 125

Lys Ala Leu Ala Glu Leu Gln Gly Leu Gln Asn Asn Phe Glu Asp Tyr
     130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                 165                 170                 175

His Phe Arg Asn Ser Met Pro Ser Phe Ala Val Ser Lys Phe Glu Val
             180                 185                 190

Leu Phe Leu Pro Thr Tyr Ala Gln Ala Ala Asn Thr His Leu Leu Leu
         195                 200                 205

Leu Lys Asp Ala Gln Val Phe Gly Glu Glu Trp Gly Tyr Ser Ser Glu
     210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                 245                 250                 255

Gly Ser Thr Tyr Asp Ala Trp Val Lys Phe Asn Arg Phe Arg Arg Glu
             260                 265                 270

Met Thr Leu Thr Val Leu Asp Leu Ile Val Leu Phe Pro Phe Tyr Asp
         275                 280                 285

Ile Arg Leu Tyr Ser Lys Gly Val Lys Thr Glu Leu Thr Arg Asp Ile
     290                 295                 300

Phe Thr Asp Pro Ile Phe Ser Leu Asn Thr Leu Gln Glu Tyr Gly Pro
305                 310                 315                 320

Thr Phe Leu Ser Ile Glu Asn Ser Ile Arg Lys Pro His Leu Phe Asp
                 325                 330                 335

Tyr Leu Gln Gly Ile Glu Phe His Thr Arg Leu Gln Pro Gly Tyr Phe
             340                 345                 350

Gly Lys Asp Ser Phe Asn Tyr Trp Ser Gly Asn Tyr Val Glu Thr Arg
         355                 360                 365

Pro Ser Ile Gly Ser Ser Lys Thr Ile Thr Ser Pro Phe Tyr Gly Asp
     370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                 405                 410                 415

Val Tyr Leu Gly Val Thr Lys Val Asp Phe Ser Gln Tyr Asp Asp Gln
```

-continued

```
                420             425             430
Lys Asn Glu Thr Ser Thr Gln Thr Tyr Asp Ser Lys Arg Asn Asn Gly
            435                 440                 445

His Val Ser Ala Gln Asp Ser Ile Asp Gln Leu Pro Pro Glu Thr Thr
        450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
    530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Asp Leu Thr Tyr Gln Thr
        595                 600                 605

Phe Asp Leu Ala Thr Thr Asn Ser Asn Met Gly Phe Ser Gly Asp Lys
    610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

<210> SEQ ID NO 3
<211> LENGTH: 1959
<212> TYPE: DNA
<213> ORGANISM: Bacillus thuringiensis
<220

-continued

| | | | | | | | | | | | | | | | | |
|---|---|---|---|---|---|---|---|---|---|---|---|---|---|---|---|---|
| | | 85 | | | | 90 | | | | | 95 | | | | | |
| gac | act | ata | tgg | cca | agt | gat | gct | gac | cca | tgg | aag | gct | ttt | atg | gca | 336 |
| Asp | Thr | Ile | Trp | Pro | Ser | Asp | Ala | Asp | Pro | Trp | Lys | Ala | Phe | Met | Ala | |
| | | 100 | | | | 105 | | | | | 110 | | | | | |
| caa | gtt | gaa | gta | ctg | ata | gat | aag | aaa | ata | gag | gag | tat | gct | aaa | agt | 384 |
| Gln | Val | Glu | Val | Leu | Ile | Asp | Lys | Lys | Ile | Glu | Glu | Tyr | Ala | Lys | Ser | |
| | | 115 | | | | 120 | | | | | 125 | | | | | |
| aaa | gct | ctt | gca | gag | tta | cag | ggt | ctt | caa | aat | aat | ttc | gaa | gat | tat | 432 |
| Lys | Ala | Leu | Ala | Glu | Leu | Gln | Gly | Leu | Gln | Asn | Asn | Phe | Glu | Asp | Tyr | |
| | 130 | | | | | 135 | | | | | 140 | | | | | |
| gtt | aat | gcg | tta | aat | tcc | tgg | aag | aaa | aca | cct | tta | agt | ttg | cga | agt | 480 |
| Val | Asn | Ala | Leu | Asn | Ser | Trp | Lys | Lys | Thr | Pro | Leu | Ser | Leu | Arg | Ser | |
| 145 | | | | | 150 | | | | | 155 | | | | | 160 | |
| aaa | aga | agc | caa | gat | cga | ata | agg | gaa | ctt | ttt | tct | caa | gca | gaa | agt | 528 |
| Lys | Arg | Ser | Gln | Asp | Arg | Ile | Arg | Glu | Leu | Phe | Ser | Gln | Ala | Glu | Ser | |
| | | | | 165 | | | | | 170 | | | | | 175 | | |
| cat | ttt | cgt | aat | tcc | atg | ccg | tca | ttt | gca | gtt | tcc | aaa | ttc | gaa | gtg | 576 |
| His | Phe | Arg | Asn | Ser | Met | Pro | Ser | Phe | Ala | Val | Ser | Lys | Phe | Glu | Val | |
| | | | 180 | | | | | 185 | | | | | 190 | | | |
| ctg | ttt | cta | cca | aca | tat | gca | caa | gct | gca | aat | aca | cat | tta | ttg | cta | 624 |
| Leu | Phe | Leu | Pro | Thr | Tyr | Ala | Gln | Ala | Ala | Asn | Thr | His | Leu | Leu | Leu | |
| | | 195 | | | | | 200 | | | | | 205 | | | | |
| tta | aaa | gat | gct | caa | gtt | ttt | gga | gaa | gaa | tgg | gga | tat | tct | tca | gaa | 672 |
| Leu | Lys | Asp | Ala | Gln | Val | Phe | Gly | Glu | Glu | Trp | Gly | Tyr | Ser | Ser | Glu | |
| | 210 | | | | | 215 | | | | | 220 | | | | | |
| gat | gtt | gct | gaa | ttt | tat | cat | aga | caa | tta | aaa | ctt | acg | caa | caa | tac | 720 |
| Asp | Val | Ala | Glu | Phe | Tyr | His | Arg | Gln | Leu | Lys | Leu | Thr | Gln | Gln | Tyr | |
| 225 | | | | | 230 | | | | | 235 | | | | | 240 | |
| act | gac | cat | tgt | gtc | aat | tgg | tat | aat | gtt | gga | tta | aat | ggt | tta | aga | 768 |
| Thr | Asp | His | Cys | Val | Asn | Trp | Tyr | Asn | Val | Gly | Leu | Asn | Gly | Leu | Arg | |
| | | | | 245 | | | | | 250 | | | | | 255 | | |
| ggt | tca | act | tat | gat | gca | tgg | gtc | aaa | ttt | aac | cgt | ttt | cgc | aga | gaa | 816 |
| Gly | Ser | Thr | Tyr | Asp | Ala | Trp | Val | Lys | Phe | Asn | Arg | Phe | Arg | Arg | Glu | |
| | | | 260 | | | | | 265 | | | | | 270 | | | |
| atg | act | tta | act | gta | tta | gat | cta | att | gta | ctt | ttc | cca | ttt | tat | gat | 864 |
| Met | Thr | Leu | Thr | Val | Leu | Asp | Leu | Ile | Val | Leu | Phe | Pro | Phe | Tyr | Asp | |
| | | 275 | | | | | 280 | | | | | 285 | | | | |
| gtt | cgg | tta | tac | tca | aaa | ggt | gtt | aaa | aca | gaa | cta | aca | aga | gac | att | 912 |
| Val | Arg | Leu | Tyr | Ser | Lys | Gly | Val | Lys | Thr | Glu | Leu | Thr | Arg | Asp | Ile | |
| | 290 | | | | | 295 | | | | | 300 | | | | | |
| ttt | acg | gat | cca | att | ttt | tca | ctc | aat | act | ctt | cag | gag | tat | gga | cca | 960 |
| Phe | Thr | Asp | Pro | Ile | Phe | Ser | Leu | Asn | Thr | Leu | Gln | Glu | Tyr | Gly | Pro | |
| 305 | | | | | 310 | | | | | 315 | | | | | 320 | |
| act | ttt | ttg | agt | ata | gaa | aac | tct | att | cga | aaa | cct | cat | tta | ttt | gat | 1008 |
| Thr | Phe | Leu | Ser | Ile | Glu | Asn | Ser | Ile | Arg | Lys | Pro | His | Leu | Phe | Asp | |
| | | | | 325 | | | | | 330 | | | | | 335 | | |
| tat | tta | cag | ggt | att | gaa | ttt | cat | acg | cgt | ctt | caa | cct | ggt | tac | tct | 1056 |
| Tyr | Leu | Gln | Gly | Ile | Glu | Phe | His | Thr | Arg | Leu | Gln | Pro | Gly | Tyr | Ser | |
| | | | 340 | | | | | 345 | | | | | 350 | | | |
| ggg | aaa | gat | tct | ttc | aat | tat | tgg | tct | ggt | aat | tat | gta | gaa | act | aga | 1104 |
| Gly | Lys | Asp | Ser | Phe | Asn | Tyr | Trp | Ser | Gly | Asn | Tyr | Val | Glu | Thr | Arg | |
| | | 355 | | | | | 360 | | | | | 365 | | | | |
| cct | agt | ata | gga | tct | agt | aag | aca | att | act | tcc | cca | ttt | tat | gga | gat | 1152 |
| Pro | Ser | Ile | Gly | Ser | Ser | Lys | Thr | Ile | Thr | Ser | Pro | Phe | Tyr | Gly | Asp | |
| | 370 | | | | | 375 | | | | | 380 | | | | | |
| aaa | tct | act | gaa | cct | gta | caa | aag | tta | agc | ttt | gat | gga | caa | aaa | gtt | 1200 |
| Lys | Ser | Thr | Glu | Pro | Val | Gln | Lys | Leu | Ser | Phe | Asp | Gly | Gln | Lys | Val | |
| 385 | | | | | 390 | | | | | 395 | | | | | 400 | |
| tat | cga | act | ata | gct | aat | aca | gac | gta | gcg | gct | tgg | ccg | aat | ggc | aag | 1248 |

-continued

| | | |
|---|---|---|
| Tyr Arg Thr Ile Ala Asn Thr Asp Val Ala Ala Trp Pro Asn Gly Lys<br>405 410 415 | | |
| ata tat ttt ggt gtt acg aaa gtt gat ttt agt caa tat gat gat caa<br>Ile Tyr Phe Gly Val Thr Lys Val Asp Phe Ser Gln Tyr Asp Asp Gln<br>420 425 430 | | 1296 |
| aaa aat gaa act agt aca caa aca tat gat tca aaa aga aac aat ggc<br>Lys Asn Glu Thr Ser Thr Gln Thr Tyr Asp Ser Lys Arg Asn Asn Gly<br>435 440 445 | | 1344 |
| cat gta ggt gca cag gat tct att gac caa tta cca cca gaa aca aca<br>His Val Gly Ala Gln Asp Ser Ile Asp Gln Leu Pro Pro Glu Thr Thr<br>450 455 460 | | 1392 |
| gat gaa cca ctt gaa aaa gca tat agt cat cag ctt aat tac gcg gaa<br>Asp Glu Pro Leu Glu Lys Ala Tyr Ser His Gln Leu Asn Tyr Ala Glu<br>465 470 475 480 | | 1440 |
| tgt ttc tta atg cag gac cgt cgt gga aca att cca ttt ttt act tgg<br>Cys Phe Leu Met Gln Asp Arg Arg Gly Thr Ile Pro Phe Phe Thr Trp<br>485 490 495 | | 1488 |
| aca cat aga agt gta gac ttt ttt aat aca att gat gct gaa aag att<br>Thr His Arg Ser Val Asp Phe Phe Asn Thr Ile Asp Ala Glu Lys Ile<br>500 505 510 | | 1536 |
| act caa ctt cca gta gtg aaa gca tat gcc ttg tct tca ggt gct tcc<br>Thr Gln Leu Pro Val Val Lys Ala Tyr Ala Leu Ser Ser Gly Ala Ser<br>515 520 525 | | 1584 |
| att att gaa ggt cca gga ttc aca gga gga aat tta cta ttc cta aaa<br>Ile Ile Glu Gly Pro Gly Phe Thr Gly Gly Asn Leu Leu Phe Leu Lys<br>530 535 540 | | 1632 |
| gaa tct agt aat tca att gct aaa ttt aaa gtt aca tta aat tca gca<br>Glu Ser Ser Asn Ser Ile Ala Lys Phe Lys Val Thr Leu Asn Ser Ala<br>545 550 555 560 | | 1680 |
| gcc ttg tta caa cga tat cgt gta aga ata cgc tat gct tct acc act<br>Ala Leu Leu Gln Arg Tyr Arg Val Arg Ile Arg Tyr Ala Ser Thr Thr<br>565 570 575 | | 1728 |
| aac tta cga ctt ttt gtg caa aat tca aac aat gat ttt att gtc atc<br>Asn Leu Arg Leu Phe Val Gln Asn Ser Asn Asn Asp Phe Ile Val Ile<br>580 585 590 | | 1776 |
| tac att aat aaa act atg aat ata gat gat gat tta aca tat caa aca<br>Tyr Ile Asn Lys Thr Met Asn Ile Asp Asp Asp Leu Thr Tyr Gln Thr<br>595 600 605 | | 1824 |
| ttt gat ctc gca act act aat tct aat atg ggg ttc tcg ggt gat acg<br>Phe Asp Leu Ala Thr Thr Asn Ser Asn Met Gly Phe Ser Gly Asp Thr<br>610 615 620 | | 1872 |
| aat gaa ctt ata ata gga gca gaa tct ttc gtt tct aat gaa aaa atc<br>Asn Glu Leu Ile Ile Gly Ala Glu Ser Phe Val Ser Asn Glu Lys Ile<br>625 630 635 640 | | 1920 |
| tat ata gat aag ata gaa ttt atc cca gta caa ttg taa<br>Tyr Ile Asp Lys Ile Glu Phe Ile Pro Val Gln Leu<br>645 650 | | 1959 |

<210> SEQ ID NO 4
<211> LENGTH: 652
<212> TYPE: PRT
<213> ORGANISM: Bacillus thuringiensis

<400> SEQUENCE: 4

Met Asn Pro Asn Asn Arg Ser Glu His Asp Thr Ile Lys Val Thr Pro
1               5                   10                  15

Asn Ser Glu Leu Pro Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

```
Thr Glu Asp Ser Ser Thr Glu Val Leu Asp Asn Ser Thr Val Lys Asp
 50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                 85                  90                  95

Asp Thr Ile Trp Pro Ser Asp Ala Asp Pro Trp Lys Ala Phe Met Ala
                100                 105                 110

Gln Val Glu Val Leu Ile Asp Lys Lys Ile Glu Glu Tyr Ala Lys Ser
                115                 120                 125

Lys Ala Leu Ala Glu Leu Gln Gly Leu Gln Asn Asn Phe Glu Asp Tyr
130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
                180                 185                 190

Leu Phe Leu Pro Thr Tyr Ala Gln Ala Ala Asn Thr His Leu Leu Leu
                195                 200                 205

Leu Lys Asp Ala Gln Val Phe Gly Glu Glu Trp Gly Tyr Ser Ser Glu
210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
                260                 265                 270

Met Thr Leu Thr Val Leu Asp Leu Ile Val Leu Phe Pro Phe Tyr Asp
                275                 280                 285

Val Arg Leu Tyr Ser Lys Gly Val Lys Thr Glu Leu Thr Arg Asp Ile
290                 295                 300

Phe Thr Asp Pro Ile Phe Ser Leu Asn Thr Leu Gln Glu Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Ser
                340                 345                 350

Gly Lys Asp Ser Phe Asn Tyr Trp Ser Gly Asn Tyr Val Glu Thr Arg
                355                 360                 365

Pro Ser Ile Gly Ser Ser Lys Thr Ile Thr Ser Pro Phe Tyr Gly Asp
370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Ile Tyr Phe Gly Val Thr Lys Val Asp Phe Ser Gln Tyr Asp Asp Gln
                420                 425                 430

Lys Asn Glu Thr Ser Thr Gln Thr Tyr Asp Ser Lys Arg Asn Asn Gly
                435                 440                 445

His Val Gly Ala Gln Asp Ser Ile Asp Gln Leu Pro Pro Glu Thr Thr
450                 455                 460
```

```
Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
            485                 490                 495

Thr His Arg Ser Val Asp Phe Phe Asn Thr Ile Asp Ala Glu Lys Ile
        500                 505                 510

Thr Gln Leu Pro Val Val Lys Ala Tyr Ala Leu Ser Ser Gly Ala Ser
    515                 520                 525

Ile Ile Glu Gly Pro Gly Phe Thr Gly Gly Asn Leu Leu Phe Leu Lys
    530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Ile Val Ile
            580                 585                 590

Tyr Ile Asn Lys Thr Met Asn Ile Asp Asp Asp Leu Thr Tyr Gln Thr
        595                 600                 605

Phe Asp Leu Ala Thr Thr Asn Ser Asn Met Gly Phe Ser Gly Asp Thr
    610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

<210> SEQ ID NO 5
<211> LENGTH: 1962
<212> TYPE: DNA
<213> ORGANISM: Artificial Sequence
<220> FEATURE:
<223> OTHER INFORMATION: Description of Artificial Sequence: synthetic
      or non-naturally occurring nucleotide sequence encoding a Cry3Bb
      amino acid sequence
<220> FEATURE:
<221> NAME/KEY: CDS
<222> LOCATION: (1)..(1956)

<400> SEQUENCE: 5 atg aac cct aac aat cgt tcc gaa cac gac acc atc aag gtt act cca       48
Met Asn Pro Asn Asn Arg Ser Glu His Asp Thr Ile Lys Val Thr Pro
  1               5                  10                  15 aac tct gag ttg caa act aat cac aac cag tac cca ttg gct gac aat       96
Asn Ser Glu Leu Gln Thr Asn His Asn Gln Tyr Pro Leu Ala Asp Asn
             20                  25                  30 cct aac agt act ctt gag gaa ctt aac tac aag gag ttt ctc cgg atg      144
Pro Asn Ser Thr Leu Glu Glu Leu Asn Tyr Lys Glu Phe Leu Arg Met
         35                  40                  45 acc gaa gat agc tcc act gag gtt ctc gat aac tct aca gtg aag gac      192
Thr Glu Asp Ser Ser Thr Glu Val Leu Asp Asn Ser Thr Val Lys Asp
     50                  55                  60 gct gtt gga act ggc att agc gtt gtg gga cag att ctt gga gtg gtt      240
Ala Val Gly Thr Gly Ile Ser Val Val Gly Gln Ile Leu Gly Val Val
 65                  70                  75                  80 ggt gtt cca ttc gct gga gct ttg acc agc ttc tac cag tcc ttt ctc      288
Gly Val Pro Phe Ala Gly Ala Leu Thr Ser Phe Tyr Gln Ser Phe Leu
                 85                  90                  95 aac acc atc tgg cct tca gat gct gat ccc tgg aag gct ttc atg gcc      336
Asn Thr Ile Trp Pro Ser Asp Ala Asp Pro Trp Lys Ala Phe Met Ala
            100                 105                 110
```

-continued

| | |
|---|---|
| caa gtg gaa gtc ttg atc gat aag aag atc gaa gag tat gcc aag tct<br>Gln Val Glu Val Leu Ile Asp Lys Lys Ile Glu Glu Tyr Ala Lys Ser<br>    115                        120                      125 | 384 |
| aaa gcc ttg gct gag ttg caa ggt ttg cag aac aac ttc gag gat tac<br>Lys Ala Leu Ala Glu Leu Gln Gly Leu Gln Asn Asn Phe Glu Asp Tyr<br>    130                        135                      140 | 432 |
| gtc aac gca ctc aac agc tgg aag aaa act ccc ttg agt ctc agg tct<br>Val Asn Ala Leu Asn Ser Trp Lys Lys Thr Pro Leu Ser Leu Arg Ser<br>145                      150                      155                  160 | 480 |
| aag cgt tcc cag gac cgt att cgt gaa ctt ttc agc caa gcc gaa tcc<br>Lys Arg Ser Gln Asp Arg Ile Arg Glu Leu Phe Ser Gln Ala Glu Ser<br>                      165                      170                      175 | 528 |
| cac ttc aga aac tcc atg cct agc ttt gcc gtt tct aag ttc gag gtg<br>His Phe Arg Asn Ser Met Pro Ser Phe Ala Val Ser Lys Phe Glu Val<br>        180                        185                      190 | 576 |
| ctc ttc ttg cca aca tac gca caa gct gcc aac act cat ctc ttg ctt<br>Leu Phe Leu Pro Thr Tyr Ala Gln Ala Ala Asn Thr His Leu Leu Leu<br>            195                        200                      205 | 624 |
| ctc aaa gac gct cag gtg ttt ggt gag gaa tgg ggt tac tcc agt gaa<br>Leu Lys Asp Ala Gln Val Phe Gly Glu Glu Trp Gly Tyr Ser Ser Glu<br>    210                        215                      220 | 672 |
| gat gtt gcc gag ttc tac cat agg cag ctc aag ttg act caa cag tac<br>Asp Val Ala Glu Phe Tyr His Arg Gln Leu Lys Leu Thr Gln Gln Tyr<br>225                      230                      235                  240 | 720 |
| aca gac cac tgc gtc aac tgg tac aac gtt ggg ctc aat ggt ctt aga<br>Thr Asp His Cys Val Asn Trp Tyr Asn Val Gly Leu Asn Gly Leu Arg<br>                      245                      250                      255 | 768 |
| gga tct acc tac gac gca tgg gtg aag ttc aac agg ttt cgt aga gag<br>Gly Ser Thr Tyr Asp Ala Trp Val Lys Phe Asn Arg Phe Arg Arg Glu<br>        260                        265                      270 | 816 |
| atg acc ttg act gtg ctc gat ctt atc gtt ctc ttt cca ttc tac gac<br>Met Thr Leu Thr Val Leu Asp Leu Ile Val Leu Phe Pro Phe Tyr Asp<br>            275                        280                      285 | 864 |
| att cgt ctt tac tcc aaa ggc gtt aag aca gag ctg acc aga gac atc<br>Ile Arg Leu Tyr Ser Lys Gly Val Lys Thr Glu Leu Thr Arg Asp Ile<br>    290                        295                      300 | 912 |
| ttc acc gat ccc atc ttc tca ctt aac acc ctg cag gaa tac ggt cca<br>Phe Thr Asp Pro Ile Phe Ser Leu Asn Thr Leu Gln Glu Tyr Gly Pro<br>305                      310                      315                  320 | 960 |
| act ttt ctc tcc att gag aac agc atc agg aag cct cac ctc ttc gac<br>Thr Phe Leu Ser Ile Glu Asn Ser Ile Arg Lys Pro His Leu Phe Asp<br>                      325                      330                      335 | 1008 |
| tat ctg caa ggc att gag ttt cac acc agg ttg caa cct ggt tac ttc<br>Tyr Leu Gln Gly Ile Glu Phe His Thr Arg Leu Gln Pro Gly Tyr Phe<br>        340                        345                      350 | 1056 |
| ggt aag gat tcc ttc aac tac tgg agc gga aac tac gtt gaa acc aga<br>Gly Lys Asp Ser Phe Asn Tyr Trp Ser Gly Asn Tyr Val Glu Thr Arg<br>            355                        360                      365 | 1104 |
| cca tcc atc gga tct agc aag acc atc act tct cca ttc tac ggt gac<br>Pro Ser Ile Gly Ser Ser Lys Thr Ile Thr Ser Pro Phe Tyr Gly Asp<br>    370                        375                      380 | 1152 |
| aag agc act gag cca gtg cag aag ttg agc ttc gat ggg cag aag gtg<br>Lys Ser Thr Glu Pro Val Gln Lys Leu Ser Phe Asp Gly Gln Lys Val<br>385                      390                      395                  400 | 1200 |
| tat aga acc atc gcc aat acc gat gtt gca gct tgg cct aat ggc aag<br>Tyr Arg Thr Ile Ala Asn Thr Asp Val Ala Ala Trp Pro Asn Gly Lys<br>                      405                      410                      415 | 1248 |
| gtc tac ctt gga gtt act aaa gtg gac ttc tcc caa tac gac gat cag<br>Val Tyr Leu Gly Val Thr Lys Val Asp Phe Ser Gln Tyr Asp Asp Gln<br>    420                        425                      430 | 1296 |

-continued

```
aag aac gag aca tct act caa acc tac gat agt aag agg aac aat ggc    1344
Lys Asn Glu Thr Ser Thr Gln Thr Tyr Asp Ser Lys Arg Asn Asn Gly
            435                 440                 445 cat gtt tcc gca caa gac tcc att gac caa ctt cca cct gaa acc act    1392
His Val Ser Ala Gln Asp Ser Ile Asp Gln Leu Pro Pro Glu Thr Thr
450                 455                 460 gat gaa cca ttg gag aag gct tac agt cac caa ctt aac tac gcc gaa    1440
Asp Glu Pro Leu Glu Lys Ala Tyr Ser His Gln Leu Asn Tyr Ala Glu
465                 470                 475                 480 tgc ttt ctc atg caa gac agg cgt ggc acc att ccg ttc ttt aca tgg    1488
Cys Phe Leu Met Gln Asp Arg Arg Gly Thr Ile Pro Phe Phe Thr Trp
                485                 490                 495 act cac agg tct gtc gac ttc ttt aac act atc gac gct gag aag att    1536
Thr His Arg Ser Val Asp Phe Phe Asn Thr Ile Asp Ala Glu Lys Ile
            500                 505                 510 acc caa ctt ccc gtg gtc aag gct tat gcc ttg tcc agc gga gct tcc    1584
Thr Gln Leu Pro Val Val Lys Ala Tyr Ala Leu Ser Ser Gly Ala Ser
        515                 520                 525 atc att gaa ggt cca ggc ttc acc ggt ggc aac ttg ctc ttc ctt aag    1632
Ile Ile Glu Gly Pro Gly Phe Thr Gly Gly Asn Leu Leu Phe Leu Lys
    530                 535                 540 gag tcc agc aac tcc atc gcc aag ttc aaa gtg aca ctt aac tca gca    1680
Glu Ser Ser Asn Ser Ile Ala Lys Phe Lys Val Thr Leu Asn Ser Ala
545                 550                 555                 560 gcc ttg ctc caa cgt tac agg gtt cgt atc aga tac gca agc act acc    1728
Ala Leu Leu Gln Arg Tyr Arg Val Arg Ile Arg Tyr Ala Ser Thr Thr
                565                 570                 575 aat ctt cgc ctc ttt gtc cag aac agc aac aat gat ttc ctt gtc atc    1776
Asn Leu Arg Leu Phe Val Gln Asn Ser Asn Asn Asp Phe Leu Val Ile
            580                 585                 590 tac atc aac aag act atg aac aaa gac gat gac ctc acc tac aac aca    1824
Tyr Ile Asn Lys Thr Met Asn Lys Asp Asp Asp Leu Thr Tyr Asn Thr
        595                 600                 605 ttc gat ctt gcc act acc aat agt aac atg gga ttc tct ggt gac aag    1872
Phe Asp Leu Ala Thr Thr Asn Ser Asn Met Gly Phe Ser Gly Asp Lys
    610                 615                 620 aac gag ctg atc ata ggt gct gag agc ttt gtc tct aat gag aag att    1920
Asn Glu Leu Ile Ile Gly Ala Glu Ser Phe Val Ser Asn Glu Lys Ile
625                 630                 635                 640 tac ata gac aag atc gag ttc att cca gtt caa ctc taatag             1962
Tyr Ile Asp Lys Ile Glu Phe Ile Pro Val Gln Leu
                645                 650
```

<210> SEQ ID NO 6
<211> LENGTH: 652
<212> TYPE: PRT
<213> ORGANISM: Artificial Sequence
<220> FEATURE:
<223> OTHER INFORMATION: Description of Artificial Sequence: synthetic or non-naturally occurring amino acid sequence encoded by SEQ ID NO:5
<220> FEATURE:
<221> NAME/KEY: PRT
<222> LOCATION: (1)..(652)

<400> SEQUENCE: 6

```
Met Asn Pro Asn Asn Arg Ser Glu His Asp Thr Ile Lys Val Thr Pro
1               5                   10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
```

-continued

```
            35                  40                  45
Thr Glu Asp Ser Ser Thr Glu Val Leu Asp Asn Ser Thr Val Lys Asp
 50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                 85                  90                  95

Asn Thr Ile Trp Pro Ser Asp Ala Asp Pro Trp Lys Ala Phe Met Ala
                100                 105                 110

Gln Val Glu Val Leu Ile Asp Lys Lys Ile Glu Tyr Ala Lys Ser
                115                 120                 125

Lys Ala Leu Ala Glu Leu Gln Gly Leu Gln Asn Asn Phe Glu Asp Tyr
            130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
        210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
            275                 280                 285

Ile Arg Leu Tyr Ser Lys Gly Val Lys Thr Glu Leu Thr Arg Asp Ile
        290                 295                 300

Phe Thr Asp Pro Ile Phe Ser Leu Asn Thr Leu Gln Glu Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
            340                 345                 350

Gly Lys Asp Ser Phe Asn Tyr Trp Ser Gly Asn Tyr Val Glu Thr Arg
        355                 360                 365

Pro Ser Ile Gly Ser Ser Lys Thr Ile Thr Ser Pro Phe Tyr Gly Asp
    370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
        435                 440                 445

His Val Ser Ala Gln Asp Ser Ile Asp Gln Leu Pro Pro Glu Thr Thr
    450                 455                 460
```

```
Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
            485                 490                 495

Thr His Arg Ser Val Asp Phe Phe Asn Thr Ile Asp Ala Glu Lys Ile
        500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
        530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
                580                 585                 590

Tyr Ile Asn Lys Thr Met Asn Lys Asp Asp Asp Leu Thr Tyr Asn Thr
            595                 600                 605

Phe Asp Leu Ala Thr Thr Asn Ser Asn Met Gly Phe Ser Gly Asp Lys
610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

<210> SEQ ID NO 7
<211> LENGTH: 1989
<212> TYPE: DNA
<213> ORGANISM: Artificial Sequence
<220> FEATURE:
<223> OTHER INFORMATION: Description of Artificial Sequence: non-
      naturally occurring nucleotide sequence encoding a variant Cry3Bb
      amino acid sequence v11231
<220> FEATURE:
<221> NAME/KEY: CDS
<222> LOCATION: (3)..(1961)
<223> OTHER INFORMATION: coding sequence for Cry3Bb variant v11231 amino
      acid sequence

<400> SEQUENCE: 7 cc atg gca aac cct aac aat cgt tcc gaa cac gac acc atc aag gtt        47
   Met Ala Asn Pro Asn Asn Arg Ser Glu His Asp Thr Ile Lys Val
   1               5                   10                  15 act cca aac tct gag ttg caa act aat cac aac cag tac cca ttg gct       95
Thr Pro Asn Ser Glu Leu Gln Thr Asn His Asn Gln Tyr Pro Leu Ala
            20                  25                  30 gac aat cct aac agt act ctt gag gaa ctt aac tac aag gag ttt ctc      143
Asp Asn Pro Asn Ser Thr Leu Glu Glu Leu Asn Tyr Lys Glu Phe Leu
        35                  40                  45 cgg atg acc gaa gat agc tcc act gag gtt ctc gat aac tct aca gtg      191
Arg Met Thr Glu Asp Ser Ser Thr Glu Val Leu Asp Asn Ser Thr Val
    50                  55                  60 aag gac gct gtt gga act ggc att agc gtt gtg gga cag att ctt gga      239
Lys Asp Ala Val Gly Thr Gly Ile Ser Val Val Gly Gln Ile Leu Gly
65                  70                  75 gtg gtt ggt gtt cca ttc gct gga gct ttg acc agc ttc tac cag tcc      287
Val Val Gly Val Pro Phe Ala Gly Ala Leu Thr Ser Phe Tyr Gln Ser
80                  85                  90                  95 ttt ctc aac acc atc tgg cct tca gat gct gat ccc tgg aag gct ttc      335
```

```
Phe Leu Asn Thr Ile Trp Pro Ser Asp Ala Asp Pro Trp Lys Ala Phe
                100                 105                 110 atg gcc caa gtg gaa gtc ttg atc gat aag aag atc gaa gag tat gcc         383
Met Ala Gln Val Glu Val Leu Ile Asp Lys Lys Ile Glu Glu Tyr Ala
                115                 120                 125 aag tct aaa gcc ttg gct gag ttg caa ggt ttg cag aac aac ttc gag         431
Lys Ser Lys Ala Leu Ala Glu Leu Gln Gly Leu Gln Asn Asn Phe Glu
        130                 135                 140 gat tac gtc aac gca ctc aac agc tgg aag aaa act ccc ttg agt ctc         479
Asp Tyr Val Asn Ala Leu Asn Ser Trp Lys Lys Thr Pro Leu Ser Leu
    145                 150                 155 agg tct aag cgt tcc cag gac cgt att cgt gaa ctt ttc agc caa gcc         527
Arg Ser Lys Arg Ser Gln Asp Arg Ile Arg Glu Leu Phe Ser Gln Ala
160                 165                 170                 175 gaa tcc cac ttc aga aac tcc atg cct agc ttt gcc gtt tct aag ttc         575
Glu Ser His Phe Arg Asn Ser Met Pro Ser Phe Ala Val Ser Lys Phe
                180                 185                 190 gag gtg ctc ttc ttg cca aca tac gca caa gct gcc aac act cat ctc         623
Glu Val Leu Phe Leu Pro Thr Tyr Ala Gln Ala Ala Asn Thr His Leu
            195                 200                 205 ttg ctt ctc aaa gac gct cag gtg ttt ggt gag gaa tgg ggt tac tcc         671
Leu Leu Leu Lys Asp Ala Gln Val Phe Gly Glu Glu Trp Gly Tyr Ser
        210                 215                 220 agt gaa gat gtt gcc gag ttc tac cgt agg cag ctc aag ttg act caa         719
Ser Glu Asp Val Ala Glu Phe Tyr Arg Arg Gln Leu Lys Leu Thr Gln
    225                 230                 235 cag tac aca gac cac tgc gtc aac tgg tac aac gtt ggg ctc aat ggt         767
Gln Tyr Thr Asp His Cys Val Asn Trp Tyr Asn Val Gly Leu Asn Gly
240                 245                 250                 255 ctt aga gga tct acc tac gac gca tgg gtg aag ttc aac agg ttt cgt         815
Leu Arg Gly Ser Thr Tyr Asp Ala Trp Val Lys Phe Asn Arg Phe Arg
                260                 265                 270 aga gag atg acc ttg act gtg ctc gat ctt atc gtt ctc ttt cca ttc         863
Arg Glu Met Thr Leu Thr Val Leu Asp Leu Ile Val Leu Phe Pro Phe
            275                 280                 285 tac gac att cgt ctt tac tcc aaa ggc gtt aag aca gag ctg acc aga         911
Tyr Asp Ile Arg Leu Tyr Ser Lys Gly Val Lys Thr Glu Leu Thr Arg
        290                 295                 300 gac atc ttc acc gat ccc atc ttc cta ctt acg acc ctg cag aaa tac         959
Asp Ile Phe Thr Asp Pro Ile Phe Leu Leu Thr Thr Leu Gln Lys Tyr
    305                 310                 315 ggt cca act ttt ctc tcc att gag aac agc atc agg aag cct cac ctc        1007
Gly Pro Thr Phe Leu Ser Ile Glu Asn Ser Ile Arg Lys Pro His Leu
320                 325                 330                 335 ttc gac tat ctg caa ggc att gag ttt cac acc agg ttg caa cct ggt        1055
Phe Asp Tyr Leu Gln Gly Ile Glu Phe His Thr Arg Leu Gln Pro Gly
                340                 345                 350 tac ttc ggt aag gat tcc ttc aac tac tgg agc gga aac tac gtt gaa        1103
Tyr Phe Gly Lys Asp Ser Phe Asn Tyr Trp Ser Gly Asn Tyr Val Glu
            355                 360                 365 acc aga cca tcc atc gga tct agc aag acc atc act tct cca ttc tac        1151
Thr Arg Pro Ser Ile Gly Ser Ser Lys Thr Ile Thr Ser Pro Phe Tyr
        370                 375                 380 ggt gac aag agc act gag cca gtg cag aag ttg agc ttc gat ggg cag        1199
Gly Asp Lys Ser Thr Glu Pro Val Gln Lys Leu Ser Phe Asp Gly Gln
    385                 390                 395 aag gtg tat aga acc atc gcc aat acc gat gtt gca gct tgg cct aat        1247
Lys Val Tyr Arg Thr Ile Ala Asn Thr Asp Val Ala Ala Trp Pro Asn
400                 405                 410                 415
```

-continued

```
ggc aag gtc tac ctt gga gtt act aaa gtg gac ttc tcc caa tac gac     1295
Gly Lys Val Tyr Leu Gly Val Thr Lys Val Asp Phe Ser Gln Tyr Asp
                420                 425                 430 gat cag aag aac gag aca tct act caa acc tac gat agt aag agg aac     1343
Asp Gln Lys Asn Glu Thr Ser Thr Gln Thr Tyr Asp Ser Lys Arg Asn
            435                 440                 445 aat ggc cat gtt tcc gca caa gac tcc att gac caa ctt cca cct gaa     1391
Asn Gly His Val Ser Ala Gln Asp Ser Ile Asp Gln Leu Pro Pro Glu
        450                 455                 460 acc act gat gaa cca ttg gag aag gct tac agt cac caa ctt aac tac     1439
Thr Thr Asp Glu Pro Leu Glu Lys Ala Tyr Ser His Gln Leu Asn Tyr
    465                 470                 475 gcc gaa tgc ttt ctc atg caa gac agg cgt ggc acc att ccg ttc ttt     1487
Ala Glu Cys Phe Leu Met Gln Asp Arg Arg Gly Thr Ile Pro Phe Phe
480                 485                 490                 495 aca tgg act cac agg tct gtc gac ttc ttt aac act atc gac gct gag     1535
Thr Trp Thr His Arg Ser Val Asp Phe Phe Asn Thr Ile Asp Ala Glu
                500                 505                 510 aag att acc caa ctt ccc gtg gtc aag gct tat gcc ttg tcc agc gga     1583
Lys Ile Thr Gln Leu Pro Val Val Lys Ala Tyr Ala Leu Ser Ser Gly
            515                 520                 525 gct tcc atc att gaa ggt cca ggc ttc acc ggt ggc aac ttg ctc ttc     1631
Ala Ser Ile Ile Glu Gly Pro Gly Phe Thr Gly Gly Asn Leu Leu Phe
        530                 535                 540 ctt aag gag tcc agc aac tcc atc gcc aag ttc aaa gtg aca ctt aac     1679
Leu Lys Glu Ser Ser Asn Ser Ile Ala Lys Phe Lys Val Thr Leu Asn
    545                 550                 555 tca gca gcc ttg ctc caa cgt tac agg gtt cgt atc aga tac gca agc     1727
Ser Ala Ala Leu Leu Gln Arg Tyr Arg Val Arg Ile Arg Tyr Ala Ser
560                 565                 570                 575 act acc aat ctt cgc ctc ttt gtc cag aac agc aac aat gat ttc ctt     1775
Thr Thr Asn Leu Arg Leu Phe Val Gln Asn Ser Asn Asn Asp Phe Leu
                580                 585                 590 gtc atc tac atc aac aag act atg aac aaa gac gat gac ctc acc tac     1823
Val Ile Tyr Ile Asn Lys Thr Met Asn Lys Asp Asp Asp Leu Thr Tyr
            595                 600                 605 caa aca ttc gat ctt gcc act acc aat agt aac atg gga ttc tct ggt     1871
Gln Thr Phe Asp Leu Ala Thr Thr Asn Ser Asn Met Gly Phe Ser Gly
        610                 615                 620 gac aag aac gag ctg atc ata ggt gct gag agc ttt gtc tct aat gag     1919
Asp Lys Asn Glu Leu Ile Ile Gly Ala Glu Ser Phe Val Ser Asn Glu
    625                 630                 635 aag att tac ata gac aag atc gag ttc att cca gtt caa ctc             1961
Lys Ile Tyr Ile Asp Lys Ile Glu Phe Ile Pro Val Gln Leu
640                 645                 650 taatagatcc cccgggctgc aggaattc                                      1989

<210> SEQ ID NO 8
<211> LENGTH: 653
<212> TYPE: PRT
<213> ORGANISM: Artificial Sequence
<220> FEATURE:
<223> OTHER INFORMATION: Description of Artificial Sequence: non-
      naturally occurring amino acid sequence encoded by SEQ ID NO:7
<220> FEATURE:
<221> NAME/KEY: PRT
<222> LOCATION: (1)..(653)
<223> OTHER INFORMATION: amino acid sequence for Cry3Bb variant v11231
      encoded by SEQ ID NO:7

<400> SEQUENCE: 8

Met Ala Asn Pro Asn Asn Arg Ser Glu His Asp Thr Ile Lys Val Thr
```

-continued

```
  1               5                   10                  15

Pro Asn Ser Glu Leu Gln Thr Asn His Asn Gln Tyr Pro Leu Ala Asp
             20                  25                  30

Asn Pro Asn Ser Thr Leu Glu Glu Leu Asn Tyr Lys Glu Phe Leu Arg
             35                  40                  45

Met Thr Glu Asp Ser Ser Thr Glu Val Leu Asp Asn Ser Thr Val Lys
             50                  55                  60

Asp Ala Val Gly Thr Gly Ile Ser Val Val Gly Gln Ile Leu Gly Val
 65                  70                  75                  80

Val Gly Val Pro Phe Ala Gly Ala Leu Thr Ser Phe Tyr Gln Ser Phe
                 85                  90                  95

Leu Asn Thr Ile Trp Pro Ser Asp Ala Asp Pro Trp Lys Ala Phe Met
                100                 105                 110

Ala Gln Val Glu Val Leu Ile Asp Lys Lys Ile Glu Glu Tyr Ala Lys
                115                 120                 125

Ser Lys Ala Leu Ala Glu Leu Gln Gly Leu Gln Asn Asn Phe Glu Asp
            130                 135                 140

Tyr Val Asn Ala Leu Asn Ser Trp Lys Lys Thr Pro Leu Ser Leu Arg
145                 150                 155                 160

Ser Lys Arg Ser Gln Asp Arg Ile Arg Glu Leu Phe Ser Gln Ala Glu
                165                 170                 175

Ser His Phe Arg Asn Ser Met Pro Ser Phe Ala Val Ser Lys Phe Glu
                180                 185                 190

Val Leu Phe Leu Pro Thr Tyr Ala Gln Ala Ala Asn Thr His Leu Leu
                195                 200                 205

Leu Leu Lys Asp Ala Gln Val Phe Gly Glu Glu Trp Gly Tyr Ser Ser
            210                 215                 220

Glu Asp Val Ala Glu Phe Tyr Arg Arg Gln Leu Lys Leu Thr Gln Gln
225                 230                 235                 240

Tyr Thr Asp His Cys Val Asn Trp Tyr Asn Val Gly Leu Asn Gly Leu
                245                 250                 255

Arg Gly Ser Thr Tyr Asp Ala Trp Val Lys Phe Asn Arg Phe Arg Arg
                260                 265                 270

Glu Met Thr Leu Thr Val Leu Asp Leu Ile Val Leu Phe Pro Phe Tyr
                275                 280                 285

Asp Ile Arg Leu Tyr Ser Lys Gly Val Lys Thr Glu Leu Thr Arg Asp
                290                 295                 300

Ile Phe Thr Asp Pro Ile Phe Leu Leu Thr Thr Leu Gln Lys Tyr Gly
305                 310                 315                 320

Pro Thr Phe Leu Ser Ile Glu Asn Ser Ile Arg Lys Pro His Leu Phe
                325                 330                 335

Asp Tyr Leu Gln Gly Ile Glu Phe His Thr Arg Leu Gln Pro Gly Tyr
                340                 345                 350

Phe Gly Lys Asp Ser Phe Asn Tyr Trp Ser Gly Asn Tyr Val Glu Thr
            355                 360                 365

Arg Pro Ser Ile Gly Ser Ser Lys Thr Ile Thr Ser Pro Phe Tyr Gly
            370                 375                 380

Asp Lys Ser Thr Glu Pro Val Gln Lys Leu Ser Phe Asp Gly Gln Lys
385                 390                 395                 400

Val Tyr Arg Thr Ile Ala Asn Thr Asp Val Ala Ala Trp Pro Asn Gly
                405                 410                 415

Lys Val Tyr Leu Gly Val Thr Lys Val Asp Phe Ser Gln Tyr Asp Asp
                420                 425                 430
```

-continued

Gln Lys Asn Glu Thr Ser Thr Gln Thr Tyr Asp Ser Lys Arg Asn Asn
        435                 440                 445

Gly His Val Ser Ala Gln Asp Ser Ile Asp Gln Leu Pro Pro Glu Thr
    450                 455                 460

Thr Asp Glu Pro Leu Glu Lys Ala Tyr Ser His Gln Leu Asn Tyr Ala
465                 470                 475                 480

Glu Cys Phe Leu Met Gln Asp Arg Arg Gly Thr Ile Pro Phe Phe Thr
                485                 490                 495

Trp Thr His Arg Ser Val Asp Phe Phe Asn Thr Ile Asp Ala Glu Lys
            500                 505                 510

Ile Thr Gln Leu Pro Val Val Lys Ala Tyr Ala Leu Ser Ser Gly Ala
        515                 520                 525

Ser Ile Ile Glu Gly Pro Gly Phe Thr Gly Gly Asn Leu Leu Phe Leu
    530                 535                 540

Lys Glu Ser Ser Asn Ser Ile Ala Lys Phe Lys Val Thr Leu Asn Ser
545                 550                 555                 560

Ala Ala Leu Leu Gln Arg Tyr Arg Val Arg Ile Arg Tyr Ala Ser Thr
                565                 570                 575

Thr Asn Leu Arg Leu Phe Val Gln Asn Ser Asn Asn Asp Phe Leu Val
            580                 585                 590

Ile Tyr Ile Asn Lys Thr Met Asn Lys Asp Asp Asp Leu Thr Tyr Gln
        595                 600                 605

Thr Phe Asp Leu Ala Thr Thr Asn Ser Asn Met Gly Phe Ser Gly Asp
    610                 615                 620

Lys Asn Glu Leu Ile Ile Gly Ala Glu Ser Phe Val Ser Asn Glu Lys
625                 630                 635                 640

Ile Tyr Ile Asp Lys Ile Glu Phe Ile Pro Val Gln Leu
                645                 650

<210> SEQ ID NO 9
<211> LENGTH: 1984
<212> TYPE: DNA
<213> ORGANISM: Artificial Sequence
<220> FEATURE:
<223> OTHER INFORMATION: Description of Artificial Sequence: non-naturally occurring nucleotide sequence encoding a Cry3Bb variant 11231mv1 amino acid sequence
<220> FEATURE:
<221> NAME/KEY: CDS
<222> LOCATION: (3)..(1961)
<223> OTHER INFORMATION: coding sequence for a Cry3Bb variant 11231mv1 amino acid sequence

<400> SEQUENCE: 9 cc atg gcc aac ccc aac aat cgc tcc gag cac gac acg atc aag gtc        47
   Met Ala Asn Pro Asn Asn Arg Ser Glu His Asp Thr Ile Lys Val
     1               5                  10                  15 acc ccc aac tcc gag ctc cag acc aac cac aac cag tac ccg ctg gcc       95
Thr Pro Asn Ser Glu Leu Gln Thr Asn His Asn Gln Tyr Pro Leu Ala
                20                  25                  30 gac aac ccc aac tcc acc ctg gaa gag ctg aac tac aag gag ttc ctg      143
Asp Asn Pro Asn Ser Thr Leu Glu Glu Leu Asn Tyr Lys Glu Phe Leu
            35                  40                  45 cgc atg acc gag gac tcc tcc acg gag gtc ctg gac aac tcc acc gtc      191
Arg Met Thr Glu Asp Ser Ser Thr Glu Val Leu Asp Asn Ser Thr Val
        50                  55                  60 aag gac gcc gtc ggg acc ggc atc tcc gtc gtt ggg cag atc ctg ggc      239
Lys Asp Ala Val Gly Thr Gly Ile Ser Val Val Gly Gln Ile Leu Gly
     65                  70                  75

```
gtc gtt ggc gtc ccc ttc gca ggt gct ctc acc tcc ttc tac cag tcc        287
Val Val Gly Val Pro Phe Ala Gly Ala Leu Thr Ser Phe Tyr Gln Ser
 80              85                  90                  95 ttc ctg aac acc atc tgg ccc tcc gac gcc gac ccc tgg aag gcc ttc        335
Phe Leu Asn Thr Ile Trp Pro Ser Asp Ala Asp Pro Trp Lys Ala Phe
                    100                 105                 110 atg gcc caa gtc gaa gtc ctg atc gac aag aag atc gag gag tac gcc        383
Met Ala Gln Val Glu Val Leu Ile Asp Lys Lys Ile Glu Glu Tyr Ala
                115                 120                 125 aag tcc aag gcc ctg gcc gag ctg caa ggc ctg caa aac aac ttc gag        431
Lys Ser Lys Ala Leu Ala Glu Leu Gln Gly Leu Gln Asn Asn Phe Glu
    130                 135                 140 gac tac gtc aac gcg ctg aac tcc tgg aag aag acg cct ctg tcc ctg        479
Asp Tyr Val Asn Ala Leu Asn Ser Trp Lys Lys Thr Pro Leu Ser Leu
    145                 150                 155 cgc tcc aag cgc tcc cag ggc cgc atc cgc gag ctg ttc tcc cag gcc        527
Arg Ser Lys Arg Ser Gln Gly Arg Ile Arg Glu Leu Phe Ser Gln Ala
160                 165                 170                 175 gag tcc cac ttc cgc aac tcc atg ccg tcc ttc gcc gtc tcc aag ttc        575
Glu Ser His Phe Arg Asn Ser Met Pro Ser Phe Ala Val Ser Lys Phe
                180                 185                 190 gag gtc ctg ttc ctg ccc acc tac gcc cag gct gcc aac acc cac ctc        623
Glu Val Leu Phe Leu Pro Thr Tyr Ala Gln Ala Ala Asn Thr His Leu
                195                 200                 205 ctg ttg ctg aag gac gcc cag gtc ttc ggc gag gaa tgg ggc tac tcc        671
Leu Leu Leu Lys Asp Ala Gln Val Phe Gly Glu Glu Trp Gly Tyr Ser
    210                 215                 220 tcg gag gac gtc gcc gag ttc tac cgt cgc cag ctg aag ctg acc caa        719
Ser Glu Asp Val Ala Glu Phe Tyr Arg Arg Gln Leu Lys Leu Thr Gln
    225                 230                 235 cag tac acc gac cac tgc gtc aac tgg tac aac gtc ggc ctg aac ggc        767
Gln Tyr Thr Asp His Cys Val Asn Trp Tyr Asn Val Gly Leu Asn Gly
240                 245                 250                 255 ctg agg ggc tcc acc tac gac gca tgg gtc aag ttc aac cgc ttc cgc        815
Leu Arg Gly Ser Thr Tyr Asp Ala Trp Val Lys Phe Asn Arg Phe Arg
                260                 265                 270 agg gag atg acc ctg acc gtc ctg gac ctg atc gtc ctg ttc ccc ttc        863
Arg Glu Met Thr Leu Thr Val Leu Asp Leu Ile Val Leu Phe Pro Phe
                275                 280                 285 tac gac atc cgc ctg tac tcc aag ggc gtc aag acc gag ctg acc cgc        911
Tyr Asp Ile Arg Leu Tyr Ser Lys Gly Val Lys Thr Glu Leu Thr Arg
                290                 295                 300 gac atc ttc acg gac ccc atc ttc ctg ctc acg acc ctc cag aag tac        959
Asp Ile Phe Thr Asp Pro Ile Phe Leu Leu Thr Thr Leu Gln Lys Tyr
305                 310                 315 ggt ccc acc ttc ctg tcc atc gag aac tcc atc cgc aag ccc cac ctg       1007
Gly Pro Thr Phe Leu Ser Ile Glu Asn Ser Ile Arg Lys Pro His Leu
320                 325                 330                 335 ttc gac tac ctc cag ggc atc gag ttc cac acg cgc ctg agg cca ggc       1055
Phe Asp Tyr Leu Gln Gly Ile Glu Phe His Thr Arg Leu Arg Pro Gly
                340                 345                 350 tac ttc ggc aag gac tcc ttc aac tac tgg tcc ggc aac tac gtc gag       1103
Tyr Phe Gly Lys Asp Ser Phe Asn Tyr Trp Ser Gly Asn Tyr Val Glu
                355                 360                 365 acc agg ccc tcc atc ggc tcc tcg aag acg atc acc tcc cct ttc tac       1151
Thr Arg Pro Ser Ile Gly Ser Ser Lys Thr Ile Thr Ser Pro Phe Tyr
                370                 375                 380 ggc gac aag tcc acc gag ccc gtc cag aag ctg tcc ttc gac ggc cag       1199
Gly Asp Lys Ser Thr Glu Pro Val Gln Lys Leu Ser Phe Asp Gly Gln
```

```
                385                 390                 395
aag gtc tac cgc acc atc gcc aac acc gac gtc gcg gct tgg ccg aac      1247
Lys Val Tyr Arg Thr Ile Ala Asn Thr Asp Val Ala Ala Trp Pro Asn
400                 405                 410                 415 ggc aag gtc tac ctg ggc gtc acg aag gtc gac ttc tcc cag tac gat      1295
Gly Lys Val Tyr Leu Gly Val Thr Lys Val Asp Phe Ser Gln Tyr Asp
                420                 425                 430 gac cag aag aat gaa acc tcc acc cag acc tac gac tcc aag cgc aac      1343
Asp Gln Lys Asn Glu Thr Ser Thr Gln Thr Tyr Asp Ser Lys Arg Asn
435                 440                 445 aat ggc cac gtc tcc gcc cag gac tcc atc gac cag ctg ccg cct gag      1391
Asn Gly His Val Ser Ala Gln Asp Ser Ile Asp Gln Leu Pro Pro Glu
    450                 455                 460 acc act gac gag ccc ctg gag aag gcc tac tcc cac cag ctg aac tac      1439
Thr Thr Asp Glu Pro Leu Glu Lys Ala Tyr Ser His Gln Leu Asn Tyr
465                 470                 475 gcg gag tgc ttc ctg atg caa gac cgc agg ggc acc atc ccc ttc ttc      1487
Ala Glu Cys Phe Leu Met Gln Asp Arg Arg Gly Thr Ile Pro Phe Phe
480                 485                 490                 495 acc tgg acc cac cgc tcc gtc gac ttc ttc aac acc atc gac gcc gag      1535
Thr Trp Thr His Arg Ser Val Asp Phe Phe Asn Thr Ile Asp Ala Glu
                500                 505                 510 aag atc acc cag ctg ccc gtg gtc aag gcc tac gcc ctg tcc tcg ggt      1583
Lys Ile Thr Gln Leu Pro Val Val Lys Ala Tyr Ala Leu Ser Ser Gly
            515                 520                 525 gcc tcc atc att gag ggt cca ggc ttc acc ggt ggc aac ctg ctg ttc      1631
Ala Ser Ile Ile Glu Gly Pro Gly Phe Thr Gly Gly Asn Leu Leu Phe
        530                 535                 540 ctg aag gag tcc tcg aac tcc atc gcc aag ttc aag gtc acc ctg aac      1679
Leu Lys Glu Ser Ser Asn Ser Ile Ala Lys Phe Lys Val Thr Leu Asn
545                 550                 555 tcc gct gcc ttg ctg caa cgc tac cgc gtc cgc atc cgc tac gcc tcc      1727
Ser Ala Ala Leu Leu Gln Arg Tyr Arg Val Arg Ile Arg Tyr Ala Ser
560                 565                 570                 575 acc acg aac ctg cgc ctg ttc gtc cag aac tcc aac aat gac ttc ctg      1775
Thr Thr Asn Leu Arg Leu Phe Val Gln Asn Ser Asn Asn Asp Phe Leu
                580                 585                 590 gtc atc tac atc aac aag acc atg aac aag gac gat gac ctg acc tac      1823
Val Ile Tyr Ile Asn Lys Thr Met Asn Lys Asp Asp Asp Leu Thr Tyr
            595                 600                 605 cag acc ttc gac ctc gcc acc acg aac tcc aac atg ggc ttc tcg ggc      1871
Gln Thr Phe Asp Leu Ala Thr Thr Asn Ser Asn Met Gly Phe Ser Gly
        610                 615                 620 gac aag aat gaa ctg atc att ggt gct gag tcc ttc gtc tcc aat gaa      1919
Asp Lys Asn Glu Leu Ile Ile Gly Ala Glu Ser Phe Val Ser Asn Glu
625                 630                 635 aag atc tac atc gac aag atc gag ttc atc ccc gtc cag ctg               1961
Lys Ile Tyr Ile Asp Lys Ile Glu Phe Ile Pro Val Gln Leu
640                 645                 650 tgataggaac tctgattgaa ttc                                            1984

<210> SEQ ID NO 10
<211> LENGTH: 653
<212> TYPE: PRT
<213> ORGANISM: Artificial Sequence
<220> FEATURE:
<223> OTHER INFORMATION: Description of Artificial Sequence: non-
      naturally occurring amino acid sequence encoded by SEQ ID NO:9
<220> FEATURE:
<221> NAME/KEY: PRT
<222> LOCATION: (1)..(653)
```

<223> OTHER INFORMATION: amino acid sequence encoded by SEQ ID NO:9

<400> SEQUENCE: 10

```
Met Ala Asn Pro Asn Arg Ser Glu His Asp Thr Ile Lys Val Thr
 1               5                  10                  15

Pro Asn Ser Glu Leu Gln Thr Asn His Asn Gln Tyr Pro Leu Ala Asp
                20                  25                  30

Asn Pro Asn Ser Thr Leu Glu Glu Leu Asn Tyr Lys Glu Phe Leu Arg
            35                  40                  45

Met Thr Glu Asp Ser Ser Thr Glu Val Leu Asp Asn Ser Thr Val Lys
50                  55                  60

Asp Ala Val Gly Thr Gly Ile Ser Val Val Gly Gln Ile Leu Gly Val
65                  70                  75                  80

Val Gly Val Pro Phe Ala Gly Ala Leu Thr Ser Phe Tyr Gln Ser Phe
                85                  90                  95

Leu Asn Thr Ile Trp Pro Ser Asp Ala Asp Pro Trp Lys Ala Phe Met
                100                 105                 110

Ala Gln Val Glu Val Leu Ile Asp Lys Lys Ile Glu Glu Tyr Ala Lys
            115                 120                 125

Ser Lys Ala Leu Ala Glu Leu Gln Gly Leu Gln Asn Asn Phe Glu Asp
130                 135                 140

Tyr Val Asn Ala Leu Asn Ser Trp Lys Lys Thr Pro Leu Ser Leu Arg
145                 150                 155                 160

Ser Lys Arg Ser Gln Gly Arg Ile Arg Glu Leu Phe Ser Gln Ala Glu
                165                 170                 175

Ser His Phe Arg Asn Ser Met Pro Ser Phe Ala Val Ser Lys Phe Glu
                180                 185                 190

Val Leu Phe Leu Pro Thr Tyr Ala Gln Ala Ala Asn Thr His Leu Leu
            195                 200                 205

Leu Leu Lys Asp Ala Gln Val Phe Gly Glu Glu Trp Gly Tyr Ser Ser
210                 215                 220

Glu Asp Val Ala Glu Phe Tyr Arg Arg Gln Leu Lys Leu Thr Gln Gln
225                 230                 235                 240

Tyr Thr Asp His Cys Val Asn Trp Tyr Asn Val Gly Leu Asn Gly Leu
                245                 250                 255

Arg Gly Ser Thr Tyr Asp Ala Trp Val Lys Phe Asn Arg Phe Arg Arg
                260                 265                 270

Glu Met Thr Leu Thr Val Leu Asp Leu Ile Val Leu Phe Pro Phe Tyr
            275                 280                 285

Asp Ile Arg Leu Tyr Ser Lys Gly Val Lys Thr Glu Leu Thr Arg Asp
290                 295                 300

Ile Phe Thr Asp Pro Ile Phe Leu Leu Thr Thr Leu Gln Lys Tyr Gly
305                 310                 315                 320

Pro Thr Phe Leu Ser Ile Glu Asn Ser Ile Arg Lys Pro His Leu Phe
                325                 330                 335

Asp Tyr Leu Gln Gly Ile Glu Phe His Thr Arg Leu Arg Pro Gly Tyr
            340                 345                 350

Phe Gly Lys Asp Ser Phe Asn Tyr Trp Ser Gly Asn Tyr Val Glu Thr
        355                 360                 365

Arg Pro Ser Ile Gly Ser Ser Lys Thr Ile Thr Ser Pro Phe Tyr Gly
            370                 375                 380

Asp Lys Ser Thr Glu Pro Val Gln Lys Leu Ser Phe Asp Gly Gln Lys
385                 390                 395                 400
```

-continued

```
Val Tyr Arg Thr Ile Ala Asn Thr Asp Val Ala Ala Trp Pro Asn Gly
            405                 410                 415

Lys Val Tyr Leu Gly Val Thr Lys Val Asp Phe Ser Gln Tyr Asp Asp
        420                 425                 430

Gln Lys Asn Glu Thr Ser Thr Gln Thr Tyr Asp Ser Lys Arg Asn Asn
    435                 440                 445

Gly His Val Ser Ala Gln Asp Ser Ile Asp Gln Leu Pro Pro Glu Thr
450                 455                 460

Thr Asp Glu Pro Leu Glu Lys Ala Tyr Ser His Gln Leu Asn Tyr Ala
465                 470                 475                 480

Glu Cys Phe Leu Met Gln Asp Arg Arg Gly Thr Ile Pro Phe Phe Thr
                485                 490                 495

Trp Thr His Arg Ser Val Asp Phe Phe Asn Thr Ile Asp Ala Glu Lys
            500                 505                 510

Ile Thr Gln Leu Pro Val Val Lys Ala Tyr Ala Leu Ser Ser Gly Ala
        515                 520                 525

Ser Ile Ile Glu Gly Pro Gly Phe Thr Gly Gly Asn Leu Leu Phe Leu
    530                 535                 540

Lys Glu Ser Ser Asn Ser Ile Ala Lys Phe Lys Val Thr Leu Asn Ser
545                 550                 555                 560

Ala Ala Leu Leu Gln Arg Tyr Arg Val Arg Ile Arg Tyr Ala Ser Thr
                565                 570                 575

Thr Asn Leu Arg Leu Phe Val Gln Asn Ser Asn Asn Asp Phe Leu Val
            580                 585                 590

Ile Tyr Ile Asn Lys Thr Met Asn Lys Asp Asp Leu Thr Tyr Gln
        595                 600                 605

Thr Phe Asp Leu Ala Thr Thr Asn Ser Asn Met Gly Phe Ser Gly Asp
    610                 615                 620

Lys Asn Glu Leu Ile Ile Gly Ala Glu Ser Phe Val Ser Asn Glu Lys
625                 630                 635                 640

Ile Tyr Ile Asp Lys Ile Glu Phe Ile Pro Val Gln Leu
                645                 650
```

<210> SEQ ID NO 11
<211> LENGTH: 1984
<212> TYPE: DNA
<213> ORGANISM: Artificial Sequence
<220> FEATURE:
<223> OTHER INFORMATION: Description of Artificial Sequence: non-
      naturally occurring nucleotide sequence encoding a Cry3Bb variant
      11231mv2 amino acid sequence
<220> FEATURE:

-continued

```
            50                  55                  60
aag gac gcc gtc ggg acc ggc atc tcc gtc gtt ggg cag atc ctg ggc       239
Lys Asp Ala Val Gly Thr Gly Ile Ser Val Val Gly Gln Ile Leu Gly
         65                  70                  75 gtc gtt ggc gtc ccc ttc gca ggt gct ctc acc tcc ttc tac cag tcc       287
Val Gly Val Pro Phe Ala Gly Ala Leu Thr Ser Phe Tyr Gln Ser
 80                  85                  90                  95 ttc ctg aac acc atc tgg ccc tcc gac gcc gac ccc tgg aag gcc ttc       335
Phe Leu Asn Thr Ile Trp Pro Ser Asp Ala Asp Pro Trp Lys Ala Phe
                    100                 105                 110 atg gcc caa gtc gaa gtc ctg atc gac aag aag atc gag gag tac gcc       383
Met Ala Gln Val Glu Val Leu Ile Asp Lys Lys Ile Glu Glu Tyr Ala
                115                 120                 125 aag tcc aag gcc ctg gcc gag ctg caa ggc ctg caa aac aac ttc gag       431
Lys Ser Lys Ala Leu Ala Glu Leu Gln Gly Leu Gln Asn Asn Phe Glu
            130                 135                 140 gac tac gtc aac gcg ctg aac tcc tgg aag aag acg cct ctg tcc ctg       479
Asp Tyr Val Asn Ala Leu Asn Ser Trp Lys Lys Thr Pro Leu Ser Leu
        145                 150                 155 cgc tcc aag cgc tcc cag gac cgc atc cgc gag ctg ttc tcc cag gcc       527
Arg Ser Lys Arg Ser Gln Asp Arg Ile Arg Glu Leu Phe Ser Gln Ala
160                 165                 170                 175 gag tcc cac ttc cgc aac tcc atg ccg tcc ttc gcc gtc tcc aag ttc       575
Glu Ser His Phe Arg Asn Ser Met Pro Ser Phe Ala Val Ser Lys Phe
                180                 185                 190 gag gtc ctg ttc ctg ccc acc tac gcc cag gct gcc aac acc cac ctc       623
Glu Val Leu Phe Leu Pro Thr Tyr Ala Gln Ala Ala Asn Thr His Leu
            195                 200                 205 ctg ttg ctg aag gac gcc cag gtc ttc ggc gag gaa tgg ggc tac tcc       671
Leu Leu Leu Lys Asp Ala Gln Val Phe Gly Glu Glu Trp Gly Tyr Ser
        210                 215                 220 tcg gag gac gtc gcc gag ttc tac cgt cgc cag ctg aag ctg acc caa       719
Ser Glu Asp Val Ala Glu Phe Tyr Arg Arg Gln Leu Lys Leu Thr Gln
225                 230                 235 cag tac acc gac cac tgc gtc aac tgg tac aac gtc ggc ctg aac ggc       767
Gln Tyr Thr Asp His Cys Val Asn Trp Tyr Asn Val Gly Leu Asn Gly
240                 245                 250                 255 ctg agg ggc tcc acc tac gac gca tgg gtc aag ttc aac cgc ttc cgc       815
Leu Arg Gly Ser Thr Tyr Asp Ala Trp Val Lys Phe Asn Arg Phe Arg
                260                 265                 270 agg gag atg acc ctg acc gtc ctg gac ctg atc gtc ctg ttc ccc ttc       863
Arg Glu Met Thr Leu Thr Val Leu Asp Leu Ile Val Leu Phe Pro Phe
            275                 280                 285 tac gac atc cgc ctg tac tcc aag ggc gtc aag acc gag ctg acc cgc       911
Tyr Asp Ile Arg Leu Tyr Ser Lys Gly Val Lys Thr Glu Leu Thr Arg
        290                 295                 300 gac atc ttc acg gac ccc atc ttc ctg ctc acg acc ctc cag aag tac       959
Asp Ile Phe Thr Asp Pro Ile Phe Leu Leu Thr Thr Leu Gln Lys Tyr
305                 310                 315 ggt ccc acc ttc ctg tcc atc gag aac tcc atc cgc aag ccc cac ctg       1007
Gly Pro Thr Phe Leu Ser Ile Glu Asn Ser Ile Arg Lys Pro His Leu
320                 325                 330                 335 ttc gac tac ctc cag ggc atc gag ttc cac acg cgc ctg agg cca ggc       1055
Phe Asp Tyr Leu Gln Gly Ile Glu Phe His Thr Arg Leu Arg Pro Gly
                340                 345                 350 tac ttc ggc aag gac tcc ttc aac tac tgg tcc ggc aac tac gtc gag       1103
Tyr Phe Gly Lys Asp Ser Phe Asn Tyr Trp Ser Gly Asn Tyr Val Glu
            355                 360                 365 acc agg ccc tcc atc ggc tcc tcg aag acg atc acc tcc cct ttc tac       1151
```

```
                Thr Arg Pro Ser Ile Gly Ser Ser Lys Thr Ile Thr Ser Pro Phe Tyr
                        370                 375                 380 ggc gac aag tcc acc gag ccc gtc cag aag ctg tcc ttc gac ggc cag                1199
Gly Asp Lys Ser Thr Glu Pro Val Gln Lys Leu Ser Phe Asp Gly Gln
385                 390                 395 aag gtc tac cgc acc atc gcc aac acc gac gtc gcg gct tgg ccg aac                1247
Lys Val Tyr Arg Thr Ile Ala Asn Thr Asp Val Ala Ala Trp Pro Asn
400                 405                 410                 415 ggc aag gtc tac ctg ggc gtc acg aag gtc gac ttc tcc cag tac gat                1295
Gly Lys Val Tyr Leu Gly Val Thr Lys Val Asp Phe Ser Gln Tyr Asp
                420                 425                 430 gac cag aag aat gaa acc tcc acc cag acc tac gac tcc aag cgc aac                1343
Asp Gln Lys Asn Glu Thr Ser Thr Gln Thr Tyr Asp Ser Lys Arg Asn
                435                 440                 445 aat ggc cac gtc tcc gcc cag gac tcc atc gac cag ctg ccg cct gag                1391
Asn Gly His Val Ser Ala Gln Asp Ser Ile Asp Gln Leu Pro Pro Glu
                450                 455                 460 acc act gac gag ccc ctg gag aag gcc tac tcc cac cag ctg aac tac                1439
Thr Thr Asp Glu Pro Leu Glu Lys Ala Tyr Ser His Gln Leu Asn Tyr
465                 470                 475 gcg gag tgc ttc ctg atg caa gac cgc agg ggc acc atc ccc ttc ttc                1487
Ala Glu Cys Phe Leu Met Gln Asp Arg Arg Gly Thr Ile Pro Phe Phe
480                 485                 490                 495 acc tgg acc cac cgc tcc gtc gac ttc ttc aac acc atc gac gcc gag                1535
Thr Trp Thr His Arg Ser Val Asp Phe Phe Asn Thr Ile Asp Ala Glu
                500                 505                 510 aag atc acc cag ctg ccc gtg gtc aag gcc tac gcc ctg tcc tcg ggt                1583
Lys Ile Thr Gln Leu Pro Val Val Lys Ala Tyr Ala Leu Ser Ser Gly
                515                 520                 525 gcc tcc atc att gag ggt cca ggc ttc acc ggt ggc aac ctg ctg ttc                1631
Ala Ser Ile Ile Glu Gly Pro Gly Phe Thr Gly Gly Asn Leu Leu Phe
                530                 535                 540 ctg aag gag tcc tcg aac tcc atc gcc aag ttc aag gtc acc ctg aac                1679
Leu Lys Glu Ser Ser Asn Ser Ile Ala Lys Phe Lys Val Thr Leu Asn
                545                 550                 555 tcc gct gcc ttg ctg caa cgc tac cgc gtc cgc atc cgc tac gcc tcc                1727
Ser Ala Ala Leu Leu Gln Arg Tyr Arg Val Arg Ile Arg Tyr Ala Ser
560                 565                 570                 575 acc acg aac ctg cgc ctg ttc gtc cag aac tcc aac aat gac ttc ctg                1775
Thr Thr Asn Leu Arg Leu Phe Val Gln Asn Ser Asn Asn Asp Phe Leu
                580                 585                 590 gtc atc tac atc aac aag acc atg aac aag gac gat gac ctg acc tac                1823
Val Ile Tyr Ile Asn Lys Thr Met Asn Lys Asp Asp Asp Leu Thr Tyr
                595                 600                 605 cag acc ttc gac ctc gcc acc acg aac tcc aac atg ggc ttc tcg ggc                1871
Gln Thr Phe Asp Leu Ala Thr Thr Asn Ser Asn Met Gly Phe Ser Gly
                610                 615                 620 gac aag aat gaa ctg atc att ggt gct gag tcc ttc gtc tcc aat gaa                1919
Asp Lys Asn Glu Leu Ile Ile Gly Ala Glu Ser Phe Val Ser Asn Glu
                625                 630                 635 aag atc tac atc gac aag atc gag ttc atc ccc gtc cag ctg                        1961
Lys Ile Tyr Ile Asp Lys Ile Glu Phe Ile Pro Val Gln Leu
640                 645                 650 tgataggaac tctgattgaa ttc                                                      1984

<210> SEQ ID NO 12
<211> LENGTH: 653
<212> TYPE: PRT
<213> ORGANISM: Artificial Sequence
<220> FEATURE:
```

```
<223> OTHER INFORMATION: Description of Artificial Sequence: non-
      naturally occurring amino acid sequence encoded by SEQ ID NO:11
<220> FEATURE:
<221> NAME/KEY: PRT
<222> LOCATION: (1)..(1653)
<223> OTHER INFORMATION: amino acid sequence encoded by SEQ ID NO:11

<400> SEQUENCE: 12
```

Met Ala Asn Pro Asn Asn Arg Ser Glu His Asp Thr Ile Lys Val Thr
 1               5                  10                  15

Pro Asn Ser Glu Leu Gln Thr Asn His Asn Gln Tyr Pro Leu Ala Asp
            20                  25                  30

Asn Pro Asn Ser Thr Leu Glu Glu Leu Asn Tyr Lys Glu Phe Leu Arg
        35                  40                  45

Met Thr Glu Asp Ser Ser Thr Glu Val Leu Asp Asn Ser Thr Val Lys
    50                  55                  60

Asp Ala Val Gly Thr Gly Ile Ser Val Val Gly Gln Ile Leu Gly Val
65                  70                  75                  80

Val Gly Val Pro Phe Ala Gly Ala Leu Thr Ser Phe Tyr Gln Ser Phe
                85                  90                  95

Leu Asn Thr Ile Trp Pro Ser Asp Ala Asp Pro Trp Lys Ala Phe Met
            100                 105                 110

Ala Gln Val Glu Val Leu Ile Asp Lys Lys Ile Glu Glu Tyr Ala Lys
        115                 120                 125

Ser Lys Ala Leu Ala Glu Leu Gln Gly Leu Gln Asn Asn Phe Glu Asp
    130                 135                 140

Tyr Val Asn Ala Leu Asn Ser Trp Lys Lys Thr Pro Leu Ser Leu Arg
145                 150                 155                 160

Ser Lys Arg Ser Gln Asp Arg Ile Arg Glu Leu Phe Ser Gln Ala Glu
                165                 170                 175

Ser His Phe Arg Asn Ser Met Pro Ser Phe Ala Val Ser Lys Phe Glu
            180                 185                 190

Val Leu Phe Leu Pro Thr Tyr Ala Gln Ala Ala Asn Thr His Leu Leu
        195                 200                 205

Leu Leu Lys Asp Ala Gln Val Phe Gly Glu Glu Trp Gly Tyr Ser Ser
    210                 215                 220

Glu Asp Val Ala Glu Phe Tyr Arg Arg Gln Leu Lys Leu Thr Gln Gln
225                 230                 235                 240

Tyr Thr Asp His Cys Val Asn Trp Tyr Asn Val Gly Leu Asn Gly Leu
                245                 250                 255

Arg Gly Ser Thr Tyr Asp Ala Trp Val Lys Phe Asn Arg Phe Arg Arg
            260                 265                 270

Glu Met Thr Leu Thr Val Leu Asp Leu Ile Val Leu Phe Pro Phe Tyr
        275                 280                 285

Asp Ile Arg Leu Tyr Ser Lys Gly Val Lys Thr Glu Leu Thr Arg Asp
    290                 295                 300

Ile Phe Thr Asp Pro Ile Phe Leu Leu Thr Thr Leu Gln Lys Tyr Gly
305                 310                 315                 320

Pro Thr Phe Leu Ser Ile Glu Asn Ser Ile Arg Lys Pro His Leu Phe
                325                 330                 335

Asp Tyr Leu Gln Gly Ile Glu Phe His Thr Arg Leu Arg Pro Gly Tyr
            340                 345                 350

Phe Gly Lys Asp Ser Phe Asn Tyr Trp Ser Gly Asn Tyr Val Glu Thr
        355                 360                 365

Arg Pro Ser Ile Gly Ser Ser Lys Thr Ile Thr Ser Pro Phe Tyr Gly

```
                    370                 375                 380
Asp Lys Ser Thr Glu Pro Val Gln Lys Leu Ser Phe Asp Gly Gln Lys
385                 390                 395                 400

Val Tyr Arg Thr Ile Ala Asn Thr Asp Val Ala Ala Trp Pro Asn Gly
                405                 410                 415

Lys Val Tyr Leu Gly Val Thr Lys Val Asp Phe Ser Gln Tyr Asp Asp
            420                 425                 430

Gln Lys Asn Glu Thr Ser Thr Gln Thr Tyr Asp Ser Lys Arg Asn Asn
        435                 440                 445

Gly His Val Ser Ala Gln Asp Ser Ile Asp Gln Leu Pro Pro Glu Thr
    450                 455                 460

Thr Asp Glu Pro Leu Glu Lys Ala Tyr Ser His Gln Leu Asn Tyr Ala
465                 470                 475                 480

Glu Cys Phe Leu Met Gln Asp Arg Arg Gly Thr Ile Pro Phe Phe Thr
                485                 490                 495

Trp Thr His Arg Ser Val Asp Phe Phe Asn Thr Ile Asp Ala Glu Lys
            500                 505                 510

Ile Thr Gln Leu Pro Val Val Lys Ala Tyr Ala Leu Ser Ser Gly Ala
        515                 520                 525

Ser Ile Ile Glu Gly Pro Gly Phe Thr Gly Gly Asn Leu Leu Phe Leu
    530                 535                 540

Lys Glu Ser Ser Asn Ser Ile Ala Lys Phe Lys Val Thr Leu Asn Ser
545                 550                 555                 560

Ala Ala Leu Leu Gln Arg Tyr Arg Val Arg Ile Arg Tyr Ala Ser Thr
                565                 570                 575

Thr Asn Leu Arg Leu Phe Val Gln Asn Ser Asn Asn Asp Phe Leu Val
            580                 585                 590

Ile Tyr Ile Asn Lys Thr Met Asn Lys Asp Asp Asp Leu Thr Tyr Gln
        595                 600                 605

Thr Phe Asp Leu Ala Thr Thr Asn Ser Asn Met Gly Phe Ser Gly Asp
    610                 615                 620

Lys Asn Glu Leu Ile Ile Gly Ala Glu Ser Phe Val Ser Asn Glu Lys
625                 630                 635                 640

Ile Tyr Ile Asp Lys Ile Glu Phe Ile Pro Val Gln Leu
                645                 650

<210> SEQ ID NO 13
<211> LENGTH: 4149
<212> TYPE: DNA
<213> ORGANISM: Artificial Sequence
<220> FEATURE:
<223> OTHER INFORMATION: Description of Artificial Sequence: expression
      cassette
<220> FEATURE:
<221> NAME/KEY: promoter
<222> LOCATION: (25)..(640)
<223> OTHER INFORMATION: P-CaMV.35S
<220> FEATURE:
<221> NAME/KEY: intron
<222> LOCATION: (669)..(1472)
<223> OTHER INFORMATION: I-Zm.Hsp70
<220> FEATURE:
<221> NAME/KEY: transit_peptide
<222> LOCATION: (1489)..(1635)
<223> OTHER INFORMATION: amino terminal TS-Zm.rbcS
<220> FEATURE:
<221> NAME/KEY: intron
<222> LOCATION: (1636)..(1798)
<223> OTHER INFORMATION: I-Zm.rbcS
<220> FEATURE:
<221> NAME/KEY: transit_peptide
```

```
<222> LOCATION: (1799)..(1885)
<223> OTHER INFORMATION: carboxy terminus TS-Zm.rbcS
<220> FEATURE:
<221> NAME/KEY: CDS
<222> LOCATION: (1885)..(3843)
<223> OTHER INFORMATION: Cry3Bb1 variant v11231
<220> FEATURE:
<221> NAME/KEY: terminator
<222> LOCATION: (3871)..(4127)
<223> OTHER INFORMATION: T-AGRtu.nos 3' transcription termination and
      polyadenylation sequence

<400> SEQUENCE: 13
gcggccgcgt taacaagctt ctgcaggtcc gatgtgagac ttttcaacaa agggtaatat      60
ccggaaacct cctcggattc cattgcccag ctatctgtca ctttattgtg aagatagtgg     120
aaaaggaagg tggctcctac aaatgccatc attgcgataa aggaaaggcc atcgttgaag     180
atgcctctgc cgacagtggt cccaaagatg gaccccgacc cacgaggagc atcgtggaaa     240
aagaagacgt tccaaccacg tcttcaaagc aagtggattg atgtgatggt ccgatgtgag     300 actttcaac aaagggtaat atccggaaac ctcctcggat tccattgccc agctatctgt     360
cactttattg tgaagatagt gaaaaggaag gtggctccta caaatgccat cattgcgata     420
aaggaaaggc catcgttgaa gatgcctctg ccgacagtgg tcccaaagat ggaccccgac     480
ccacgaggag catcgtggaa aaagaagacg ttccaaccac gtcttcaaag caagtggatt     540
gatgtgatat ctccactgac gtaagggatg acgcacaatc ccactatcct tcgcaagacc     600
cttcctctat ataaggaagt tcatttcatt tggagaggac acgctgacaa gctgactcta     660
gcagatctac cgtcttcggt acgcgctcac tccgcctct gcctttgtta ctgccacgtt     720
tctctgaatg ctctcttgtg tggtgattgc tgagagtggt ttagctggat ctagaattac     780
actctgaaat cgtgttctgc ctgtgctgat tacttgccgt cctttgtagc agcaaaatat     840
agggacatgg tagtacgaaa cgaagataga acctacacag caatacgaga atgtgtaat      900 ttggtgctta gcggtattta tttaagcaca tgttggtgtt atagggcact tggattcaga     960
agtttgctgt taatttaggc acaggcttca tactacatgg gtcaatagta tagggattca    1020
tattataggc gatactataa taatttgttc gtctgcagag cttattattt gccaaaatta    1080
gatattccta ttctgttttt gtttgtgtgc tgttaaattg ttaacgcctg aaggaataaa    1140
tataaatgac gaaattttga tgtttatctc tgctccttta ttgtgaccat aagtcaagat    1200
cagatgcact tgttttaaat attgttgtct gaagaaataa gtactgacag tattttgatg    1260
cttgatctgc ttgtttgttg taacaaaatt taaaaataaa gagtttcctt tttgttgctc    1320
tccttacctc ctgatggtat ctagtatcta ccaactgaca ctatattgct tctctttaca    1380
tacgtatctt gctcgatgcc ttctccctag tgttgaccag tgttactcac atagtctttg    1440
ctcatttcat tgtaatgcag ataccaagcg gcctctagag gatcagcatg gcgcccaccg    1500
tgatgatggc ctcgtcggcc accgccgtcg ctccgttcct ggggctcaag tccaccgcca    1560
gcctccccgt cgcccgccgc tcctccagaa gcctcggcaa cgtcagcaac ggcggaagga    1620
tccggtgcat gcaggtaaca aatgcatcct agctagtagt tctttgcatt gcagcagctg    1680
cagctagcga gttagtaata ggaagggaac tgatgatcca tgcatggact gatgtgtgtt    1740
gcccatccca tccatccca tttcccaaac gaaccgaaaa caccgtacta cgtgcaggtg    1800
tggccctacg gcaacaagaa gttcgagacg ctgtcgtacc tgccgccgct gtcgaccggc    1860
gggcgcatcc gctgcatgca ggcc atg gca aac cct aac aat cgt tcc gaa      1911
                                  Met Ala Asn Pro Asn Asn Arg Ser Glu
                                    1               5
```

```
cac gac acc atc aag gtt act cca aac tct gag ttg caa act aat cac      1959
His Asp Thr Ile Lys Val Thr Pro Asn Ser Glu Leu Gln Thr Asn His
 10              15                  20                  25 aac cag tac cca ttg gct gac aat cct aac agt act ctt gag gaa ctt      2007
Asn Gln Tyr Pro Leu Ala Asp Asn Pro Asn Ser Thr Leu Glu Glu Leu
             30                  35                  40 aac tac aag gag ttt ctc cgg atg acc gaa gat agc tcc act gag gtt      2055
Asn Tyr Lys Glu Phe Leu Arg Met Thr Glu Asp Ser Ser Thr Glu Val
                 45                  50                  55 ctc gat aac tct aca gtg aag gac gct gtt gga act ggc att agc gtt      2103
Leu Asp Asn Ser Thr Val Lys Asp Ala Val Gly Thr Gly Ile Ser Val
             60                  65                  70 gtg gga cag att ctt gga gtg gtt ggt gtt cca ttc gct gga gct ttg      2151
Val Gly Gln Ile Leu Gly Val Val Gly Val Pro Phe Ala Gly Ala Leu
 75                  80                  85 acc agc ttc tac cag tcc ttt ctc aac acc atc tgg cct tca gat gct      2199
Thr Ser Phe Tyr Gln Ser Phe Leu Asn Thr Ile Trp Pro Ser Asp Ala
 90                  95                 100                 105 gat ccc tgg aag gct ttc atg gcc caa gtg gaa gtc ttg atc gat aag      2247
Asp Pro Trp Lys Ala Phe Met Ala Gln Val Glu Val Leu Ile Asp Lys
                110                 115                 120 aag atc gaa gag tat gcc aag tct aaa gcc ttg gct gag ttg caa ggt      2295
Lys Ile Glu Glu Tyr Ala Lys Ser Lys Ala Leu Ala Glu Leu Gln Gly
             125                 130                 135 ttg cag aac aac ttc gag gat tac gtc aac gca ctc aac agc tgg aag      2343
Leu Gln Asn Asn Phe Glu Asp Tyr Val Asn Ala Leu Asn Ser Trp Lys
             140                 145                 150 aaa act ccc ttg agt ctc agg tct aag cgt tcc cag gac cgt att cgt      2391
Lys Thr Pro Leu Ser Leu Arg Ser Lys Arg Ser Gln Asp Arg Ile Arg
 155                 160                 165 gaa ctt ttc agc caa gcc gaa tcc cac ttc aga aac tcc atg cct agc      2439
Glu Leu Phe Ser Gln Ala Glu Ser His Phe Arg Asn Ser Met Pro Ser
170                 175                 180                 185 ttt gcc gtt tct aag ttc gag gtg ctc ttc ttg cca aca tac gca caa      2487
Phe Ala Val Ser Lys Phe Glu Val Leu Phe Leu Pro Thr Tyr Ala Gln
                190                 195                 200 gct gcc aac act cat ctc ttg ctt ctc aaa gac gct cag gtg ttt ggt      2535
Ala Ala Asn Thr His Leu Leu Leu Leu Lys Asp Ala Gln Val Phe Gly
             205                 210                 215 gag gaa tgg ggt tac tcc agt gaa gat gtt gcc gag ttc tac cgt agg      2583
Glu Glu Trp Gly Tyr Ser Ser Glu Asp Val Ala Glu Phe Tyr Arg Arg
             220                 225                 230 cag ctc aag ttg act caa cag tac aca gac cac tgc gtc aac tgg tac      2631
Gln Leu Lys Leu Thr Gln Gln Tyr Thr Asp His Cys Val Asn Trp Tyr
 235                 240                 245 aac gtt ggg ctc aat ggt ctt aga gga tct acc tac gac gca tgg gtg      2679
Asn Val Gly Leu Asn Gly Leu Arg Gly Ser Thr Tyr Asp Ala Trp Val
250                 255                 260                 265 aag ttc aac agg ttt cgt aga gag atg acc ttg act gtg ctc gat ctt      2727
Lys Phe Asn Arg Phe Arg Arg Glu Met Thr Leu Thr Val Leu Asp Leu
                270                 275                 280 atc gtt ctc ttt cca ttc tac gac att cgt ctt tac tcc aaa ggc gtt      2775
Ile Val Leu Phe Pro Phe Tyr Asp Ile Arg Leu Tyr Ser Lys Gly Val
             285                 290                 295 aag aca gag ctg acc aga gac atc ttc acc gat ccc atc ttc cta ctt      2823
Lys Thr Glu Leu Thr Arg Asp Ile Phe Thr Asp Pro Ile Phe Leu Leu
             300                 305                 310 acg acc ctg cag aaa tac ggt cca act ttt ctc tcc att gag aac agc      2871
Thr Thr Leu Gln Lys Tyr Gly Pro Thr Phe Leu Ser Ile Glu Asn Ser
```

```
              315                 320                 325
atc agg aag cct cac ctc ttc gac tat ctg caa ggc att gag ttt cac     2919
Ile Arg Lys Pro His Leu Phe Asp Tyr Leu Gln Gly Ile Glu Phe His
330                 335                 340                 345 acc agg ttg caa cct ggt tac ttc ggt aag gat tcc ttc aac tac tgg     2967
Thr Arg Leu Gln Pro Gly Tyr Phe Gly Lys Asp Ser Phe Asn Tyr Trp
            350                 355                 360 agc gga aac tac gtt gaa acc aga cca tcc atc gga tct agc aag acc     3015
Ser Gly Asn Tyr Val Glu Thr Arg Pro Ser Ile Gly Ser Ser Lys Thr
        365                 370                 375 atc act tct cca ttc tac ggt gac aag agc act gag cca gtg cag aag     3063
Ile Thr Ser Pro Phe Tyr Gly Asp Lys Ser Thr Glu Pro Val Gln Lys
    380                 385                 390 ttg agc ttc gat ggg cag aag gtg tat aga acc atc gcc aat acc gat     3111
Leu Ser Phe Asp Gly Gln Lys Val Tyr Arg Thr Ile Ala Asn Thr Asp
395                 400                 405 gtt gca gct tgg cct aat ggc aag gtc tac ctt gga gtt act aaa gtg     3159
Val Ala Ala Trp Pro Asn Gly Lys Val Tyr Leu Gly Val Thr Lys Val
410                 415                 420                 425 gac ttc tcc caa tac gat gat cag aag aac gag aca tct act caa acc     3207
Asp Phe Ser Gln Tyr Asp Asp Gln Lys Asn Glu Thr Ser Thr Gln Thr
            430                 435                 440 tac gat agt aag agg aac aat ggc cat gtt tcc gca caa gac tcc att     3255
Tyr Asp Ser Lys Arg Asn Asn Gly His Val Ser Ala Gln Asp Ser Ile
        445                 450                 455 gac caa ctt cca cct gaa acc act gat gaa cca ttg gag aag gct tac     3303
Asp Gln Leu Pro Pro Glu Thr Thr Asp Glu Pro Leu Glu Lys Ala Tyr
    460                 465                 470 agt cac caa ctt aac tac gcc gaa tgc ttt ctc atg caa gac agg cgt     3351
Ser His Gln Leu Asn Tyr Ala Glu Cys Phe Leu Met Gln Asp Arg Arg
475                 480                 485 ggc acc att ccg ttc ttt aca tgg act cac agg tct gtc gac ttc ttt     3399
Gly Thr Ile Pro Phe Phe Thr Trp Thr His Arg Ser Val Asp Phe Phe
490                 495                 500                 505 aac act atc gac gct gag aag att acc caa ctt ccc gtg gtc aag gct     3447
Asn Thr Ile Asp Ala Glu Lys Ile Thr Gln Leu Pro Val Val Lys Ala
            510                 515                 520 tat gcc ttg tcc agc gga gct tcc atc att gaa ggt cca ggc ttc acc     3495
Tyr Ala Leu Ser Ser Gly Ala Ser Ile Ile Glu Gly Pro Gly Phe Thr
        525                 530                 535 ggt ggc aac ttg ctc ttc ctt aag gag tcc agc aac tcc atc gcc aag     3543
Gly Gly Asn Leu Leu Phe Leu Lys Glu Ser Ser Asn Ser Ile Ala Lys
    540                 545                 550 ttc aaa gtg aca ctt aac tca gca gcc ttg ctc caa cgt tac agg gtt     3591
Phe Lys Val Thr Leu Asn Ser Ala Ala Leu Leu Gln Arg Tyr Arg Val
555                 560                 565 cgt atc aga tac gca agc act acc aat ctt cgc ctc ttt gtc cag aac     3639
Arg Ile Arg Tyr Ala Ser Thr Thr Asn Leu Arg Leu Phe Val Gln Asn
570                 575                 580                 585 agc aac aat gat ttc ctt gtc atc tac atc aac aag act atg aac aaa     3687
Ser Asn Asn Asp Phe Leu Val Ile Tyr Ile Asn Lys Thr Met Asn Lys
            590                 595                 600 gac gat gac ctc acc tac caa aca ttc gat ctt gcc act acc aat agt     3735
Asp Asp Asp Leu Thr Tyr Gln Thr Phe Asp Leu Ala Thr Thr Asn Ser
        605                 610                 615 aac atg gga ttc tct ggt gac aag aac gag ctg atc ata ggt gct gag     3783
Asn Met Gly Phe Ser Gly Asp Lys Asn Glu Leu Ile Ile Gly Ala Glu
    620                 625                 630 agc ttt gtc tct aat gag aag att tac ata gac aag atc gag ttc att     3831
```

```
Ser Phe Val Ser Asn Glu Lys Ile Tyr Ile Asp Lys Ile Glu Phe Ile
    635                 640                 645 cca gtt caa ctc taatagatcc cccgggctgc aggaattccc gatcgttcaa        3883
Pro Val Gln Leu
650 acatttggca ataaagtttc ttaagattga atcctgttgc cggtcttgcg atgattatca   3943 tataatttct gttgaattac gttaagcatg taataattaa catgtaatgc atgacgttat   4003 ttatgagatg ggtttttatg attagagtcc cgcaattata catttaatac gcgatagaaa   4063 acaaaatata gcgcgcaaac taggataaat tatcgcgcgc ggtgtcatct atgttactag   4123 atcggggata tccccggggc ggccgc                                       4149

<210> SEQ ID NO 14
<211> LENGTH: 653
<212> TYPE: PRT
<213> ORGANISM: Artificial Sequence
<220> FEATURE:
<223> OTHER INFORMATION: Description of Artificial Sequence: peptide
      encoded by SEQ ID NO:13
<220> FEATURE:
<221> NAME/KEY: PRT
<222> LOCATION: (1)..(653)
<223> OTHER INFORMATION: Cry3Bb1 variant v11231

<400> SEQUENCE: 14

Met Ala Asn Pro Asn Asn Arg Ser Glu His Asp Thr Ile Lys Val Thr
 1               5                  10                  15

Pro Asn Ser Glu Leu Gln Thr Asn His Asn Gln Tyr Pro Leu Ala Asp
            20                  25                  30

Asn Pro Asn Ser Thr Leu Glu Glu Leu Asn Tyr Lys Glu Phe Leu Arg
        35                  40                  45

Met Thr Glu Asp Ser Ser Thr Glu Val Leu Asp Asn Ser Thr Val Lys
    50                  55                  60

Asp Ala Val Gly Thr Gly Ile Ser Val Val Gly Gln Ile Leu Gly Val
65                  70                  75                  80

Val Gly Val Pro Phe Ala Gly Ala Leu Thr Ser Phe Tyr Gln Ser Phe
                85                  90                  95

Leu Asn Thr Ile Trp Pro Ser Asp Ala Asp Pro Trp Lys Ala Phe Met
            100                 105                 110

Ala Gln Val Glu Val Leu Ile Asp Lys Lys Ile Glu Glu Tyr Ala Lys
        115                 120                 125

Ser Lys Ala Leu Ala Glu Leu Gln Gly Leu Gln Asn Asn Phe Glu Asp
    130                 135                 140

Tyr Val Asn Ala Leu Asn Ser Trp Lys Lys Thr Pro Leu Ser Leu Arg
145                 150                 155                 160

Ser Lys Arg Ser Gln Asp Arg Ile Arg Glu Leu Phe Ser Gln Ala Glu
                165                 170                 175

Ser His Phe Arg Asn Ser Met Pro Ser Phe Ala Val Ser Lys Phe Glu
            180                 185                 190

Val Leu Phe Leu Pro Thr Tyr Ala Gln Ala Ala Asn Thr His Leu Leu
        195                 200                 205

Leu Leu Lys Asp Ala Gln Val Phe Gly Glu Glu Trp Gly Tyr Ser Ser
    210                 215                 220

Glu Asp Val Ala Glu Phe Tyr Arg Arg Gln Leu Lys Leu Thr Gln Gln
225                 230                 235                 240

Tyr Thr Asp His Cys Val Asn Trp Tyr Asn Val Gly Leu Asn Gly Leu
                245                 250                 255
```

```
Arg Gly Ser Thr Tyr Asp Ala Trp Val Lys Phe Asn Arg Phe Arg Arg
            260                 265                 270

Glu Met Thr Leu Thr Val Leu Asp Leu Ile Val Leu Phe Pro Phe Tyr
        275                 280                 285

Asp Ile Arg Leu Tyr Ser Lys Gly Val Lys Thr Glu Leu Thr Arg Asp
    290                 295                 300

Ile Phe Thr Asp Pro Ile Phe Leu Leu Thr Thr Leu Gln Lys Tyr Gly
305                 310                 315                 320

Pro Thr Phe Leu Ser Ile Glu Asn Ser Ile Arg Lys Pro His Leu Phe
                325                 330                 335

Asp Tyr Leu Gln Gly Ile Glu Phe His Thr Arg Leu Gln Pro Gly Tyr
            340                 345                 350

Phe Gly Lys Asp Ser Phe Asn Tyr Trp Ser Gly Asn Tyr Val Glu Thr
        355                 360                 365

Arg Pro Ser Ile Gly Ser Ser Lys Thr Ile Thr Ser Pro Phe Tyr Gly
    370                 375                 380

Asp Lys Ser Thr Glu Pro Val Gln Lys Leu Ser Phe Asp Gly Gln Lys
385                 390                 395                 400

Val Tyr Arg Thr Ile Ala Asn Thr Asp Val Ala Ala Trp Pro Asn Gly
                405                 410                 415

Lys Val Tyr Leu Gly Val Thr Lys Val Asp Phe Ser Gln Tyr Asp Asp
            420                 425                 430

Gln Lys Asn Glu Thr Ser Thr Gln Thr Tyr Asp Ser Lys Arg Asn Asn
        435                 440                 445

Gly His Val Ser Ala Gln Asp Ser Ile Asp Gln Leu Pro Pro Glu Thr
    450                 455                 460

Thr Asp Glu Pro Leu Glu Lys Ala Tyr Ser His Gln Leu Asn Tyr Ala
465                 470                 475                 480

Glu Cys Phe Leu Met Gln Asp Arg Arg Gly Thr Ile Pro Phe Phe Thr
                485                 490                 495

Trp Thr His Arg Ser Val Asp Phe Phe Asn Thr Ile Asp Ala Glu Lys
            500                 505                 510

Ile Thr Gln Leu Pro Val Val Lys Ala Tyr Ala Leu Ser Ser Gly Ala
        515                 520                 525

Ser Ile Ile Glu Gly Pro Gly Phe Thr Gly Gly Asn Leu Leu Phe Leu
    530                 535                 540

Lys Glu Ser Ser Asn Ser Ile Ala Lys Phe Lys Val Thr Leu Asn Ser
545                 550                 555                 560

Ala Ala Leu Leu Gln Arg Tyr Arg Val Arg Ile Arg Tyr Ala Ser Thr
                565                 570                 575

Thr Asn Leu Arg Leu Phe Val Gln Asn Ser Asn Asn Asp Phe Leu Val
            580                 585                 590

Ile Tyr Ile Asn Lys Thr Met Asn Lys Asp Asp Leu Thr Tyr Gln
        595                 600                 605

Thr Phe Asp Leu Ala Thr Thr Asn Ser Asn Met Gly Phe Ser Gly Asp
    610                 615                 620

Lys Asn Glu Leu Ile Ile Gly Ala Glu Ser Phe Val Ser Asn Glu Lys
625                 630                 635                 640

Ile Tyr Ile Asp Lys Ile Glu Phe Ile Pro Val Gln Leu
                645                 650

<210> SEQ ID NO 15
<211> LENGTH: 3754
```

```
<212> TYPE: DNA
<213> ORGANISM: Artificial Sequence
<220> FEATURE:
<223> OTHER INFORMATION: Description of Artificial Sequence: expression
      cassette
<220> FEATURE:
<221> NAME/KEY: promoter
<222> LOCATION: (25)..(640)
<223> OTHER INFORMATION: P-CaMV.35S
<220> FEATURE:
<221> NAME/KEY: intron
<222> LOCATION: (669)..(1472)
<223> OTHER INFORMATION: I-Zm.Hsp70
<220> FEATURE:
<221> NAME/KEY: CDS
<222> LOCATION: (1490)..(3448)
<223> OTHER INFORMATION: Cry3Bb1 variant v11231
<220> FEATURE:
<221> NAME/KEY: terminator
<222> LOCATION: (3475)..(3730)
<223> OTHER INFORMATION: Agrobacterium tumefaciens nos 3' transcription
      termination and polyadenylation sequence

<400> SEQUENCE: 15
gcggccgcgt taacaagctt ctgcaggtcc gatgtgagac ttttcaacaa agggtaatat    60
ccggaaacct cctcggattc cattgcccag ctatctgtca ctttattgtg aagatagtgg   120
aaaaggaagg tggctcctac aaatgccatc attgcgataa aggaaaggcc atcgttgaag   180
atgcctctgc cgacagtggt cccaaagatg acccccacc cacgaggagc atcgtggaaa   240
aagaagacgt tccaaccacg tcttcaaagc aagtggattg atgtgatggt ccgatgtgag   300 actttcaac aaagggtaat atccggaaac ctcctcggat tccattgccc agctatctgt   360
cactttattg tgaagatagt ggaaaaggaa ggtggctcct acaaatgcca tcattgcgat   420
aaaggaaagg ccatcgttga agatgcctct gccgacagtg gtcccaaaga tgaccccca   480 cccacgagga gcatcgtgga aaaagaagac gttccaacca cgtcttcaaa gcaagtggat   540
tgatgtgata tctccactga cgtaagggat gacgcacaat cccactatcc ttcgcaagac   600
ccttcctcta tataaggaag ttcatttcat tggagagga cacgctgaca agctgactct   660
agcagatcta ccgtcttcgg tacgcgctca ctccgccctc tgcctttgtt actgccacgt   720
ttctctgaat gctctcttgt gtggtgattg ctgagagtgg tttagctgga tctagaatta   780
cactctgaaa tcgtgttctg cctgtgctga ttacttgccg tcctttgtag cagcaaaata   840
tagggacatg gtagtacgaa acgaagatag aacctacaca gcaatacgag aaatgtgtaa   900
tttggtgctt agcggtattt atttaagcac atgttggtgt tatagggcac ttggattcag   960
aagtttgctg ttaatttagg cacaggcttc atactacatg ggtcaatagt atagggattc  1020
atattatagg cgatactata ataatttgtt cgtctgcaga gcttattatt tgccaaaatt  1080
agatattcct attctgtttt tgtttgtgtg ctgttaaatt gttaacgcct gaaggaataa  1140
atataaatga cgaaattttg atgtttatct ctgctccttt attgtgacca taagtcaaga  1200
tcagatgcac ttgttttaaa tattgttgtc tgaagaaata agtactgaca gtattttgat  1260
gcattgatct gcttgtttgt tgtaacaaaa tttaaaaata aagagtttcc ttttgttgc   1320 tctccttacc tcctgatggt atctagtatc taccaactga cactatattg cttctcttta  1380
catacgtatc ttgctcgatg ccttctccct agtgttgacc agtgttactc acatagtctt  1440
tgctcatttc attgtaatgc agataccaag cggcctctag aggatctcc atg gca aac  1498
                                                      Met Ala Asn
                                                        1 cct aac aat cgt tcc gaa cac gac acc atc aag gtt act cca aac tct    1546
Pro Asn Asn Arg Ser Glu His Asp Thr Ile Lys Val Thr Pro Asn Ser
```

```
              5                   10                  15
gag ttg caa act aat cac aac cag tac cca ttg gct gac aat cct aac    1594
Glu Leu Gln Thr Asn His Asn Gln Tyr Pro Leu Ala Asp Asn Pro Asn
 20                  25                  30                  35 agt act ctt gag gaa ctt aac tac aag gag ttt ctc cgg atg acc gaa    1642
Ser Thr Leu Glu Glu Leu Asn Tyr Lys Glu Phe Leu Arg Met Thr Glu
                 40                  45                  50 gat agc tcc act gag gtt ctc gat aac tct aca gtg aag gac gct gtt    1690
Asp Ser Ser Thr Glu Val Leu Asp Asn Ser Thr Val Lys Asp Ala Val
             55                  60                  65 gga act ggc att agc gtt gtg gga cag att ctt gga gtg gtt ggt gtt    1738
Gly Thr Gly Ile Ser Val Val Gly Gln Ile Leu Gly Val Val Gly Val
         70                  75                  80 cca ttc gct gga gct ttg acc agc ttc tac cag tcc ttt ctc aac acc    1786
Pro Phe Ala Gly Ala Leu Thr Ser Phe Tyr Gln Ser Phe Leu Asn Thr
     85                  90                  95 atc tgg cct tca gat gct gat ccc tgg aag gct ttc atg gcc caa gtg    1834
Ile Trp Pro Ser Asp Ala Asp Pro Trp Lys Ala Phe Met Ala Gln Val
100                 105                 110                 115 gaa gtc ttg atc gat aag aag atc gaa gag tat gcc aag tct aaa gcc    1882
Glu Val Leu Ile Asp Lys Lys Ile Glu Glu Tyr Ala Lys Ser Lys Ala
                120                 125                 130 ttg gct gag ttg caa ggt ttg cag aac aac ttc gag gat tac gtc aac    1930
Leu Ala Glu Leu Gln Gly Leu Gln Asn Asn Phe Glu Asp Tyr Val Asn
            135                 140                 145 gca ctc aac agc tgg aag aaa act ccc ttg agt ctc agg tct aag cgt    1978
Ala Leu Asn Ser Trp Lys Lys Thr Pro Leu Ser Leu Arg Ser Lys Arg
        150                 155                 160 tcc cag gac cgt att cgt gaa ctt ttc agc caa gcc gaa tcc cac ttc    2026
Ser Gln Asp Arg Ile Arg Glu Leu Phe Ser Gln Ala Glu Ser His Phe
    165                 170                 175 aga aac tcc atg cct agc ttt gcc gtt tct aag ttc gag gtg ctc ttc    2074
Arg Asn Ser Met Pro Ser Phe Ala Val Ser Lys Phe Glu Val Leu Phe
180                 185                 190                 195 ttg cca aca tac gca caa gct gcc aac act cat ctc ttg ctt ctc aaa    2122
Leu Pro Thr Tyr Ala Gln Ala Ala Asn Thr His Leu Leu Leu Leu Lys
                200                 205                 210 gac gct cag gtg ttt ggt gag gaa tgg ggt tac tcc agt gaa gat gtt    2170
Asp Ala Gln Val Phe Gly Glu Glu Trp Gly Tyr Ser Ser Glu Asp Val
            215                 220                 225 gcc gag ttc tac cgt agg cag ctc aag ttg act caa cag tac aca gac    2218
Ala Glu Phe Tyr Arg Arg Gln Leu Lys Leu Thr Gln Gln Tyr Thr Asp
        230                 235                 240 cac tgc gtc aac tgg tac aac gtt ggg ctc aat ggt ctt aga gga tct    2266
His Cys Val Asn Trp Tyr Asn Val Gly Leu Asn Gly Leu Arg Gly Ser
    245                 250                 255 acc tac gac gca tgg gtg aag ttc aac agg ttt cgt aga gag atg acc    2314
Thr Tyr Asp Ala Trp Val Lys Phe Asn Arg Phe Arg Arg Glu Met Thr
260                 265                 270                 275 ttg act gtg ctc gat ctt atc gtt ctc ttt cca ttc tac gac att cgt    2362
Leu Thr Val Leu Asp Leu Ile Val Leu Phe Pro Phe Tyr Asp Ile Arg
                280                 285                 290 ctt tac tcc aaa ggc gtt aag aca gag ctg acc aga gac atc ttc acc    2410
Leu Tyr Ser Lys Gly Val Lys Thr Glu Leu Thr Arg Asp Ile Phe Thr
            295                 300                 305 gat ccc atc ttc cta ctt acg acc ctg cag aaa tac ggt cca act ttt    2458
Asp Pro Ile Phe Leu Leu Thr Thr Leu Gln Lys Tyr Gly Pro Thr Phe
        310                 315                 320 ctc tcc att gag aac agc atc agg aag cct cac ctc ttc gac tat ctg    2506
```

```
Leu Ser Ile Glu Asn Ser Ile Arg Lys Pro His Leu Phe Asp Tyr Leu
    325                 330                 335 caa ggc att gag ttt cac acc agg ttg caa cct ggt tac ttc ggt aag        2554
Gln Gly Ile Glu Phe His Thr Arg Leu Gln Pro Gly Tyr Phe Gly Lys
340                 345                 350                 355 gat tcc ttc aac tac tgg agc gga aac tac gtt gaa acc aga cca tcc        2602
Asp Ser Phe Asn Tyr Trp Ser Gly Asn Tyr Val Glu Thr Arg Pro Ser
                360                 365                 370 atc gga tct agc aag acc atc act tct cca ttc tac ggt gac aag agc        2650
Ile Gly Ser Ser Lys Thr Ile Thr Ser Pro Phe Tyr Gly Asp Lys Ser
            375                 380                 385 act gag cca gtg cag aag ttg agc ttc gat ggg cag aag gtg tat aga        2698
Thr Glu Pro Val Gln Lys Leu Ser Phe Asp Gly Gln Lys Val Tyr Arg
        390                 395                 400 acc atc gcc aat acc gat gtt gca gct tgg cct aat ggc aag gtc tac        2746
Thr Ile Ala Asn Thr Asp Val Ala Ala Trp Pro Asn Gly Lys Val Tyr
    405                 410                 415 ctt gga gtt act aaa gtg gac ttc tcc caa tac gac gat cag aag aac        2794
Leu Gly Val Thr Lys Val Asp Phe Ser Gln Tyr Asp Asp Gln Lys Asn
420                 425                 430                 435 gag aca tct act caa acc tac gat agt aag agg aac aat ggc cat gtt        2842
Glu Thr Ser Thr Gln Thr Tyr Asp Ser Lys Arg Asn Asn Gly His Val
                440                 445                 450 tcc gca caa gac tcc att gac caa ctt cca cct gaa acc act gat gaa        2890
Ser Ala Gln Asp Ser Ile Asp Gln Leu Pro Pro Glu Thr Thr Asp Glu
            455                 460                 465 cca ttg gag aag gct tac agt cac caa ctt aac tac gcc gaa tgc ttt        2938
Pro Leu Glu Lys Ala Tyr Ser His Gln Leu Asn Tyr Ala Glu Cys Phe
        470                 475                 480 ctc atg caa gac agg cgt ggc acc att ccg ttc ttt aca tgg act cac        2986
Leu Met Gln Asp Arg Arg Gly Thr Ile Pro Phe Phe Thr Trp Thr His
    485                 490                 495 agg tct gtc gac ttc ttt aac act atc gac gct gag aag att acc caa        3034
Arg Ser Val Asp Phe Phe Asn Thr Ile Asp Ala Glu Lys Ile Thr Gln
500                 505                 510                 515 ctt ccc gtg gtc aag gct tat gcc ttg tcc agc gga gct tcc atc att        3082
Leu Pro Val Val Lys Ala Tyr Ala Leu Ser Ser Gly Ala Ser Ile Ile
                520                 525                 530 gaa ggt cca ggc ttc acc ggt ggc aac ttg ctc ttc ctt aag gag tcc        3130
Glu Gly Pro Gly Phe Thr Gly Gly Asn Leu Leu Phe Leu Lys Glu Ser
            535                 540                 545 agc aac tcc atc gcc aag ttc aaa gtg aca ctt aac tca gca gcc ttg        3178
Ser Asn Ser Ile Ala Lys Phe Lys Val Thr Leu Asn Ser Ala Ala Leu
        550                 555                 560 ctc caa cgt tac agg gtt cgt atc aga tac gca agc act acc aat ctt        3226
Leu Gln Arg Tyr Arg Val Arg Ile Arg Tyr Ala Ser Thr Thr Asn Leu
    565                 570                 575 cgc ctc ttt gtc cag aac agc aac aat gat ttc ctt gtc atc tac atc        3274
Arg Leu Phe Val Gln Asn Ser Asn Asn Asp Phe Leu Val Ile Tyr Ile
580                 585                 590                 595 aac aag act atg aac aaa gac gat gac ctc acc tac caa aca ttc gat        3322
Asn Lys Thr Met Asn Lys Asp Asp Asp Leu Thr Tyr Gln Thr Phe Asp
                600                 605                 610 ctt gcc act acc aat agt aac atg gga ttc tct ggt gac aag aac gag        3370
Leu Ala Thr Thr Asn Ser Asn Met Gly Phe Ser Gly Asp Lys Asn Glu
            615                 620                 625 ctg atc ata ggt gct gag agc ttt gtc tct aat gag aag att tac ata        3418
Leu Ile Ile Gly Ala Glu Ser Phe Val Ser Asn Glu Lys Ile Tyr Ile
        630                 635                 640
```

-continued

```
gac aag atc gag ttc att cca gtt caa ctc taatagatcc cccgggctgc      3468
Asp Lys Ile Glu Phe Ile Pro Val Gln Leu
    645                 650 aggaattccc gatcgttcaa acatttggca ataaagtttc ttaagattga atcctgttgc   3528
cggtcttgcg atgattatca tataatttct gttgaattac gttaagcatg taataattaa   3588
catgtaatgc atgacgttat ttatgagatg ggttttatg attagagtcc cgcaattata    3648
catttaatac gcgatagaaa acaaaatata gcgcgcaaac taggataaat tatcgcgcgc   3708
ggtgtcatct atgttactag atcggggata tccccggggc ggccgc                  3754

<210> SEQ ID NO 16
<211> LENGTH: 653
<212> TYPE: PRT
<213> ORGANISM: Artificial Sequence
<220> FEATURE:
<221> NAME/KEY: PRT
<222> LOCATION: (1)..(653)
<223> OTHER INFORMATION: Cry3Bb1 variant v11231

<400> SEQUENCE: 16

Met Ala Asn Pro Asn Asn Arg Ser Glu His Asp Thr Ile Lys Val Thr
 1               5                   10                  15

Pro Asn Ser Glu Leu Gln Thr Asn His Asn Gln Tyr Pro Leu Ala Asp
             20                  25                  30

Asn Pro Asn Ser Thr Leu Glu Glu Leu Asn Tyr Lys Glu Phe Leu Arg
         35                  40                  45

Met Thr Glu Asp Ser Ser Thr Glu Val Leu Asp Asn Ser Thr Val Lys
     50                  55                  60

Asp Ala Val Gly Thr Gly Ile Ser Val Val Gly Gln Ile Leu Gly Val
 65                  70                  75                  80

Val Gly Val Pro Phe Ala Gly Ala Leu Thr Ser Phe Tyr Gln Ser Phe
                 85                  90                  95

Leu Asn Thr Ile Trp Pro Ser Asp Ala Asp Pro Trp Lys Ala Phe Met
            100                 105                 110

Ala Gln Val Glu Val Leu Ile Asp Lys Lys Ile Glu Glu Tyr Ala Lys
        115                 120                 125

Ser Lys Ala Leu Ala Glu Leu Gln Gly Leu Gln Asn Asn Phe Glu Asp
    130                 135                 140

Tyr Val Asn Ala Leu Asn Ser Trp Lys Lys Thr Pro Leu Ser Leu Arg
145                 150                 155                 160

Ser Lys Arg Ser Gln Asp Arg Ile Arg Glu Leu Phe Ser Gln Ala Glu
                165                 170                 175

Ser His Phe Arg Asn Ser Met Pro Ser Phe Ala Val Ser Lys Phe Glu
            180                 185                 190

Val Leu Phe Leu Pro Thr Tyr Ala Gln Ala Ala Asn Thr His Leu Leu
        195                 200                 205

Leu Leu Lys Asp Ala Gln Val Phe Gly Glu Glu Trp Gly Tyr Ser Ser
    210                 215                 220

Glu Asp Val Ala Glu Phe Tyr Arg Arg Gln Leu Lys Leu Thr Gln Gln
225                 230                 235                 240

Tyr Thr Asp His Cys Val Asn Trp Tyr Asn Val Gly Leu Asn Gly Leu
                245                 250                 255

Arg Gly Ser Thr Tyr Asp Ala Trp Val Lys Phe Asn Arg Phe Arg Arg
            260                 265                 270

Glu Met Thr Leu Thr Val Leu Asp Leu Ile Val Leu Phe Pro Phe Tyr
        275                 280                 285
```

```
Asp Ile Arg Leu Tyr Ser Lys Gly Val Lys Thr Glu Leu Thr Arg Asp
    290                 295                 300

Ile Phe Thr Asp Pro Ile Phe Leu Leu Thr Thr Leu Gln Lys Tyr Gly
305                 310                 315                 320

Pro Thr Phe Leu Ser Ile Glu Asn Ser Ile Arg Lys Pro His Leu Phe
                325                 330                 335

Asp Tyr Leu Gln Gly Ile Glu Phe His Thr Arg Leu Gln Pro Gly Tyr
            340                 345                 350

Phe Gly Lys Asp Ser Phe Asn Tyr Trp Ser Gly Asn Tyr Val Glu Thr
        355                 360                 365

Arg Pro Ser Ile Gly Ser Ser Lys Thr Ile Thr Ser Pro Phe Tyr Gly
    370                 375                 380

Asp Lys Ser Thr Glu Pro Val Gln Lys Leu Ser Phe Asp Gly Gln Lys
385                 390                 395                 400

Val Tyr Arg Thr Ile Ala Asn Thr Asp Val Ala Ala Trp Pro Asn Gly
                405                 410                 415

Lys Val Tyr Leu Gly Val Thr Lys Val Asp Phe Ser Gln Tyr Asp Asp
            420                 425                 430

Gln Lys Asn Glu Thr Ser Thr Gln Thr Tyr Asp Ser Lys Arg Asn Asn
        435                 440                 445

Gly His Val Ser Ala Gln Asp Ser Ile Asp Gln Leu Pro Pro Glu Thr
    450                 455                 460

Thr Asp Glu Pro Leu Glu Lys Ala Tyr Ser His Gln Leu Asn Tyr Ala
465                 470                 475                 480

Glu Cys Phe Leu Met Gln Asp Arg Arg Gly Thr Ile Pro Phe Phe Thr
                485                 490                 495

Trp Thr His Arg Ser Val Asp Phe Phe Asn Thr Ile Asp Ala Glu Lys
            500                 505                 510

Ile Thr Gln Leu Pro Val Val Lys Ala Tyr Ala Leu Ser Ser Gly Ala
        515                 520                 525

Ser Ile Ile Glu Gly Pro Gly Phe Thr Gly Gly Asn Leu Leu Phe Leu
    530                 535                 540

Lys Glu Ser Ser Asn Ser Ile Ala Lys Phe Lys Val Thr Leu Asn Ser
545                 550                 555                 560

Ala Ala Leu Leu Gln Arg Tyr Arg Val Arg Ile Arg Tyr Ala Ser Thr
                565                 570                 575

Thr Asn Leu Arg Leu Phe Val Gln Asn Ser Asn Asn Asp Phe Leu Val
            580                 585                 590

Ile Tyr Ile Asn Lys Thr Met Asn Lys Asp Asp Leu Thr Tyr Gln
        595                 600                 605

Thr Phe Asp Leu Ala Thr Thr Asn Ser Asn Met Gly Phe Ser Gly Asp
    610                 615                 620

Lys Asn Glu Leu Ile Ile Gly Ala Glu Ser Phe Val Ser Asn Glu Lys
625                 630                 635                 640

Ile Tyr Ile Asp Lys Ile Glu Phe Ile Pro Val Gln Leu
                645                 650

<210> SEQ ID NO 17
<211> LENGTH: 3450
<212> TYPE: DNA
<213> ORGANISM: Artificial Sequence
<220> FEATURE:
<223> OTHER INFORMATION: Description of Artificial Sequence: expression
      cassette
<220> FEATURE:
```

-continued

```
<221> NAME/KEY: promoter
<222> LOCATION: (14)..(235)
<223> OTHER INFORMATION: P-CaMV.AS4
<220> FEATURE:
<221> NAME/KEY: 5'UTR
<222> LOCATION: (240)..(304)
<223> OTHER INFORMATION: L-Ta.hcb1
<220> FEATURE:
<221> NAME/KEY: intron
<222> LOCATION: (318)..(805)
<223> OTHER INFORMATION: I-Os.Act1
<220> FEATURE:
<221> NAME/KEY: transit_peptide
<222> LOCATION: (825)..(971)
<223> OTHER INFORMATION: amino terminal TS-Zm.rbcS
<220> FEATURE:
<221> NAME/KEY: intron
<222> LOCATION: (972)..(1134)
<223> OTHER INFORMATION: I-Zm.rbcS
<220> FEATURE:
<221> NAME/KEY: transit_peptide
<222> LOCATION: (1135)..(1221)
<223> OTHER INFORMATION: carboxy terminus TS-Zm.rbcS
<220> FEATURE:
<221> NAME/KEY: CDS
<222> LOCATION: (1222)..(3180)
<223> OTHER INFORMATION: Cry3Bb1 variant 11231mv1
<220> FEATURE:
<221> NAME/KEY: terminator
<222> LOCATION: (3198)..(3431)
<223> OTHER INFORMATION: T-Ta.hsp17

<400> SEQUENCE: 17
gcggccgcgt taacaagctt ctgacgtaag ggatgacgca cctgacgtaa gggatgacgc     60
acctgacgta agggatgacg cacctgacgt aagggatgac gcactcgaga tccccatctc    120
cactgacgta agggatgacg cacaatccca ctatccttcg caagaccctt cctctatata    180
aggaagttca tttcatttgg agaggacacg ctgacaagct agcttggctg caggtagatc    240
ctagaaccat cttccacaca ctcaagccac actattggag aacacacagg gacaacacac    300
cataagatcc aagggaggcc tccgccgccg ccggtaacca ccccgcccct ctcctctttc    360
tttctccgtt ttttttccg tctcggtctc gatctttggc cttggtagtt tgggtgggcg    420
agaggcggct tcgtgcgcgc ccagatcggt gcgcgggagg ggcgggatct cgcggctggg    480
gctctcgccg gcgtggatcc ggcccggatc tcgcggggaa tggggctctc ggatgtagat    540
ctgcgatccg ccgttgttgg gggagatgat ggggggttta aaatttccgc cgtgctaaac    600
aagatcagga agaggggaaa agggcactat ggtttatatt tttatatatt tctgctgctt    660
cgtcaggctt agatgtgcta gatctttctt tcttcttttt gtgggtagaa tttgaatccc    720
tcagcattgt tcatcggtag tttttctttt catgatttgt gacaaatgca gcctcgtgcg    780
gagctttttt gtaggtagaa gtgatcaacc tctagaggat cagcatggcg cccaccgtga    840
tgatggcctc gtcggccacc gccgtcgctc cgttcctggg gctcaagtcc accgccagcc    900
tccccgtcgc ccgccgctcc tccagaagcc tcggcaacgt cagcaacggc ggaaggatcc    960
ggtgcatgca ggtaacaaat gcatcctagc tagtagttct ttgcattgca gcagctgcag   1020
ctagcgagtt agtaatagga agggaactga tgatccatgc atggactgat gtgtgttgcc   1080
catcccatcc catcccattt cccaaacgaa ccgaaaacac cgtactacgt gcaggtgtgg   1140
ccctacggca acaagaagtt cgagacgctg tcgtacctgc cgccgctgtc gaccggcggg   1200
cgcatccgct gcatgcaggc c atg gcc aac ccc aac aat cgc tcc gag cac     1251
                        Met Ala Asn Pro Asn Asn Arg Ser Glu His
                          1               5                  10 gac acg atc aag gtc acc ccc aac tcc gag ctc cag acc aac cac aac     1299
```

-continued

| | | | | | | | | | | | | | | | |
|---|---|---|---|---|---|---|---|---|---|---|---|---|---|---|---|
| Asp | Thr | Ile | Lys | Val | Thr | Pro | Asn | Ser | Glu | Leu | Gln | Thr | Asn | His | Asn |
| | | | 15 | | | | | 20 | | | | | 25 | | | cag tac ccg ctg gcc gac aac ccc aac tcc acc ctg gaa gag ctg aac     1347
Gln Tyr Pro Leu Ala Asp Asn Pro Asn Ser Thr Leu Glu Glu Leu Asn
            30                  35                  40 tac aag gag ttc ctg cgc atg acc gag gac tcc tcc acg gag gtc ctg     1395
Tyr Lys Glu Phe Leu Arg Met Thr Glu Asp Ser Ser Thr Glu Val Leu
            45                  50                  55 gac aac tcc acc gtc aag gac gcc gtc ggg acc ggc atc tcc gtc gtt     1443
Asp Asn Ser Thr Val Lys Asp Ala Val Gly Thr Gly Ile Ser Val Val
      60                  65                  70 ggg cag atc ctg ggc gtc gtt ggc gtc ccc ttc gca ggt gct ctc acc     1491
Gly Gln Ile Leu Gly Val Val Gly Val Pro Phe Ala Gly Ala Leu Thr
75                  80                  85                  90 tcc ttc tac cag tcc ttc ctg aac acc atc tgg ccc tcc gac gcc gac     1539
Ser Phe Tyr Gln Ser Phe Leu Asn Thr Ile Trp Pro Ser Asp Ala Asp
                  95                  100              105 ccc tgg aag gcc ttc atg gcc caa gtc gaa gtc ctg atc gac aag aag     1587
Pro Trp Lys Ala Phe Met Ala Gln Val Glu Val Leu Ile Asp Lys Lys
          110                 115                120 atc gag gag tac gcc aag tcc aag gcc ctg gcc gag ctg caa ggc ctg     1635
Ile Glu Glu Tyr Ala Lys Ser Lys Ala Leu Ala Glu Leu Gln Gly Leu
              125                130                135 caa aac aac ttc gag gac tac gtc aac gcg ctg aac tcc tgg aag aag     1683
Gln Asn Asn Phe Glu Asp Tyr Val Asn Ala Leu Asn Ser Trp Lys Lys
140                  145                  150 acg cct ctg tcc ctg cgc tcc aag cgc tcc cag ggc cgc atc cgc gag     1731
Thr Pro Leu Ser Leu Arg Ser Lys Arg Ser Gln Gly Arg Ile Arg Glu
155                  160                  165                170 ctg ttc tcc cag gcc gag tcc cac ttc cgc aac tcc atg ccg tcc ttc     1779
Leu Phe Ser Gln Ala Glu Ser His Phe Arg Asn Ser Met Pro Ser Phe
              175                180                185 gcc gtc tcc aag ttc gag gtc ctg ttc ctg ccc acc tac gcc cag gct     1827
Ala Val Ser Lys Phe Glu Val Leu Phe Leu Pro Thr Tyr Ala Gln Ala
                  190                195                200 gcc aac acc cac ctc ctg ttg ctg aag gac gcc cag gtc ttc ggc gag     1875
Ala Asn Thr His Leu Leu Leu Leu Lys Asp Ala Gln Val Phe Gly Glu
                  205                210                215 gaa tgg ggc tac tcc tcg gag gac gtc gcc gag ttc tac cgt cgc cag     1923
Glu Trp Gly Tyr Ser Ser Glu Asp Val Ala Glu Phe Tyr Arg Arg Gln
220                  225                  230 ctg aag ctg acc caa cag tac acc gac cac tgc gtc aac tgg tac aac     1971
Leu Lys Leu Thr Gln Gln Tyr Thr Asp His Cys Val Asn Trp Tyr Asn
235                  240                  245                250 gtc ggc ctg aac ggc ctg agg ggc tcc acc tac gac gca tgg gtc aag     2019
Val Gly Leu Asn Gly Leu Arg Gly Ser Thr Tyr Asp Ala Trp Val Lys
                  255                260                265 ttc aac cgc ttc cgc agg gag atg acc ctg acc gtc ctg gac ctg atc     2067
Phe Asn Arg Phe Arg Arg Glu Met Thr Leu Thr Val Leu Asp Leu Ile
              270                275                280 gtc ctg ttc ccc ttc tac gac atc cgc ctg tac tcc aag ggc gtc aag     2115
Val Leu Phe Pro Phe Tyr Asp Ile Arg Leu Tyr Ser Lys Gly Val Lys
          285                 290                295 acc gag ctg acc cgc gac atc ttc acg gac ccc atc ttc ctg ctc acg     2163
Thr Glu Leu Thr Arg Asp Ile Phe Thr Asp Pro Ile Phe Leu Leu Thr
300                  305                  310 acc ctc cag aag tac ggt ccc acc ttc ctg tcc atc gag aac tcc atc     2211
Thr Leu Gln Lys Tyr Gly Pro Thr Phe Leu Ser Ile Glu Asn Ser Ile
315                  320                  325                330

```
cgc aag ccc cac ctg ttc gac tac ctc cag ggc atc gag ttc cac acg    2259
Arg Lys Pro His Leu Phe Asp Tyr Leu Gln Gly Ile Glu Phe His Thr
            335                 340                 345 cgc ctg agg cca ggc tac ttc ggc aag gac tcc ttc aac tac tgg tcc    2307
Arg Leu Arg Pro Gly Tyr Phe Gly Lys Asp Ser Phe Asn Tyr Trp Ser
        350                 355                 360 ggc aac tac gtc gag acc agg ccc tcc atc ggc tcg aag acg atc        2355
Gly Asn Tyr Val Glu Thr Arg Pro Ser Ile Gly Ser Lys Thr Ile
    365                 370                 375 acc tcc cct ttc tac ggc gac aag tcc acc gag ccc gtc cag aag ctg    2403
Thr Ser Pro Phe Tyr Gly Asp Lys Ser Thr Glu Pro Val Gln Lys Leu
380                 385                 390 tcc ttc gac ggc cag aag gtc tac cgc acc atc gcc aac acc gac gtc    2451
Ser Phe Asp Gly Gln Lys Val Tyr Arg Thr Ile Ala Asn Thr Asp Val
395                 400                 405                 410 gcg gct tgg ccg aac ggc aag gtc tac ctg ggc gtc acg aag gtc gac    2499
Ala Ala Trp Pro Asn Gly Lys Val Tyr Leu Gly Val Thr Lys Val Asp
                415                 420                 425 ttc tcc cag tac gat gac cag aag aat gaa acc tcc acc cag acc tac    2547
Phe Ser Gln Tyr Asp Asp Gln Lys Asn Glu Thr Ser Thr Gln Thr Tyr
            430                 435                 440 gac tcc aag cgc aac aat ggc cac gtc tcc gcc cag gac tcc atc gac    2595
Asp Ser Lys Arg Asn Asn Gly His Val Ser Ala Gln Asp Ser Ile Asp
        445                 450                 455 cag ctg ccg cct gag acc act gac gag ccc ctg gag aag gcc tac tcc    2643
Gln Leu Pro Pro Glu Thr Thr Asp Glu Pro Leu Glu Lys Ala Tyr Ser
    460                 465                 470 cac cag ctg aac tac gcg gag tgc ttc ctg atg caa gac cgc agg ggc    2691
His Gln Leu Asn Tyr Ala Glu Cys Phe Leu Met Gln Asp Arg Arg Gly
475                 480                 485                 490 acc atc ccc ttc ttc acc tgg acc cac cgc tcc gtc gac ttc ttc aac    2739
Thr Ile Pro Phe Phe Thr Trp Thr His Arg Ser Val Asp Phe Phe Asn
                495                 500                 505 acc atc gac gcc gag aag atc acc cag ctg ccc gtg gtc aag gcc tac    2787
Thr Ile Asp Ala Glu Lys Ile Thr Gln Leu Pro Val Val Lys Ala Tyr
            510                 515                 520 gcc ctg tcc tcg ggt gcc tcc atc att gag ggt cca ggc ttc acc ggt    2835
Ala Leu Ser Ser Gly Ala Ser Ile Ile Glu Gly Pro Gly Phe Thr Gly
        525                 530                 535 ggc aac ctg ctg ttc ctg aag gag tcc tcg aac tcc atc gcc aag ttc    2883
Gly Asn Leu Leu Phe Leu Lys Glu Ser Ser Asn Ser Ile Ala Lys Phe
    540                 545                 550 aag gtc acc ctg aac tcc gct gcc ttg ctg caa cgc tac cgc gtc cgc    2931
Lys Val Thr Leu Asn Ser Ala Ala Leu Leu Gln Arg Tyr Arg Val Arg
555                 560                 565                 570 atc cgc tac gcc tcc acc acg aac ctg cgc ctg ttc gtc cag aac tcc    2979
Ile Arg Tyr Ala Ser Thr Thr Asn Leu Arg Leu Phe Val Gln Asn Ser
                575                 580                 585 aac aat gac ttc ctg gtc atc tac atc aac aag acc atg aac aag gac    3027
Asn Asn Asp Phe Leu Val Ile Tyr Ile Asn Lys Thr Met Asn Lys Asp
            590                 595                 600 gat gac ctg acc tac cag acc ttc gac ctc gcc acc acg aac tcc aac    3075
Asp Asp Leu Thr Tyr Gln Thr Phe Asp Leu Ala Thr Thr Asn Ser Asn
        605                 610                 615 atg ggc ttc tcg ggc gac aag aat gaa ctg atc att ggt gct gag tcc    3123
Met Gly Phe Ser Gly Asp Lys Asn Glu Leu Ile Ile Gly Ala Glu Ser
    620                 625                 630 ttc gtc tcc aat gaa aag atc tac atc gac aag atc gag ttc atc ccc    3171
Phe Val Ser Asn Glu Lys Ile Tyr Ile Asp Lys Ile Glu Phe Ile Pro
635                 640                 645                 650
```

```
                          gtc cag ctg tgataggaac tctgattgaa ttctgcatgc gtttggacgt          3220
                          Val Gln Leu atgctcattc aggttggagc caatttggtt gatgtgtgtg cgagttcttg cgagtctgat                          3280
gagacatctc tgtattgtgt ttctttcccc agtgttttct gtacttgtgt aatcggctaa                          3340
tcgccaacag attcggcgat gaataaatga gaaataaatt gttctgattt tgagtgcaaa                          3400
aaaaaaggaa ttagatctgt gtgtgttttt tggatccccg gggcggccgc                                     3450

<210> SEQ ID NO 18
<211> LENGTH: 653
<212> TYPE: PRT
<213> ORGANISM: Artificial Sequence
<220> FEATURE:
<221> NAME/KEY: PRT
<222> LOCATION: (1)..(653)
<223> OTHER INFORMATION: Cry3Bb1 variant 11231mv1

<400> SEQUENCE: 18

Met Ala Asn Pro Asn Asn Arg Ser Glu His Asp Thr Ile Lys Val Thr
  1               5                  10                  15

Pro Asn Ser Glu Leu Gln Thr Asn His Asn Gln Tyr Pro Leu Ala Asp
             20                  25                  30

Asn Pro Asn Ser Thr Leu Glu Glu Leu Asn Tyr Lys Glu Phe Leu Arg
         35                  40                  45

Met Thr Glu Asp Ser Ser Thr Glu Val Leu Asp Asn Ser Thr Val Lys
     50                  55                  60

Asp Ala Val Gly Thr Gly Ile Ser Val Val Gly Gln Ile Leu Gly Val
 65                  70                  75                  80

Val Gly Val Pro Phe Ala Gly Ala Leu Thr Ser Phe Tyr Gln Ser Phe
                 85                  90                  95

Leu Asn Thr Ile Trp Pro Ser Asp Ala Asp Pro Trp Lys Ala Phe Met
            100                 105                 110

Ala Gln Val Glu Val Leu Ile Asp Lys Lys Ile Glu Glu Tyr Ala Lys
        115                 120                 125

Ser Lys Ala Leu Ala Glu Leu Gln Gly Leu Gln Asn Asn Phe Glu Asp
    130                 135                 140

Tyr Val Asn Ala Leu Asn Ser Trp Lys Lys Thr Pro Leu Ser Leu Arg
145                 150                 155                 160

Ser Lys Arg Ser Gln Gly Arg Ile Arg Glu Leu Phe Ser Gln Ala Glu
                165                 170                 175

Ser His Phe Arg Asn Ser Met Pro Ser Phe Ala Val Ser Lys Phe Glu
            180                 185                 190

Val Leu Phe Leu Pro Thr Tyr Ala Gln Ala Ala Asn Thr His Leu Leu
        195                 200                 205

Leu Leu Lys Asp Ala Gln Val Phe Gly Glu Glu Trp Gly Tyr Ser Ser
    210                 215                 220

Glu Asp Val Ala Glu Phe Tyr Arg Arg Gln Leu Lys Leu Thr Gln Gln
225                 230                 235                 240

Tyr Thr Asp His Cys Val Asn Trp Tyr Asn Val Gly Leu Asn Gly Leu
                245                 250                 255

Arg Gly Ser Thr Tyr Asp Ala Trp Val Lys Phe Asn Arg Phe Arg Arg
            260                 265                 270

Glu Met Thr Leu Thr Val Leu Asp Leu Ile Val Leu Phe Pro Phe Tyr
        275                 280                 285

Asp Ile Arg Leu Tyr Ser Lys Gly Val Lys Thr Glu Leu Thr Arg Asp
```

```
                 290                 295                 300
Ile Phe Thr Asp Pro Ile Phe Leu Leu Thr Thr Leu Gln Lys Tyr Gly
305                 310                 315                 320

Pro Thr Phe Leu Ser Ile Glu Asn Ser Ile Arg Lys Pro His Leu Phe
                325                 330                 335

Asp Tyr Leu Gln Gly Ile Glu Phe His Thr Arg Leu Arg Pro Gly Tyr
            340                 345                 350

Phe Gly Lys Asp Ser Phe Asn Tyr Trp Ser Gly Asn Tyr Val Glu Thr
        355                 360                 365

Arg Pro Ser Ile Gly Ser Ser Lys Thr Ile Thr Ser Pro Phe Tyr Gly
370                 375                 380

Asp Lys Ser Thr Glu Pro Val Gln Lys Leu Ser Phe Asp Gly Gln Lys
385                 390                 395                 400

Val Tyr Arg Thr Ile Ala Asn Thr Asp Val Ala Ala Trp Pro Asn Gly
                405                 410                 415

Lys Val Tyr Leu Gly Val Thr Lys Val Asp Phe Ser Gln Tyr Asp Asp
            420                 425                 430

Gln Lys Asn Glu Thr Ser Thr Gln Thr Tyr Asp Ser Lys Arg Asn Asn
        435                 440                 445

Gly His Val Ser Ala Gln Asp Ser Ile Asp Gln Leu Pro Pro Glu Thr
    450                 455                 460

Thr Asp Glu Pro Leu Glu Lys Ala Tyr Ser His Gln Leu Asn Tyr Ala
465                 470                 475                 480

Glu Cys Phe Leu Met Gln Asp Arg Arg Gly Thr Ile Pro Phe Phe Thr
                485                 490                 495

Trp Thr His Arg Ser Val Asp Phe Phe Asn Thr Ile Asp Ala Glu Lys
            500                 505                 510

Ile Thr Gln Leu Pro Val Val Lys Ala Tyr Ala Leu Ser Ser Gly Ala
        515                 520                 525

Ser Ile Ile Glu Gly Pro Gly Phe Thr Gly Gly Asn Leu Leu Phe Leu
    530                 535                 540

Lys Glu Ser Ser Asn Ser Ile Ala Lys Phe Lys Val Thr Leu Asn Ser
545                 550                 555                 560

Ala Ala Leu Leu Gln Arg Tyr Arg Val Arg Ile Arg Tyr Ala Ser Thr
                565                 570                 575

Thr Asn Leu Arg Leu Phe Val Gln Asn Ser Asn Asn Asp Phe Leu Val
            580                 585                 590

Ile Tyr Ile Asn Lys Thr Met Asn Lys Asp Asp Asp Leu Thr Tyr Gln
        595                 600                 605

Thr Phe Asp Leu Ala Thr Thr Asn Ser Asn Met Gly Phe Ser Gly Asp
    610                 615                 620

Lys Asn Glu Leu Ile Ile Gly Ala Glu Ser Phe Val Ser Asn Glu Lys
625                 630                 635                 640

Ile Tyr Ile Asp Lys Ile Glu Phe Ile Pro Val Gln Leu
                645                 650

<210> SEQ ID NO 19
<211> LENGTH: 3039
<212> TYPE: DNA
<213> ORGANISM: Artificial Sequence
<220> FEATURE:
<223> OTHER INFORMATION: Description of Artificial Sequence: expression
      cassette
<220> FEATURE:
<221> NAME/KEY: promoter
<222> LOCATION: (14)..(235)
```

-continued

```
<223> OTHER INFORMATION: P-CaMV.AS4
<220> FEATURE:
<221> NAME/KEY: 5'UTR
<222> LOCATION: (240)..(304)
<223> OTHER INFORMATION: L-Ta.hcb1
<220> FEATURE:
<221> NAME/KEY: intron
<222> LOCATION: (318)..(805)
<223> OTHER INFORMATION: I-Os.Act1
<220> FEATURE:
<221> NAME/KEY: CDS
<222> LOCATION: (811)..(2769)
<223> OTHER INFORMATION: Cry3Bb1 variant 11231mv1
<220> FEATURE:
<221> NAME/KEY: terminator
<222> LOCATION: (2787)..(3020)
<223> OTHER INFORMATION: T-Ta.hsp17

<400> SEQUENCE: 19
gcggccgcgt taacaagctt ctgacgtaag ggatgacgca cctgacgtaa gggatgacgc     60
acctgacgta agggatgacg cacctgacgt aagggatgac gcactcgaga tccccatctc    120
cactgacgta agggatgacg cacaatccca ctatccttcg caagaccctt cctctatata    180
aggaagttca tttcatttgg agaggacacg ctgacaagct agcttggctg caggtagatc    240
ctagaaccat cttccacaca ctcaagccac actattggag aacacacagg gacaacacac    300
cataagatcc aagggaggcc tccgccgccg ccggtaacca ccccgcccct ctcctctttc    360
tttctccgtt ttttttccg tctcggtctc gatctttggc cttggtagtt tgggtgggcg    420
agaggcggct tcgtgcgcgc ccagatcggt gcgcgggagg ggcgggatct cgcggctggg    480
gctctcgccg gcgtggatcc ggcccggatc tcgcggggaa tggggctctc ggatgtagat    540
ctgcgatccg ccgttgttgg gggagatgat ggggggttta aaatttccgc cgtgctaaac    600
aagatcagga agaggggaaa agggcactat ggtttatatt tttatatatt tctgctgctt    660
cgtcaggctt agatgtgcta gatctttctt tcttcttttt gtgggtagaa tttgaatccc    720
tcagcattgt tcatcggtag tttttctttt catgatttgt gacaaatgca gcctcgtgcg    780
gagctttttt gtaggtagaa gtgatcaacc atg gcc aac ccc aac aat cgc tcc     834
                                 Met Ala Asn Pro Asn Asn Arg Ser
                                   1               5 gag cac gac acg atc aag gtc acc ccc aac tcc gag ctc cag acc aac      882
Glu His Asp Thr Ile Lys Val Thr Pro Asn Ser Glu Leu Gln Thr Asn
     10                  15                  20 cac aac cag tac ccg ctg gcc gac aac ccc aac tcc acc ctg gaa gag      930
His Asn Gln Tyr Pro Leu Ala Asp Asn Pro Asn Ser Thr Leu Glu Glu
 25                  30                  35                  40 ctg aac tac aag gag ttc ctg cgc atg acc gag gac tcc tcc acg gag      978
Leu Asn Tyr Lys Glu Phe Leu Arg Met Thr Glu Asp Ser Ser Thr Glu
                 45                  50                  55 gtc ctg gac aac tcc acc gtc aag gac gcc gtc ggg acc ggc atc tcc     1026
Val Leu Asp Asn Ser Thr Val Lys Asp Ala Val Gly Thr Gly Ile Ser
             60                  65                  70 gtc gtt ggg cag atc ctg ggc gtc gtt ggc gtc ccc ttc gca ggt gct     1074
Val Val Gly Gln Ile Leu Gly Val Val Gly Val Pro Phe Ala Gly Ala
         75                  80                  85 ctc acc tcc ttc tac cag tcc ttc ctg aac acc atc tgg ccc tcc gac     1122
Leu Thr Ser Phe Tyr Gln Ser Phe Leu Asn Thr Ile Trp Pro Ser Asp
     90                  95                 100 gcc gac ccc tgg aag gcc ttc atg gcc caa gtc gaa gtc ctg atc gac     1170
Ala Asp Pro Trp Lys Ala Phe Met Ala Gln Val Glu Val Leu Ile Asp
105                 110                 115                 120 aag aag atc gag gag tac gcc aag tcc aag gcc ctg gcc gag ctg caa     1218
```

```
                Lys Lys Ile Glu Glu Tyr Ala Lys Ser Lys Ala Leu Ala Glu Leu Gln
                                125                 130                 135 ggc ctg caa aac aac ttc gag gac tac gtc aac gcg ctg aac tcc tgg           1266
Gly Leu Gln Asn Asn Phe Glu Asp Tyr Val Asn Ala Leu Asn Ser Trp
            140                 145                 150 aag aag acg cct ctg tcc ctg cgc tcc aag cgc tcc cag ggc cgc atc           1314
Lys Lys Thr Pro Leu Ser Leu Arg Ser Lys Arg Ser Gln Gly Arg Ile
            155                 160                 165 cgc gag ctg ttc tcc cag gcc gag tcc cac ttc cgc aac tcc atg ccg           1362
Arg Glu Leu Phe Ser Gln Ala Glu Ser His Phe Arg Asn Ser Met Pro
            170                 175                 180 tcc ttc gcc gtc tcc aag ttc gag gtc ctg ttc ctg ccc acc tac gcc           1410
Ser Phe Ala Val Ser Lys Phe Glu Val Leu Phe Leu Pro Thr Tyr Ala
185                 190                 195                 200 cag gct gcc aac acc cac ctc ctg ttg ctg aag gac gcc cag gtc ttc           1458
Gln Ala Ala Asn Thr His Leu Leu Leu Leu Lys Asp Ala Gln Val Phe
                205                 210                 215 ggc gag gaa tgg ggc tac tcc tcg gag gac gtc gcc gag ttc tac cgt           1506
Gly Glu Glu Trp Gly Tyr Ser Ser Glu Asp Val Ala Glu Phe Tyr Arg
            220                 225                 230 cgc cag ctg aag ctg acc caa cag tac acc gac cac tgc gtc aac tgg           1554
Arg Gln Leu Lys Leu Thr Gln Gln Tyr Thr Asp His Cys Val Asn Trp
            235                 240                 245 tac aac gtc ggc ctg aac ggc ctg agg ggc tcc acc tac gac gca tgg           1602
Tyr Asn Val Gly Leu Asn Gly Leu Arg Gly Ser Thr Tyr Asp Ala Trp
250                 255                 260 gtc aag ttc aac cgc ttc cgc agg gag atg acc ctg acc gtc ctg gac           1650
Val Lys Phe Asn Arg Phe Arg Arg Glu Met Thr Leu Thr Val Leu Asp
265                 270                 275                 280 ctg atc gtc ctg ttc ccc ttc tac gac atc cgc ctg tac tcc aag ggc           1698
Leu Ile Val Leu Phe Pro Phe Tyr Asp Ile Arg Leu Tyr Ser Lys Gly
                285                 290                 295 gtc aag acc gag ctg acc cgc gac atc ttc acg gac ccc atc ttc ctg           1746
Val Lys Thr Glu Leu Thr Arg Asp Ile Phe Thr Asp Pro Ile Phe Leu
            300                 305                 310 ctc acg acc ctc cag aag tac ggt ccc acc ttc ctg tcc atc gag aac           1794
Leu Thr Thr Leu Gln Lys Tyr Gly Pro Thr Phe Leu Ser Ile Glu Asn
            315                 320                 325 tcc atc cgc aag ccc cac ctg ttc gac tac ctc cag ggc atc gag ttc           1842
Ser Ile Arg Lys Pro His Leu Phe Asp Tyr Leu Gln Gly Ile Glu Phe
            330                 335                 340 cac acg cgc ctg agg cca ggc tac ttc ggc aag gac tcc ttc aac tac           1890
His Thr Arg Leu Arg Pro Gly Tyr Phe Gly Lys Asp Ser Phe Asn Tyr
345                 350                 355                 360 tgg tcc ggc aac tac gtc gag acc agg ccc tcc atc ggc tcc tcg aag           1938
Trp Ser Gly Asn Tyr Val Glu Thr Arg Pro Ser Ile Gly Ser Ser Lys
                365                 370                 375 acg atc acc tcc cct ttc tac ggc gac aag tcc acc gag ccc gtc cag           1986
Thr Ile Thr Ser Pro Phe Tyr Gly Asp Lys Ser Thr Glu Pro Val Gln
            380                 385                 390 aag ctg tcc ttc gac ggc cag aag gtc tac cgc acc atc gcc aac acc           2034
Lys Leu Ser Phe Asp Gly Gln Lys Val Tyr Arg Thr Ile Ala Asn Thr
            395                 400                 405 gac gtc gcg gct tgg ccg aac ggc aag gtc tac ctg ggc gtc acg aag           2082
Asp Val Ala Ala Trp Pro Asn Gly Lys Val Tyr Leu Gly Val Thr Lys
            410                 415                 420 gtc gac ttc tcc cag tac gat gac cag aag aat gaa acc tcc acc cag           2130
Val Asp Phe Ser Gln Tyr Asp Asp Gln Lys Asn Glu Thr Ser Thr Gln
425                 430                 435                 440
```

```
acc tac gac tcc aag cgc aac aat ggc cac gtc tcc gcc cag gac tcc    2178
Thr Tyr Asp Ser Lys Arg Asn Asn Gly His Val Ser Ala Gln Asp Ser
                445                 450                 455 atc gac cag ctg ccg cct gag acc act gac gag ccc ctg gag aag gcc    2226
Ile Asp Gln Leu Pro Pro Glu Thr Thr Asp Glu Pro Leu Glu Lys Ala
            460                 465                 470 tac tcc cac cag ctg aac tac gcg gag tgc ttc ctg atg caa gac cgc    2274
Tyr Ser His Gln Leu Asn Tyr Ala Glu Cys Phe Leu Met Gln Asp Arg
        475                 480                 485 agg ggc acc atc ccc ttc ttc acc tgg acc cac cgc tcc gtc gac ttc    2322
Arg Gly Thr Ile Pro Phe Phe Thr Trp Thr His Arg Ser Val Asp Phe
    490                 495                 500 ttc aac acc atc gac gcc gag aag atc acc cag ctg ccc gtg gtc aag    2370
Phe Asn Thr Ile Asp Ala Glu Lys Ile Thr Gln Leu Pro Val Val Lys
505                 510                 515                 520 gcc tac gcc ctg tcc tcg ggt gcc tcc atc att gag ggt cca ggc ttc    2418
Ala Tyr Ala Leu Ser Ser Gly Ala Ser Ile Ile Glu Gly Pro Gly Phe
                525                 530                 535 acc ggt ggc aac ctg ctg ttc ctg aag gag tcc tcg aac tcc atc gcc    2466
Thr Gly Gly Asn Leu Leu Phe Leu Lys Glu Ser Ser Asn Ser Ile Ala
            540                 545                 550 aag ttc aag gtc acc ctg aac tcc gct gcc ttg ctg caa cgc tac cgc    2514
Lys Phe Lys Val Thr Leu Asn Ser Ala Ala Leu Leu Gln Arg Tyr Arg
        555                 560                 565 gtc cgc atc cgc tac gcc tcc acc acg aac ctg cgc ctg ttc gtc cag    2562
Val Arg Ile Arg Tyr Ala Ser Thr Thr Asn Leu Arg Leu Phe Val Gln
    570                 575                 580 aac tcc aac aat gac ttc ctg gtc atc tac atc aac aag acc atg aac    2610
Asn Ser Asn Asn Asp Phe Leu Val Ile Tyr Ile Asn Lys Thr Met Asn
585                 590                 595                 600 aag gac gat gac ctg acc tac cag acc ttc gac ctc gcc acc acg aac    2658
Lys Asp Asp Asp Leu Thr Tyr Gln Thr Phe Asp Leu Ala Thr Thr Asn
                605                 610                 615 tcc aac atg ggc ttc tcg ggc gac aag aat gaa ctg atc att ggt gct    2706
Ser Asn Met Gly Phe Ser Gly Asp Lys Asn Glu Leu Ile Ile Gly Ala
            620                 625                 630 gag tcc ttc gtc tcc aat gaa aag atc tac atc gac aag atc gag ttc    2754
Glu Ser Phe Val Ser Asn Glu Lys Ile Tyr Ile Asp Lys Ile Glu Phe
        635                 640                 645 atc ccc gtc cag ctg tgataggaac tctgattgaa ttctgcatgc gtttggacgt    2809
Ile Pro Val Gln Leu
        650 atgctcattc aggttggagc caatttggtt gatgtgtgtg cgagttcttg cgagtctgat    2869 gagacatctc tgtattgtgt ttctttcccc agtgttttct gtacttgtgt aatcggctaa    2929 tcgccaacag attcggcgat gaataaatga gaaataaatt gttctgattt tgagtgcaaa    2989 aaaaaaggaa ttagatctgt gtgtgttttt tggatccccg gggcggccgc              3039

<210> SEQ ID NO 20
<211> LENGTH: 653
<212> TYPE: PRT
<213> ORGANISM: Artificial Sequence
<220> FEATURE:
<221> NAME/KEY: PRT
<222> LOCATION: (1)..(653)
<223> OTHER INFORMATION: Cry3Bb1 variant 11231mv1

<400> SEQUENCE: 20

Met Ala Asn Pro Asn Asn Arg Ser Glu His Asp Thr Ile Lys Val Thr
 1               5                  10                  15
```

```
Pro Asn Ser Glu Leu Gln Thr Asn His Asn Gln Tyr Pro Leu Ala Asp
             20                  25                  30
Asn Pro Asn Ser Thr Leu Glu Glu Leu Asn Tyr Lys Glu Phe Leu Arg
         35                  40                  45
Met Thr Glu Asp Ser Ser Thr Glu Val Leu Asp Asn Ser Thr Val Lys
     50                  55                  60
Asp Ala Val Gly Thr Gly Ile Ser Val Val Gly Gln Ile Leu Gly Val
 65                  70                  75                  80
Val Gly Val Pro Phe Ala Gly Ala Leu Thr Ser Phe Tyr Gln Ser Phe
                 85                  90                  95
Leu Asn Thr Ile Trp Pro Ser Asp Ala Asp Pro Trp Lys Ala Phe Met
             100                 105                 110
Ala Gln Val Glu Val Leu Ile Asp Lys Lys Ile Glu Glu Tyr Ala Lys
         115                 120                 125
Ser Lys Ala Leu Ala Glu Leu Gln Gly Leu Gln Asn Asn Phe Glu Asp
     130                 135                 140
Tyr Val Asn Ala Leu Asn Ser Trp Lys Lys Thr Pro Leu Ser Leu Arg
145                 150                 155                 160
Ser Lys Arg Ser Gln Gly Arg Ile Arg Glu Leu Phe Ser Gln Ala Glu
                 165                 170                 175
Ser His Phe Arg Asn Ser Met Pro Ser Phe Ala Val Ser Lys Phe Glu
             180                 185                 190
Val Leu Phe Leu Pro Thr Tyr Ala Gln Ala Ala Asn Thr His Leu Leu
         195                 200                 205
Leu Leu Lys Asp Ala Gln Val Phe Gly Glu Glu Trp Gly Tyr Ser Ser
     210                 215                 220
Glu Asp Val Ala Glu Phe Tyr Arg Arg Gln Leu Lys Leu Thr Gln Gln
225                 230                 235                 240
Tyr Thr Asp His Cys Val Asn Trp Tyr Asn Val Gly Leu Asn Gly Leu
                 245                 250                 255
Arg Gly Ser Thr Tyr Asp Ala Trp Val Lys Phe Asn Arg Phe Arg Arg
             260                 265                 270
Glu Met Thr Leu Thr Val Leu Asp Leu Ile Val Leu Phe Pro Phe Tyr
         275                 280                 285
Asp Ile Arg Leu Tyr Ser Lys Gly Val Lys Thr Glu Leu Thr Arg Asp
     290                 295                 300
Ile Phe Thr Asp Pro Ile Phe Leu Leu Thr Thr Leu Gln Lys Tyr Gly
305                 310                 315                 320
Pro Thr Phe Leu Ser Ile Glu Asn Ser Ile Arg Lys Pro His Leu Phe
                 325                 330                 335
Asp Tyr Leu Gln Gly Ile Glu Phe His Thr Arg Leu Arg Pro Gly Tyr
             340                 345                 350
Phe Gly Lys Asp Ser Phe Asn Tyr Trp Ser Gly Asn Tyr Val Glu Thr
         355                 360                 365
Arg Pro Ser Ile Gly Ser Ser Lys Thr Ile Thr Ser Pro Phe Tyr Gly
     370                 375                 380
Asp Lys Ser Thr Glu Pro Val Gln Lys Leu Ser Phe Asp Gly Gln Lys
385                 390                 395                 400
Val Tyr Arg Thr Ile Ala Asn Thr Asp Val Ala Ala Trp Pro Asn Gly
                 405                 410                 415
Lys Val Tyr Leu Gly Val Thr Lys Val Asp Phe Ser Gln Tyr Asp Asp
             420                 425                 430
Gln Lys Asn Glu Thr Ser Thr Gln Thr Tyr Asp Ser Lys Arg Asn Asn
```

-continued

```
        435                 440                 445

Gly His Val Ser Ala Gln Asp Ser Ile Asp Gln Leu Pro Pro Glu Thr
    450                 455                 460

Thr Asp Glu Pro Leu Glu Lys Ala Tyr Ser His Gln Leu Asn Tyr Ala
465                 470                 475                 480

Glu Cys Phe Leu Met Gln Asp Arg Arg Gly Thr Ile Pro Phe Phe Thr
                485                 490                 495

Trp Thr His Arg Ser Val Asp Phe Phe Asn Thr Ile Asp Ala Glu Lys
            500                 505                 510

Ile Thr Gln Leu Pro Val Val Lys Ala Tyr Ala Leu Ser Ser Gly Ala
        515                 520                 525

Ser Ile Ile Glu Gly Pro Gly Phe Thr Gly Gly Asn Leu Leu Phe Leu
    530                 535                 540

Lys Glu Ser Ser Asn Ser Ile Ala Lys Phe Lys Val Thr Leu Asn Ser
545                 550                 555                 560

Ala Ala Leu Leu Gln Arg Tyr Arg Val Arg Ile Arg Tyr Ala Ser Thr
                565                 570                 575

Thr Asn Leu Arg Leu Phe Val Gln Asn Ser Asn Asn Asp Phe Leu Val
            580                 585                 590

Ile Tyr Ile Asn Lys Thr Met Asn Lys Asp Asp Asp Leu Thr Tyr Gln
        595                 600                 605

Thr Phe Asp Leu Ala Thr Thr Asn Ser Asn Met Gly Phe Ser Gly Asp
    610                 615                 620

Lys Asn Glu Leu Ile Ile Gly Ala Glu Ser Phe Val Ser Asn Glu Lys
625                 630                 635                 640

Ile Tyr Ile Asp Lys Ile Glu Phe Ile Pro Val Gln Leu
                645                 650

<210> SEQ ID NO 21
<211> LENGTH: 3039
<212> TYPE: DNA
<213> ORGANISM: Artificial Sequence
<220> FEATURE:
<223> OTHER INFORMATION: Description of Artificial Sequence: expression
      cassette
<220> FEATURE:
<221> NAME/KEY: promoter
<222> LOCATION: (14)..(235)
<223> OTHER INFORMATION: P-CaMV.AS4
<220> FEATURE:
<221> NAME/KEY: 5'UTR
<222> LOCATION: (240)..(304)
<223> OTHER INFORMATION: L-Ta.hcb1
<220> FEATURE:
<221> NAME/KEY: intron
<222> LOCATION: (318)..(805)
<223> OTHER INFORMATION: I-Os.Act1
<220> FEATURE:
<221> NAME/KEY: CDS
<222> LOCATION: (811)..(2769)
<223> OTHER INFORMATION: Cry3Bb1 variant 11231mv2
<220> FEATURE:
<221> NAME/KEY: terminator
<222> LOCATION: (2787)..(3020)
<223> OTHER INFORMATION: T-Ta.hsp17

<400> SEQUENCE: 21
gcggccgcgt taacaagctt ctgacgtaag ggatgacgca cctgacgtaa gggatgacgc     60
acctgacgta agggatgacg cacctgacgt aagggatgac gcactcgaga tccccatctc    120
cactgacgta agggatgacg cacaatccca ctatccttcg caagaccctt cctctatata    180
aggaagttca tttcatttgg agaggacacg ctgacaagct agcttggctg caggtagatc    240
```

-continued

```
ctagaaccat cttccacaca ctcaagccac actattggag aacacacagg gacaacacac      300
cataagatcc aagggaggcc tccgccgccg ccggtaacca ccccgcccct ctcctctttc      360
tttctccgtt ttttttttccg tctcggtctc gatctttggc cttggtagtt tgggtgggcg     420
agaggcggct tcgtgcgcgc ccagatcggt gcgcgggagg ggcgggatct cgcggctggg     480
gctctcgccg gcgtggatcc ggcccggatc tcgcggggaa tggggctctc ggatgtagat     540
ctgcgatccg ccgttgttgg gggagatgat ggggggttta aaatttccgc cgtgctaaac     600
aagatcagga agaggggaaa aaggcactat ggtttatatt tttatatatt tctgctgctt     660
cgtcaggctt agatgtgcta gatctttctt tcttcttttt gtgggtagaa tttgaatccc     720
tcagcattgt tcatcggtag tttttctttt catgatttgt gacaaatgca gcctcgtgcg     780
gagctttttt gtaggtagaa gtgatcaacc atg gcc aac ccc aac aat cgc tcc     834
                                Met Ala Asn Pro Asn Asn Arg Ser
                                 1               5 gag cac gac acg atc aag gtc acc ccc aac tcc gag ctc cag acc aac      882
Glu His Asp Thr Ile Lys Val Thr Pro Asn Ser Glu Leu Gln Thr Asn
        10                  15                  20 cac aac cag tac ccg ctg gcc gac aac ccc aac tcc acc ctg gaa gag      930
His Asn Gln Tyr Pro Leu Ala Asp Asn Pro Asn Ser Thr Leu Glu Glu
 25                  30                  35                  40 ctg aac tac aag gag ttc ctg cgc atg acc gag gac tcc tcc acg gag      978
Leu Asn Tyr Lys Glu Phe Leu Arg Met Thr Glu Asp Ser Ser Thr Glu
                45                  50                  55 gtc ctg gac aac tcc acc gtc aag gac gcc gtg ggg acc ggc atc tcc     1026
Val Leu Asp Asn Ser Thr Val Lys Asp Ala Val Gly Thr Gly Ile Ser
            60                  65                  70 gtc gtt ggg cag atc ctg ggc gtc gtt ggc gtc ccc ttc gca ggt gct     1074
Val Val Gly Gln Ile Leu Gly Val Val Gly Val Pro Phe Ala Gly Ala
        75                  80                  85 ctc acc tcc ttc tac cag tcc ttc ctg aac acc atc tgg ccc tcc gac     1122
Leu Thr Ser Phe Tyr Gln Ser Phe Leu Asn Thr Ile Trp Pro Ser Asp
 90                  95                 100 gcc gac ccc tgg aag gcc ttc atg gcc caa gtc gaa gtc ctg atc gac     1170
Ala Asp Pro Trp Lys Ala Phe Met Ala Gln Val Glu Val Leu Ile Asp
105                 110                 115                 120 aag aag atc gag gag tac gcc aag tcc aag gcc ctg gcc gag ctg caa     1218
Lys Lys Ile Glu Glu Tyr Ala Lys Ser Lys Ala Leu Ala Glu Leu Gln
                125                 130                 135 ggc ctg caa aac aac ttc gag gac tac gtc aac gcg ctg aac tcc tgg     1266
Gly Leu Gln Asn Asn Phe Glu Asp Tyr Val Asn Ala Leu Asn Ser Trp
            140                 145                 150 aag aag acg cct ctg tcc ctg cgc tcc aag cgc tcc cag gac cgc atc     1314
Lys Lys Thr Pro Leu Ser Leu Arg Ser Lys Arg Ser Gln Asp Arg Ile
        155                 160                 165 cgc gag ctg ttc tcc cag gcc gag tcc cac ttc cgc aac tcc atg ccg     1362
Arg Glu Leu Phe Ser Gln Ala Glu Ser His Phe Arg Asn Ser Met Pro
170                 175                 180 tcc ttc gcc gtc tcc aag ttc gag gtc ctg ttc ctg ccc acc tac gcc     1410
Ser Phe Ala Val Ser Lys Phe Glu Val Leu Phe Leu Pro Thr Tyr Ala
185                 190                 195                 200 cag gct gcc aac acc cac ctc ctg ttg ctg aag gac gcc cag gtc ttc     1458
Gln Ala Ala Asn Thr His Leu Leu Leu Leu Lys Asp Ala Gln Val Phe
                205                 210                 215 ggc gag gaa tgg ggc tac tcc tcg gag gac gtc gcc gag ttc tac cgt     1506
Gly Glu Glu Trp Gly Tyr Ser Ser Glu Asp Val Ala Glu Phe Tyr Arg
            220                 225                 230
```

```
cgc cag ctg aag ctg acc caa cag tac acc gac cac tgc gtc aac tgg    1554
Arg Gln Leu Lys Leu Thr Gln Gln Tyr Thr Asp His Cys Val Asn Trp
        235                 240                 245 tac aac gtc ggc ctg aac ggc ctg agg ggc tcc acc tac gac gca tgg    1602
Tyr Asn Val Gly Leu Asn Gly Leu Arg Gly Ser Thr Tyr Asp Ala Trp
250                 255                 260 gtc aag ttc aac cgc ttc cgg gag atg acc ctg acc gtc ctg gac        1650
Val Lys Phe Asn Arg Phe Arg Arg Glu Met Thr Leu Thr Val Leu Asp
265                 270                 275                 280 ctg atc gtc ctg ttc ccc ttc tac gac atc cgc ctg tac tcc aag ggc    1698
Leu Ile Val Leu Phe Pro Phe Tyr Asp Ile Arg Leu Tyr Ser Lys Gly
                285                 290                 295 gtc aag acc gag ctg acc cgc gac atc ttc acg gac ccc atc ttc ctg    1746
Val Lys Thr Glu Leu Thr Arg Asp Ile Phe Thr Asp Pro Ile Phe Leu
            300                 305                 310 ctc acg acc ctc cag aag tac ggt ccc acc ttc ctg tcc atc gag aac    1794
Leu Thr Thr Leu Gln Lys Tyr Gly Pro Thr Phe Leu Ser Ile Glu Asn
        315                 320                 325 tcc atc cgc aag ccc cac ctg ttc gac tac ctc cag ggc atc gag ttc    1842
Ser Ile Arg Lys Pro His Leu Phe Asp Tyr Leu Gln Gly Ile Glu Phe
    330                 335                 340 cac acg cgc ctg agg cca ggc tac ttc ggc aag gac tcc ttc aac tac    1890
His Thr Arg Leu Arg Pro Gly Tyr Phe Gly Lys Asp Ser Phe Asn Tyr
345                 350                 355                 360 tgg tcc ggc aac tac gtc gag acc agg ccc tcc atc ggc tcc tcg aag    1938
Trp Ser Gly Asn Tyr Val Glu Thr Arg Pro Ser Ile Gly Ser Ser Lys
                365                 370                 375 acg atc acc tcc cct ttc tac ggc gac aag tcc acc gag ccc gtc cag    1986
Thr Ile Thr Ser Pro Phe Tyr Gly Asp Lys Ser Thr Glu Pro Val Gln
            380                 385                 390 aag ctg tcc ttc gac ggc cag aag gtc tac cgc acc atc gcc aac acc    2034
Lys Leu Ser Phe Asp Gly Gln Lys Val Tyr Arg Thr Ile Ala Asn Thr
        395                 400                 405 gac gtc gcg gct tgg ccg aac ggc aag gtc tac ctg ggc gtc acg aag    2082
Asp Val Ala Ala Trp Pro Asn Gly Lys Val Tyr Leu Gly Val Thr Lys
    410                 415                 420 gtc gac ttc tcc cag tac gat gac cag aag aat gaa acc tcc acc cag    2130
Val Asp Phe Ser Gln Tyr Asp Asp Gln Lys Asn Glu Thr Ser Thr Gln
425                 430                 435                 440 acc tac gac tcc aag cgc aac aat ggc cac gtc tcc gcc cag gac tcc    2178
Thr Tyr Asp Ser Lys Arg Asn Asn Gly His Val Ser Ala Gln Asp Ser
                445                 450                 455 atc gac cag ctg ccg cct gag acc act gac gag ccc ctg gag aag gcc    2226
Ile Asp Gln Leu Pro Pro Glu Thr Thr Asp Glu Pro Leu Glu Lys Ala
            460                 465                 470 tac tcc cac cag ctg aac tac gcg gag tgc ttc ctg atg caa gac cgc    2274
Tyr Ser His Gln Leu Asn Tyr Ala Glu Cys Phe Leu Met Gln Asp Arg
        475                 480                 485 agg ggc acc atc ccc ttc ttc acc tgg acc cac cgc tcc gtc gac ttc    2322
Arg Gly Thr Ile Pro Phe Phe Thr Trp Thr His Arg Ser Val Asp Phe
    490                 495                 500 ttc aac acc atc gac gcc gag aag atc acc cag ctg ccc gtg gtc aag    2370
Phe Asn Thr Ile Asp Ala Glu Lys Ile Thr Gln Leu Pro Val Val Lys
505                 510                 515                 520 gcc tac gcc ctg tcc tcg ggt gcc tcc atc att gag ggt cca ggc ttc    2418
Ala Tyr Ala Leu Ser Ser Gly Ala Ser Ile Ile Glu Gly Pro Gly Phe
                525                 530                 535 acc ggt ggc aac ctg ctg ttc ctg aag gag tcc tcg aac tcc atc gcc    2466
Thr Gly Gly Asn Leu Leu Phe Leu Lys Glu Ser Ser Asn Ser Ile Ala
            540                 545                 550
```

-continued

```
aag ttc aag gtc acc ctg aac tcc gct gcc ttg ctg caa cgc tac cgc     2514
Lys Phe Lys Val Thr Leu Asn Ser Ala Ala Leu Leu Gln Arg Tyr Arg
            555                 560                 565 gtc cgc atc cgc tac gcc tcc acc acg aac ctg cgc ctg ttc gtc cag     2562
Val Arg Ile Arg Tyr Ala Ser Thr Thr Asn Leu Arg Leu Phe Val Gln
        570                 575                 580 aac tcc aac aat gac ttc ctg gtc atc tac atc aac aag acc atg aac     2610
Asn Ser Asn Asn Asp Phe Leu Val Ile Tyr Ile Asn Lys Thr Met Asn
585                 590                 595                 600 aag gac gat gac ctg acc tac cag acc ttc gac ctc gcc acc acg aac     2658
Lys Asp Asp Asp Leu Thr Tyr Gln Thr Phe Asp Leu Ala Thr Thr Asn
                605                 610                 615 tcc aac atg ggc ttc tcg ggc gac aag aat gaa ctg atc att ggt gct     2706
Ser Asn Met Gly Phe Ser Gly Asp Lys Asn Glu Leu Ile Ile Gly Ala
            620                 625                 630 gag tcc ttc gtc tcc aat gaa aag atc tac atc gac aag atc gag ttc     2754
Glu Ser Phe Val Ser Asn Glu Lys Ile Tyr Ile Asp Lys Ile Glu Phe
        635                 640                 645 atc ccc gtc cag ctg tgataggaac tctgattgaa ttctgcatgc gtttggacgt     2809
Ile Pro Val Gln Leu
    650 atgctcattc aggttggagc caatttggtt gatgtgtgtg cgagttcttg cgagtctgat    2869 gagacatctc tgtattgtgt ttctttcccc agtgttttct gtacttgtgt aatcggctaa    2929 tcgccaacag attcggcgat gaataaatga gaaataaatt gttctgattt tgagtgcaaa    2989 aaaaaaggaa ttagatctgt gtgtgttttt tggatccccg gggcggccgc             3039

<210> SEQ ID NO 22
<211> LENGTH: 653
<212> TYPE: PRT
<213> ORGANISM: Artificial Sequence
<220> FEATURE:
<221> NAME/KEY: PRT
<222> LOCATION: (1)..(653)
<223> OTHER INFORMATION: Cry3Bb1 variant 11231mv2

<400> SEQUENCE: 22

Met Ala Asn Pro Asn Asn Arg Ser Glu His Asp Thr Ile Lys Val Thr
1               5                   10                  15

Pro Asn Ser Glu Leu Gln Thr Asn His Asn Gln Tyr Pro Leu Ala Asp
            20                  25                  30

Asn Pro Asn Ser Thr Leu Glu Glu Leu Asn Tyr Lys Glu Phe Leu Arg
        35                  40                  45

Met Thr Glu Asp Ser Ser Thr Glu Val Leu Asp Asn Ser Thr Val Lys
    50                  55                  60

Asp Ala Val Gly Thr Gly Ile Ser Val Val Gly Gln Ile Leu Gly Val
65                  70                  75                  80

Val Gly Val Pro Phe Ala Gly Ala Leu Thr Ser Phe Tyr Gln Ser Phe
                85                  90                  95

Leu Asn Thr Ile Trp Pro Ser Asp Ala Asp Pro Trp Lys Ala Phe Met
            100                 105                 110

Ala Gln Val Glu Val Leu Ile Asp Lys Lys Ile Glu Glu Tyr Ala Lys
        115                 120                 125

Ser Lys Ala Leu Ala Glu Leu Gln Gly Leu Gln Asn Asn Phe Glu Asp
    130                 135                 140

Tyr Val Asn Ala Leu Asn Ser Trp Lys Lys Thr Pro Leu Ser Leu Arg
145                 150                 155                 160
```

-continued

```
Ser Lys Arg Ser Gln Asp Arg Ile Arg Glu Leu Phe Ser Gln Ala Glu
                165                 170                 175

Ser His Phe Arg Asn Ser Met Pro Ser Phe Ala Val Ser Lys Phe Glu
            180                 185                 190

Val Leu Phe Leu Pro Thr Tyr Ala Gln Ala Ala Asn Thr His Leu Leu
        195                 200                 205

Leu Leu Lys Asp Ala Gln Val Phe Gly Glu Glu Trp Gly Tyr Ser Ser
    210                 215                 220

Glu Asp Val Ala Glu Phe Tyr Arg Arg Gln Leu Lys Leu Thr Gln Gln
225                 230                 235                 240

Tyr Thr Asp His Cys Val Asn Trp Tyr Asn Val Gly Leu Asn Gly Leu
                245                 250                 255

Arg Gly Ser Thr Tyr Asp Ala Trp Val Lys Phe Asn Arg Phe Arg Arg
            260                 265                 270

Glu Met Thr Leu Thr Val Leu Asp Leu Ile Val Leu Phe Pro Phe Tyr
        275                 280                 285

Asp Ile Arg Leu Tyr Ser Lys Gly Val Lys Thr Glu Leu Thr Arg Asp
    290                 295                 300

Ile Phe Thr Asp Pro Ile Phe Leu Leu Thr Thr Leu Gln Lys Tyr Gly
305                 310                 315                 320

Pro Thr Phe Leu Ser Ile Glu Asn Ser Ile Arg Lys Pro His Leu Phe
                325                 330                 335

Asp Tyr Leu Gln Gly Ile Glu Phe His Thr Arg Leu Arg Pro Gly Tyr
            340                 345                 350

Phe Gly Lys Asp Ser Phe Asn Tyr Trp Ser Gly Asn Tyr Val Glu Thr
        355                 360                 365

Arg Pro Ser Ile Gly Ser Lys Thr Ile Thr Ser Pro Phe Tyr Gly
    370                 375                 380

Asp Lys Ser Thr Glu Pro Val Gln Lys Leu Ser Phe Asp Gly Gln Lys
385                 390                 395                 400

Val Tyr Arg Thr Ile Ala Asn Thr Asp Val Ala Ala Trp Pro Asn Gly
                405                 410                 415

Lys Val Tyr Leu Gly Val Thr Lys Val Asp Phe Ser Gln Tyr Asp Asp
            420                 425                 430

Gln Lys Asn Glu Thr Ser Thr Gln Thr Tyr Asp Ser Lys Arg Asn Asn
        435                 440                 445

Gly His Val Ser Ala Gln Asp Ser Ile Asp Gln Leu Pro Pro Glu Thr
    450                 455                 460

Thr Asp Glu Pro Leu Glu Lys Ala Tyr Ser His Gln Leu Asn Tyr Ala
465                 470                 475                 480

Glu Cys Phe Leu Met Gln Asp Arg Arg Gly Thr Ile Pro Phe Phe Thr
                485                 490                 495

Trp Thr His Arg Ser Val Asp Phe Phe Asn Thr Ile Asp Ala Glu Lys
            500                 505                 510

Ile Thr Gln Leu Pro Val Val Lys Ala Tyr Ala Leu Ser Ser Gly Ala
        515                 520                 525

Ser Ile Ile Glu Gly Pro Gly Phe Thr Gly Gly Asn Leu Leu Phe Leu
    530                 535                 540

Lys Glu Ser Ser Asn Ser Ile Ala Lys Phe Lys Val Thr Leu Asn Ser
545                 550                 555                 560

Ala Ala Leu Leu Gln Arg Tyr Arg Val Arg Ile Arg Tyr Ala Ser Thr
                565                 570                 575

Thr Asn Leu Arg Leu Phe Val Gln Asn Ser Asn Asn Asp Phe Leu Val
```

```
                580              585              590
Ile Tyr Ile Asn Lys Thr Met Asn Lys Asp Asp Leu Thr Tyr Gln
            595              600              605
Thr Phe Asp Leu Ala Thr Thr Asn Ser Asn Met Gly Phe Ser Gly Asp
        610              615              620
Lys Asn Glu Leu Ile Ile Gly Ala Glu Ser Phe Val Ser Asn Glu Lys
625              630              635              640
Ile Tyr Ile Asp Lys Ile Glu Phe Ile Pro Val Gln Leu
                645              650

<210> SEQ ID NO 23
<211> LENGTH: 3469
<212> TYPE: DNA
<213> ORGANISM: Artificial Sequence
<220> FEATURE:
<223> OTHER INFORMATION: Description of Artificial Sequence: expression
      cassette
<220> FEATURE:
<221> NAME/KEY: promoter
<222> LOCATION: (25)..(640)
<223> OTHER INFORMATION: P-CaMV.35S
<220> FEATURE:
<221> NAME/KEY: 5'UTR
<222> LOCATION: (664)..(734)
<223> OTHER INFORMATION: L-Ta.hcb1
<220> FEATURE:
<221> NAME/KEY: intron
<222> LOCATION: (748)..(1238)
<223> OTHER INFORMATION: I-Os.Act1
<220> FEATURE:
<221> NAME/KEY: CDS
<222> LOCATION: (1241)..(3199)
<223> OTHER INFORMATION: Cry3Bb1 variant 11231mv2
<220> FEATURE:
<221> NAME/KEY: terminator
<222> LOCATION: (3217)..(3450)
<223> OTHER INFORMATION: T-Ta.hsp17

<400> SEQUENCE: 23
gcggccgcgt taacaagctt ctgcaggtcc gatgtgagac ttttcaacaa agggtaatat    60
ccggaaacct cctcggattc cattgcccag ctatctgtca ctttattgtg aagatagtgg   120
aaaaggaagg tggctcctac aaatgccatc attgcgataa aggaaaggcc atcgttgaag   180
atgcctctgc cgacagtggt cccaaagatg acccccacc cacgaggagc atcgtggaaa   240
agaagacgt tccaaccacg tcttcaaagc aagtggattg atgtgatggt ccgatgtgag   300
acttttcaac aaagggtaat atccggaaac ctcctcggat tccattgccc agctatctgt   360
cactttattg tgaagatagt ggaaaaggaa ggtggctcct acaaatgcca tcattgcgat   420
aaaggaaagg ccatcgttga agatgcctct gccgacagtg gtcccaaaga tgaccccca   480
cccacgagga gcatcgtgga aaaagaagac gttccaacca cgtcttcaaa gcaagtggat   540
tgatgtgata tctccactga cgtaagggat gacgcacaat cccactatcc ttcgcaagac   600
ccttcctcta tataaggaag ttcatttcat ttggagagga cacgctgaca agctgactct   660
agcagatcct ctagaaccat cttccacaca ctcaagccac actattggag aacacacagg   720
gacaacacac cataagatcc aagggaggcc tccgccgccg ccggtaacca ccccgcccct   780
ctcctctttc tttctccgtt ttttttttccg tctcggtctc gatctttggc cttggtagtt   840
tgggtgggcg agaggcggct tcgtgcgcgc ccagatcggc gcgcgggagg ggcgggatct   900
cgcggctggg gctctcgccg gcgtggatcc ggcccggatc tcgcgggaa tggggctctc   960
ggatgtagat ctgcgatccg ccgttgttgg gggagatgat gggggggttta aaatttccgc  1020
```

```
                                      -continued
cgtgctaaac aagatcagga agagggaaa aggggcactat ggtttatatt tttatatatt  1080
tctgctgctt cgtcaggctt agatgtgcta gatctttctt tcttctttt gtgggtagaa   1140 tttgaatccc tcagcattgt tcatcggtag ttttcttttt catgatttgt gacaaatgca   1200
gcctcgtgcg gagctttttt gtaggtagaa gtgatcaacc atg gcc aac ccc aac    1255
                                              Met Ala Asn Pro Asn
                                              1               5 aat cgc tcc gag cac gac acg atc aag gtc acc ccc aac tcc gag ctc    1303
Asn Arg Ser Glu His Asp Thr Ile Lys Val Thr Pro Asn Ser Glu Leu
            10                  15                  20 cag acc aac cac aac cag tac ccg ctg gcc gac aac ccc aac tcc acc    1351
Gln Thr Asn His Asn Gln Tyr Pro Leu Ala Asp Asn Pro Asn Ser Thr
                25                  30                  35 ctg gaa gag ctg aac tac aag gag ttc ctg cgc atg acc gag gac tcc    1399
Leu Glu Glu Leu Asn Tyr Lys Glu Phe Leu Arg Met Thr Glu Asp Ser
        40                  45                  50 tcc acg gag gtc ctg gac aac tcc acc gtc aag gac gcc gtc ggg acc    1447
Ser Thr Glu Val Leu Asp Asn Ser Thr Val Lys Asp Ala Val Gly Thr
    55                  60                  65 ggc atc tcc gtc gtt ggg cag atc ctg ggc gtc gtt ggc gtc ccc ttc    1495
Gly Ile Ser Val Val Gly Gln Ile Leu Gly Val Val Gly Val Pro Phe
70                  75                  80                  85 gca ggt gct ctc acc tcc ttc tac cag tcc ttc ctg aac acc atc tgg    1543
Ala Gly Ala Leu Thr Ser Phe Tyr Gln Ser Phe Leu Asn Thr Ile Trp
                90                  95                  100 ccc tcc gac gcc gac ccc tgg aag gcc ttc atg gcc caa gtc gaa gtc    1591
Pro Ser Asp Ala Asp Pro Trp Lys Ala Phe Met Ala Gln Val Glu Val
                105                 110                 115 ctg atc gac aag aag atc gag gag tac gcc aag tcc aag gcc ctg gcc    1639
Leu Ile Asp Lys Lys Ile Glu Glu Tyr Ala Lys Ser Lys Ala Leu Ala
        120                 125                 130 gag ctg caa ggc ctg caa aac aac ttc gag gac tac gtc aac gcg ctg    1687
Glu Leu Gln Gly Leu Gln Asn Asn Phe Glu Asp Tyr Val Asn Ala Leu
    135                 140                 145 aac tcc tgg aag aag acg cct ctg tcc ctg cgc tcc aag cgc tcc cag    1735
Asn Ser Trp Lys Lys Thr Pro Leu Ser Leu Arg Ser Lys Arg Ser Gln
150                 155                 160                 165 gac cgc atc cgc gag ctg ttc tcc cag gcc gag tcc cac ttc cgc aac    1783
Asp Arg Ile Arg Glu Leu Phe Ser Gln Ala Glu Ser His Phe Arg Asn
                170                 175                 180 tcc atg ccg tcc ttc gcc gtc tcc aag ttc gag gtc ctg ttc ctg ccc    1831
Ser Met Pro Ser Phe Ala Val Ser Lys Phe Glu Val Leu Phe Leu Pro
                185                 190                 195 acc tac gcc cag gct gcc aac acc cac ctc ctg ttg ctg aag gac gcc    1879
Thr Tyr Ala Gln Ala Ala Asn Thr His Leu Leu Leu Leu Lys Asp Ala
        200                 205                 210 cag gtc ttc ggc gag gaa tgg ggc tac tcc tcg gag gac gtc gcc gag    1927
Gln Val Phe Gly Glu Glu Trp Gly Tyr Ser Ser Glu Asp Val Ala Glu
    215                 220                 225 ttc tac cgt cgc cag ctg aag ctg acc caa cag tac acc gac cac tgc    1975
Phe Tyr Arg Arg Gln Leu Lys Leu Thr Gln Gln Tyr Thr Asp His Cys
230                 235                 240                 245 gtc aac tgg tac aac gtc ggc ctg aac ggc ctg agg ggc tcc acc tac    2023
Val Asn Trp Tyr Asn Val Gly Leu Asn Gly Leu Arg Gly Ser Thr Tyr
                250                 255                 260 gac gca tgg gtc aag ttc aac cgc ttc cgc agg gag atg acc ctg acc    2071
Asp Ala Trp Val Lys Phe Asn Arg Phe Arg Arg Glu Met Thr Leu Thr
                265                 270                 275 gtc ctg gac ctg atc gtc ctg ttc ccc ttc tac gac atc cgc ctg tac    2119
```

```
                    Val Leu Asp Leu Ile Val Leu Phe Pro Phe Tyr Asp Ile Arg Leu Tyr
                                280                 285                 290 tcc aag ggc gtc aag acc gag ctg acc cgc gac atc ttc acg gac ccc          2167
Ser Lys Gly Val Lys Thr Glu Leu Thr Arg Asp Ile Phe Thr Asp Pro
295                 300                 305 atc ttc ctg ctc acg acc ctc cag aag tac ggt ccc acc ttc ctg tcc          2215
Ile Phe Leu Leu Thr Thr Leu Gln Lys Tyr Gly Pro Thr Phe Leu Ser
310                 315                 320                 325 atc gag aac tcc atc cgc aag ccc cac ctg ttc gac tac ctc cag ggc          2263
Ile Glu Asn Ser Ile Arg Lys Pro His Leu Phe Asp Tyr Leu Gln Gly
                330                 335                 340 atc gag ttc cac acg cgc ctg agg cca ggc tac ttc ggc aag gac tcc          2311
Ile Glu Phe His Thr Arg Leu Arg Pro Gly Tyr Phe Gly Lys Asp Ser
                345                 350                 355 ttc aac tac tgg tcc ggc aac tac gtc gag acc agg ccc tcc atc ggc          2359
Phe Asn Tyr Trp Ser Gly Asn Tyr Val Glu Thr Arg Pro Ser Ile Gly
                360                 365                 370 tcc tcg aag acg atc acc tcc cct ttc tac ggc gac aag tcc acc gag          2407
Ser Ser Lys Thr Ile Thr Ser Pro Phe Tyr Gly Asp Lys Ser Thr Glu
375                 380                 385 ccc gtc cag aag ctg tcc ttc gac ggc cag aag gtc tac cgc acc atc          2455
Pro Val Gln Lys Leu Ser Phe Asp Gly Gln Lys Val Tyr Arg Thr Ile
390                 395                 400                 405 gcc aac acc gac gtc gcg gct tgg ccg aac ggc aag gtc tac ctg ggc          2503
Ala Asn Thr Asp Val Ala Ala Trp Pro Asn Gly Lys Val Tyr Leu Gly
                410                 415                 420 gtc acg aag gtc gac ttc tcc cag tac gat gac cag aag aat gaa acc          2551
Val Thr Lys Val Asp Phe Ser Gln Tyr Asp Asp Gln Lys Asn Glu Thr
                425                 430                 435 tcc acc cag acc tac gac tcc aag cgc aac aat ggc cac gtc tcc gcc          2599
Ser Thr Gln Thr Tyr Asp Ser Lys Arg Asn Asn Gly His Val Ser Ala
                440                 445                 450 cag gac tcc atc gac cag ctg ccg cct gag acc act gac gag ccc ctg          2647
Gln Asp Ser Ile Asp Gln Leu Pro Pro Glu Thr Thr Asp Glu Pro Leu
455                 460                 465 gag aag gcc tac tcc cac cag ctg aac tac gcg gag tgc ttc ctg atg          2695
Glu Lys Ala Tyr Ser His Gln Leu Asn Tyr Ala Glu Cys Phe Leu Met
470                 475                 480                 485 caa gac cgc agg ggc acc atc ccc ttc ttc acc tgg acc cac cgc tcc          2743
Gln Asp Arg Arg Gly Thr Ile Pro Phe Phe Thr Trp Thr His Arg Ser
                490                 495                 500 gtc gac ttc ttc aac acc atc gac gcc gag aag atc acc cag ctg ccc          2791
Val Asp Phe Phe Asn Thr Ile Asp Ala Glu Lys Ile Thr Gln Leu Pro
                505                 510                 515 gtg gtc aag gcc tac gcc ctg tcc tcg ggt gcc tcc atc att gag ggt          2839
Val Val Lys Ala Tyr Ala Leu Ser Ser Gly Ala Ser Ile Ile Glu Gly
                520                 525                 530 cca ggc ttc acc ggt ggc aac ctg ctg ttc ctg aag gag tcc tcg aac          2887
Pro Gly Phe Thr Gly Gly Asn Leu Leu Phe Leu Lys Glu Ser Ser Asn
535                 540                 545 tcc atc gcc aag ttc aag gtc acc ctg aac tcc gct gcc ttg ctg caa          2935
Ser Ile Ala Lys Phe Lys Val Thr Leu Asn Ser Ala Ala Leu Leu Gln
550                 555                 560                 565 cgc tac cgc gtc cgc atc cgc tac gcc tcc acc acg aac ctg cgc ctg          2983
Arg Tyr Arg Val Arg Ile Arg Tyr Ala Ser Thr Thr Asn Leu Arg Leu
                570                 575                 580 ttc gtc cag aac tcc aac aat gac ttc ctg gtc atc tac atc aac aag          3031
Phe Val Gln Asn Ser Asn Asn Asp Phe Leu Val Ile Tyr Ile Asn Lys
                585                 590                 595
```

-continued

```
acc atg aac aag gac gat gac ctg acc tac cag acc ttc gac ctc gcc      3079
Thr Met Asn Lys Asp Asp Asp Leu Thr Tyr Gln Thr Phe Asp Leu Ala
        600                 605                 610 acc acg aac tcc aac atg ggc ttc tcg ggc gac aag aat gaa ctg atc      3127
Thr Thr Asn Ser Asn Met Gly Phe Ser Gly Asp Lys Asn Glu Leu Ile
    615                 620                 625 att ggt gct gag tcc ttc gtc tcc aat gaa aag atc tac atc gac aag      3175
Ile Gly Ala Glu Ser Phe Val Ser Asn Glu Lys Ile Tyr Ile Asp Lys
630                 635                 640                 645 atc gag ttc atc ccc gtc cag ctg tgataggaac tctgattgaa ttctgcatgc     3229
Ile Glu Phe Ile Pro Val Gln Leu
                650 gtttggacgt atgctcattc aggttggagc caatttggtt gatgtgtgtg cgagttcttg    3289 cgagtctgat gagacatctc tgtattgtgt ttctttcccc agtgttttct gtacttgtgt    3349 aatcggctaa tcgccaacag attcggcgat gaataaatga gaaataaatt gttctgattt    3409 tgagtgcaaa aaaaaggaa ttagatctgt gtgtgttttt tggatccccg gggcggccgc     3469
```

<210> SEQ ID NO 24
<211> LENGTH: 653
<212> TYPE: PRT
<213> ORGANISM: Artificial Sequence
<220> FEATURE:
<221> NAME/KEY: PRT
<222> LOCATION: (1)..(653)
<223> OTHER INFORMATION: Cry3Bb1 variant 11231mv2

<400> SEQUENCE: 24

```
Met Ala Asn Pro Asn Asn Arg Ser Glu His Asp Thr Ile Lys Val Thr
  1               5                  10                  15

Pro Asn Ser Glu Leu Gln Thr Asn His Asn Gln Tyr Pro Leu Ala Asp
                 20                  25                  30

Asn Pro Asn Ser Thr Leu Glu Glu Leu Asn Tyr Lys Glu Phe Leu Arg
             35                  40                  45

Met Thr Glu Asp Ser Ser Thr Glu Val Leu Asp Asn Ser Thr Val Lys
         50                  55                  60

Asp Ala Val Gly Thr Gly Ile Ser Val Val Gly Gln Ile Leu Gly Val
 65                  70                  75                  80

Val Gly Val Pro Phe Ala Gly Ala Leu Thr Ser Phe Tyr Gln Ser Phe
                 85                  90                  95

Leu Asn Thr Ile Trp Pro Ser Asp Ala Asp Pro Trp Lys Ala Phe Met
                100                 105                 110

Ala Gln Val Glu Val Leu Ile Asp Lys Lys Ile Glu Glu Tyr Ala Lys
            115                 120                 125

Ser Lys Ala Leu Ala Glu Leu Gln Gly Leu Gln Asn Asn Phe Glu Asp
        130                 135                 140

Tyr Val Asn Ala Leu Asn Ser Trp Lys Lys Thr Pro Leu Ser Leu Arg
145                 150                 155                 160

Ser Lys Arg Ser Gln Asp Arg Ile Arg Glu Leu Phe Ser Gln Ala Glu
                165                 170                 175

Ser His Phe Arg Asn Ser Met Pro Ser Phe Ala Val Ser Lys Phe Glu
            180                 185                 190

Val Leu Phe Leu Pro Thr Tyr Ala Gln Ala Ala Asn Thr His Leu Leu
        195                 200                 205

Leu Leu Lys Asp Ala Gln Val Phe Gly Glu Glu Trp Gly Tyr Ser Ser
    210                 215                 220

Glu Asp Val Ala Glu Phe Tyr Arg Arg Gln Leu Lys Leu Thr Gln Gln
```

-continued

```
                225                 230                 235                 240
Tyr Thr Asp His Cys Val Asn Trp Tyr Asn Val Gly Leu Asn Gly Leu
                    245                 250                 255
Arg Gly Ser Thr Tyr Asp Ala Trp Val Lys Phe Asn Arg Phe Arg Arg
                260                 265                 270
Glu Met Thr Leu Thr Val Leu Asp Leu Ile Val Leu Phe Pro Phe Tyr
                275                 280                 285
Asp Ile Arg Leu Tyr Ser Lys Gly Val Lys Thr Glu Leu Thr Arg Asp
            290                 295                 300
Ile Phe Thr Asp Pro Ile Phe Leu Leu Thr Thr Leu Gln Lys Tyr Gly
305                 310                 315                 320
Pro Thr Phe Leu Ser Ile Glu Asn Ser Ile Arg Lys Pro His Leu Phe
                325                 330                 335
Asp Tyr Leu Gln Gly Ile Glu Phe His Thr Arg Leu Arg Pro Gly Tyr
            340                 345                 350
Phe Gly Lys Asp Ser Phe Asn Tyr Trp Ser Gly Asn Tyr Val Glu Thr
        355                 360                 365
Arg Pro Ser Ile Gly Ser Ser Lys Thr Ile Thr Ser Pro Phe Tyr Gly
370                 375                 380
Asp Lys Ser Thr Glu Pro Val Gln Lys Leu Ser Phe Asp Gly Gln Lys
385                 390                 395                 400
Val Tyr Arg Thr Ile Ala Asn Thr Asp Val Ala Ala Trp Pro Asn Gly
                405                 410                 415
Lys Val Tyr Leu Gly Val Thr Lys Val Asp Phe Ser Gln Tyr Asp Asp
            420                 425                 430
Gln Lys Asn Glu Thr Ser Thr Gln Thr Tyr Asp Ser Lys Arg Asn Asn
        435                 440                 445
Gly His Val Ser Ala Gln Asp Ser Ile Asp Gln Leu Pro Pro Glu Thr
    450                 455                 460
Thr Asp Glu Pro Leu Glu Lys Ala Tyr Ser His Gln Leu Asn Tyr Ala
465                 470                 475                 480
Glu Cys Phe Leu Met Gln Asp Arg Arg Gly Thr Ile Pro Phe Phe Thr
                485                 490                 495
Trp Thr His Arg Ser Val Asp Phe Phe Asn Thr Ile Asp Ala Glu Lys
            500                 505                 510
Ile Thr Gln Leu Pro Val Val Lys Ala Tyr Ala Leu Ser Ser Gly Ala
        515                 520                 525
Ser Ile Ile Glu Gly Pro Gly Phe Thr Gly Gly Asn Leu Leu Phe Leu
    530                 535                 540
Lys Glu Ser Ser Asn Ser Ile Ala Lys Phe Lys Val Thr Leu Asn Ser
545                 550                 555                 560
Ala Ala Leu Leu Gln Arg Tyr Arg Val Arg Ile Arg Tyr Ala Ser Thr
                565                 570                 575
Thr Asn Leu Arg Leu Phe Val Gln Asn Ser Asn Asn Asp Phe Leu Val
            580                 585                 590
Ile Tyr Ile Asn Lys Thr Met Asn Lys Asp Asp Asp Leu Thr Tyr Gln
        595                 600                 605
Thr Phe Asp Leu Ala Thr Thr Asn Ser Asn Met Gly Phe Ser Gly Asp
    610                 615                 620
Lys Asn Glu Leu Ile Ile Gly Ala Glu Ser Phe Val Ser Asn Glu Lys
625                 630                 635                 640
Ile Tyr Ile Asp Lys Ile Glu Phe Ile Pro Val Gln Leu
                645                 650
```

```
<210> SEQ ID NO 25
<211> LENGTH: 416
<212> TYPE: DNA
<213> ORGANISM: Artificial Sequence
<220> FEATURE:
<223> OTHER INFORMATION: Description of Artificial Sequence: non-
      naturally occurring nucleotide sequence encoding Zea mays ribulose
      bis-phosphate carboxylase chloroplast targeting peptide
<220> FEATURE:
<221> NAME/KEY: CDS
<222> LOCATION: (16)..(162)
<220> FEATURE:
<221> NAME/KEY: CDS
<222> LOCATION: (326)..(415)
<220> FEATURE:
<221> NAME/KEY: intron
<222> LOCATION: (163)..(325)
<223> OTHER INFORMATION: I-Zm.rbcS

<400> SEQUENCE: 25
ttctagagga tcagc atg gcg ccc acc gtg atg atg gcc tcg tcg gcc acc         51
                Met Ala Pro Thr Val Met Met Ala Ser Ser Ala Thr
                  1               5                  10 gcc gtc gct ccg ttc ctg ggg ctc aag tcc acc gcc agc ctc ccc gtc          99
Ala Val Ala Pro Phe Leu Gly Leu Lys Ser Thr Ala Ser Leu Pro Val
         15                  20                  25 gcc cgc cgc tcc tcc aga agc ctc ggc aac gtc agc aac ggc gga agg         147
Ala Arg Arg Ser Ser Arg Ser Leu Gly Asn Val Ser Asn Gly Gly Arg
 30                  35                  40 atc cgg tgc atg cag gtaacaaatg catcctagct agtagttctt tgcattgcag         202
Ile Arg Cys Met Gln
 45 cagctgcagc tagcgagtta gtaataggaa gggaactgat gatccatgca tggactgatg        262 tgtgttgccc atcccatccc atcccatttc ccaaacgaac cgaaaacacc gtactacgtg        322 cag gtg tgg ccc tac ggc aac aag aag ttc gag acg ctg tcg tac ctg         370
    Val Trp Pro Tyr Gly Asn Lys Lys Phe Glu Thr Leu Ser Tyr Leu
         50                  55                  60 ccg ccg ctg tcg acc ggc ggg cgc atc cgc tgc atg cag gcc atg g           416
Pro Pro Leu Ser Thr Gly Gly Arg Ile Arg Cys Met Gln Ala Met
 65                  70                  75

<210> SEQ ID NO 26
<211> LENGTH: 79
<212> TYPE: PRT
<213> ORGANISM: Artificial Sequence
<220> FEATURE:
<221> NAME/KEY: PRT
<222> LOCATION: (1)..(48)
<223> OTHER INFORMATION: full length zea mays transit peptide

<400> SEQUENCE: 26

Met Ala Pro Thr Val Met Met Ala Ser Ser Ala Thr Ala Val Ala Pro
  1               5                  10                  15

Phe Leu Gly Leu Lys Ser Thr Ala Ser Leu Pro Val Ala Arg Arg Ser
                 20                  25                  30

Ser Arg Ser Leu Gly Asn Val Ser Asn Gly Gly Arg Ile Arg Cys Met
             35                  40                  45

Gln Val Trp Pro Tyr Gly Asn Lys Lys Phe Glu Thr Leu Ser Tyr Leu
         50                  55                  60

Pro Pro Leu Ser Thr Gly Gly Arg Ile Arg Cys Met Gln Ala Met
 65                  70                  75
```

<210> SEQ ID NO 27
<211> LENGTH: 49
<212> TYPE: PRT
<213> ORGANISM: Artificial Sequence
<220> FEATURE:
<221> NAME/KEY: PRT
<222> LOCATION: (1)..(49)
<223> OTHER INFORMATION: Zea mays targeting peptide sequence encoded 5'
      of the intronic sequence indicated in SEQID NO:25

<400> SEQUENCE: 27

Met Ala Pro Thr Val Met Met Ala Ser Ser Ala Thr Ala Val Ala Pro
 1               5                  10                  15

Phe Leu Gly Leu Lys Ser Thr Ala Ser Leu Pro Val Ala Arg Arg Ser
                20                  25                  30

Ser Arg Ser Leu Gly Asn Val Ser Asn Gly Gly Arg Ile Arg Cys Met
        35                  40                  45

Gln

<210> SEQ ID NO 28
<211> LENGTH: 30
<212> TYPE: PRT
<213> ORGANISM: Artificial Sequence
<220> FEATURE:
<221> NAME/KEY: PRT
<222> LOCATION: (1)..(30)
<223> OTHER INFORMATION: Zea mays targeting peptide sequence encoded 3'
      of the intronic sequence indicated in SEQID NO:25

<400> SEQUENCE: 28

Val Trp Pro Tyr Gly Asn Lys Lys Phe Glu Thr Leu Ser Tyr Leu Pro
 1               5                  10                  15

Pro Leu Ser Thr Gly Gly Arg Ile Arg Cys Met Gln Ala Met
                20                  25                  30

<210> SEQ ID NO 29
<211> LENGTH: 202
<212> TYPE: DNA
<213> ORGANISM: Cauliflower mosaic virus
<220> FEATURE:
<221> NAME/KEY: PRT
<222> LOCATION: (1)..(30)
<223> OTHER INFORMATION: a cauliflower mosaic virus 35S promoter
      sequence, P-CaMV.35S

<400> SEQUENCE: 29
gacgcacctg acgtaaggga tgacgcacct gacgtaaggg atgacgcacc tgacgtaagg      60
gatgacgcac tcgagatccc catctccact gacgtaaggg atgacgcaca atcccactat     120
ccttcgcaag acccttcctc tatataagga agttcatttc atttggagag gacacgctga     180
caagctagct tggctgcagg ta                                              202

<210> SEQ ID NO 30
<211> LENGTH: 416
<212> TYPE: DNA
<213> ORGANISM: Artificial Sequence
<220> FEATURE:
<223> OTHER INFORMATION: Description of Artificial Sequence: modified
      cauliflower mosaic virus promoter AS4

<400> SEQUENCE: 30
ttctagagga tcagcatggc gcccaccgtg atgatggcct cgtcggccac cgccgtcgct      60
ccgttcctgg ggctcaagtc caccgccagc ctccccgtcg cccgccgctc tccagaagc     120 ctcggcaacg tcagcaacgg cggaaggatc cggtgcatgc aggtaacaaa tgcatcctag    180

```
ctagtagttc tttgcattgc agcagctgca gctagcgagt tagtaatagg aagggaactg    240
atgatccatg catggactga tgtgtgttgc ccatcccatc ccatcccatt tcccaaacga    300
accgaaaaca ccgtactacg tgcaggtgtg gccctacggc aacaagaagt tcgagacgct    360
gtcgtacctg ccgccgctgt cgaccggcgg gcgcatccgc tgcatgcagg ccatgg       416
```

<210> SEQ ID NO 31
<211> LENGTH: 75
<212> TYPE: DNA
<213> ORGANISM: Triticum aestivum

<400> SEQUENCE: 31

```
ctagaaccat cttccacaca ctcaagccac actattggag aacacacagg gacaacacac     60
cataagatcc aaggg                                                      75
```

<210> SEQ ID NO 32
<211> LENGTH: 804
<212> TYPE: DNA
<213> ORGANISM: Oryza sp.

<400> SEQUENCE: 32

```
accgtcttcg gtacgcgctc actccgccct ctgcctttgt tactgccacg tttctctgaa     60
tgctctcttg tgtggtgatt gctgagagtg gtttagctgg atctagaatt acactctgaa    120
atcgtgttct gcctgtgctg attacttgcc gtcctttgta gcagcaaaat atagggacat    180
ggtagtacga aacgaagata gaacctacac agcaatacga gaaatgtgta atttggtgct    240
tagcggtatt tatttaagca catgttggtg ttatagggca cttggattca gaagtttgct    300
gttaatttag gcacaggctt catactacat gggtcaatag tatagggatt catattatag    360
gcgatactat aataatttgt tcgtctgcag agcttattat ttgccaaaat tagatattcc    420
tattctgttt tgtttgtgt gctgttaaat tgttaacgcc tgaaggaata aatataaatg     480
acgaaatttt gatgtttatc tctgctcctt tattgtgacc ataagtcaag atcagatgca    540
cttgttttaa atattgttgt ctgaagaaat aagtactgac agtattttga tgcattgatc    600
tgcttgtttg ttgtaacaaa atttaaaaat aaagagtttc cttttttgttg ctctccttac    660 ctcctgatgg tatctagtat ctaccaactg acactatatt gcttctcttt acatacgtat    720
cttgctcgat gccttctccc tagtgttgac cagtgttact cacatagtct ttgctcattt    780
cattgtaatg cagataccaa gcgg                                            804
```

<210> SEQ ID NO 33
<211> LENGTH: 804
<212> TYPE: DNA
<213> ORGANISM: Zea mays

<400> SEQUENCE: 33

```
accgtcttcg gtacgcgctc actccgccct ctgcctttgt tactgccacg tttctctgaa     60
tgctctcttg tgtggtgatt gctgagagtg gtttagctgg atctagaatt acactctgaa    120
atcgtgttct gcctgtgctg attacttgcc gtcctttgta gcagcaaaat atagggacat    180
ggtagtacga aacgaagata gaacctacac agcaatacga gaaatgtgta atttggtgct    240
tagcggtatt tatttaagca catgttggtg ttatagggca cttggattca gaagtttgct    300
gttaatttag gcacaggctt catactacat gggtcaatag tatagggatt catattatag    360
gcgatactat aataatttgt tcgtctgcag agcttattat ttgccaaaat tagatattcc    420
```

```
tattctgttt ttgtttgtgt gctgttaaat tgttaacgcc tgaaggaata aatataaatg    480
acgaaatttt gatgtttatc tctgctcctt tattgtgacc ataagtcaag atcagatgca    540
cttgttttaa atattgttgt ctgaagaaat aagtactgac agtatttga tgcattgatc     600 tgcttgtttg ttgtaacaaa atttaaaaat aaagagtttc ctttttgttg ctctccttac    660
ctcctgatgg tatctagtat ctaccaactg acactatatt gcttctcttt acatacgtat    720
cttgctcgat gccttctccc tagtgttgac cagtgttact cacatagtct ttgctcattt    780
cattgtaatg cagataccaa gcgg                                            804

<210> SEQ ID NO 34
<211> LENGTH: 257
<212> TYPE: DNA
<213> ORGANISM: Agrobacterium tumefaciens

<400> SEQUENCE: 34
tcccgatcgt tcaaacattt ggcaataaag tttcttaaga ttgaatcctg ttgccggtct     60
tgcgatgatt atcatataat ttctgttgaa ttacgttaag catgtaataa ttaacatgta    120
atgcatgacg ttatttatga gatgggtttt tatgattaga gtcccgcaat tatacattta    180
atacgcgata gaaaacaaaa tatagcgcgc aaactaggat aaattatcgc gcgcggtgtc    240
atctatgtta ctagatc                                                    257

<210> SEQ ID NO 35
<211> LENGTH: 234
<212> TYPE: DNA
<213> ORGANISM: Triticum aestivum

<400> SEQUENCE: 35
aattctgcat gcgtttggac gtatgctcat tcaggttgga gccaatttgg ttgatgtgtg     60
tgcgagttct tgcgagtctg atgagacatc tctgtattgt gtttctttcc ccagtgtttt    120
ctgtacttgt gtaatcggct aatcgccaac agattcggcg atgaataaat gagaaataaa    180
ttgttctgat tttgagtgca aaaaaaagg aattagatct gtgtgtgttt tttg           234

<210> SEQ ID NO 36
<211> LENGTH: 3455
<212> TYPE: DNA
<213> ORGANISM: Artificial Sequence
<220> FEATURE:
<223> OTHER INFORMATION: Description of Artificial Sequence: expression
      cassette
<220> FEATURE:
<221> NAME/KEY: promoter
<222> LOCATION: (14)..(235)
<223> OTHER INFORMATION: P.CaMV.AS4
<220> FEATURE:
<221> NAME/KEY: 5'UTR
<222> LOCATION: (240)..(304)
<223> OTHER INFORMATION: L-Ta.hcb1
<220> FEATURE:
<221> NAME/KEY: intron
<222> LOCATION: (318)..(805)
<223> OTHER INFORMATION: I-Os.Act1
<220> FEATURE:
<221> NAME/KEY: transit_peptide
<222> LOCATION: (825)..(971)
<223> OTHER INFORMATION: TS-Zm.rbcS amino terminal coding sequence
      upstream of Zea mays rbcS intron
<220> FEATURE:
<221> NAME/KEY: intron
<222> LOCATION: (972)..(1134)
<223> OTHER INFORMATION: I-Zm.rbcS
<220> FEATURE:
<221> NAME/KEY: transit_peptide
```

```
<222> LOCATION: (1135)..(1221)
<223> OTHER INFORMATION: TS-Zm.rbcS carboxy terminus coding sequence
      downstream of Zea mays rbcS intron
<220> FEATURE:
<221> NAME/KEY: CDS
<222> LOCATION: (1222)..(3180)
<223> OTHER INFORMATION: variant Cry3BB1 coding sequence encoding v11231
<220> FEATURE:
<221> NAME/KEY: terminator
<222> LOCATION: (3198)..(3431)
<223> OTHER INFORMATION: T-Ta.hsp17

<400> SEQUENCE: 36
```

| | |
|---|---|
| gcggccgcgt taacaagctt ctgacgtaag ggatgacgca cctgacgtaa gggatgacgc | 60 |
| acctgacgta agggatgacg cacctgacgt aagggatgac gcactcgaga tccccatctc | 120 |
| cactgacgta agggatgacg cacaatccca ctatccttcg caagacccct cctctatata | 180 |
| aggaagttca tttcatttgg agaggacacg ctgacaagct agcttggctg caggtagatc | 240 |
| ctagaaccat cttccacaca ctcaagccac actattggag aacacacagg acaacacac | 300 |
| cataagatcc aagggaggcc tccgccgccg ccggtaacca ccccgcccct ctcctctttc | 360 |
| tttctccgtt tttttttccg tctcggtctc gatctttggc cttggtagtt tgggtgggcg | 420 |
| agaggcggct tcgtgcgcgc ccagatcggt gcgcgggagg ggcgggatct cgcggctggg | 480 |
| gctctcgccg gcgtggatcc ggcccggatc tcgcggggaa tggggctctc ggatgtagat | 540 |
| ctgcgatccg ccgttgttgg gggagatgat gggggggttta aaatttccgc cgtgctaaac | 600 |
| aagatcagga agaggggaaa agggcactat ggtttatatt tttatatatt tctgctgctt | 660 |
| cgtcaggctt agatgtgcta gatctttctt tcttcttttt gtgggtagaa tttgaatccc | 720 |
| tcagcattgt tcatcggtag tttttctttt catgatttgt gacaaatgca gcctcgtgcg | 780 |
| gagcttttt gtaggtagaa gtgatcaacc tctagaggat cagcatggcg cccaccgtga | 840 |
| tgatggcctc gtcggccacc gccgtcgctc cgttcctggg gctcaagtcc accgccagcc | 900 |
| tccccgtcgc ccgccgctcc tccagaagcc tcggcaacgt cagcaacggc ggaaggatcc | 960 |
| ggtgcatgca ggtaacaaat gcatcctagc tagtagttct ttgcattgca gcagctgcag | 1020 |
| ctagcgagtt agtaatagga agggaactga tgatccatgc atggactgat gtgtgttgcc | 1080 |
| catcccatcc catcccattt cccaaacgaa ccgaaaacac cgtactacgt gcaggtgtgg | 1140 |
| ccctacggca acaagaagtt cgagacgctg tcgtacctgc cgccgctgtc gaccggcggg | 1200 |
| cgcatccgct gcatgcaggc c atg gca aac cct aac aat cgt tcc gaa cac | 1251 |
|                                      Met Ala Asn Pro Asn Asn Arg Ser Glu His<br>                                       1             5                   10 | |
| gac acc atc aag gtt act cca aac tct gag ttg caa act aat cac aac<br>Asp Thr Ile Lys Val Thr Pro Asn Ser Glu Leu Gln Thr Asn His Asn<br>               15                     20                    25 | 1299 |
| cag tac cca ttg gct gac aat cct aac agt act ctt gag gaa ctt aac<br>Gln Tyr Pro Leu Ala Asp Asn Pro Asn Ser Thr Leu Glu Glu Leu Asn<br>        30                         35                       40 | 1347 |
| tac aag gag ttt ctc cgg atg acc gaa gat agc tcc act gag gtt ctc<br>Tyr Lys Glu Phe Leu Arg Met Thr Glu Asp Ser Ser Thr Glu Val Leu<br>        45                         50                       55 | 1395 |
| gat aac tct aca gtg aag gac gct gtt gga act ggc att agc gtt gtg<br>Asp Asn Ser Thr Val Lys Asp Ala Val Gly Thr Gly Ile Ser Val Val<br>       60                         65                     70 | 1443 |
| gga cag att ctt gga gtg gtt ggt gtt cca ttc gct gga gct ttg acc<br>Gly Gln Ile Leu Gly Val Val Gly Val Pro Phe Ala Gly Ala Leu Thr<br>75                     80                       85                     90 | 1491 |
| agc ttc tac cag tcc ttt ctc aac acc atc tgg cct tca gat gct gat | 1539 |

```
                  Ser Phe Tyr Gln Ser Phe Leu Asn Thr Ile Trp Pro Ser Asp Ala Asp
                                   95                 100                 105 ccc tgg aag gct ttc atg gcc caa gtg gaa gtc ttg atc gat aag aag                1587
Pro Trp Lys Ala Phe Met Ala Gln Val Glu Val Leu Ile Asp Lys Lys
            110                 115                 120 atc gaa gag tat gcc aag tct aaa gcc ttg gct gag ttg caa ggt ttg                1635
Ile Glu Glu Tyr Ala Lys Ser Lys Ala Leu Ala Glu Leu Gln Gly Leu
        125                 130                 135 cag aac aac ttc gag gat tac gtc aac gca ctc aac agc tgg aag aaa                1683
Gln Asn Asn Phe Glu Asp Tyr Val Asn Ala Leu Asn Ser Trp Lys Lys
    140                 145                 150 act ccc ttg agt ctc agg tct aag cgt tcc cag gac cgt att cgt gaa                1731
Thr Pro Leu Ser Leu Arg Ser Lys Arg Ser Gln Asp Arg Ile Arg Glu
155                 160                 165                 170 ctt ttc agc caa gcc gaa tcc cac ttc aga aac tcc atg cct agc ttt                1779
Leu Phe Ser Gln Ala Glu Ser His Phe Arg Asn Ser Met Pro Ser Phe
                175                 180                 185 gcc gtt tct aag ttc gag gtg ctc ttc ttg cca aca tac gca caa gct                1827
Ala Val Ser Lys Phe Glu Val Leu Phe Leu Pro Thr Tyr Ala Gln Ala
            190                 195                 200 gcc aac act cat ctc ttg ctt ctc aaa gac gct cag gtg ttt ggt gag                1875
Ala Asn Thr His Leu Leu Leu Leu Lys Asp Ala Gln Val Phe Gly Glu
        205                 210                 215 gaa tgg ggt tac tcc agt gaa gat gtt gcc gag ttc tac cgt agg cag                1923
Glu Trp Gly Tyr Ser Ser Glu Asp Val Ala Glu Phe Tyr Arg Arg Gln
    220                 225                 230 ctc aag ttg act caa cag tac aca gac cac tgc gtc aac tgg tac aac                1971
Leu Lys Leu Thr Gln Gln Tyr Thr Asp His Cys Val Asn Trp Tyr Asn
235                 240                 245                 250 gtt ggg ctc aat ggt ctt aga gga tct acc tac gac gca tgg gtg aag                2019
Val Gly Leu Asn Gly Leu Arg Gly Ser Thr Tyr Asp Ala Trp Val Lys
                255                 260                 265 ttc aac agg ttt cgt aga gag atg acc ttg act gtg ctc gat ctt atc                2067
Phe Asn Arg Phe Arg Arg Glu Met Thr Leu Thr Val Leu Asp Leu Ile
            270                 275                 280 gtt ctc ttt cca ttc tac gac att cgt ctt tac tcc aaa ggc gtt aag                2115
Val Leu Phe Pro Phe Tyr Asp Ile Arg Leu Tyr Ser Lys Gly Val Lys
        285                 290                 295 aca gag ctg acc aga gac atc ttc acc gat ccc atc ttc cta ctt acg                2163
Thr Glu Leu Thr Arg Asp Ile Phe Thr Asp Pro Ile Phe Leu Leu Thr
    300                 305                 310 acc ctg cag aaa tac ggt cca act ttt ctc tcc att gag aac agc atc                2211
Thr Leu Gln Lys Tyr Gly Pro Thr Phe Leu Ser Ile Glu Asn Ser Ile
315                 320                 325                 330 agg aag cct cac ctc ttc gac tat ctg caa ggc att gag ttt cac acc                2259
Arg Lys Pro His Leu Phe Asp Tyr Leu Gln Gly Ile Glu Phe His Thr
                335                 340                 345 agg ttg caa cct ggt tac ttc ggt aag gat tcc ttc aac tac tgg agc                2307
Arg Leu Gln Pro Gly Tyr Phe Gly Lys Asp Ser Phe Asn Tyr Trp Ser
            350                 355                 360 gga aac tac gtt gaa acc aga cca tcc atc gga tct agc aag acc atc                2355
Gly Asn Tyr Val Glu Thr Arg Pro Ser Ile Gly Ser Ser Lys Thr Ile
        365                 370                 375 act tct cca ttc tac ggt gac aag agc act gag cca gtg cag aag ttg                2403
Thr Ser Pro Phe Tyr Gly Asp Lys Ser Thr Glu Pro Val Gln Lys Leu
    380                 385                 390 agc ttc gat ggg cag aag gtg tat aga acc atc gcc aat acc gat gtt                2451
Ser Phe Asp Gly Gln Lys Val Tyr Arg Thr Ile Ala Asn Thr Asp Val
395                 400                 405                 410
```

```
gca gct tgg cct aat ggc aag gtc tac ctt gga gtt act aaa gtg gac     2499
Ala Ala Trp Pro Asn Gly Lys Val Tyr Leu Gly Val Thr Lys Val Asp
            415                 420                 425 ttc tcc caa tac gac gat cag aag aac gag aca tct act caa acc tac     2547
Phe Ser Gln Tyr Asp Asp Gln Lys Asn Glu Thr Ser Thr Gln Thr Tyr
        430                 435                 440 gat agt aag agg aac aat ggc cat gtt tcc gca caa gac tcc att gac     2595
Asp Ser Lys Arg Asn Asn Gly His Val Ser Ala Gln Asp Ser Ile Asp
    445                 450                 455 caa ctt cca cct gaa acc act gat gaa cca ttg gag aag gct tac agt     2643
Gln Leu Pro Pro Glu Thr Thr Asp Glu Pro Leu Glu Lys Ala Tyr Ser
460                 465                 470 cac caa ctt aac tac gcc gaa tgc ttt ctc atg caa gac agg cgt ggc     2691
His Gln Leu Asn Tyr Ala Glu Cys Phe Leu Met Gln Asp Arg Arg Gly
475                 480                 485                 490 acc att ccg ttc ttt aca tgg act cac agg tct gtc gac ttc ttt aac     2739
Thr Ile Pro Phe Phe Thr Trp Thr His Arg Ser Val Asp Phe Phe Asn
                495                 500                 505 act atc gac gct gag aag att acc caa ctt ccc gtg gtc aag gct tat     2787
Thr Ile Asp Ala Glu Lys Ile Thr Gln Leu Pro Val Val Lys Ala Tyr
            510                 515                 520 gcc ttg tcc agc gga gct tcc atc att gaa ggt cca ggc ttc acc ggt     2835
Ala Leu Ser Ser Gly Ala Ser Ile Ile Glu Gly Pro Gly Phe Thr Gly
        525                 530                 535 ggc aac ttg ctc ttc ctt aag gag tcc agc aac tcc atc gcc aag ttc     2883
Gly Asn Leu Leu Phe Leu Lys Glu Ser Ser Asn Ser Ile Ala Lys Phe
    540                 545                 550 aaa gtg aca ctt aac tca gca gcc ttg ctc caa cgt tac agg gtt cgt     2931
Lys Val Thr Leu Asn Ser Ala Ala Leu Leu Gln Arg Tyr Arg Val Arg
555                 560                 565                 570 atc aga tac gca agc act acc aat ctt cgc ctc ttt gtc cag aac agc     2979
Ile Arg Tyr Ala Ser Thr Thr Asn Leu Arg Leu Phe Val Gln Asn Ser
                575                 580                 585 aac aat gat ttc ctt gtc atc tac atc aac aag act atg aac aaa gac     3027
Asn Asn Asp Phe Leu Val Ile Tyr Ile Asn Lys Thr Met Asn Lys Asp
            590                 595                 600 gat gac ctc acc tac caa aca ttc gat ctt gcc act acc aat agt aac     3075
Asp Asp Leu Thr Tyr Gln Thr Phe Asp Leu Ala Thr Thr Asn Ser Asn
        605                 610                 615 atg gga ttc tct ggt gac aag aac gag ctg atc ata ggt gct gag agc     3123
Met Gly Phe Ser Gly Asp Lys Asn Glu Leu Ile Ile Gly Ala Glu Ser
    620                 625                 630 ttt gtc tct aat gag aag att tac ata gac aag atc gag ttc att cca     3171
Phe Val Ser Asn Glu Lys Ile Tyr Ile Asp Lys Ile Glu Phe Ile Pro
635                 640                 645                 650 gtt caa ctc taatagatcc cccgggctgc aggaattctg catgcgtttg             3220
Val Gln Leu gacgtatgct cattcaggtt ggagccaatt tggttgatgt gtgtgcgagt tcttgcgagt   3280
ctgatgagac atctctgtat tgtgtttctt tccccagtgt tttctgtact tgtgtaatcg   3340
gctaatcgcc aacagattcg gcgatgaata aatgagaaat aaattgttct gattttgagt   3400
gcaaaaaaaa aggaattaga tctgtgtgtg ttttttggat ccccggggcg gccgc         3455

<210> SEQ ID NO 37
<211> LENGTH: 653
<212> TYPE: PRT
<213> ORGANISM: Artificial Sequence
<220> FEATURE:
<221> NAME/KEY: PRT
<222> LOCATION: (1)..(653)
```

-continued

<223> OTHER INFORMATION: variant Cry3BB1 coding sequence encoding v11231

<400> SEQUENCE: 37

```
Met Ala Asn Pro Asn Asn Arg Ser Glu His Asp Thr Ile Lys Val Thr
  1               5                  10                  15

Pro Asn Ser Glu Leu Gln Thr Asn His Asn Gln Tyr Pro Leu Ala Asp
             20                  25                  30

Asn Pro Asn Ser Thr Leu Glu Glu Leu Asn Tyr Lys Glu Phe Leu Arg
         35                  40                  45

Met Thr Glu Asp Ser Ser Thr Glu Val Leu Asp Asn Ser Thr Val Lys
     50                  55                  60

Asp Ala Val Gly Thr Gly Ile Ser Val Val Gly Gln Ile Leu Gly Val
 65                  70                  75                  80

Val Gly Val Pro Phe Ala Gly Ala Leu Thr Ser Phe Tyr Gln Ser Phe
                 85                  90                  95

Leu Asn Thr Ile Trp Pro Ser Asp Ala Asp Pro Trp Lys Ala Phe Met
            100                 105                 110

Ala Gln Val Glu Val Leu Ile Asp Lys Lys Ile Glu Glu Tyr Ala Lys
        115                 120                 125

Ser Lys Ala Leu Ala Glu Leu Gln Gly Leu Gln Asn Asn Phe Glu Asp
    130                 135                 140

Tyr Val Asn Ala Leu Asn Ser Trp Lys Lys Thr Pro Leu Ser Leu Arg
145                 150                 155                 160

Ser Lys Arg Ser Gln Asp Arg Ile Arg Glu Leu Phe Ser Gln Ala Glu
                165                 170                 175

Ser His Phe Arg Asn Ser Met Pro Ser Phe Ala Val Ser Lys Phe Glu
            180                 185                 190

Val Leu Phe Leu Pro Thr Tyr Ala Gln Ala Ala Asn Thr His Leu Leu
        195                 200                 205

Leu Leu Lys Asp Ala Gln Val Phe Gly Glu Glu Trp Gly Tyr Ser Ser
    210                 215                 220

Glu Asp Val Ala Glu Phe Tyr Arg Arg Gln Leu Lys Leu Thr Gln Gln
225                 230                 235                 240

Tyr Thr Asp His Cys Val Asn Trp Tyr Asn Val Gly Leu Asn Gly Leu
                245                 250                 255

Arg Gly Ser Thr Tyr Asp Ala Trp Val Lys Phe Asn Arg Phe Arg Arg
            260                 265                 270

Glu Met Thr Leu Thr Val Leu Asp Leu Ile Val Leu Phe Pro Phe Tyr
        275                 280                 285

Asp Ile Arg Leu Tyr Ser Lys Gly Val Lys Thr Glu Leu Thr Arg Asp
    290                 295                 300

Ile Phe Thr Asp Pro Ile Phe Leu Leu Thr Thr Leu Gln Lys Tyr Gly
305                 310                 315                 320

Pro Thr Phe Leu Ser Ile Glu Asn Ser Ile Arg Lys Pro His Leu Phe
                325                 330                 335

Asp Tyr Leu Gln Gly Ile Glu Phe His Thr Arg Leu Gln Pro Gly Tyr
            340                 345                 350

Phe Gly Lys Asp Ser Phe Asn Tyr Trp Ser Gly Asn Tyr Val Glu Thr
        355                 360                 365

Arg Pro Ser Ile Gly Ser Ser Lys Thr Ile Thr Ser Pro Phe Tyr Gly
    370                 375                 380

Asp Lys Ser Thr Glu Pro Val Gln Lys Leu Ser Phe Asp Gly Gln Lys
385                 390                 395                 400

```
Val Tyr Arg Thr Ile Ala Asn Thr Asp Val Ala Ala Trp Pro Asn Gly
            405                 410                 415

Lys Val Tyr Leu Gly Val Thr Lys Val Asp Phe Ser Gln Tyr Asp Asp
        420                 425                 430

Gln Lys Asn Glu Thr Ser Thr Gln Thr Tyr Asp Ser Lys Arg Asn Asn
            435                 440                 445

Gly His Val Ser Ala Gln Asp Ser Ile Asp Gln Leu Pro Pro Glu Thr
        450                 455                 460

Thr Asp Glu Pro Leu Glu Lys Ala Tyr Ser His Gln Leu Asn Tyr Ala
465                 470                 475                 480

Glu Cys Phe Leu Met Gln Asp Arg Arg Gly Thr Ile Pro Phe Phe Thr
                485                 490                 495

Trp Thr His Arg Ser Val Asp Phe Phe Asn Thr Ile Asp Ala Glu Lys
                500                 505                 510

Ile Thr Gln Leu Pro Val Val Lys Ala Tyr Ala Leu Ser Ser Gly Ala
            515                 520                 525

Ser Ile Ile Glu Gly Pro Gly Phe Thr Gly Gly Asn Leu Leu Phe Leu
        530                 535                 540

Lys Glu Ser Ser Asn Ser Ile Ala Lys Phe Lys Val Thr Leu Asn Ser
545                 550                 555                 560

Ala Ala Leu Leu Gln Arg Tyr Arg Val Arg Ile Arg Tyr Ala Ser Thr
                565                 570                 575

Thr Asn Leu Arg Leu Phe Val Gln Asn Ser Asn Asn Asp Phe Leu Val
                580                 585                 590

Ile Tyr Ile Asn Lys Thr Met Asn Lys Asp Asp Asp Leu Thr Tyr Gln
            595                 600                 605

Thr Phe Asp Leu Ala Thr Thr Asn Ser Asn Met Gly Phe Ser Gly Asp
        610                 615                 620

Lys Asn Glu Leu Ile Ile Gly Ala Glu Ser Phe Val Ser Asn Glu Lys
625                 630                 635                 640

Ile Tyr Ile Asp Lys Ile Glu Phe Ile Pro Val Gln Leu
            645                 650

<210> SEQ ID NO 38
<211> LENGTH: 3044
<212> TYPE: DNA
<213> ORGANISM: Artificial Sequence
<220> FEATURE:
<223> OTHER INFORMATION: Description of Artificial Sequence: expression
      cassette
<220> FEATURE:
<221> NAME/KEY: promoter
<222> LOCATION: (14)..(235)
<223> OTHER INFORMATION: P-CaMV.AS4
<220> FEATURE:
<221> NAME/KEY: 5'UTR
<222> LOCATION: (240)..(304)
<223> OTHER INFORMATION: L-Ta.hcb1
<220> FEATURE:
<221> NAME/KEY: intron
<222> LOCATION: (318)..(805)
<223> OTHER INFORMATION: I-Os.Act1
<220> FEATURE:
<221> NAME/KEY: CDS
<222> LOCATION: (811)..(2769)
<223> OTHER INFORMATION: variant Cry3Bb1 coding sequence encoding v11231
<220> FEATURE:
<221> NAME/KEY: terminator
<222> LOCATION: (2792)..(3025)
<223> OTHER INFORMATION: T-Ta.hsp17

<400> SEQUENCE: 38
```

```
gcggccgcgt taacaagctt ctgacgtaag ggatgacgca cctgacgtaa gggatgacgc      60
acctgacgta agggatgacg cacctgacgt aagggatgac gcactcgaga tccccatctc     120
cactgacgta agggatgacg cacaatccca ctatccttcg caagaccctt cctctatata     180
aggaagttca tttcatttgg agaggacacg ctgacaagct agcttggctg caggtagatc     240
ctagaaccat cttccacaca ctcaagccac actattggag aacacacagg acaacacac      300 cataagatcc aagggaggcc tccgccgccg ccggtaacca ccccgcccct ctcctctttc     360
tttctccgtt ttttttttccg tctcggtctc gatctttggc cttggtagtt tgggtgggcg     420
agaggcggct tcgtgcgcgc ccagatcggt gcgcggagg ggcgggatct cgcggctggg      480
gctctcgccg cgtggatcc ggcccggatc tcgcggggaa tggggctctc ggatgtagat     540
ctgcgatccg ccgttgttgg gggagatgat ggggggttta aaatttccgc cgtgctaaac    600
aagatcagga agaggggaaa agggcactat ggtttatatt tttatatatt tctgctgctt    660
cgtcaggctt agatgtgcta gatctttctt tcttcttttt gtgggtagaa tttgaatccc    720
tcagcattgt tcatcggtag tttttctttt catgatttgt gacaaatgca gcctcgtgcg    780 gagcttttt gtaggtagaa gtgatcaacc atg gca aac cct aac aat cgt tcc      834
                                  Met Ala Asn Pro Asn Asn Arg Ser
                                   1               5 gaa cac gac acc atc aag gtt act cca aac tct gag ttg caa act aat      882
Glu His Asp Thr Ile Lys Val Thr Pro Asn Ser Glu Leu Gln Thr Asn
         10                  15                  20 cac aac cag tac cca ttg gct gac aat cct aac agt act ctt gag gaa      930
His Asn Gln Tyr Pro Leu Ala Asp Asn Pro Asn Ser Thr Leu Glu Glu
 25                  30                  35                  40 ctt aac tac aag gag ttt ctc cgg atg acc gaa gat agc tcc act gag      978
Leu Asn Tyr Lys Glu Phe Leu Arg Met Thr Glu Asp Ser Ser Thr Glu
             45                  50                  55 gtt ctc gat aac tct aca gtg aag gac gct gtt gga act ggc att agc     1026
Val Leu Asp Asn Ser Thr Val Lys Asp Ala Val Gly Thr Gly Ile Ser
         60                  65                  70 gtt gtg gga cag att ctt gga gtg gtt ggt gtt cca ttc gct gga gct     1074
Val Val Gly Gln Ile Leu Gly Val Val Gly Val Pro Phe Ala Gly Ala
 75                  80                  85 ttg acc agc ttc tac cag tcc ttt ctc aac acc atc tgg cct tca gat     1122
Leu Thr Ser Phe Tyr Gln Ser Phe Leu Asn Thr Ile Trp Pro Ser Asp
             90                  95                 100 gct gat ccc tgg aag gct ttc atg gcc caa gtg gaa gtc ttg atc gat     1170
Ala Asp Pro Trp Lys Ala Phe Met Ala Gln Val Glu Val Leu Ile Asp
105                 110                 115                 120 aag aag atc gaa gag tat gcc aag tct aaa gcc ttg gct gag ttg caa     1218
Lys Lys Ile Glu Glu Tyr Ala Lys Ser Lys Ala Leu Ala Glu Leu Gln
                125                 130                 135 ggt ttg cag aac aac ttc gag gat tac gtc aac gca ctc aac agc tgg     1266
Gly Leu Gln Asn Asn Phe Glu Asp Tyr Val Asn Ala Leu Asn Ser Trp
            140                 145                 150 aag aaa act ccc ttg agt ctc agg tct aag cgt tcc cag gac cgt att     1314
Lys Lys Thr Pro Leu Ser Leu Arg Ser Lys Arg Ser Gln Asp Arg Ile
155                 160                 165 cgt gaa ctt ttc agc caa gcc gaa tcc cac ttc aga aac tcc atg cct     1362
Arg Glu Leu Phe Ser Gln Ala Glu Ser His Phe Arg Asn Ser Met Pro
        170                 175                 180 agc ttt gcc gtt tct aag ttc gag gtg ctc ttc ttg cca aca tac gca     1410
Ser Phe Ala Val Ser Lys Phe Glu Val Leu Phe Leu Pro Thr Tyr Ala
185                 190                 195                 200 caa gct gcc aac act cat ctc ttg ctt ctc aaa gac gct cag gtg ttt     1458
```

```
                                         -continued

Gln Ala Ala Asn Thr His Leu Leu Leu Lys Asp Ala Gln Val Phe
                205                 210                 215 ggt gag gaa tgg ggt tac tcc agt gaa gat gtt gcc gag ttc tac cgt       1506
Gly Glu Glu Trp Gly Tyr Ser Ser Glu Asp Val Ala Glu Phe Tyr Arg
                220                 225                 230 agg cag ctc aag ttg act caa cag tac aca gac cac tgc gtc aac tgg       1554
Arg Gln Leu Lys Leu Thr Gln Gln Tyr Thr Asp His Cys Val Asn Trp
                235                 240                 245 tac aac gtt ggg ctc aat ggt ctt aga gga tct acc tac gac gca tgg       1602
Tyr Asn Val Gly Leu Asn Gly Leu Arg Gly Ser Thr Tyr Asp Ala Trp
                250                 255                 260 gtg aag ttc aac agg ttt cgt aga gag atg acc ttg act gtg ctc gat       1650
Val Lys Phe Asn Arg Phe Arg Arg Glu Met Thr Leu Thr Val Leu Asp
265                 270                 275                 280 ctt atc gtt ctc ttt cca ttc tac gac att cgt ctt tac tcc aaa ggc       1698
Leu Ile Val Leu Phe Pro Phe Tyr Asp Ile Arg Leu Tyr Ser Lys Gly
                285                 290                 295 gtt aag aca gag ctg acc aga gac atc ttc acc gat ccc atc ttc cta       1746
Val Lys Thr Glu Leu Thr Arg Asp Ile Phe Thr Asp Pro Ile Phe Leu
                300                 305                 310 ctt acg acc ctg cag aaa tac ggt cca act ttt ctc tcc att gag aac       1794
Leu Thr Thr Leu Gln Lys Tyr Gly Pro Thr Phe Leu Ser Ile Glu Asn
                315                 320                 325 agc atc agg aag cct cac ctc ttc gac tat ctg caa ggc att gag ttt       1842
Ser Ile Arg Lys Pro His Leu Phe Asp Tyr Leu Gln Gly Ile Glu Phe
                330                 335                 340 cac acc agg ttg caa cct ggt tac ttc ggt aag gat tcc ttc aac tac       1890
His Thr Arg Leu Gln Pro Gly Tyr Phe Gly Lys Asp Ser Phe Asn Tyr
345                 350                 355                 360 tgg agc gga aac tac gtt gaa acc aga cca tcc atc gga tct agc aag       1938
Trp Ser Gly Asn Tyr Val Glu Thr Arg Pro Ser Ile Gly Ser Ser Lys
                365                 370                 375 acc atc act tct cca ttc tac ggt gac aag agc act gag cca gtg cag       1986
Thr Ile Thr Ser Pro Phe Tyr Gly Asp Lys Ser Thr Glu Pro Val Gln
                380                 385                 390 aag ttg agc ttc gat ggg cag aag gtg tat aga acc atc gcc aat acc       2034
Lys Leu Ser Phe Asp Gly Gln Lys Val Tyr Arg Thr Ile Ala Asn Thr
                395                 400                 405 gat gtt gca gct tgg cct aat ggc aag gtc tac ctt gga gtt act aaa       2082
Asp Val Ala Ala Trp Pro Asn Gly Lys Val Tyr Leu Gly Val Thr Lys
                410                 415                 420 gtg gac ttc tcc caa tac gac gat cag aag aac gag aca tct act caa       2130
Val Asp Phe Ser Gln Tyr Asp Asp Gln Lys Asn Glu Thr Ser Thr Gln
425                 430                 435                 440 acc tac gat agt aag agg aac aat ggc cat gtt tcc gca caa gac tcc       2178
Thr Tyr Asp Ser Lys Arg Asn Asn Gly His Val Ser Ala Gln Asp Ser
                445                 450                 455 att gac caa ctt cca cct gaa acc act gat gaa cca ttg gag aag gct       2226
Ile Asp Gln Leu Pro Pro Glu Thr Thr Asp Glu Pro Leu Glu Lys Ala
                460                 465                 470 tac agt cac caa ctt aac tac gcc gaa tgc ttt ctc atg caa gac agg       2274
Tyr Ser His Gln Leu Asn Tyr Ala Glu Cys Phe Leu Met Gln Asp Arg
                475                 480                 485 cgt ggc acc att ccg ttc ttt aca tgg act cac agg tct gtc gac ttc       2322
Arg Gly Thr Ile Pro Phe Phe Thr Trp Thr His Arg Ser Val Asp Phe
                490                 495                 500 ttt aac act atc gac gct gag aag att acc caa ctt ccc gtg gtc aag       2370
Phe Asn Thr Ile Asp Ala Glu Lys Ile Thr Gln Leu Pro Val Val Lys
505                 510                 515                 520
```

-continued

```
gct tat gcc ttg tcc agc gga gct tcc atc att gaa ggt cca ggc ttc     2418
Ala Tyr Ala Leu Ser Ser Gly Ala Ser Ile Ile Glu Gly Pro Gly Phe
                525                 530                 535 acc ggt ggc aac ttg ctc ttc ctt aag gag tcc agc aac tcc atc gcc     2466
Thr Gly Gly Asn Leu Leu Phe Leu Lys Glu Ser Ser Asn Ser Ile Ala
            540                 545                 550 aag ttc aaa gtg aca ctt aac tca gca gcc ttg ctc caa cgt tac agg     2514
Lys Phe Lys Val Thr Leu Asn Ser Ala Ala Leu Leu Gln Arg Tyr Arg
        555                 560                 565 gtt cgt atc aga tac gca agc act acc aat ctt cgc ctc ttt gtc cag     2562
Val Arg Ile Arg Tyr Ala Ser Thr Thr Asn Leu Arg Leu Phe Val Gln
    570                 575                 580 aac agc aac aat gat ttc ctt gtc atc tac atc aac aag act atg aac     2610
Asn Ser Asn Asn Asp Phe Leu Val Ile Tyr Ile Asn Lys Thr Met Asn
585                 590                 595                 600 aaa gac gat gac ctc acc tac caa aca ttc gat ctt gcc act acc aat     2658
Lys Asp Asp Asp Leu Thr Tyr Gln Thr Phe Asp Leu Ala Thr Thr Asn
                605                 610                 615 agt aac atg gga ttc tct ggt gac aag aac gag ctg atc ata ggt gct     2706
Ser Asn Met Gly Phe Ser Gly Asp Lys Asn Glu Leu Ile Ile Gly Ala
            620                 625                 630 gag agc ttt gtc tct aat gag aag att tac ata gac aag atc gag ttc     2754
Glu Ser Phe Val Ser Asn Glu Lys Ile Tyr Ile Asp Lys Ile Glu Phe
        635                 640                 645 att cca gtt caa ctc taatagatcc cccgggctgc aggaattctg catgcgtttg     2809
Ile Pro Val Gln Leu
    650 gacgtatgct cattcaggtt ggagccaatt tggttgatgt gtgtgcgagt tcttgcgagt   2869 ctgatgagac atctctgtat tgtgtttctt tccccagtgt tttctgtact tgtgtaatcg   2929 gctaatcgcc aacagattcg gcgatgaata aatgagaaat aaattgttct gattttgagt   2989 gcaaaaaaaa aggaattaga tctgtgtgtg ttttttggat ccccggggcg gccgc        3044

<210> SEQ ID NO 39
<211> LENGTH: 653
<212> TYPE: PRT
<213> ORGANISM: Artificial Sequence
<220> FEATURE:
<221> NAME/KEY: PRT
<222> LOCATION: (1)..(653)
<223> OTHER INFORMATION: variant Cry3Bb1 coding sequence encoding v11231

<400> SEQUENCE: 39

Met Ala Asn Pro Asn Asn Arg Ser Glu His Asp Thr Ile Lys Val Thr
  1               5                  10                  15

Pro Asn Ser Glu Leu Gln Thr Asn His Asn Gln Tyr Pro Leu Ala Asp
            20                  25                  30

Asn Pro Asn Ser Thr Leu Glu Glu Leu Asn Tyr Lys Glu Phe Leu Arg
        35                  40                  45

Met Thr Glu Asp Ser Ser Thr Glu Val Leu Asp Asn Ser Thr Val Lys
     50                  55                  60

Asp Ala Val Gly Thr Gly Ile Ser Val Val Gly Gln Ile Leu Gly Val
 65                  70                  75                  80

Val Gly Val Pro Phe Ala Gly Ala Leu Thr Ser Phe Tyr Gln Ser Phe
                85                  90                  95

Leu Asn Thr Ile Trp Pro Ser Asp Ala Asp Pro Trp Lys Ala Phe Met
            100                 105                 110

Ala Gln Val Glu Val Leu Ile Asp Lys Lys Ile Glu Glu Tyr Ala Lys
        115                 120                 125
```

```
Ser Lys Ala Leu Ala Glu Leu Gln Gly Leu Gln Asn Asn Phe Glu Asp
    130                 135                 140

Tyr Val Asn Ala Leu Asn Ser Trp Lys Lys Thr Pro Leu Ser Leu Arg
145                 150                 155                 160

Ser Lys Arg Ser Gln Asp Arg Ile Arg Glu Leu Phe Ser Gln Ala Glu
                165                 170                 175

Ser His Phe Arg Asn Ser Met Pro Ser Phe Ala Val Ser Lys Phe Glu
                180                 185                 190

Val Leu Phe Leu Pro Thr Tyr Ala Gln Ala Ala Asn Thr His Leu Leu
            195                 200                 205

Leu Leu Lys Asp Ala Gln Val Phe Gly Glu Glu Trp Gly Tyr Ser Ser
        210                 215                 220

Glu Asp Val Ala Glu Phe Tyr Arg Arg Gln Leu Lys Leu Thr Gln Gln
225                 230                 235                 240

Tyr Thr Asp His Cys Val Asn Trp Tyr Asn Val Gly Leu Asn Gly Leu
                245                 250                 255

Arg Gly Ser Thr Tyr Asp Ala Trp Val Lys Phe Asn Arg Phe Arg Arg
            260                 265                 270

Glu Met Thr Leu Thr Val Leu Asp Leu Ile Val Leu Phe Pro Phe Tyr
        275                 280                 285

Asp Ile Arg Leu Tyr Ser Lys Gly Val Lys Thr Glu Leu Thr Arg Asp
290                 295                 300

Ile Phe Thr Asp Pro Ile Phe Leu Leu Thr Thr Leu Gln Lys Tyr Gly
305                 310                 315                 320

Pro Thr Phe Leu Ser Ile Glu Asn Ser Ile Arg Lys Pro His Leu Phe
                325                 330                 335

Asp Tyr Leu Gln Gly Ile Glu Phe His Thr Arg Leu Gln Pro Gly Tyr
            340                 345                 350

Phe Gly Lys Asp Ser Phe Asn Tyr Trp Ser Gly Asn Tyr Val Glu Thr
        355                 360                 365

Arg Pro Ser Ile Gly Ser Ser Lys Thr Ile Thr Ser Pro Phe Tyr Gly
370                 375                 380

Asp Lys Ser Thr Glu Pro Val Gln Lys Leu Ser Phe Asp Gly Gln Lys
385                 390                 395                 400

Val Tyr Arg Thr Ile Ala Asn Thr Asp Val Ala Ala Trp Pro Asn Gly
                405                 410                 415

Lys Val Tyr Leu Gly Val Thr Lys Val Asp Phe Ser Gln Tyr Asp Asp
            420                 425                 430

Gln Lys Asn Glu Thr Ser Thr Gln Thr Tyr Asp Ser Lys Arg Asn Asn
        435                 440                 445

Gly His Val Ser Ala Gln Asp Ser Ile Asp Gln Leu Pro Pro Glu Thr
        450                 455                 460

Thr Asp Glu Pro Leu Glu Lys Ala Tyr Ser His Gln Leu Asn Tyr Ala
465                 470                 475                 480

Glu Cys Phe Leu Met Gln Asp Arg Arg Gly Thr Ile Pro Phe Phe Thr
                485                 490                 495

Trp Thr His Arg Ser Val Asp Phe Phe Asn Thr Ile Asp Ala Glu Lys
            500                 505                 510

Ile Thr Gln Leu Pro Val Val Lys Ala Tyr Ala Leu Ser Ser Gly Ala
        515                 520                 525

Ser Ile Ile Glu Gly Pro Gly Phe Thr Gly Gly Asn Leu Leu Phe Leu
530                 535                 540
```

```
Lys Glu Ser Ser Asn Ser Ile Ala Lys Phe Lys Val Thr Leu Asn Ser
545                 550                 555                 560

Ala Ala Leu Leu Gln Arg Tyr Arg Val Arg Ile Arg Tyr Ala Ser Thr
                565                 570                 575

Thr Asn Leu Arg Leu Phe Val Gln Asn Ser Asn Asp Phe Leu Val
            580                 585                 590

Ile Tyr Ile Asn Lys Thr Met Asn Lys Asp Asp Leu Thr Tyr Gln
        595                 600                 605

Thr Phe Asp Leu Ala Thr Thr Asn Ser Asn Met Gly Phe Ser Gly Asp
    610                 615                 620

Lys Asn Glu Leu Ile Ile Gly Ala Glu Ser Phe Val Ser Asn Glu Lys
625                 630                 635                 640

Ile Tyr Ile Asp Lys Ile Glu Phe Ile Pro Val Gln Leu
                645                 650

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 40
taggcctcca tccatggcaa accctaacaa tc                                    32

<210> SEQ ID NO 41
<211> LENGTH: 42
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 41
tcccatcttc ctacttagca ccctgcagaa atacggtcca ac                         42

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 42
gacctcacct accaaacatt cgatcttg                                         28

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 43
cgagttctac cgtaggcagc tcaag                                            25
```

EXPRESSION OF CRY3B INSECTICIDAL PROTEIN IN PLANTS

CROSS REFERENCE TO RELATED APPLICATIONS

This application is a divisional of U.S. application Ser. No. 10/232,665, filed Aug. 29, 2002 now U.S. Pat. No. 6,943,281 which is a divisional of U.S. application Ser. No. 09/377,466 filed Aug. 19, 1999 now U.S. Pat. No. 6,501,009, all of which are incorporated herein by reference.

1.0 BACKGROUND OF THE INVENTION

1.1 Field of the Invention

The present invention discloses transgenic plants expressing substantially higher levels of insect controlling *Bacillus thuringiensis* δ-endotoxin. Methods for obtaining such plants and compositions, and methods for using such plants and compositions are described. Also disclosed are improved polynucleotide cassettes containing preferred protein coding sequences which impart the substantially higher levels of insect controlling δ-endotoxins. The preferred embodiments of the invention surprisingly provide up to ten fold higher levels of insect controlling protein relative to the highest levels obtained using prior compositions. In particular, transgenic maize expressing higher levels of a protein designed to exhibit increased toxicity toward *Coleopteran* pests deliver superior levels of insect protection and are less likely to sponsor development of populations of target insects that are resistant to the insecticidally active protein.

1.2 Description of the Related Art

Almost all field crops, plants, and commercial farming areas are susceptible to attack by one or more insect pests. Particularly problematic are *Coleopteran* and *Lepidopteran* pests. Because crops of commercial interest are often the target of insect attack, environmentally-sensitive methods for controlling or eradicating insect infestation are desirable. This is particularly true for farmers, nurserymen, growers, and commercial and residential areas which seek to control insect populations using ecologically friendly compositions.

The most widely used environmentally-sensitive insecticidal formulations developed in recent years have been composed of microbial protein pesticides derived from the bacterium *Bacillus thuringiensis*, a Gram-positive bacterium that produces crystal proteins or inclusion bodies which are specifically toxic to certain orders and species of insects. Many different strains of *B. thuringiensis* have been identified which produce one or more insecticidal crystal proteins as well as other insecticidal non-crystal forming proteins. Compositions including *B. thuringiensis* strains which produce insecticidal proteins have been commercially available and used as environmentally acceptable insecticides because they are quite toxic to specific target insect pests, but are harmless to plants and to vertebrate and invertebrate animals. More importantly, because these insect controlling proteins have to be ingested by susceptible target insect pests in order to exert their insecticidal or toxic effects, judicious application of such protein compositions limits or prevents non-target insect members of the susceptible order which may also be susceptible to the composition from significant exposure to the proteins (for example, non-target *Lepidopteran* species where *Lepidopteran* specific B.t. crystal protein is used in an insecticidal formulation). Additionally, insects of various orders have been shown to totally lack susceptibility to specifically targeted insecticidal proteins even when ingested in large amounts.

1.2.1 δ-Endotoxins

δ-endotoxins are used to control a wide range of plant-eating caterpillars and beetles, as well as mosquitoes. These proteins, also referred to as insecticidal crystal proteins, crystal proteins, and Bt toxins, represent a large collection of insecticidal proteins produced by *B. thuringiensis* that are toxic upon ingestion by a susceptible insect host. Over the past decade research on the structure and function of *B. thuringiensis* toxins has covered all of the major toxin categories, and while these toxins differ in specific structure and function, general similarities in the structure and function are assumed. A recent review describes the genetics, biochemistry, and molecular biology of Bt toxins (Schnepf et al., *Bacillus thuringiensis* and its Pesticidal Crystal Proteins, Microbiol. Mol. Biol. Rev. 62:775-806, 1998). Based on the accumulated knowledge of *B. thuringiensis* toxins, a generalized mode of action for *B. thuringiensis* toxins has been created and includes: ingestion by the insect, solubilization in the insect midgut (a combination stomach and small intestine), resistance to digestive enzymes sometimes with partial digestion by gut specific proteases catalyzing specifically a cleavage at a peptide site within a protoxin structure which "activates" the toxin, binding of the toxin to the midgut cells' brush border, formation of a pore in the insect midgut cell, and the disruption of cellular homeostasis (English and Slatin, 1992).

1.2.2 Genes Encoding Crystal Proteins

Many of the δ-endotoxins are related to various degrees by similarities in their amino acid sequences. Historically, the proteins and the genes which encode them were classified based largely upon their spectrum of insecticidal activity. A review by Höfte and Whiteley (1989) discusses the genes and proteins that were identified in *B. thuringiensis* prior to 1990, and sets forth the nomenclature and classification scheme which has traditionally been applied to *B. thuringiensis* genes and proteins. The original nomenclature took advantage of the discovery that the few Bt Cry proteins known at the time generally fell into a limited number of classes, wherein each class represented proteins having specificity for specific orders of insects. For example, cry1 genes encoded *Lepidopteran*-toxic Cry1 proteins. cry2 genes encoded Cry2 proteins that were generally toxic to both *Lepidopteran* as well as to *Dipterans*. cry3 genes encoded *Coleopteran*-toxic Cry3 proteins, while cry4 genes encoded *Dipteran*-specific toxic Cry4 proteins. The nomenclature has, for the past decade or more become rather confusing with the discovery of more distantly related classes of insecticidal Bt proteins. More recently, a simplified homogeneous nomenclature and basis for classifications of Bt proteins has been adopted and has been reviewed by Schnepf et al. (1998). Schnepf et al. (1998) also provides a structural solution for a Cry1 crystal. This simplified nomenclature will be adopted herein. The convention of identifying Bt genes with lower case, italicized letters (eg. cry1Ab1) and identifying Bt proteins with uppercase first character (eg. Cry1Ab1) will also be observed herein.

Based on the degree of sequence similarity, the proteins have been further classified into subfamilies. Proteins which appeared to be more closely related within each family were assigned divisional letters such as Cry1A, Cry1B, Cry1C, etc. Even more closely related proteins within each division were given names such as Cry1Ca, Cry1Cb, etc. and still even more closely related proteins within each division were designated with names such as Cry1Bb1, Cry1Bb2, etc.

The modern nomenclature systematically classifies the Cry proteins based upon amino acid sequence homology rather than upon insect target specificities. The classification scheme for many known toxins, not including allelic variations in individual proteins, is summarized in regularly updated tables which can be obtained from Dr. Neil Crickmore at http://cpunix.biols.susx.ac.uk/Home/Neil_Crickmore/Bt/index.html.

1.2.3 Bio-Insecticide, Polypeptide Compositions

The utility of bacterial crystal proteins as insecticides was extended beyond *Lepidopterans* and *Dipteran* larvae when the first isolation of a *Coleopteran*-toxic *B. thuringiensis* strain was reported (Krieg et al., 1983; 1984). This strain (described in U.S. Pat. No. 4,766,203, specifically incorporated herein by reference), designated *B. thuringiensis* var. *tenebrionis*, was reported to be toxic to larvae of the *Coleopteran* insects *Agelastica alni* (blue alder leaf beetle) and *Leptinotarsa decemlineata* (Colorado potato beetle).

U.S. Pat. No. 5,024,837 also describes hybrid *B. thuringiensis* var. *kurstaki* strains which showed activity against *Lepidopteran* insects. U.S. Pat. No. 4,797,279 (corresponding to EP 0221024) discloses a hybrid *B. thuringiensis* containing a plasmid from *B. thuringiensis* var. *kurstaki* encoding a *Lepidopteran*-toxic crystal protein-encoding gene and a plasmid from *B. thuringiensis tenebrionis* encoding a *Coleopteran*-toxic crystal protein-encoding gene. The hybrid *B. thuringiensis* strain produces crystal proteins characteristic of those made by both *B. thuringiensis kurstaki* and *B. thuringiensis tenebrionis*. U.S. Pat. No. 4,910,016 (corresponding to EP 0303379) discloses a *B. thuringiensis* isolate identified as *B. thuringiensis* MT 104 which has insecticidal activity against *Coleopterans* and *Lepidopterans*. More recently, Osman et al. disclosed a natural *Bacillus thuringiensis* isolate which displayed activity against at least two orders of insects and against nematodes (WO 98/30700).

It has been known for more than two decades that compositions comprising Bt insecticidal proteins are effective in providing protection from insect infestation to plants treated with such compositions. More recently, molecular genetic techniques have enabled the expression of Bt insecticidal proteins from nucleotide sequences stably inserted into plant genomes (Perlak et al., Brown & Santino, etc.). However, expression of transgenes in plants has provided an avenue for increased insect resistance to Bt's produced in plants because plants have not been shown to produce high levels of insecticidal proteins. It was initially believed that gross morphological or topological differences in gene structure and architecture between plant and bacterial systems was the limitation which prevented over-expression of Bt transgenes in plants. These differences were seemingly overcome as disclosed by Perlak et al. (U.S. Pat. No. 5,500,365) and by Brown et al. (U.S. Pat. Nos. 5,424,412 and 5,689,052) wherein transgenes encoding Bt insecticidal protein which contained plant preferred codons were shown to improve the levels of expression. Alternatively, truncating the protoxin coding domain to the shortest peptide coding domain which still encoded an insecticidal protein was also deemed sufficient to overcome the limitation of vanishingly low expression levels of the Bt encoding transgene in planta. Expression levels of Bt proteins in planta from transgenes has varied widely independent of the means used for expression, and accumulated protein levels have ranged from virtually undetectable to 2 parts per million to around 20 to 30 parts per million. However, even though all of these approaches provided improved levels of Bt protein accumulation in plants, none provided levels of expression which could ensure that insect resistance would not become a problem without the necessity of coordinate expression of one or more additional insecticidal toxins by the transgenic plant, or alternatively without the coordinate topical application of additional supplemental Bt or insecticidal chemical compositions.

The importance of accumulation of higher levels of Bt toxin for preventing insect resistance to individual Bt toxins has been understood for some time. Various laboratory studies in which selection against Bt was applied over several generations of insects have confirmed that resistance against Bt insecticidal proteins is seldom obtained. It should be emphasized that laboratory conditions represent rather low but constant selection pressure conditions, allowing for the survival of a sub-population of insects which have been subjected to insecticidal pressure and which produce the subsequent generations of insects. Succeeding generations are also maintained on media containing low but constant concentrations of insecticidal protein. Generally, concentrations used for selection pressures range from LC40 to around LC60 or so, however, LC95 concentrations have also tested for the development of resistance. In most cases, resistance is acquired slowly, generally developing within a reasonably few generations, for example 10-50 generations. However, such resistance is not observed where substantially higher levels of toxin are used, or in situations in which multiple toxins are provided.

At present, recombinant plants expressing commercially useful levels of Bt insecticidal protein generally contain only one gene encoding a single class of Bt. Such plants are anticipated to have a very limited duration of use for two reasons. First, these plants are expressing insufficient levels of the insecticidal protein to ensure that all target insects exposed to and feeding from the plant tissues will succumb due to the dose of toxin ingested. Second, because of the insufficient insecticidal protein levels, the potential for development of resistance is unreasonably increased. This is not to say that the level of toxin produced by such transgenic plants is insufficient to be effective. This merely represents the limitations of expression of δ-endotoxins in planta even when using sequences encoding Bt δ-endotoxin which have been modified to conform to plant preferred sequences. One limitation which has been observed for many Bt δ-endotoxin encoding sequences modified for expression in plants is that is has been impossible to predict which Bt δ-endotoxin would be effective for expression in plants. (For example, expression of Cry2Aa in cotton plants results in phytotoxicity when targeted to the chloroplast, however expression of a closely related cry2Ab sequence is not phytotoxic when targeted to the chloroplast. (Corbin et al., U.S. patent application, Ser. No. 09/186,002). Even so, levels of δ-endotoxin protein produced in plants is not sufficient to be effective against all desired target insect species known to be susceptible to a given type and class of δ-endotoxin.

As indicated above, alternative approaches to development of resistance to insecticidal proteins has included ineffective attempts to increase the expression levels of transgenes in plants. Alternatively, additional insecticidal genes could be engineered into plants so that multiple toxins are coordinately expressed. This would provide a more effective means for delaying the onset of resistance to any one combination of Bt's, however, this still does not overcome the limitation of insufficient levels of insecticidal protein accumulating in the recombinant plant(s). An additional alternative to insufficient levels of expression has been to engineer genes encoding Bt insecticidal crystal proteins which demonstrate improved insecticidal properties, having either a broader host range or an increased biological activity, which could conceivably result in requiring less of the recombinant protein to control a target insect species than was required of the native form of the protein.

The combination of structural analyses of *B. thuringiensis* toxins followed by an investigation of the function of such structures, motifs, and the like has taught that specific regions of crystal protein endotoxins are, in a general way, responsible for particular functions.

Domain 1. for example, from Cry3Bb and Cry1Ac has been found to be responsible for ion channel activity, the initial step in formation of a pore (Walters et al., 1993; Von Tersch et al., 1994). Domains 2 and 3 have been found to be responsible for receptor binding and insecticidal specificity (Aronson et al., 1995; Caramori et al., 1991; Chen et al. 1993; de Maagd et al., 1996; et al., 1991; Lee et al., 1992; Lee et al., 1995; Lu et al., 1994; Smedley and Ellar, 1996; Smith and Ellar, 1994; Rajamohan et al., 1995; Rajamohan et al., 1996; Wu and Dean, 1996). Regions in domain 2 and 3 can also impact the ion channel activity of some toxins (Chen et al., 1993, Wolfersberger et al., 1996; Von Terschet al., 1994).

Unfortunately, while many investigators have attempted, few have succeeded in making mutated crystal proteins with improved insecticidal toxicity. In almost all of the examples of genetically-engineered *B. thuringiensis* toxins in the literature, the biological activity of the mutated crystal protein is no better than that of the wild-type protein, and in many cases, the activity is decreased or destroyed altogether (Almond and Dean, 1993; Aronson et al., 1995; Chen et al., 1993, Chen et al., 1995; Ge et al., 1991; Kwak et al., 1995; Lu et al., 1994; Rajamohan et al., 1995; Rajamohan et al., 1996; Smedley and Ellar, 1996; Smith and Ellar, 1994; Wolfersberger et al., 1996; Wu and Aronson, 1992). However, Van Rie et al. have recently accomplished the improvement of a Cry3A δ-endotoxin having increased *Coleopteran* insecticidal activity by identifying a single mutant having increased insecticidal activity. Van Rie et al. propose a method for identifying mutants having increased insecticidal activity in which the method consists of identifying amino acid mutations which decrease the insecticidal activity, and selectively altering those residues by site directed mutagenesis to incorporate one or more of the naturally occurring 20 amino acids at those positions, and feeding the various forms of the resulting altered protein to western or northern corn rootworms to identify those having improved activity (U.S. Pat. No. 5,659, 123). While no sequences were enabled using the method, as mentioned above, Van Rie et al. succeeded in identifying only one sequence having increased activity and did not demonstrate an increase in expression of the mutant form as compared to the native sequence.

For a crystal protein having approximately 650 amino acids in the sequence of its active toxin, and the possibility of 20 different amino acids at each position in this sequence, the likelihood of arbitrarily creating a successful new structure is remote, even if a general function to a stretch of 250-300 amino acids can be assigned. Indeed, the above prior art with respect to crystal protein gene mutagenesis has been concerned primarily with studying the structure and function of the crystal proteins, using mutagenesis to perturb some step in the mode of action, rather than with engineering improved toxins.

Collectively, the limited successes in the art to develop non-naturally occurring toxins with improved insecticidal activity have stifled progress in this area and confounded the search for improved endotoxins or crystal proteins. Rather than following simple and predictable rules, the successful engineering of an improved to crystal protein may involve different strategies, depending on the crystal protein being improved and the insect pests being targeted. Thus, the process is highly empirical.

Accordingly, traditional recombinant DNA technology is clearly not routine experimentation for providing improved insecticidal crystal proteins. What has been lacking in the prior art are rational methods for producing genetically-engineered *B. thuringiensis* crystal proteins that have improved insecticidal activity and, in particular, improved toxicity towards a wide range of *Lepidopteran, Coleopteran*, or *Dipteran* insect pests. Methods and compositions which address these concerns were disclosed in U.S. patent application Ser. No. 08/993,170 (Dec. 18, 1997; English et al.) and other related U.S. application Ser. No. (08/993,722, Dec. 18, 1997, English et al.; Ser. No. 08/993,755, Dec. 18, 1997, English et al.; and Ser. No. 08/996,441, Dec. 18, 1997, English et al.) and in Van Rie et al. (U.S. Pat. No. 5,659,123, Jun. 1, 1999). In addition, recombinantly improved δ-endotoxins have continued to be expressed poorly and/or cause phytotoxic effects when expressed in plants, thus leading to the recovery of fewer commercially useful transgenic events.

2.0 SUMMARY OF THE INVENTION

Described herein are novel compositions and methods for expressing in transformed plants variant Cry3 *B. thuringiensis* δ-endotoxins having significant *Coleopteran* inhibitory activity. These compositions and methods advantageously result in plants expressing *B. thuringiensis* Cry3 δ-endotoxins at increased levels not previously observed for Cry δ-endotoxins. Increased levels of Cry3 δ-endotoxin expression are reflected in the attainment of higher maximal expression levels in individual transgenic insertion events. Unexpectedly, the particular compositions disclosed herein result in the recovery of an increased percentage of transgenic events which manifest expression levels that far exceed threshold levels of expression necessary for *Coleopteran* insect control and which provide sufficient toxin levels capable of supporting a resistance management strategy. Since Cry3 δ-endotoxins are typically less potent than other δ-endotoxins commonly used to control *Lepidopteran* or *Dipteran* target pests when expressed in transgenic plants, attainment of higher maximal levels of Cry3 δ-endotoxin expression and recovery of more transgenic events with effective expression levels are both critical in isolating transgenic events expressing Cry3 δ-endotoxin which exhibit commercially useful levels-of target insect control.

Another limitation of the prior art addressed by the present invention is the development of insect resistance to δ-endotoxins provided by plant expression. Specifically, the instant invention provides a superior strategy for the delay or elimination of the development of resistance to Cry3 δ-endotoxins through improved accumulation of δ-endotoxin within plant cells so that levels of the δ-endotoxin are maintained in-planta above a threshold level of protein, typically measured in parts per million (ppm). Improved expression of δ-endotoxins, which also should be taken to mean increased expression in view of what has been previously observed in the art, is believed to result in delayed onset of insect resistance and thus extends the utility of plant expressed δ-endotoxins as insect control agents.

Figure 2:
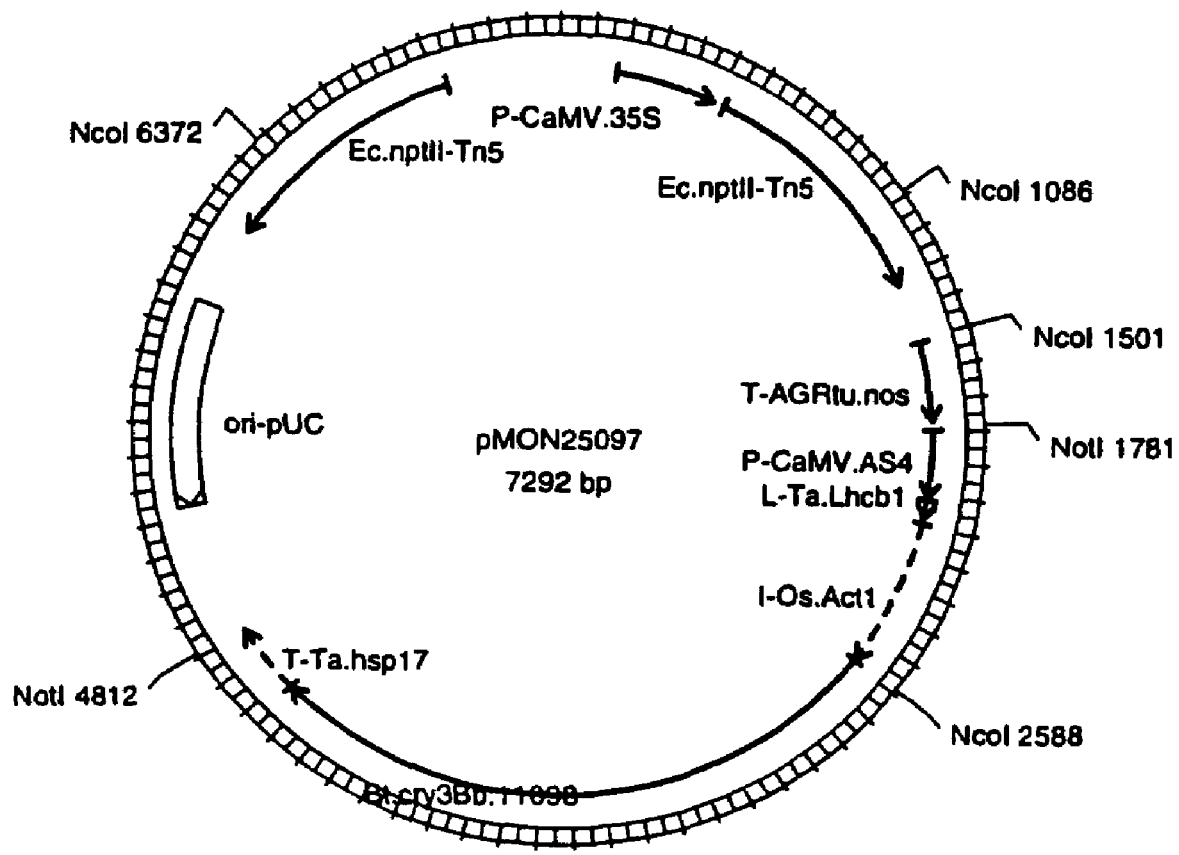

In preferred embodiments, the present invention provides isolated and purified novel Cry3B δ-endotoxin proteins exhibiting particularly effective insecticidal activity directed toward controlling *Coleopteran* pest insect species. Such δ-endotoxin proteins of the present invention are provided by expression from isolated, purified and improved or enhanced DNA or polynucleotide sequences each comprising a Cry3 δ-endotoxin coding sequence placed under the control of preferred plant functional gene expression elements such as a promoter, an untranslated leader sequence, an intron and a transcription termination and polyadenylation sequence. Some preferred DNA or polynucleotide sequences may also provide for plastid or chloroplast targeting protein sequences. Preferred DNA constructs of the present invention include those constructs which encode Cry3 δ-endotoxins exhibiting *Coleopteran*-inhibitory or *Coleopteran*-controlling activity. In an illustrative embodiment, polynucleotide sequences arc assembled into an expression cassette for introduction into plant genomic DNA, wherein the expression cassette comprises a Cry3Bb δ-endotoxin variant coding sequence operably linked to a sequence comprising a promoter, an untranslated leader sequence, an intron and a transcription termination and polyadenylation sequence. In particular, a transgene localized within a plant operable polynucleotide expression cassette or polynucleotide sequence comprising an expression cassette which is comprised of genetic elements which function in plant cells to express a desired protein from a nucleic acid coding sequence (the transgene) which is operably localized within said expression cassette. The coding sequence is linked upstream to at least a promoter sequence, an untranslated leader sequence (UTL), an intron sequence, and in-frame in certain indicated embodiments to a sequence encoding a plastid or chloroplast targeting peptide. The coding sequence is also linked downstream to at least a plant functional transcription termination and polyadenylation sequence. Polynucleotide sequences comprising such an expression cassette are shown herein to improve expression of the desired protein encoded from within the cassette, improve the number of events obtained from the use of the polynucleotide sequence in plant transformation, wherein said improved number of events contain the desired transgene localized within the expression cassette and exhibit improved levels of expression of one or more desired proteins. The improved number of events are also surprisingly observed to express the desired protein at levels above 2 to 5 parts per million but in general below 200 to 500 parts per million of total cell protein. Even more surprising were some events in particular which expressed the desired protein at levels well above 500 ppm. Indicated embodiments disclose a sequence encoding a variant Cry3Bb δ-endotoxin comprising the isolated and purified SEQ ID NO:9, from NcoI to EcoRI as set forth in FIG. 1 illustrating plasmid pMON25096. Yet other embodiments disclose a variant Cry3Bb δ-endotoxin coding sequence comprising an isolated and purified SEQ ID NO:11, from NcoI to EcoRI as set forth in FIG. 2 illustrating plasmid pMON33741. It is contemplated, however, that any Cry3 δ-endotoxin exhibiting substantial *Coleopteran*-inhibitory or *Coleopteran*-controlling activity greater than or equal to that disclosed in the present invention could be utilized according to the embodiments of the present invention. with those Cry3 proteins bearing substantial homologies to Cry3Bb being particularly preferred.

In a preferred embodiment, the invention provides for transgenic plants which have been transformed with a DNA construct or expression cassette of the present invention that is expressed and translated at unexpectedly high levels by the plant which results in surprisingly high levels of δ-endotoxin accumulation. Monocotyledenous plants may be transformed according to the methods and with the DNA constructs disclosed herein. However, it is also anticipated that dicotyledenous plants could also be transformed with DNA sequences disclosed herein by one skilled in the art in order to obtain transgenic plants providing unexpectedly useful levels of insect resistance without the risk of development of insect resistance to the δ-endotoxin. The plant transformed by the instant invention may be prepared, in a further preferred embodiment, by a process including obtainment of the isolated and purified DNA construct contained within the expression cassette, and then transforming the plant with the construct so that the plant expresses the protein for which the construct encodes. Alternatively, the plant transformed by the instant invention may be prepared, in a further preferred embodiment, by a process including introduction of the isolated and purified DNA construct into a transformation competent *Agrobacterium* strain, and then transforming the plant with the *Agrobacterium* strain containing the construct so that the plant expresses the proteins for which the construct encodes. It has been observed herein that transformation of plants by the disclosed compositions and methods results surprisingly in increased frequencies of transformants exhibiting transgene expression as well as in the recovery of individual transgenic events exhibiting unexpectedly higher absolute levels of transgene expression.

It is contemplated that the increased expression levels observed in the disclosed invention will allow for reduced development of insect resistance to Bt δ-endotoxins presented to target insect pests. This may be achieved by transforming a plant with the preferred DNA construct to achieve high rates of Cry3 expression alone, or by simultaneously exposing target insects to the disclosed Cry3 δ-endotoxins along with other compositions effective in controlling *Coleopteran* species such as variants of Cry3B (English et al., WO 99/31248), variant Cry3A or variant Cry3D (U.S. Pat. No. 5,659,123), CryET33 and CryET34 (Donovan et al., WO 97/17600), CryET70 (U.S. application Ser. No. 09/184,748; Mettus et al., Nov. 2, 1998), Cry6A. Cry6B, Cry8B (U.S. Pat. No. 5,277,905), CryET29 (Ruparet al., WO 97/21587), insecticidal acyl lipid hydrolases, combinations of amino acid oxidases and tedanalactam synthases (Romano et al. U.S. application Ser. No. 09/063,733, filed Apr. 21, 1998), or insecticidal proteins such as VIP1 (Gay, WO 97/26339; Gourlet et al., WO 98/02453) and VIP3 (Estruch et al., U.S. Pat. No. 5,877,012; 1999) among others. Susceptible target insects include *Diabroticus* spp. Wire Worm in *Zea mays* and *Leptinotarsa decemlineata* (Say) in *Solanum tuberosum*, and Boll Weevil in *Gossypium* species (cotton).

It is therefore contemplated that the compositions and methods disclosed by the present invention will provide many advantages over the prior art including those specifically outlined above. Other advantages include improved control of susceptible target insect pests and achieving season long protection from insect pathogens. An additional advantage of the present invention provides for reducing the number of transgenic events that have to be screened in order to identify one which contains beneficial levels of one or more insect controlling compositions. The present invention also encompasses cells transformed with the DNA constructs disclosed herein. Also, transformation vectors such as plasmids, bacmids, artificial chromosomes; viral vectors and such are contemplated as elements for use in delivering the nucleotide compositions of the present invention into contemplated cells in order to obtain transformed host cells, both prokaryotic and eukaryotic, which express the δ-endotoxin proteins encoded by the novel DNA construct disclosed herein. It is further contemplated that in some instances the genome of a transgenic plant of the present invention will have been augmented through the stable integration of an expression cassette encoding a *Coleopteran* inhibitory or controlling *B. thuringiensis* δ-endotoxin or variants thereof as described herein. Furthermore, more than one transgene encoding an insecticidal composition will be incorporated into the nuclear genome, or alternatively, into the chloroplast or plastid genome of the transformed host plant cell. It is envisioned that more than one polynucleotide encoding an insecticidal crystal protein will be incorporated into the genome of a plant cell and it may be desirable to have two or even more sequences encoding insecticidal or other plant beneficial proteins within the nucleotide sequences contained within the cell. Such recombinantly derived proteins may exist as precursors, protoxins, or as fusions of beneficial proteins linked by flexible amino acid linker sequences or by protease specific cleavage sequences well known in the art. Chimeras comprising fusions of insecticidal proteins are also envisioned. The offspring of transgenic plant host cells can be manipulated artificially to produce whole recombinant plants exhibiting improved insecticidal properties, and the recombinant nucleotide sequences are shown herein to be heritable. The heritability of the elements is a preferred aspect of this invention, so that the expression elements are able to be delivered to lineal descendants of the original transformed host plant cell, giving rise first to a stably transformed plant whose constituent cells express the desired transgene, albeit tissue specific expression can be selectively manipulated generally through the choice of plant operable promoter selected for use in a given expression cassette, as described above. Transformed plants give rise to seeds containing the heritable expression cassette, and the seeds thus give rise to plants in lineal fashion which contain the expression cassette, generally in Mendelian fashion, particularly when selfed according to well known methods in the art.

3.0 BRIEF DESCRIPTION OF THE DRAWINGS

Figure 3:
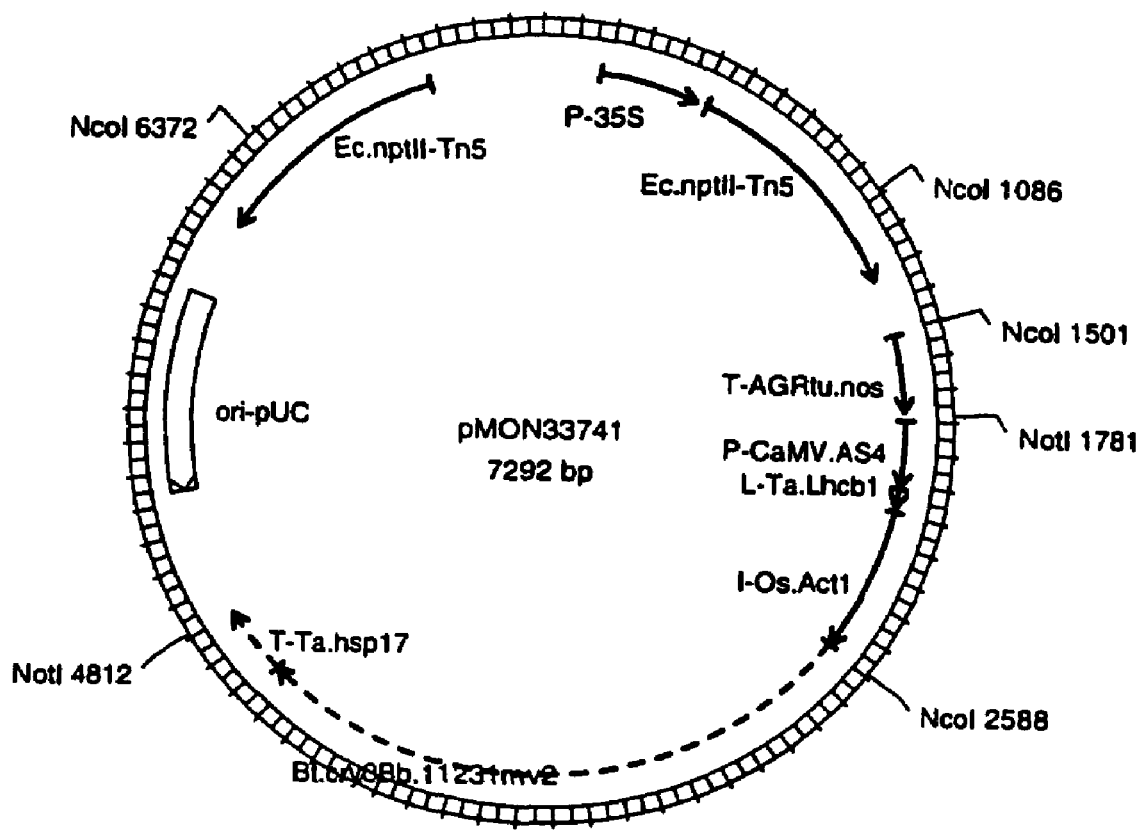
Figure 4:
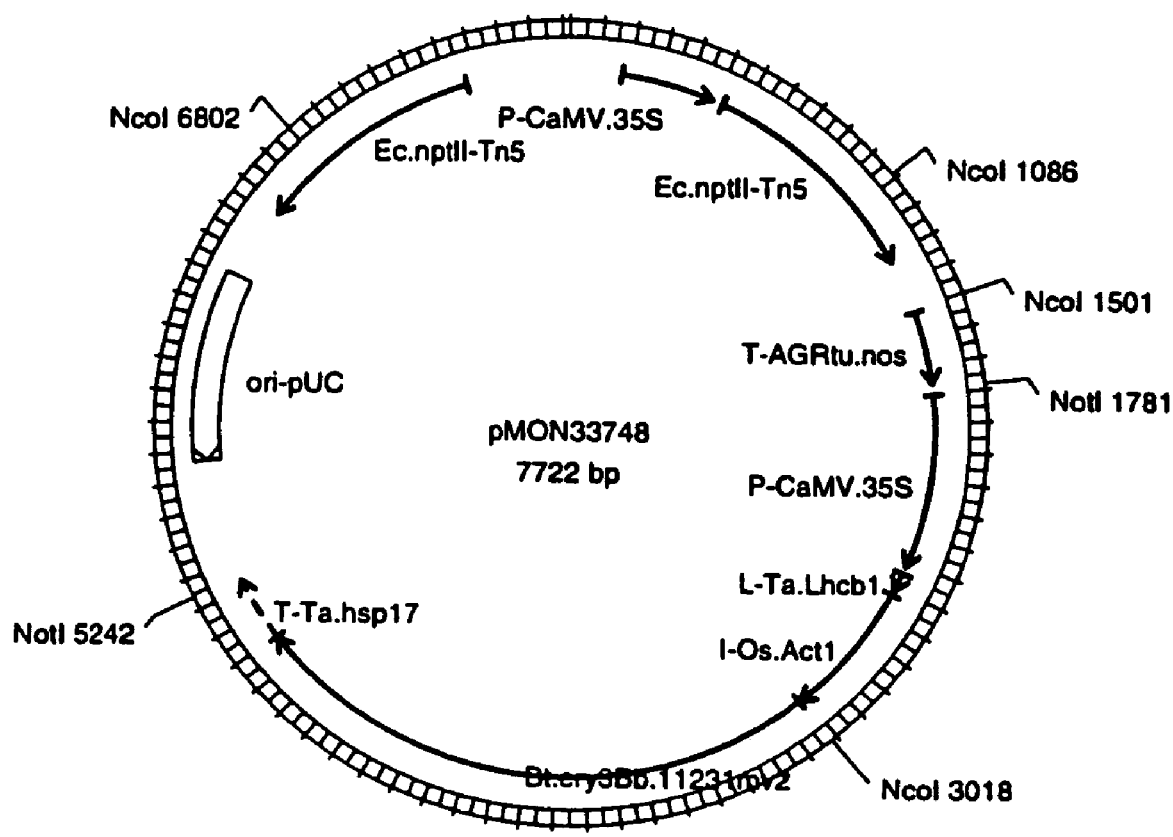

FIG. 1 illustrates plasmid pMON25096.
FIG. 2 illustrates plasmid pMON33741.
FIG. 3 illustrates plasmid pMON25097.
FIG. 4 illustrates plasmid pMON33748.
FIG. 5 illustrates the nucleotide and amino acid sequence translation of a variant Cry3Bb.11098 insecticidal protein as shown in SEQ ID NO:9.
FIG. 6 illustrates the nucleotide and amino acid sequence translation of a variant Cry3Bb.11231 insecticidal protein as shown in SEQ ID NO:11.

4.0 DETAILED DESCRIPTION OF THE INVENTION

The following detailed description of the invention is provided to aid those skilled in the art in practicing the present invention. Even so, the following detailed description should not be construed to unduly limit the present invention as modifications and variations in the embodiments discussed herein may be made by those of ordinary skill in the art without departing from the spirit and scope of the present invention.

4.1 Definitions

The following words and phrases have the meanings set forth below.

Biological functional equivalents. As used herein such equivalents with respect to the insecticidal proteins of the present invention are peptides, polypeptides and proteins that contain a sequence or moiety exhibiting sequence similarity to the novel peptides of the present invention, such as Cry3Bb.11231, and which exhibit the same or similar functional properties as that of the polypeptides disclosed herein, including insecticidal activity. Biological equivalents also include peptides, polypeptides and proteins that react with, i.e. specifically bind to antibodies raised against Cry3Bb and that exhibit the same or similar insecticidal activity, including both monoclonal and polyclonal antibodies.

Combating or Controlling Insect Damage in an agricultural context refers to reduction of damage in relative units to a crop or plant part caused by infestation of an insect pest. More generally, this phrase refers to reduction in the adverse effects caused by the presence of an undesired insect in any particular location.

Event refers to a transgenic plant derived from one of the following:
1. the insertion of foreign DNA into one or more unique sites in the nuclear genomic DNA;
2. the insertion of foreign DNA into one or more unique sites in the plastid, chloroplast or mitochondrial genome;
3. the introduction of a stable, heritable, epigenetic vector into the cytoplasm of a plastid, chloroplast, or mitochondria; or
4. a combination of any of the foregoing processes.

Events derived from these processes contain an expression cassette expressing a desired coding sequence as described herein. Events are also referred to as ITE's (independent transformation events).

Expression: The combination of intracellular processes, including transcription, translation, and other intracellular protein and RNA processing and stabilization functions, undergone by a nucleic acid coding sequence controlled by genetic sequences which function in plant cells to achieve production of a desired product, such as a structural gene encoding an RNA molecule, or an RNA molecule being used as a substrate for a reverse transcriptase enzyme or enzyme complex.

Improved or enhanced expression cassette refers to the specific combination and order of genetic elements associated with the insecticidal protein encoding sequence which, when expressed within a plant cell:
  gives rise to the surprising average level of that protein expressed in plants, plant tissue, or plant cells;
  gives rise to the unexpected number of transformation events expressing a surprisingly higher average level of insecticidal protein;
  gives rise to individual plants, plant tissue, or plant cells expressing an unexpectedly high level of the insecticidal protein; and
  gives rise to plants expressing unexpected levels of insecticidal protein effective in controlling or combating *Coleopteran* pests and preventing development of resistance by the *Coleopteran* pest to the particular insecticidal protein.

Insecticidal polypeptide refers to a polypeptide having insecticidal properties, e.g., a polypeptide which exhibits the properties of inhibiting the growth, development, viability or fecundity of target insect pests.

Operably Linked: Nucleic acid or polynucleotide sequences connected sequentially in linear form, so that the properties of one influence the expression characteristics of the other. A promoter, for example, operably linked to other polynucleotide sequences (which may consist of operator or enhancer sequences, untranslated or translated leader sequences, intron sequences, structural gene coding sequences, non-structural genes, transcription and translation termination sequences, and polyadenylation sequences) influences the expression of a coding or noncoding sequence, whether the product is RNA, protein, or other product. Similarly, an intron or an untranslated leader sequence can influence the expression and stability of sequences operably linked to them, and structural or non-structural gene sequences can be influenced by elements operably linked upstream, within, or downstream.

Plant-Expressible Coding Regions: Amino acid coding regions or open reading frames (ORF's) which are expressible in planta because they contain typical plant regulatory elements facilitating their expression, and often include changes to the coding sequence such that plant preferred codons are utilized in place of non-preferred codons where heterologous coding regions are contemplated.

Plastid Transit Peptide: Any amino acid sequence useful in targeting a linked amino acid, such as a protein fusion, to a subcellular compartment or organelle such as a plastid or chloroplast.

Polynucleotide sequence: Any DNA or RNA sequence of four or more consecutive nucleotides or ribonucleotides. Generally polynucleotide sequences as disclosed herein comprise at least 50 or more nucleotides or ribonucleotides.

Progeny: "Progeny" includes any offspring or descendant of the transgenic plant, or any subsequent plant which contains the transgene(s) in operable form. Progeny is not limited to one generation, but rather encompasses the transformant's descendants so long as they contain or express the transgene(s). Seeds containing transgenic embryos as well as seeds from the transgenic plants and their offspring or descendants which, after Mendelian segregation continue to contain the transgene(s), are also important parts of the invention.

Promoter: A recognition site on a DNA sequence or group of DNA sequences that provide an expression control element for a preferred polynucleotide sequence and to which RNA polymerase specifically binds and initiates RNA synthesis (transcription) of that preferred sequence.

$R_0$ is the primary regenerant plant derived from transformation of plant tissue or cells in culture. Subsequent progeny or generations derived from the $R_0$ are referred to as $R_1$ (first generation), $R_2$ (second generation), etc.

Regeneration: The process of growing a plant from a plant cell or group of plant cells (e.g., plant protoplast, embryo, callus, or explant).

Structural Coding Sequence refers to a DNA sequence that encodes a peptide, polypeptide, or protein that is made by a cell following transcription of the structural coding sequence to messenger RNA (mRNA), followed by translation of the mRNA to the desired peptide, polypeptide, or protein product.

Structural gene: A gene or polynucleotide sequence containing the coding sequence of a desired polypeptide that is expressed by transcription and translation to produce the desired polypeptide.

Synthetic gene: Synthetic genes encoding the *B. thuringiensis* δ-endotoxins of the present invention are those prepared in a manner involving any sort of genetic isolation or manipulation which alters the naturally occurring coding sequence of the δ-endotoxin gene. This includes isolation of the gene from its naturally occuring state, manipulation of the gene as by codon modification (as described herein), or site-specific mutagenesis (as described herein), truncation of the gene or any other manipulative or isolative method. A synthetic gene can also be a polynucleotide sequence which is not known to be naturally occurring but which encodes a useful polypeptide or other product such as a tRNA or an antisense polynucleotide. A non-naturally occurring polynucleotide sequence.

Substantial homology: As this term is used herein, it refers to nucleic acid or polypeptide sequences which are about 86% homologous, to about 90% homologous, to about 95% homologous, to about 99% homologous. More specifically, the inventors envision substantial homologues to be about 86, 87, 88, 89, 90, 91, 92, 93, 94, 95, 96, 97, 98, and 99 percent homologous to the referent nucleic acid sequence of polypeptide.

Terminator: With reference to eukaryotic nuclear gene expression processes, the operable 3' end transcription termination and polyadenylation sequence. With reference to prokaryotic gene expression, and including plastid or chloroplast gene expression, the operable DNA sequence at the 3' end of an open reading frame which, for ORF's expressing protein product, at least one termination codon in frame with the coding sequence of the ORF, which may also be followed by a DNA sequence encoding a transcription termination signal which may cause the translated RNA or mRNA product to form a hairpin or other three dimensional structure which may or may not act together with one or more soluble structural proteins to cause transcription to be interrupted.

Transformation: A process of introducing an exogenous polynucleotide sequence (e.g., a vector, or a recombinant or non-recombinant DNA or RNA molecule) into a cell or protoplast in which that exogenous polynucleotide is incorporated into a heritable genetic element or is capable of autonomous replication and thus stably maintained within that cell or protoplast as well as in the progeny of that cell or protoplast.

Transformed cell: A cell which contains a heritable genetic element altered by the introduction of one or more exogenous DNA molecules. A transgenic cell. Exemplary transformed or transgenic cells include plant calli derived from a transformed plant cell and particular cells such as leaf, root, stem, e.g., somatic cells, or reproductive (germ) cells obtained from a transgenic plant.

Transgene: A gene construct, expression cassette, or DNA segment or sequence comprising an ORF which is desired to be expressed in the recipient cell, tissue or organism. This may include an entire plasmid, or other vector, or may simply include the functional coding sequence, region, domain, or segment of the transferred DNA sequence.

Transgenic event: A plant or progeny thereof derived from a plant cell or protoplast manufactured or constructed to contain one or more exogenous DNA molecules inserted into the nuclear or other genome of the plant cell, or introduced and stably maintained within the cytoplasm of a plastid, chloroplast, or mitochondria, which confers some physically detectable phenotype upon the plant or progeny thereof.

Transgenic plant: A plant or progeny thereof which has been genetically modified to contain and express heterologous DNA sequences either as proteins or as nucleic acids. As specifically exemplified herein, a transgenic corn plant is genetically modified to contain and express at least one heterologous DNA sequence operably linked to and under the regulatory control of transcriptional control sequences which function together in plant cells or tissue or in whole plants to achieve expression from a nucleic acid sequence encoding an insecticidal δ-endotoxin protein or an amino acid sequence variant thereof. A transgenic plant may also be referred to as a transformed plant. A transgenic plant also refers to progeny of the initial transgenic plant where those progeny contain and express the heterologous coding sequence under the regulatory control of the plant-expressible transcription control sequences described herein.

Vector: A polynucleotide capable of replication in a host cell and/or to which another polynucleotide sequence can be operatively linked so as to bring about replication of the linked sequence. A plasmid is an exemplary vector.

The present invention discloses novel DNA constructs comprising polynucleotide sequences encoding *B. thuringiensis* δ-endotoxins. Methods for the construction and expression of synthetic *B. thuringiensis* genes in plants are well known by those of skill in the art and are described in detail in U.S. Pat. No. 5,500,365. The present invention contemplates the use of Cry3B *B. thuringiensis* genes in the transformation of both monocotyledonous and dicotyledonous plants. To potentiate the expression of these genes, the present invention provides DNA constructs comprising polynucleotide segments encoding plastid targeting peptides positioned upstream of and in frame with the polynucleotide sequences encoding the desired *B. thuringiensis* δ-endotoxins, along with various combinations of untranslated leader sequences, plant functional intron sequences, and transcription termination and polyadenylation sequences.

In one aspect, nucleotide sequence information provided by the invention allows for the preparation of relatively short DNA sequences having the ability to specifically hybridize to gene sequences of the selected polynucleotides disclosed herein. In these aspects, nucleic acid probes of an appropriate length are prepared based on a consideration of selected polypeptide sequences encoding *Coleopteran* inhibitory Cry3B δ-endotoxin polypeptides, e.g., a sequence such as that shown in SEQ ID NO:2, SEQ ID NO:4, SEQ ID NO:6, SEQ ID NO:8, SEQ ID NO:10, and SEQ ID NO:12. These nucleic acid probes may also be prepared based on a consideration of selected polynucleotide sequences encoding a plastid targeting peptide, such as those shown in SEQ ID NO:26 The ability of such nucleic acid probes to specifically hybridize to a gene sequence encoding a δ-endotoxin polypeptide or a plastid targeting peptide sequence lends to them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a crystal protein gene from *B. thuringiensis* using thermal amplification technology. The process may also be used to detect, amplify or mutate a defined segment of the polynucleotide encoding a plastid targeting peptide. Segments of genes related to the polynucleotides encoding the δ-endotoxin polypeptides and plastid targeting peptides of the present invention may also be amplified by using such primers and thermal amplification methods.

To provide certain of the advantages in accordance with the present invention, a preferred nucleic acid sequence employed for hybridization studies or assays includes a polynucleotide sequences at least about 14 to 30 or so nucleotides in length complimentary to a nucleotide sequence encoding a crystal protein, or polynucleotide sequences at least about 14 to 30 or so nucleotides in length complimentary to a nucleotide sequence encoding a plastid targeting peptide.

A size of at least 14 nucleotides in length helps to ensure that the fragment will be of sufficient length to form a duplex molecule that is both stable and selective. Molecules having complementary sequences over segments greater than 14 bases in length are generally preferred. In order to increase stability and selectivity of the hybrid, and thereby improve the quality and degree of specific hybrid molecules obtained, one will generally prefer to design nucleic acid molecules having gene-complementary sequences of 14 to 20 nucleotides, or even longer where desired. Such fragments may be readily prepared by, for example, directly synthesizing the fragment by chemical means, by application of nucleic acid reproduction technology, such as the PCR™ technology of U.S. Pat. Nos. 4,683,195, and 4,683,202, or by excising selected DNA fragments from recombinant plasmids containing appropriate inserts and suitable restriction sites.

The present invention also contemplates an expression vector comprising a polynucleotide of the present invention. Thus, in one embodiment an expression vector is an isolated and purified DNA molecule comprising a promoter operatively linked to a coding region that encodes a polypeptide of the present invention, which coding region is operatively linked to a transcription-terminating region, whereby the promoter drives the transcription of the coding region. The coding region may include a segment encoding a *B. thuringiensis* δ-endotoxin and a segment encoding a plastid target peptide. The DNA molecule comprising the expression vector may also contain a functional intron. As used herein, the terms "operatively linked" or "operably linked" mean that a promoter is connected to a coding region in such a way that the transcription of that coding region is controlled and regulated by that promoter. Means for operatively linking a promoter to a coding region to regulate both upstream and downstream are well known in the art.

Preferred plant transformation vectors include those derived from a Ti plasmid of *Agrobacterium tumefaciens*, as well as those disclosed, e.g., by Herrera-Estrella (1983), Bevan (1983), Klee (1985) and Eur. Pat Appl. No. EP 0120516.

Promoters that function in bacteria are well known in the art. Exemplary and preferred promoters for the *B. thuringiensis* crystal proteins include the sigA, sigE, and sigK gene promoters. Alternatively, native, mutagenized, heterologous, or recombinant promoters derived from *Bacillus thuringiensis* δ-endotoxin protein coding sequences can be used.

Where an expression vector of the present invention is to be used to transform a plant, a promoter is selected that has the ability to drive expression in that particular species of plant. Promoters that function in different plant species are also well known in the art. Promoters useful in expression of polypeptide coding sequences in plants are those which are inducible, viral, synthetic or constitutive as described (Poszkowski et al., 1989; Odell et al., 1985), and/or temporally regulated, spatially regulated, and spatio-temporally regulated (Chau et al., 1989). Preferred promoters include the enhanced CaMV35S promoters, and the FMV35S promoter. Other promoters include the POX promoter, the ScbDNA virus early promoter and the yellow mottle virus promoter.

In accordance with the present invention, expression vectors designed to specifically potentiate the expression of the polypeptide in the transformed plant may include certain regions encoding plastid targeting peptides (PTP). These regions allow for the cellular processes involved in transcription, translation and expression of the encoded protein to be fully exploited when associated with certain *B. thuringiensis* δ-endotoxins. Such plastid targeting peptides function in a variety of ways, such as for example, by transferring the expressed protein to the cell structure in which it most effectively operates, or by transferring the expressed protein to areas of the cell in which cellular processes necessary for expression are concentrated.

In the case of Cry3B, elevated expression is critical in obtaining transgenic corn with CRW control since the $LC_{50}$ of Cry3B against CRW is significantly higher than the $LC_{50}$ of the *B. thuringiensis* toxins currently used to control target pests such as Colorado Potato Beetle in potato (Cry3A) or European Corn Borer in corn (Cry1Ab).

Increased expression is also especially valuable in that it provides additional protection against development of resistance via a high dose strategy (McGaughey and Whalon, 1993; Roush, 1994). High level expression is even further desirable as it provides sustained insect protection in instances where insecticidal gene expression decreases due to environmental conditions. Additionally and unexpectedly, corn plants transformed with vectors expressing Coleopteran inhibitory Cry3B or variant proteins exhibited normal growth and development.

An example of a plastid or chloroplast targeting peptide (CTP) is a chloroplast targeting peptide. Chloroplast targeting peptides have been found particularly useful in the glyphosate resistant selectable marker system. In this system plants transformed to express a protein conferring glyphosate resistance are transformed with a PTP that targets the peptide to the cell's cholorplasts. Glyphosate inhibits the shikimic acid pathway which leads to the biosynthesis of aromatic compounds including amino acids and vitamins. Specifically, glyphosate inhibits the conversion of phosphoenolpyruvic acid and 3-phosphoshikimic acid to 5-enolpyruvyl-3-phosphoshikimic acid by inhibiting the enzyme 5-enolpyruvyl-3-phosphoshikimic acid synthase (EPSP synthase or EPSPS). Supplemental EPSPS, conferred via insertion of a transgene encoding this enzyme, allows the cell to resist the effects of to the gylphosate. Thus, as the herbicide glyphosate functions to kill the cell by interrupting aromatic amino acid biosynthesis, particularly in the cell's chloroplast, the CTP allows increased resistance to the herbicide by concentrating what glyphosate resistance enzyme the cell expresses in the chloroplast, i.e. in the target organelle of the cell. Exemplary herbicide resistance enzymes include EPSPS as noted above, glyphosate oxido-reductase (GOX) and the aro-A gene (U.S. Pat. No. 4,535,060).

CTP's can target proteins to chloroplasts and other plastids. For example, the target organelle may be the amyloplast. Preferred CTP's of the present invention include those targeting both chloroplasts as well as other plastids. Specific examples of preferred CTP's include the maize RUBISCO SSU protein CTP, and functionally related peptides. An exemplary CTP polypeptide is shown in SEQ ID NO:26. A polynucleotide sequence encoding for this CTP polypeptide is shown in SEQ ID NO:25.

The expression of a gene which exists in double-stranded DNA form involves transcription of messenger RNA (mRNA) from the coding strand of the DNA by an RNA polymerase enzyme, and the subsequent processing of the mRNA primary transcript inside the nucleus. Transcription of DNA into mRNA is regulated by a region of DNA usually referred to as the "promoter". The promoter region contains a sequence of bases that signals RNA polymerase to associate with the DNA and to initiate the transcription of mRNA using one of the DNA strands as a template to make a corresponding strand of RNA. The particular promoter selected should be capable of causing sufficient expression of the enzyme coding sequence to result in the production of an effective insecticidal amount of the B. thuringiensis protein.

The 3' non-translated region of the chimeric plant genes of the present invention also contains a polyadenylation signal which functions in plants to cause the addition of adenylate nucleotides to the 3' end of the RNA. Examples of preferred 3' regions are (1) the 3' transcribed, non-translated regions containing the polyadenylation signal of *Agrobacterium* tumor-inducing (Ti) plasmid genes, such as the nopaline synthase (NOS) gene and (2) the 3' ends of plant genes such as the pea ssRUBISCO E9 gene (Fischhoff et al., 1987).

A promoter is selected for its ability to direct the transformed plant cell's or transgenic plant's transcriptional activity to the coding region, to ensure sufficient expression of the enzyme coding sequence to result in the production of insecticidal amounts of the *B. thuringiensis* protein. Structural genes can be driven by a variety of promoters in plant tissues. Promoters can be near-constitutive (i.e. they drive transcription of the transgene in all tissue), such as the CaMV35S promoter, or tissue-specific or developmentally specific promoters affecting dicots or monocots. Where the promoter is a near-constitutive promoter such as CaMV35S or FMV35S, increases in polypeptide expression are found in a variety of transformed plant tissues and most plant organs (e.g., callus, leaf, seed and root). Enhanced or duplicate versions of the CaMV35S and FMV35S promoters are particularly useful in the practice of this invention (Kay et al., 1987; Rogers, U.S. Pat. No. 5,378,619). Tandemly duplicated enhancer sequences have been demonstrated to be of particular significance, for example, as described in Neuhaus et al. (Tissue-specific expression from promoter AS-1 in transgenic tobacco. Plant Cell 6:827-834; 1994).

Those skilled in the art will recognize that there are a number of promoters which are active in plant cells, and have been described in the literature. Such promoters may be obtained from plants or plant viruses and include, but are not limited to, the nopaline synthase (NOS) and octopine synthase (OCS) promoters (which are carried on tumor-inducing plasmids of *A. tumefaciens*), the cauliflower mosaic virus (CaMV) 19S and 35S promoters, the light-inducible promoter from the small subunit of ribulose 1.5-bisphosphate carboxylase (ssRUBISCO, a very abundant plant polypeptide), the rice Act1 promoter, POX promoter, yellow mottle virus promoter, ScBV virus early promoter, the Figwort Mosaic Virus (FMV) 35S promoter, and the AS4 35S promoter (root enhanced expression from 35S promoter linked to multiple tandem as-1 sequences as in Neuhaus et al.). All of these promoters have been used to create various types of DNA constructs which have been expressed in plants (see e.g., McElroy et al., 1990. U.S. Pat. No. 5,463,175).

In addition, it may also be preferred to bring about expression of the *B. thuringiensis* δ-endotoxin in specific tissues of the plant by using plant integrating vectors containing a tissue-specific promoter. Specific target tissues may include the leaf, stem, root, tuber, seed, fruit, etc., and the promoter chosen should have the desired tissue and developmental specificity. Therefore, promoter function should be optimized by selecting a promoter with the desired tissue expression capabilities and approximate promoter strength and selecting a transformant which produces the to desired insecticidal activity in the target tissues. This selection approach from the pool of transformants is routinely employed in expression of heterologous structural genes in plants since there is variation between transformants containing the same heterologous gene due to the site of gene insertion within the plant genome (commonly referred to as "position effect"). In addition to promoters which are known to cause transcription (constitutive or tissue-specific) of DNA in plant cells, other promoters may be identified for use in the current invention by screening a plant cDNA library for genes which are selectively or preferably expressed in the target tissues and then determine the promoter regions.

An exemplary tissue-specific promoter is the lectin promoter, which is specific for seed tissue. The lectin protein in soybean seeds is encoded by a single gene (Le1) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983, Lindstrom et al., 1990). An expression vector containing a coding region that encodes a polypeptide of interest can be engineered to be under control of the lectin promoter and that vector may be introduced into plants using, for example, a protoplast transformation method (Dhir et al., 1991). The expression of the polypeptide would then be directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Other exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP carboxylase (Poulsen et al., 1986; Cashmore et al., 1983), Ti plasmid mannopine synthase (McBride and Summerfelt, 1989), Ti plasmid nopaline synthase (Langridge et al., 1989), *petunia* chalcone isomerase (Van Tunen et al., 1988), bean glycine rich protein 1 (Keller et al., 1989), CaMV 35s transcript (Odell et al., 1985) and Potato patatin (Wenzler et al., 1989). Preferred promoters are the cauliflower mosaic virus (CaMV 35S) promoter and the S-E9 small subunit RuBP carboxylase promoter.

The promoters used in the DNA constructs of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression. Examples of such enhancer sequences have been reported by Kay et al. (1987) and Neuhaus et al. (1994).

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNAs, from suitable eukaryotic genes, or from a synthetic gene sequence. The present invention is not limited to constructs wherein the non-translated region is derived from the 5' non-translated sequence that accompanies the promoter sequence. As shown below, a plant gene leader sequence which is useful in the present invention is the petunia heat shock protein 70 (hsp70) leader (Winter et al., 1988), the wheat CAB leader or the wheat PER leader.

An exemplary embodiment of the invention involves the plastid targeting of the *B. thuringiensis* sequence. Such plastid targeting sequences have been isolated from numerous nuclear encoded plant genes and have been shown to direct importation of cytoplasmically synthesized proteins into plastids (reviewed in Keegstra and Olsen, 1989). A variety of plastid targeting sequences, well known in the art, including but not limited to ADPGPP, EPSP synthase, or ssRUBISCO, may be utilized in practicing this invention. In alternative embodiments preferred, plastidic targeting sequences (peptide and nucleic acid) for monocotyledonous crops may consist of a genomic fragment coding containing art intronic sequence as well as a duplicated proteolytic cleavage site in the encoded plastidic targeting sequences.

The most preferred CTP encoding nucleic acid sequence, referred to herein as zmSSU CTP (SEQ ID NO:25), consisting of a genomic fragment containing an intronic sequence as well as a duplicated proteolytic cleavage site in the encoded plastidic targeting sequences, was derived from plastidic targeting sequence zmS1 (Russell et al., 1993). Direct translational fusions of zmSSU CTP peptide sequence (SEQ ID NO:26) to the amino terminus of the sequence has been shown to be useful in obtaining elevated levels of the polypeptide in transgenic maize. In-frame fusions of the zmSSU CTP nucleic acid sequence (SEQ ID NO:25) to a cry3b gene (SEQ ID NO:1) or gene variant can be effected by ligation of an NcoI site engineered into the 3' (C-terminal encoding) end of the zmSSU CTP sequence to a 5' NcoI site engineered into the N-terminal encoding end of the cry3B or variant coding sequence.

The preferred CTP sequence for dicotyledonous crops consists of a genomic coding fragment containing the chloroplast targeting peptide sequence from the EPSP synthase gene of *Arabidopsis thaliana* in which the transit peptide cleavage site of the pea ssRUBISCO CTP replaces the native EPSP synthase CTP cleavage site (Klee et al., 1987).

As noted above, the 3' non-translated region of the chimeric plant genes of the present invention contains a polyadenylation signal which functions in plants to cause the addition of adenylate nucleotides to the 3' end of the RNA. Examples of preferred 3' regions are (1) the 3' transcribed, non-translated regions containing the polyadenylate signal of *Agrobacterium* tumor-inducing (Ti) plasmid genes, such as the nopaline synthase (NOS) gene and (2) plant genes such as the pea ssRUBISCO E9 gene (Fischhoffet et al., 1987).

For optimized expression in monocotyledonous plants, an intron may also be included in the DNA expression construct. Such an intron is typically placed near the 5'-end of the mRNA in an untranslated sequence. This intron could be obtained from, but not limited to, a set of introns consisting of the maize Heat Shock Protein (HSP) 70 intron (U.S. Pat. No. 5,424,412; 1995), the rice Act1 intron (McElroy et al., 1990), the Adh intron 1 (Callis et al., 1987), or the sucrose synthase intron (Vasil et al., 1989). As shown herein, the maize HSP70 intron (SEQID NO:33) and the rice actin intron (SEQID NO:32) are particularly useful in the present invention.

RNA polymerase transcribes through a coding DNA sequence to a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Constructs will typically include the gene of interest along with a 3' end DNA sequence that acts as a signal to terminate transcription and allow for the poly-adenylation of the resultant mRNA. The most preferred 3' elements are contemplated to be those from the nopaline synthase gene of *A. tumefaciens* (nos 3' end) (Bevan et al., 1983), the terminator for the T7 transcript from the octopine synthase gene of *A. tumefaciens*, and the 3' end of the protease inhibitor i or ii genes from potato or tomato. Regulatory elements such as TMV Ω element (Gallie, et al., 1989), may further be included where desired.

Another type of element which can regulate gene expression is the DNA sequence-between the transcription initiation site and the start of the coding sequence, termed the untranslated leader sequence. The leader sequence can influence gene expression. Compilations of leader sequences have been made to predict optimum or sub-optimum sequences and generate "consensus" and preferred leader sequences (Joshi, 1987). Preferred leader sequences are contemplated to include those which comprise sequences predicted to direct optimum expression of the linked structural gene. i.e. to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants and in maize in particular, will be most preferred. One particularly preferred leader may be the wheat CAB leader (SEQ ID NO:31).

Transcription enhancers or duplications of enhancers could be used to increase expression. These enhancers often are found 5' to the start of transcription in a promoter that functions in eukaryotic cells, but can often be inserted in the forward or reverse orientation 5' or 3' to the coding sequence. Examples of enhancers include elements from the CAMV 35S promoter, octopine synthase genes (Ellis et al., 1987), the rice actin gene, and promoter from non-plant eukaryotes (e.g., yeast; Ma et al., 1988).

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *A. tumefaciens* described (Rogers et al., 1987). However, several other plant integrating vector systems are known to function in plants including pCaMVCN transfer control vector described (Fromm et a., 1985). pCaMVCN (available from Pharmacia, Piscataway, N.J.) includes the CaMV35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e. the chimeric gene containing the nopaline synthase promoter, Tn5 neomycin phosphotransferase II (nptII) and nopaline synthase 3' non-translated region described (Rogers et al., 1988).

Means for preparing expression vectors are well known in the art. Expression (transformation) vectors used to transform plants and methods of making those vectors are described in U S. Pat. Nos. 4,971,908, 4,940,835, 4,769,061 and 4,757, 011. Those vectors can be modified to include a coding sequence in accordance with the present invention.

A coding region that encodes a polypeptide having the ability to confer insecticidal activity to a cell is preferably a polynucleotide encoding a *B. thuringiensis* δ-endotoxin or a functional equivalent of such a polynucleotide. In accordance with such embodiments, a coding region comprising the DNA sequences of SEQ ID NO:1, SEQ ID NO:3, SEQ ID NO:5, SEQ ID NO:7, SEQ ID NO:9, and SEQ ID NO:11 are also preferred.

Specific *B. thuringiensis* δ-endotoxin polypeptide-encoding ORF's contained within expression cassettes that have been shown to to express the *B. thuringiensis* δ-endotoxins at high levels in transformed plants. Preferred cassettes include those contained in plasmids pMON33709, pMON33710, pMON33722, pMON33723, pMON25096, pMON25097, pMON33741, and pMON33748. The expression cassettes in these plasmids are respectively encoded for by the sequences shown in SEQ ID NO:13, SEQ ID NO:15, SEQ ID NO:36, SEQ ID NO:38, SEQ ID NO:17, SEQ ID NO:19, SEQ ID NO:21, and SEQ ID NO:23. More preferably, plants may be successfully transformed with any expression cassettes comprising the nucleotide sequences of nucleotide 14 to 3431 of SEQ ID NO:36, 14 to 3025 of SEQ ID NO:38, 14 to 3431 of SEQ ID NO:17, 14 to 3020 of SEQ ID NO:19, 14 to 3020 of SEQ ID NO:21, or 25 to 3450 of SEQ ID NO:23 (pMON33722, pMON33723, pMON25096, pMON25097, pMON33741, and pMON33748). Most preferably, plants may be successfully transformed with any expression cassettes comprising the nucleotide sequences of nucleotide 14 to 3431 of SEQ ID NO:17, 14 to 3020 of SEQ ID NO:19, 14 to 3020 of SEQ ID NO:21, or 25 to 3450 of SEQ ID NO:23 (pMON25096, pMON25097, pMON33741, and pMON33748).

The work described herein has identified methods of potentiating in planta expression of *B. thuringiensis* δ-endotoxins, which confer resistance to insect pathogens when incorporated into the genome of susceptible plants. U.S. Pat. No. 5,500,365 describes a method for synthesizing plant genes to optimize the expression level of the protein for which the synthesized gene encodes. This method relates to the modification of the structural gene sequences of the exogenous transgene, to make them more "plant-like" and therefore more likely to be translated and expressed by the plant. A similar method for enhanced expression of transgenes in monocotyledonous plants is disclosed in U.S. Pat. No. 5,689, 052. Agronomic, horticultural, ornamental, and other economically or commercially useful plants can be made in accordance with the methods described herein, to express *B. thuringiensis* δ-endotoxins at levels high enough to confer resistance to insect pathogens.

Such plants may co-express the *B. thuringiensis* δ-endotoxin polypeptide along with other antifungal, antibacterial or antiviral pathogenesis-related peptides, polypeptides, or proteins insecticidal proteins; proteins conferring herbicide resistance; and proteins involved in improving the quality of plant products or agronomic performance of plants. Simultaneous co-expression of multiple proteins in plants is advantageous in that it exploits more than one mode of action to control plant pathogenic damage. This can minimize the possibility of developing resistant pathogen strains, broaden the scope of resistance, and potentially result in a synergistic insecticidal effect, thereby enhancing plants ability to resist insect infestation (WO 92/17591).

Ultimately, the most desirable DNA segments for introduction into a monocot genome may be homologous genes or gene families which encode a desired trait (for example, increased yield), and which are introduced under the control of novel promoters or enhancers, etc., or perhaps even homologous or tissue specific (e.g., root-collar/sheath-, whorl-, stalk-, earshank-, kernel- or leaf-specific) promoters or control elements. Indeed, it is envisioned that a particular use of the present invention may be the production of transformants comprising a transgene which is targeted in a tissue-specific manner. For example, insect resistant genes may be expressed specifically in the whorl and collar/sheath tissues which are targets for the first and second broods, respectively, of ECB. Likewise, it is desireable that genes encoding proteins with particular activity against rootworm be preferentially expressed in root tissues.

Vectors for use in tissue-specific targeting of gene expression in transgenic plants typically will include tissue-specific promoters and also may include other tissue-specific control elements such as enhancer sequences. Promoters which direct specific or enhanced expression in certain plant tissues will be known to those of skill in the art in light of the present disclosure.

It also is contemplated that tissue specific expression may be functionally accomplished by introducing a constitutively expressed gene (all tissues) in combination with an antisense gene that is expressed only in those tissues where the gene product is not desired. For example, a gene coding for the crystal toxin protein from B. thuringiensis may be introduced such that it is expressed in all tissues using the 35S promoter from Cauliflower Mosaic Virus. Alternatively, a rice actin promoter or a histone promoter from a dicot or monocot species also could be used for constitutive expression of a gene. Furthermore, it is contemplated that promoters combining elements from more than one promoter may be useful. For example, U.S. Pat. No. 5,491,288 discloses combining a Cauliflower Mosaic Virus promoter with a histone promoter. Therefore, expression of an antisense transcript of a Bt δ-endotoxin gene in a maize kernel, using for example a zein promoter, would prevent accumulation of the δ-endotoxin in seed. Hence the protein encoded by the introduced gene would be present in all tissues except the kernel. It is specifically contemplated by the inventors that a similar strategy could be used with the instant invention to direct expression of a screenable or selectable marker in seed tissue.

Alternatively, one may wish to obtain novel tissue-specific promoter sequences for use in accordance with the present invention. To achieve this, one may first isolate cDNA clones from the tissue concerned and identify those clones which are expressed specifically in that tissue, for example, using Northern blotting. Ideally, one would like to identify a gene that is not present in a high copy number, but which gene product is relatively abundant in specific tissues. The promoter and control elements of corresponding genomic clones may thus be localized using the techniques of molecular biology known to those of skill in the art.

It is contemplated that expression of some genes in transgenic plants will be desired only under specified conditions. For example, it is proposed that expression of certain genes that confer resistance to environmentally stress factors such as drought will be desired only under actual stress conditions. It further is contemplated that expression of such genes throughout a plants development may have detrimental effects. It is known that a large number of genes exist that respond to the environment. For example, expression of some genes such as rbcS, encoding the small subunit of ribulose bisphosphate carboxylase, is regulated by light as mediated through phytochrome. Other genes are induced by secondary stimuli. For example, synthesis of abscisic acid (ABA) is induced by certain environmental factors, including but not limited to water stress. A number of genes have been shown to be induced by ABA (Skriver and Mundy, 1990). It also is expected that expression of genes conferring resistance to insect predation would be desired only under conditions of actual insect infestation. Therefore, for some desired traits, inducible expression of genes in transgenic plants will be desired.

It is proposed that, in some embodiments of the present invention, expression of a gene in a transgenic plant will be desired only in a certain time period during the development of the plant. Developmental timing frequently is correlated with tissue specific gene expression. For example expression of zein storage proteins is initiated in the endosperm about 15 days after pollination.

It is contemplated that the method described in this invention could be used to obtain substantially improved expression of a number of novel B. thuringiensis endotoxins isolated as described below. Identification of new Bacillus thuringiensis strains encoding crystalline endotoxins with insecticidal activity has been described previously (Donovan et al., 1992). Isolation of the B. thuringiensis endotoxin, followed by amino terminal amino acid sequencing, back-translation of the amino acid sequence to design an oligonucleotide probe or use of a related B. thuringiensis gene as a probe, followed by cloning of the gene encoding the endotoxin by hybridization are familiar to those skilled in the art and have been described (see e.g., Donovan et al., 1992, U.S. Pat. No. 5,264,364). Cry3Bb Bacillus thuringiensis δ-endotoxins with improved Coleopteran inhibitory activity can be achieved using the methods described in English et al. (WO 99/31248).

A plant transformed with an expression vector of the present invention is also contemplated. A transgenic plant derived from such a transformed or transgenic cell is also contemplated. Those skilled in the art will recognize that a chimeric plant gene containing a structural coding sequence of the present invention can be inserted into the genome of a plant by methods well known in the art. Such methods for DNA transformation of plant cells include Agrobacterium-mediated plant transformation, the use of liposomes, transformation using viruses or pollen, electroporation, protoplast transformation, gene transfer into pollen, injection or vacuum infiltration (Bechtold et al., Meth. Mo. Biol., 82:259-266; 1998) into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

Technology for introduction of DNA into cells is well-known to those of skill in the art. Four general methods for delivering a gene into cells have been described: (1) chemical methods (Graham and van der Eb, 1973); (2) physical methods such as microinjection (Capecchi, 1980), electroporation (Wong and Neumann, 1982; Fromm et al., 1985) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

An advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like. Using these particles, DNA is carried through the cell wall and into the cytoplasm on the surface of small metal particles as described (Klein et al., 1987; Klein et al., 1988; Kawata et al., 1988). The metal particles penetrate through several layers of cells and thus allow the transformation of cells within tissue explants.

An advantage of microprojectile bombardment, in addition to it being an effective means of reproducibly stably transforming plant cells, is that neither the isolation of protoplasts (Cristou et al., 1988) nor the susceptibility to Agrobacterium infection is required. An illustrative embodiment of a method for delivering DNA into plant cells by acceleration is a Biolistics Particle Delivery System, which can be used to propel particles coated with DNA or cells through a screen, such as a stainless steel or Nytex screen, onto a filter surface covered with the plant cultured cells in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature plant embryos.

Accordingly, it is contemplated that one may desire to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

The methods of particle-mediated transformation is well-known to those of skill in the art. U.S. Pat. No. 5,015,580 describes the transformation of soybeans using such a technique.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described (Fraley et al., 1985; Rogers et al., 1987). The genetic engineering of cotton plants using Agrobacteriun-mediated transfer is described in U.S. Pat. No. 5,004,863; like transformation of lettuce plants is described in U.S. Pat. No. 5,349,124: and the Agrobacterium-mediated transformation of soybean is described in U.S. Pat. No. 5,416,011. Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern Agrobacterium transformation vectors are capable of replication in E. coli as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant varieties where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described (Bytebier et al., 1987). Other monocots recently have also been transformed with Agrobacterium. Included in this group are corn (Ishida et al.) and rice (Cheng et al.).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added exogenous gene segregates independently during mitosis and meiosis.

An independent segregant may be preferred when the plant is commercialized as a hybrid, such as corn. In this case an independent segregant containing the gene is crossed with another plant, to form a hybrid plant that is heterozygous for the gene of interest.

An alternate preference is for a transgenic plant that is homozygous for the added structural gene; i.e. a transgenic plant that contains two added genes, one gene at the same locus on each chromosome of a chromosome pair. A homozygous transgenic plant can be obtained by sexually mating (selling) an independent segregant transgenic plant that contains a single added gene, germinating some of the seed produced and analyzing the resulting plants produced for gene of interest activity and mendelian inheritance indicating homozygosity relative to a control (native, non-transgenic) or an independent segregant transgenic plant.

Two different transgenic plants can be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments (see e.g., Potrykus et al., 1985; Lorz et al, 1985; Fromm et al., 1985; Uchimiya et al., 1986; Callis et al., 1987; Marcotte et al., 1988). Application of these systems to different plant germplasm depends upon the ability to regenerate that particular plant variety from protoplasts. Illustrative methods for the regeneration of cereals from protoplasts are described (see, e.g., Fujimura et at., 1985; Toriyama et al., 1986; Yamada et al., 1986; Abdullah et al., 1986). To transform plant germplasm that cannot be successfully regenerated from protoplasts, other ways to introduce DNA into intact cells or tissues can be utilized. For example, regeneration of cereals from immature embryos or explants can be effected as described (Vasil, 1988). DNA can also be introduced into plants by direct DNA transfer into pollen as described (Zhou et al., 1983; Hess, 1987). Expression of polypeptide coding genes can be obtained by injection of the DNA into reproductive organs of a plant as described (Pena et al., 1987). DNA can also be injected directly into the cells of immature embryos and the rehydration of desiccated embryos as described (Neuhaus et al., 1987; Benbrook et al., 1986).

Unmodified bacterial genes are often poorly expressed in transgenic plant cells. Several reports have disclosed methods for improving expression of recombinant genes in plants (Murray et al., 1989; Diehn et al., 1996; lannacone et al., 1997; Rouwendal et al., 1997; Futterer et al., 1997; and Futterer and Hohn, 1996). These reports disclose various methods for engineering coding sequences to represent sequences which are more efficiently translated based on plant codon frequency tables, improvements in codon third base position bias, using recombinant sequences which avoid suspect polyadenylation or A/T rich domains or intron splicing consensus sequences. While these methods for synthetic gene construction are notable, synthetic genes of the present invention were prepared according to the method of Brown et al., (U.S. Pat. No. 5,689,052; 1997). Thus, the present invention provides a method for preparing synthetic plant genes express in planta a desired protein product at levels significantly higher than the wild-type genes. Briefly, according to Brown et al., the frequency of rare and semi-rare monocotyledonous codons in a polynucleotide sequence encoding a desired protein are reduced and replaced with more preferred monocotyledonous codons. Enhanced accumulation of a desired polypeptide encoded by a modified polynucleotide sequence in a monocotyledonous plant is the result of increasing the frequency of preferred codons by analyzing the coding sequence in successive six nucleotide fragments and altering the sequence based on the frequency of appearance of the six-mers as to the frequency of appearance of the rarest 284, 484, and 664 six-mers in monocotyledenous plants. Furthermore, Brown et al. disclose the enhanced expression of a recombinant gene by applying the method for reducing the frequency of rare codons with methods for reducing the occurrence of polyadenylation signals and intron splice sites in the nucleotide sequence, removing self-complementary sequences in the nucleotide sequence and replacing such sequences with non-self-complementary nucleotides while maintaining a structural gene encoding the polypeptide, and reducing the frequency of occurrence of 5'-CG-3' dinucleotide pairs in the nucleotide sequence. These steps are performed sequentially and have a cumulative effect resulting in a nucleotide sequence containing a preferential utilization of the more-preferred monocotyledonous codons for monocotyledonous plants for a majority of the amino acids present in the desired polypeptide.

Thus, the amount of a gene coding for a polypeptide of interest (i.e. a bacterial crystal protein or δ-endotoxin polypeptide or such δ-endotoxin linked to a plastid targeting peptide) can be increased in plants by transforming those plants using transformation methods such as those disclosed herein.

After effecting delivery of exogenous DNA to recipient cells, the next step to obtain a transgenic plant generally concern identifying the transformed cells for further culturing and plant regeneration. As mentioned herein, in order to improve the ability to identify transformants, it is preferable to employ a selectable or screenable marker gene as, or in addition to, the expressible gene of interest. In this case, one would then generally assay the potentially transformed cell population by exposing the cells to a selective agent or agents, or one would screen the cells for the desired marker gene trait.

An exemplary embodiment of methods for identifying transformed cells involves exposing the transformed cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing. One example of a preferred marker gene encoding an EPSPS synthase which is resistant to glyphosate inhibition. When this gene is used as a selectable marker, the putatively transformed cell culture is treated with glyphosate. Upon treatment, transgenic cells will be available for further culturing while sensitive, or non-transformed cells, will not. This method is described in detail in U.S. Pat. No. 5,569,834. Another example of a preferred selectable marker system is the nptII system by which resistance to the antibiotics kanamycin, neomycin, and paromomycin or related antibiotics is conferred, as described in U.S. Pat. No. 5,569,834. Again, after transformation with this system transformed cells containing a plant expressible nptII gene will be available for further culturing upon treatment with kanamycin or related antibiotic, while non-transformed cells will not. Use of this type of a selectable marker system is described in Brown et al. (U.S. Pat. No. 5,424,412). Another screenable marker which may be used is the gene coding for green fluorescent protein. All contemplated assays are nondestructive and transformed cells may be cultured further following identification.

It is further contemplated that combinations of screenable and selectable markers will be useful for identification of transformed cells. In some cell or tissue types a selection agent, such as glyphosate or kanamycin, may either not provide enough killing activity to clearly recognize transformed cells or may cause substantial nonselective inhibition of transformants and non-transformants alike, thus causing the selection technique to not be effective. It is proposed that selection with a growth inhibiting compound, such as glyphosate at concentrations below those that cause 100% inhibition followed by screening of growing tissue for expression of a screenable marker gene such as kanamycin would allow one to recover transformants from cell or tissue types that are not amenable to selection alone. It is proposed that combinations of selection and screening may enable one to identify transformants in a wider variety of cell and tissue types.

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983). In particular, U.S. Pat. No. 5,349,124 details the creation of genetically transformed lettuce cells and plants resulting therefrom which express hybrid crystal proteins conferring insecticidal activity against *Lepidopteran* larvae to such plants. This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

A transgenic plant of this invention thus has an increased amount of a coding region encoding a *B. thuringiensis* δ-endotoxin polypeptide or variant thereof or may encode such a δ-endotoxin linked to a plastid targeting peptide. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for increased expression of the transgene encoding the δ-endotoxin.

To identify a transgenic plant expressing high levels of the δ-endotoxin of interest, it is necessary to screen the herbicide or antibiotic resistant transgenic, regenerated plants ($R_0$ generation) for insecticidal activity and/or expression of the gene of interest. This can be accomplished by various methods well known to those skilled in the art, including but not limited to: 1) obtaining small tissue samples from the transgenic $R_0$ plant and directly assaying the tissue for activity against susceptible insects in parallel with tissue derived from a non-expressing, negative control plant. For example, $R_0$ transgenic corn plants expressing *B. thuringiensis* endotoxins such as Cry3B can be identified by assaying leaf tissue or root tissue derived from such plants for activity against CRW; 2) analysis of protein extracts by enzyme linked immunoassays (ELISAs) specific for the gene of interest (Cry3B); or 3) reverse transcriptase thermal amplification to identify events expressing the gene of interest.

The genes and δ-endotoxins according to the subject invention include not only the full length sequences disclosed herein but also fragments of these sequences, or fusion proteins, which retain the characteristic insecticidal activity of the sequences specifically exemplified herein.

It should be apparent to a person of skill in the art that insecticidal δ-endotoxins can be identified and obtained through several means. The specific genes, or portions thereof, may be obtained from a culture depository, or constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these δ-endotoxins.

Equivalent δ-endotoxins and/or genes encoding these δ-endotoxins can also be isolated from *Bacillus* strains and/or DNA libraries using the teachings provided herein. For example, antibodies to the δ-endotoxins disclosed and claimed herein can be used to identify and isolate other δ-endotoxins from a mixture of proteins. Specifically, antibodies may be raised to the portions of the δ-endotoxins which are most constant and most distinct from other *B. thuringiensis* δ-endotoxins. These antibodies can then be used to specifically identify equivalent δ-endotoxins with the characteristic insecticidal activity by immunoprecipitation, enzyme linked immunoassay (ELISA), or Western blotting.

A further method for identifying the δ-endotoxins and genes of the subject invention is through the use of oligonucleotide probes. These probes are nucleotide sequences having a detectable label. As is well known in the art, if the probe molecule and nucleic acid sample hybridize when together in a sample by forming hydrogen bonds between the two molecules, it can be reasonably assumed that the probe and sample are essentially identical or substantially similar or homologous at least along the length of the probe. The probe's detectable label provides a means for determining in a known manner whether hybridization has occurred. Such a probe analysis provides a rapid method for identifying insecticidal δ-endotoxin genes of the subject invention.

Duplex formation and stability depend on substantial complementary between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations. insertions, and deletions can be produced in a given polynucleotide sequence in many ways, by methods currently known to an ordinarily skilled artisan, and perhaps by other methods which may become known in the future.

The potential variations in the probes listed is due, in part, to the redundancy of the genetic code. Because of the redundancy of the genetic code, more than one coding nucleotide triplet (codon) can be used for most of the amino acids used to make proteins. Therefore different nucleotide sequences can code for a particular amino acid. Thus, the amino acid sequences of the *B. thuringiensis* δ-endotoxins and peptides, and the plastid targeting peptides and the polynucleotides which code for them, can be prepared by equivalent nucleotide sequences encoding the same amino acid sequence of the protein or peptide.

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage or plasmids containing an M13 origin of replication. These phage are readily commercially available and their use is generally well known to those skilled in the art.

Modification and changes may be made in the structure of the peptides of the present invention and DNA segments which encode them and still obtain a functional molecule that encodes a protein or peptide with desirable characteristics. The biologically functional equivalent peptides, polypeptides, and proteins contemplated herein should possess about 80% or greater sequence similarity, preferably about 85% or greater sequence similarity, and most preferably about 90% or greater sequence similarity, to the sequence of, or corresponding moiety within, the fundamental Cry3B amino acid sequence.

The following is a discussion based upon changing the amino acids of a protein to create an equivalent, or even an improved, second-generation molecule. In particular embodiments of the invention, mutated crystal proteins are contemplated to be useful for increasing the insecticidal activity of the protein, and consequently increasing the insecticidal activity and/or expression of the recombinant transgene in a plant cell. The amino acid changes may be achieved by changing the codons of the DNA sequence, according to the codons given in readily available amino acid codon tables.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is known in the art that certain amino acids may be substituted by other amino acids having a similar hydropathic index or score and still result in a protein with similar biological activity, i.e. still obtain a biological functionally equivalent protein. It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. It is understood that an amino acid can be substituted for another having a similar hydrophilicity value and still obtain a biologically equivalent, and in particular, an immunologically equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Polynucleotides encoding δ-endotoxins derived from B. thuringiensis are known by those skilled in the art, to be poorly expressed when incorporated into the nuclear DNA of transgenic plants (reviewed by Diehn et al., 1996). Preferably, a nucleotide sequence encoding the δ-endotoxin of interest is designed essentially as described in U.S. Pat. Nos. 5,500,365 and 5,689,052. Examples of nucleotide sequences useful for expression include but are not limited to, cry3B (SEQ ID NO:5), cry3Bb1 (SEQ ID NO:1), cry3Bb2 (SEQ ID NO:3), v11231 (SEQ ID NO:7), 11231mv1 (SEQ ID NO:9), and 11231mv2 (SEQ ID NO:11).

Peptides, polypeptides, and proteins biologically functionally equivalent to Cry3B include amino acid sequences containing conservative amino acid changes in the fundamental sequence shown in SEQ ID NO:2, SEQ ID NO:4, SEQ ID NO:8., SEQ ID NO:10, and SEQ ID NO:12 (Cry3Bb1, Cry3Bb2, v11231, 11231mv1, 11231mv2, Cry3Bb.11231, or Cry3Bb.11098, etc). In such amino acid sequences, one or more amino acids in the fundamental sequence is (are) substituted with another amino acid(s), the charge and polarity of which is similar to that of the native amino acid, i.e. a conservative amino acid substitution, resulting in a silent change.

Substitutes for an amino acid within the fundamental polypeptide sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine. histidine, and lysine; (3) neutral polar amino acids such as glycine, serine, threonine, cyteine, cystine, tyrosine, asparagine, and glutamine; (4) neutral nonpolar (hydrophobic) amino acids such as alanine, leucine, isoleucine, valine, proline, phenylalanine, tryptophan, and methionine.

Conservative amino acid changes within the fundamental polypeptide sequence can be made by substituting one amino acid within one of these groups with another amino acid within the same group. Biologically functional equivalents of Cry3B can have 10 or fewer conservative amino acid changes, more preferably seven or fewer conservative amino acid changes, and most preferably five or fewer conservative amino acid changes. The encoding nucleotide sequence (gene, plasmid DNA, cDNA, non-naturally occurring, or synthetic DNA) will thus have corresponding base substitutions, permitting it to encode biologically functional equivalent forms of Cry3B.

The present invention provides methods and compositions for expressing Coleopteran inhibitory Cry3B B. thuringiensis δ-endotoxins or amino acid sequence variants thereof at unexpectedly high levels in transgenic plants. The disclosed methods and compositions may exploit any of the DNA constructs disclosed as well as any of the transformation vectors disclosed herein. The contemplated methods and compositions enable Cry3Bb δ-endotoxins or amino acid sequence variants thereof to be expressed in plants without negatively affecting the recovery of agronomic qualities of transgenic plants. The inventions described herein also enables expression of Cry3B δ-endotoxins and variants at levels up to 500 times higher than that achieved by previous methods and compositions.

The methods described here thus enables plants expressing Cry3B or variants to be used as either an alternative or supplement to plants expressing other Cry proteins such as a Cry3B variant, a Cry3A or Cry3D or variant, CryET33 and CryET34 or variants thereof, a CryET70 or variant, a CryET29 or variant, a Cry6A or Cry6B or variant, a Cry8B or variant, insecticidal acyl lipid hydrolases, combinations of amino acid oxidases and tedanalactam synthases, and other insecticidal proteins such as VIP1 and VIP3 and various combinations isolated from *Heterorhabdus, Photorhabdus*, and *Xenorhabdus* species for both control and resistance management of key insect pests, including *Ostrinia* sp, *Diatraea* sp, *Diabrotica, Helicoverpa* sp, *Spodoptera* sp in *Zea mays*; *Heliothis virescens, Helicoverpa* sp, *Pectinophora* sp, in *Gossypium hirsutum*; and *Anticarsia* sp *Pseudoplusia* sp, *Epinotia* sp in *Glycine max*. It is also contemplated that the methods described may be used to dramatically increase expression of *B. thuringiensis* δ-endotoxins including and related to Cry3, thus increasing its effectiveness against target pests and decreasing the likelihood of evolved resistance to these proteins. In one embodiment of the present invention, a Cry3 δ-endotoxin is expressed. Target pests of this protein and their common hosts are shown below in Table 1.

TABLE 1

Target Pests Affected by Coleopteran Active (Inhibitory) Cry3B δ-Endotoxin and Common Plant Hosts of Those Pests

| Pests | Hosts |
|---|---|
| *Leptinotarsa decemlineata* (Colorado Potato Beetle) | Potato |
| *Diabrotica barberi* (Northern Corn Rootworm) | Corn |
| *Diabrotica undecimpunctata* (Southern Corn Rootworm) | Corn |
| *Diabrotica virgifera* (Western Corn Rootworm) | Corn |
| *Anthonomis grandis* (Boll Weevil) | Cotton |
| *Triboleum castaneum* (Red Flour Beetle) | Wheat |
| *Popilla japonica* (Japanese Flour Beetle) | Wheat |

Antibodies were required for studies comparing expression of various Cry3 coding sequences, so polyclonal serum was generated as follows. Cry3 Bt crystals were collected from a sporulated fermentation of *Bacillus thuringiensis* recombinant strain 11037 expressing native Cry3Bb. Crystals were solubilized in 100 mM sodium carbonate buffer, pH10.5, to give a concentration of 2.7 mg protein per mL as measured by a colorimetric bicinchoninic acid assay (Smith et al, 1985). A sample was diluted to a concentration of 0.4 mg/mL and mixed with an equal volume of Freund's complete adjuvant. A 1 milliliter inoculum of this mixture was used for the first intradermal injection into a rabbit. A first bleed was collected two weeks later. Subsequent injections of Cry3Bb protein designed to boost the immune titer were prepared by mixing equal volumes of 0.2 mg/mL protein with equal volumes of Freund's incomplete adjuvant. 1 milliliter injections were administered at four week intervals, and additional bleeds were obtained every two weeks. Immune serum adequate for analytical purposes was prepared from rabbit #783 after purification over a Protein A Sepharose CL4B affinity chromatography according to the manufacturers' instructions (Sigma Chemical Co, St. Louis, Mo.) and concentrated to 1 milligram of IgG protein per milliliter and stored in the dark at 4° C. A sample of this antiserum was conjugated to alkaline phosphatase enzyme for subsequent use in quantitative ELISA assays.

Leaf and root samples were collected from plants expressing Cry3Bb variant proteins 11231, 11084, 11098, and 11247. Extracts of plant samples were prepared as follows. Plant tissue, root or leaf parts, was harvested and weighed on a gram scale. Leaf tissue was mixed with 20 parts TBA buffer, weight to volume. Root tissue was mixed with 10 parts TBA buffer, weight to volume. Tissues were ground into an emulsion using a Wheaton™ overhead grinder and stored on ice or at −20° C. 250 microliters of rabbit anti-Cry3Bb antiserum diluted 1:1000 in carbonate coating buffer, pH9.6, was distributed onto each well of a 96-well microtiter plate and incubated overnight at 4° C. The plate was then washed with PBST (3×5 min). Tissue extract samples were loaded in duplicate at 20 microliters per well and at varying dilutions in order to obtain a value within a standard curve established using Cry3Bb variant 11231. Plates were incubated overnight at 4° C., then washed with PBST three times, five minutes each time. 50 microliters of the rabbit anti-Cry3B alkaline phosphatase conjugated polyclonal antibody was added to each well, followed by the addition of 180 uL of PBST containing 1% PVP-40 (Sigma). After overnight incubation, plates were washed with PBST (3×5 min) and developed with alkaline phosphatase color development solution consisting of 20 mg para-nitrophenyl phosphate in 25 mL diethanolamine, pH9.8, 200 uL/well). Plates were read at λ405 after 15-20 minutes, using a quadratic curve fit to a protein standard curve where the optical density of the highest standard was approximately 1.00.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Isolation, Characterization, and Identification of Cry3 Proteins and Genes, and Construction of Amino Acid Sequence Variants Thereof Means for identifying and characterizing *Coleopteran* toxic gene products are well documented in the art, and methods for isolating, characterizing and identifying the genes which encode such gene products are also well known in the art. In addition, the means for producing amino acid sequence variants of such *Coleopteran* toxic δ-endotoxin proteins are also well known. In particular, Van Rie et al. (U.S. Pat. No. 5,659,123; 1997) identify Cry3A and D toxins which exhibit *Coleopteran* inhibitory properties, and also set forth a method for identifying mutants which can be constructed which have reduced insecticidal activity with reference to the wild type protein. Van Rie et al. describe how those particular mutants can be further manipulated to identify amino acid sequence variant toxins which exhibit increased insecticidal activity with reference to the wild type protein. English et al. (WO 99/31248) describe other methods and compositions, in particular for Cry3B, which enable the identification of Cry3 encoding genes and gene products and the methods which can be used to construct and identify amino acid sequence variants exhibiting improved insecticidal activity with reference to that of the wild type Cry3 protein. Several coding sequences used herein were derived from those described in English et al. and the proteins produced from these coding sequences represent in particular the variants 11231 or 11098 as described therein.

5.2

Example 2

Construction of Monocot Plant Expression Vectors for the Cry3Bb Variants

Design of cry3Bb Variant Genes for Plant Expression:

For efficient expression of the Cry3Bb variants in transgenic plants, the gene encoding the variants must have a suitable sequence composition (Diehn et al, 1996). One example of such a sequence is shown for the v11231 gene (SEQID NO:7) which encodes the 11231 variant of the Cry3Bb protein (SEQID NO: 8) exhibiting *Diabroticus* activity. This gene was derived via mutagenesis (Kunkel, 1985) of a Cry3Bb synthetic gene (SEQID NO:5) encoding a protein essentially homologous to the protein encoded by the native Cry3Bb gene (Gen Bank Accession Number m89794; SEQID NO:1). The following oligonucleotides were used in the mutagenesis of the original Cry3Bb synthetic gene (SEQID NO:5) to create the v11231 gene (SEQID NO:7)

```
Oligo #1:
                                        (SEQID NO:40)
TAGGCCTCCATCCATGGCAAACCCTAACAATC Oligo #2:
                                        (SEQID NO:41)
TCCCATCTTCCTACTTACGACCCTGCAGAAATACGGTCCAAC Oligo #3:
                                        (SEQID NO:42)
GACCTCACCTACCAAACATTCGATCTTG Oligo #4:
                                        (SEQID NO:43)
CGAGTTCTACCGTAGGCAGCTCAAG
```

Construction of cry3Bb Monocot Plant Expression Vector:

To place the Cry3Bb variant gene v11231 in a vector suitable for expression in monocotyledonous plants (i.e. under control of the enhanced Cauliflower Mosaic Virus 35S promoter and linker to the hsp70 intron followed by a nopaline synthase polyadenylation site as in Brown and Santino U.S. Pat. No. 5,424,412; 1995), the vector pMON19469 was digested with NcoI and EcoRI. The larger vector band of approximately 4.6 kb was isolated after electrophoresis of the digestion products through an agarose gel, purified, and ligated with T4 DNA ligase to the NcoI-EcoRI fragment of approximately 2 kb containing the v11231 gene (SEQID NO:7). The ligation mix was transformed into a useful laboratory strain of *E coli*, and carbenicillin resistant colonies were recovered. Plasmid DNA was recovered by miniprep DNA procedures from subsequent overnight cultures of carbenicillin resistant colonies selected into broth containing antibiotics. This DNA was subjected to restriction endonuclease analysis with enzymes such as NcoI and EcoRI, NotI, and PstI to identify clones containing the v11231 coding sequence fused to the hsp70 intron under control of the enhanced CaMV35S promoter. Clones identified as such were designated as pMON33708.

To place the v11231 gene in a vector suitable for recovery of stably transformed and insect resistant plants, the 3.75 kb NotI restriction fragment from pMON33708 containing the lysine oxidase coding sequence fused to the hsp70 intron under control of the enhanced CaMV35S promoter was isolated and purified after extraction from an agarose gel. This fragment was ligated with pMON30460 treated with NotI and calf intestinal alkaline phosphatase. pMON30460 contains the neomycin phosphotransferase coding sequence under control of the CaMV35S promoter. Kanamycin resistant colonies were obtained by transformation of this ligation mix into *E. coli* and colonies containing the appropriate band were identified by restriction endonuclease digestion and designated as pMON33710. Restriction enzymes such as NotI, EcoRV, HindIII, NcoI, EcoRI, and BglII were used to identify the appropriate clones containing the NotI fragment of pMON33708 in the NotI site of pMON30460 (i.e. pMON33710) in the orientation such that both genes are in tandem (i.e. the 3' end of the v11231 expression cassette is linked to the 5' end of the nptII expression cassette). Expression of the v11231 protein by pMON33710 in corn protoplasts was confirmed by electroporation of pMON33710 covalently closed circular plasmid DNA into protoplasts followed by protein blot and ELISA analysis. This vector can be introduced into the genomic DNA of corn embryos by particle gun bombardment followed by paromomycin selection to obtain corn plants expressing the v11231 gene essentially as described in Brown and Santino U.S. Pat. No. 5,424,412. In this example, the vector was introduced into immature embryo scutella (IES) of maize via co-bombardment along with with a plasmid conferring hygromycin resistance, followed by hygromycin selection, and regeneration. Transgenic corn lines expressing the v11231 protein were identified by ELISA analysis scoring for both the presence and amount of v11231 protein present in each extract sample. Plants were selfed and allowed to go to seed. Progeny seed were cured and planted to produce seedling corn plants which were subsequently tested for protection from *Diabroticus* feeding.

In Plant Performance of Cry3Bb Variant 11231:

Transformed corn plants expressing Cry3Bb variant 11231 protein were challenged with western corn rootworm (WCR) larvae in both a seedling and 10 inch pot assay. The transformed genotype was A634, where the progeny of the R0 cross by A634 was evaluated. Observations included effect on larval development (weight), root damage rating (RDR), and protein expression. The transformation vector containing the Cry3Bb variant gene was pMON33710. Treatments included the positive and negative iso-populations for each event and an A634 check.

The seedling assay consisted of the following steps; i. single seeds were placed in 1 oz cups containing potting soil; ii. at spiking, each seedling was infested with 4 neonate larvae, and iii, after infestation, seedlings were incubated for 7 days at 25° C., 50% RH, and 14:10 (L:D) photo period. Adequate moisture was added to the potting soil during the incubation period to maintain seedling vigor.

The 10 inch pot assay consisted of the following steps; i. single seeds were placed in 10 inch pots containing potting soil; ii. at 14 days post planting, each pot was infested with 800 eggs which have been pre-incubated such that hatch would occur 5-7 days post infestation, and iii. after infestation, plants were incubated for 4 weeks under the same environmental conditions as the seedling assay. Pots were both sub & top irrigated daily.

For the seedling assay, on day 7 plants were given a root damage rating (Table 1.) and surviving larvae were weighed. Also at this time, Cry3Bb protein concentrations in the roots were determined by ELISA.

TABLE 1

Root Damage Rating Scale for seedling assay.

| RDR | 0 = no visible feeding |
| --- | --- |
| | 1 = very light feeding |
| | 2 = light feeding |
| | 3 = moderate feeding |
| | 4 = heavy feeding |
| | 5 = very heavy feeding |

Results of the seedling assay are shown in Table 2. Plants expressing Cry3Bb protein were completely protected by WCR feeding, where surviving larvae within this treatment had not grown. Mean larval weights ranged from 2.03-2.73 mg for the non-expressing treatments, where the surviving larval average weight was 0.11 mg on the expressing Cry3Bb treatment. Root damage ratings were 3.86 and 0.33 for the non-expressing and expressing iso-populations, respectively. Larval survival ranged from 75-85% for the negative and check treatments, where only 25% of the larvae survived on the Cry3Bb treatment.

TABLE 2

Effect of Cry3Bb expressing plants on WCR larvae in a seedling assay.

| | | Plants | | | Larvae | |
| --- | --- | --- | --- | --- | --- | --- |
| Event | Treatment | N | Root (ppm) | RDR ± SD | N | % Surv | Mean ± SD Wt. (mg) |
| 16 | Negative | 7 | 0.0 | 3.86 ± 0.65 | 21 | 75 | 2.73 ± 1.67 |
| 16 | Positive | 3 | 29.01 | 0.33 ± 0.45 | 3 | 25 | 0.11 ± 0.07 |
| A634 | Check | 4 | 0.0 | — | 13 | 81 | 2.03 ± 0.83 |

For the 10 inch pot assay, at 4 weeks post infestation plant height was recorded and a root damage rating was given (Iowa 1-6 scale; Hills, T. M. and D. C. Peters. 1971; A method of evaluating post planting insecticide treatments for control of western corn rootworm larvae. Journal of Economic Entomology 64: 764-765.).

Results of the 10 inch pot assay are shown in Table 3. Plants expressing Cry3Bb protein had significantly less feeding damage and were taller than the non-expressing plants. Event 16, the higher of the two expressing events provided nearly complete control. The negative treatments had very high root damage ratings indicating very high insect pressure. The positive mean root damage ratings were 3.4 and 2.2 for event 6 & 16, respectively. Mean RDR for the negative treatment was 5.0 & 5.6.

TABLE 3

Effect of Cry3Bb expressed in corn in controlling WCR larval feeding in a 10 inch pot assay.

| Event | Treatment | N | Root (ppm) | RDR ± SD | Plant Height (cm) |
| --- | --- | --- | --- | --- | --- |
| 6 | Negative | 7 | 0.0 | 5.0 ± 1.41 | 49.7 ± 18.72 |
| 6 | Positive | 5 | 7.0 | 3.4 ± 1.14 | 73.9 ± 8.67 |
| 16 | Negative | 5 | 0.0 | 5.6 ± 0.89 | 61.2 ± 7.75 |
| 16 | Positive | 5 | 55.0 | 2.2 ± 0.84 | 83.8 ± 27.15 |

In summary, corn plants expressing Cry3Bb protein have a significant biological effect on WCR larval development as seen in the seedling assay. When challenged with very high infestation levels, plants expressing the Cry3Bb protein were protected from WCR larval feeding damage as illustrated in the 10 inch pot assay.

Example 3

Increased Expression of a Cry3Bb Protein in Transgenic Maize

Expression of a Cry3Bb protein was compared in corn plants transformed with standard or preferred Cry3Bb expression vectors. Plants transformed with the improved vectors consistently demonstrated significantly higher levels of expression of Cry3Bb when compared to plants transformed with the standard Cry3Bb vectors. A standard Cry3Bb plant expression vector pMON33710 contains an expression cassette composed of an enhanced CaMV35S promoter sequence (P-CaMV.35S, SEQID NO:29), a Zea mays Hsp70 intron sequence (I-Zm.Hsp70, SEQID NO:33), a non-naturally occurring sequence encoding Cry3Bb variant protein v11231 (Bt.cry3Bb.v11231, SEQID NO: 7), and a nopaline synthase transcription termination and polyadenylation sequence (T-AGRtu.nos, SEQID NO:34). Another standard Cry3Bb plant expression vector pMON33709 contains an expression cassette composed of an enhanced CaMV35S promoter sequence (P-CaMV.35S, SEQID NO:29), a Zea mays Hsp70intron sequence (I-Zm.Hsp70, SEQID NO:33), a Zea mays CTP encoding sequence (TS-Zm.rbc1, SEQID NO:25), a non-naturally occurring sequence encoding Cry3Bb variant protein v11231 (Bt.cry3Bb.v11231, SEQID NO:7), and a nopaline synthase transcription termination and polyadenylation sequence (T-AGRtu.nos, SEQID NO:34). The plant expression vector pMON25097 is improved compared to pMON33710 as judged by Cry3Bb expression levels in planta, and contains an expression cassette comprising a non-naturally occurring CaMV35S AS4 promoter sequence (P-CaMV .AS4, SEQID NO:30), a wheat chlorophyll A/B binding protein untranslated leader sequence (L-Ta.hcb1, SEQID NO:31), a rice actin intron sequence (I-Os.Act1, SEQID NO:32), and a non-naturally occurring sequence encoding Cry3Bb variant protein 11231mv1 (11098) (Bt.cry3Bb.11231mv1, SEQID NO:9) linked to a wheat heat shock Hsp17 transcription termination and polyadenylation sequence (T-Ta.Hsp17, SEQID NO:35). Another preferred vector is pMON25096, which contains an expression cassette (SEQID NO:17) comprising a non-naturally occurring CaMV35S AS4 promoter sequence (P-CaMV.AS4, SEQID NO:30), a wheat chlorophyll A/B binding protein untranslated leader sequence (L-Ta.hcb1, SEQID NO:31), a rice actin intron sequence (I-Os.Act1, SEQID NO:32), a Zea mays CTP encoding sequence (TS-Zm.rbc1. SEQID NO:25), and a non-naturally occurring sequence encoding Cry3Bb variant protein 11231mv1 (Bt.cry3Bb.11231mv1, SEQID NO:9) linked to a wheat heat shock Hsp17 transcription termination and polyadenylation sequence (T-Ta.Hsp17, SEQID NO:35). All vectors contain an identical cassette linked to the Cry3Bb expression cassette which confers paromomycin resistance to transformed plant tissue. This resistance cassette consists of an enhanced CaMV35S promoter sequence, and a neomycin phosphotransferase coding sequence linked to a nopaline synthase transcription termination and polyadenylation sequence. A summary of the standard and improved vectors is presented in Table 4. Transgenic corn plants resistant to paromomycin were derived essentially as described in U.S. Pat. No. 5,424,412 (1995).

TABLE 4

Plant Expression Vector Summary

| Vector | Expression Cassette | Selection Cassette |
|---|---|---|
| pMON33709 | 35S/HSP70/ZmRBC/v11231/NOS | e35S/nptII/nos |
| pMON33710 | e35S/HSP70/11231v/nos | e35S/nptII/nos |
| pMON33722 | AS4/TaCAB/OsAct1/ZmRBC/v11231/tahsp17 | e35S/nptII/nos |
| pMON33723 | AS4//TaCAB/OsAct1/v11231/tahsp17 | e35S/nptII/nos |
| pMON25096 | AS4/TaCAB/OsAct1/ZmRBC/11231mv1/tahsp17 | e35S/nptII/nos |
| pMON25097 | AS4/TaCAB/OsAct1/11231mv1/tahsp17 | e35S/nptII/nos |
| pMON33741 | AS4/TaCAB/OsAct1/11231mv2/tahsp17 | e35S/nptII/nos |
| pMON33748 | e35S/TaCAB/OsAct1/11231mv2/tahsp17 | e35S/nptII/nos |

Maize leaf protoplasts were electroporated with standard vectors (pMON33709 or pMON33710) or improved vectors (pMON33722, pMON33723, pMON25096, pMON25097, pMON33741) as described (Sheen. Plant Cell 2:1027-1038, 1990) and transient expression of Cry3Bb variant proteins was compared by ELISA and Western Blot analysis methods. The ELISA used a rabbit anti-Cry3B chromatography purified IgG capture antibody raised against Cry3B 11231, a sample of that antibody conjugated to alkaline phosphatase as the secondary detecting antibody, and a purified Cry3Bb native protein as a standard. Comparison of the ratio of Cry3Bb to neomycin phosphotransferase (Npt II) expression levels by ELISA indicated that approximately two-fold increases in the normalized expression levels of Cry3Bb variant protein 11231 were obtained with improved vectors pMON33723 and pMON33722 relative to the standard vectors pMON33710 and pMON33709, respectively. (Expt. 1, Table 5). Differences in Cry3Bb expression are directly ascribed to the improved expression cassette in the improved vectors rather than to differences in protoplast electroporation efficiency since expression of Cry3Bb protein is normalized to Npt II produced by the identical linked nptII gene present in all vectors. The most preferred improved vectors such as pMON25096, pMON25097, and pMON33741 expressed approximately 10-fold higher normalized levels of Cry3Bb and variant Cry3Bb protein than the preferred improved vectors such as pMON33722 or pMON33723 (Table 5, Expt. 2, 3). Finally, the equally preferred pMON33741 and pMON25097 vectors yielded roughly equivalent normalized Cry3Bb expression (Table 5, Expt. 4)

TABLE 5

Transient Cry3Bb and Cry3Bb Variant Expression in Corn Leaf Protoplasts (normalized to NptII expression)

| Expt. 1 | pMON33710 | pMON33723 |
| | 5.79 | 12.3 |
| | pMON33709 | pMON33722 |
| | 2.7 | 7.7 |
| Expt. 2 | pMON33722 | pMON25096 |
| | 1.9 | 26.2 |
| | pMON33723 | pMON25097 |
| | 3.7 | 37.5 |
| Expt. 3 | pMON33723 | pMON33741 |
| | 30 | 319 |
| Expt. 4 | pMON33741 | pMON25097 |
| | 20 | 25 |

Since the improved expression cassette in pMON25097 encodes the Cry3Bb 11231mv1 (11098) variant toxin, and the standard cassette in pMON33710 encodes the Cry3Bb v11231 variant which differ by a single amino acid, the intrinsic immunoreactivity of the two proteins in the ELISA assay was compared. Subsequent ELISA experiments with Cry3Bb v11231 and 11231mv 1 (11098) variant proteins produced in and purified from B. thuringiensis indicate that the two proteins have similar levels of immunoreactivity. Consequently, the observed increase in levels of Cry3Bb 11231mv1 (11098) protein produced from the expression cassette in pMON25097 is due to increased expression levels rather than a difference in immunoreactivity. Protein blot analyses confirm that the increased level of cross reactive material produced in maize protoplasts from the improved Cry3Bb expression cassette in pMON25097 were due to increased accumulation of an approximately 60,000 Mr protein immunoreactive with Cry3B antiserum that also co-migrates with Cry3Bb variant 11231 protein produced in a recombinant cry-B. thuringiensis strain from pEG7174. Equally preferred and improved Cry3Bb variant protein expression cassettes in pMON33741 and pMON33748 that encode Cry3Bb.11231 also exhibit increased expression levels of Cry3Bb relative to expression observed from the standard cassette in pMON33710. These results confirm that expression differences are due to the improved compositions disclosed herein rather than to differences in the intrinsic immunoreactivity of the different variants.

Root tissue from transgenic plants in the $R_0$ stage independently obtained after transformation with an improved vectors (pMON33723, 25097,) or with a standard vector (pMON 33710) was subjected to quantitative analysis of Cry3Bb protein levels by a quantitative ELISA assay. Comparison of Cry3Bb or Cry3Bb protein variant expression levels in improved and standard vector transformed corn plants show that Cry3Bb.11231 variant expression does not exceed 50 ppm in the standard pMON33710 transgenics while Cry3Bb.11098 (11231mv1) expression in the improved pMON25097 transgenics is frequently higher than 50 ppm (Table 6). Protein blot analyses confirm that the increased level of cross reactive material produced by pMON25097 (improved) were due to increased accumulation of an approximately Mr 60,000 protein that migrates with Cry3Bb1 standard from B. thuringiensis. Other improved Cry3Bb protein variant expression cassettes found in pMON33741 and 33748 also consistently yield select independently transformed events (ITE's) with Cry3Bb protein variant levels greater than 100 PPM whereas the standard vectors have never given rise to ITE's with greater than 50 PPM of Cry3Bb protein variant (Table 7). High level expression is evident in both the H99 and A634 maize genotypes, indicating that the compositions disclosed herein have broad utility to many varieties of commercially cultivated maize. Such select high expressing Cry3 protein variant lines obtained with the vectors described herein are expected to be especially advantageous in conferring high levels of protection to insect feeding damage and in reducing the incidence of insect resistance to Cry3 insecticidal proteins.

TABLE 6

Comparison of Cry3Bb Expression in $R_0$ Corn Transformed with Standard and Improved Cry3Bb Protein Variant Expression Cassettes Cry3B Expression Level (ppm)

| Vector (genotype) | Total Events | 5-10 ppm | 10-50 ppm | 50-100 ppm | 100-200 ppm | >200 ppm |
|---|---|---|---|---|---|---|
| L25097 | | | | | | |
| A634 | 45 | 3 | 7 | | | 3 |
| H99 | 589 | 32 | 36 | 5 | 3 | 5 |

TABLE 6-continued

Comparison of Cry3Bb Expression in $R_0$ Corn Transformed with Standard and Improved Cry3Bb Protein Variant Expression Cassettes Cry3B Expression Level (ppm)

| Vector (genotype) | Total Events | 5-10 ppm | 10-50 ppm | 50-100 ppm | 100-200 ppm | >200 ppm |
|---|---|---|---|---|---|---|
| L33710 | | | | | | |
| A634 | 22 | 2 | 2 | | | |
| H99 | 336 | 13 | 15 | | | |
| L33723 | | | | | | |
| A634 | 0 | | | | | |
| H99 | 67 | 6 | 9 | | | |

TABLE 7

Cry3Bb Expression in $R_0$ Corn Transformed with Improved Cry3Bb Protein Variant Expression Cassettes Cry3B Expression Level (ppm)

| Vector | Total Events | 5-10 ppm | 10-50 ppm | 50-100 ppm | 100-200 ppm | >200 ppm |
|---|---|---|---|---|---|---|
| L25097 | | | | | | |
| A634 | 112 | 7 | 4 | 5 | 1 | 4 |
| H99 | 45 | 1 | 4 | 2 | | |
| L33741 | | | | | | |
| H99 | 108 | 11 | 5 | 2 | | 4 |
| L33748 | | | | | | |
| A634 | 82 | 1 | 11 | 2 | 2 | 1 |
| H99 | 209 | 23 | 13 | 3 | 3 | 11 |

Progeny derived from corn plants transformed with both the standard (pMON33709 and pMON33710) and preferred (pMON25096, 25097, 33722, 33723, 33726, 33741, and 33748) cassettes expressing 10 ppm or more of Cry3Bb protein were further tested for resistance to Corn Rootworm (CRW) feeding damage in greenhouse or growth chamber based bioassays as previously described (English et al., WO 99/31248). Corn Rootworm resistant transgenic corn plants were obtained from essentially all of the preferred vectors (Table 8). For example, the improved pMON25096 vector was used to generate 89 independently transformed events (ITE's), 14 independent pMON25096 $F_1$ progeny lines expressing 10 ppm or more of Cry3Bb and 7 $F_1$ progeny lines displaying significant levels of CRW resistance (an RDR rating $\geq 3.5$ on a rating scale of 0-6). In contrast, not a single event with a RDR rating $\leq 3.5$ was obtained from 12 of the standard pMON33710 cassette $F_1$ progeny lines expressing 10 PPM or more of Cry3Bb protein variant. Failure to obtain CRW resistant lines with either of the standard vectors (pMON33709 or pMON33710) was not due to insufficient numbers of ITE's as over 300 ITE's from each of these two vectors were generated and screened for CRW resistant $F_1$ progeny. Far fewer ITE's were generated with preferred vectors such as pMON33722, pMON33723, and pMON25096, yet all ultimately gave rise to CRW resistant $F_1$ progeny lines

TABLE 8

Numbers of CRW resistant independent transformation events obtained with the standard and improved Cry3Bb Protein Variant expression cassettes

| Expression cassette | Genotype | Total Number of ITE's | Number of ITE's Tested | Number and Percent of ITEs with RDR $\leq 3.5$ |
|---|---|---|---|---|
| L33709 | H99 | 318 | 11 | 0 |
| L33710 | H99 | 336 | 10 | 0 |
| | A634 | 22 | 2 | 0 |
| L25096 | H99 | 52 | 4 | 2 (50%) |
| | A634 | 37 | 10 | 5 (50%) |
| L25097 | H99 | 634 | 17 | 10 (59%) |
| | A634 | 157 | 18 | 8 (44%) |
| L33722 | H99 | 107 | 10 | 6 (60%) |
| L33723 | H99 | 93 | 7 | 3 (43%) |
| L33726 | H99 | 65 | 6 | 5 (83%) |
| | A634 | 10 | 0 | |
| L33727 | H99 | 86 | 0 | |
| | A634 | 1 | 1 | 0 |
| 33736ABI | H99 | 3 | 3 | 2 (67%) |
| L33741 | H99 | 108 | 1 | 0 |
| L33748 | H99 | 223 | 6 | 3 (50%) |
| | A634 | 82 | 7 | 4 (57%) |
| L33749ABI | H99 | 73 | 14 | 13 (93%) |

In examples provided herein, experimental evidence that substantially equivalent compositions based on the improvements disclosed herein yield equivalent improvements in performance relative to the previously disclosed standards. More specifically, we demonstrate that improved compositions encoding both the Cry3Bb. 11098 and Cry3Bb. 11231 variants both yield equivalently improved performance relative to the previously disclosed standard compositions encoding Cry3Bb.11231. It thus follows that use of other Cry3B variants with specific biological activities that are greater than or equal to Cry3Bb.11098 or Cry3Bb.11231 is contemplated by and within the scope of this invention. For example, improved vector compositions encoding Cry3Bb variants include 11231, 11084, 11098, 11247, and others as set forth in English et al., U.S. application Ser. Nos. 08/993,170, 08/993, 722, 08/993,755, and 08/996,441, all filed Dec. 18, 1997 can be derived from pMON25095 using standard mutagenesis procedures in a manner essentially equivalent to the construction of pMON33740.

5.4

Example 4

Preferred Expression Cassettes Confer Resistance to CRW Damage in Field Tests

Corn plants genetically modified to express Cry3Bb protein variants derived from the preferred vectors pMON33722, pMON33723, pMON25096, and pMON25097 were evaluated in the field for control of western corn rootworm, *Diabrotica vergifera vergifera* LeConte (WCR). None of the corn plants transformed with the standard vectors were advanced to field testing as none displayed adequate Corn Rootworm control in greenhouse tests (Example 3. Table 8). The efficacy trials were held at a Monsanto research farm in Jerseyville, Ill. and at the Northern Grain Insects Research Laboratory, USDA ARS research station in Brookings, S.Dak. These trials serve to evaluate performance of the preferred cassettes in the field under heavy insect pressure and to compare their performance to the current commercially available insecticides.

Seventeen independent transformation events (ITE) were selected for field evaluation based on greenhouse performance. The amount of seed available for the field evaluation varied for each ITE. Of these 17 events, only seven were planted at the Brookings research station. The field design for the Brookings' location was a randomized complete block (RCB) with 2 replications, where each plot was a single row containing a maximum of 30 plants. All 17 ITE's were planted at the Jerseyville location, where the design was a RCB with a maximum of 4 replications. 1 row plots each, where the number of replications depended on the seed available from each ITE. Because of this, the number of replications at Jerseyville ranged from two to four. Additional treatments included an untreated check (nontransgenic corn) and commercial insecticides, including Counter®, Lorsban®, and Force®. The insecticide treatments were only at the Jerseyville location. The insecticides were applied as an eight inch band at planting using the recommended rates.

Planting dates where May $28^{th}$ and June $3^{rd}$ for the Jerseyville & Brookings, respectively. The study was performed as follows; plots were infested with CRW eggs at planting with 1,600 eggs per foot of row, approximately 800 eggs per plant. At the V1-V2 plant growth stage, plants were analyzed for presence of the Cry3Bb protein variant expression using an ELISA. Plants negative for the gene were culled from the plot.

At the end of the CRW larval feeding stage, when maximum damage would have occurred, all remaining plants in each plot were evaluated for root feeding injury using a 1-6 root damage rating (RDR) scale described by Hills and Peters (1971). The RDR scale is as follows;

Root Damage Rating:
1. No feeding scars
2. Visible feeding scars, but no roots pruned to within 4 cm of the stalk
3. One or more nodal roots pruned to within 4 cm of the stalk, but less than one nodes worth of roots
4. One node worth of pruned roots
5. Two nodes worth of pruned roots
6. Three or more nodes worth of pruned roots On July $25^{th}$ and August $3^{rd}$ the field trials were evaluated at Jerseyville and Brookings, respectively. The average RDR's for all treatments are illustrated in Table 9. Of the seventeen ITE's evaluated, 16 ITE's controlled CRW feeding, $\leq$3.0 RDR. Two of the three chemical standards had a RDR less than 3.0. Force® had a root damage rating of 3.2. Except for one ITE, WCR20, all treatments were significantly better than the checks (p<0.01) but did not differ significantly from each other. Figure one illustrates the difference in larval feeding damage between a transgenic CRW resistant plant and an untreated check.

Even though the ITE's did not differ significantly from the chemical standards with respect to root damage rating, the amount of feeding injury observed on roots from the insecticide treatments were greater than the roots expressing Monsanto's proprietary gene. The lack of difference between root damage rating is an artifact of the root rating scale, where this scale is based on "pruned" roots. Hills and Peters describe a pruned root as being less than 4 cm in length due to CRW feeding. Therefore, root masses without a "pruned" root but visible feeding scares are given a rating of 2. Roots outside of the zone of protection from the insecticide treatments had many more feeding scars and in most cases the root tips were destroyed as compared to the ITE's. Unlike the insecticide treatments, the transgenic plants express the CRW resistant gene throughout the entire root mass. But because the mechanism for control of the transgenic plant is orally mediated, a minimum amount of feeding is required to control any further injury by the CRW larvae. This minimal feeding requirement resulted in a RDR of 2.

In summary, corn plants expressing Cry3Bb protein variants were fully protected from CRW larval feeding. This level of protection eliminates the need for an insecticide treatment. Insecticides, including organophosphates, carbamates and pyrethroids are incorporated into the soil on over 16 million corn acres annually to control CRW. CRW resistance technology has the potential to significantly reduce the current exposure level of these insecticides to the environment. The benefits of shifting away from soil insecticides to a transgenic approach are impressive and include a reduction in potential human health and safety risks, reduced direct impacts on nontarget organisms, reduced contamination of surface and ground water supplies, decreased pesticide container disposal problems, and general compatibility with other pest management and agronomic programs.

TABLE 9

Corn rootworm root feeding damage (RDR) means for corn independent transformation events containing Monsanto's proprietary CRW resistant gene.
Root Damage Rating (RDR)

| Treatment | Jerseyville | Brookings | Average (RDR) |
| --- | --- | --- | --- |
| pMON 25097-1 | 2.3 | 1.9 | 2.1 |
| pMON 33722-1 | 2.6 | 2.3 | 2.5 |
| PMON 33723-1 | 2.6 | 2.9 | 2.8 |
| pMON 33723-2 | 2.6 | 2.0 | 2.3 |
| pMON 33722-2 | 2.5 | 1.9 | 2.2 |
| pMON 25096-1 | 2.8 | 2.5 | 2.7 |
| pMON 25097-2 | 2.5 | 2.3 | 2.4 |
| pMON 25096-2 | 2.4 | n/a | 2.4 |
| pMON 25097-3 | 2.6 | n/a | 2.6 |
| pMON 25096-3 | 2.2 | n/a | 2.2 |
| pMON 25097-4 | 2.2 | n/a | 2.2 |
| pMON 25096-4 | 2.6 | n/a | 2.6 |
| pMON 33723-3 | 2.5 | n/a | 2.5 |
| pMON 25097-5 | 3.0 | n/a | 3.0 |
| pMON 25097-6 | 4.0 | n/a | 4.0 |
| pMON 25097-7 | 2.2 | n/a | 2.2 |
| pMON 33722-3 | 2.6 | n/a | 2.6 |
| COUNTER ® | 2.4 | n/a | 2.4 |
| LORSBAN ® | 2.4 | n/a | 2.4 |
| FORCE ® | 3.2 | n/a | 3.2 |
| CHECK | 4.1 | 4.1 | 4.1 |

5.5

Example 5

Transformation of Tobacco Chloroplast with a cry3B Gene

Recombinant plants can be produced in which only the mitochondrial or chloroplast DNA has been altered to incorporate the molecules envisioned in this application. Promoters which function in chloroplasts have been known in the art (Hanley-Bowden et al., Trends in Biochemical Sciences 12:67-70, 1987). Methods and compositions for obtaining cells containing chloroplasts into which heterologous DNA has been inserted have been described, for example by Daniell et al. (U.S. Pat. No. 5,693,507: 1997) and Maliga et al. (U.S. Pat. No. 5,451,513: 1995). A vector can be constructed which contains an expression cassette from which a Cry3B protein could be produced. A cassette could contain a chloroplast operable promoter sequence driving expression of a cry3B crystal protein gene, constructed in much the same manner as other polynucleotides herein, using thermal amplification methodologies, restriction endonuclease digestion, and ligation etc. A chloroplast expressible gene would provide a promoter and a 5' untranslated region from a heterologous gene or chloroplast gene such as psbA, which would provide for transcription and translation of a DNA sequence encoding a Cry3B protein in the chloroplast; a DNA sequence encoding Cry3B protein; and a transcriptional and translational termination region such as a 3' inverted repeat region of a chloroplast gene that could stabilize an expressed cry3B mRNA. Expression from within the chloroplast would enhance cry3B gene product accumulation. A host cell containing chloroplasts or plastids can be transformed with the expression cassette and then the resulting cell containing the transformed chloroplasts can be grown to express the Cry3B protein. A cassette may also include an antibiotic, herbicide tolerance, or other selectable marker gene in addition to the cry3B gene. The expression cassette may be flanked by DNA sequences obtained from a chloroplast DNA which would facilitate stable integration of the expression cassette into the chloroplast genome, particularly by homologous recombination. Alternatively, the expression cassette may not integrate, but by including an origin of replication obtained from a chloroplast DNA, would be capable of providing for replication of the heterologous cry3B gene in the chloroplast. Plants can be generated from cells containing transformed chloroplasts and can then be grown to produce seeds, from which additional plants can be generated. Such transformation methods are advantageous over nuclear genome transformation, in particular where chloroplast transformation is effected by integration into the chloroplast genome, because chloroplast genes in general are maternally inherited. This provides environmentally "safer" transgenic plants, virtually eliminating the possibility of escapes into the environment. Furthermore, chloroplasts can be transformed multiple times to produce functional chloroplast genomes which express multiple desired recombinant proteins, whereas nuclear genomic transformation has been shown to be rather limited when multiple genes are desired. Segregational events are thus avoided using chloroplast or plastid transformation. Unlike plant nuclear genome expression, expression in chloroplasts or plastids can be initiated from only one promoter and continue through a polycistronic region to produce multiple peptides from a single mRNA.

The expression cassette would be produced in much the same way that other plant transformation vectors are constructed. Plant chloroplast operable DNA sequences can be inserted into a bacterial plasmid and linked to DNA sequences expressing desired gene products, such as Cry3B proteins, so that Cry3B protein is produced within the chloroplast, obviating the requirement for nuclear gene regulation, capping, splicing, or polyadenylation of nuclear regulated genes, or chloroplast or plastid targeting sequences. An expression cassette comprising a cry3B gene, which is either synthetically constructed or a native gene derived directly from a B. thuringiensis genome or a B. thuringiensis episomal element, would be inserted into a restriction site in a vector constructed for the purpose of chloroplast or plastid transformation. The cassette would be flanked upstream by a chloroplast or plastid functional promoter and downstream by a chloroplast or plastid functional transcription and translation termination sequence. The resulting cassette would be incorporated into the chloroplast or plastid genome using well known homologous recombination methods.

Alternatively, chloroplast or plastid transformation could be obtained by using an autonomously replicating plasmid or other vector capable of propagation within the chloroplast or plastid. One means of effectuating this method would be to utilize a portion of the chloroplast or plastid genome required for chloroplast or plastid replication initiation as a means for maintaining the plasmid or vector in the transformed chloroplast or plastid. A sequence enabling stable replication of a chloroplast or plastid epigenetic element would easily be identified from random cloning of a chloroplast or plastid genome into a standard bacterial vector which also contains a chloroplast or plastid selectable marker gene, followed by transformation of chloroplasts or plastids and selection for transformed cells on an appropriate selection medium. Introduction of an expression cassette as described herein into a chloroplast or plastid replicable epigenetic element would thus provide an effective means for localizing a Cry3B B. thuringiensis δ-endotoxin to the chloroplast or plastid.

5.6

Example 6

Targeting Cry3Bb or Variant Cry3Bb Protein to Plastids

Improved expression by targeting recombinant insecticidal protein to the chloroplast may result in tissues which are light exposed and which accumulate mature chloroplasts as a result. Improving expression in leaf tissue to inhibit leaf-feeding pests susceptible to the insecticidal protein could be advantageous. To test this, two plasmids, pMON33709 and pMON33710 were constructed which were isogenic with respect to all elements with the exception of a plastid or chloroplast targeting sequence linked in frame to the insecticidal Cry3Bb improved variant in pMON33709. $R_0$ corn plants were recovered and were shown to contain and express the transgene by ELISA. Six pMON33709 lines and sixteen pMON33710 lines were recovered which expressed the transgene in both the root and the leaves. Leaf and root tissue were recovered and analyzed for the presence and amount of Cry3Bb variant protein, measured in parts per million. The results are shown in Table 10.

TABLE 10

Comparison of Non-Targeted and Plastid Targeted Leaf vs Root Expression of Cry3Bb Variant v11231 in $R_0$ Corn Transformation Events

| R0 # | Event # | Construct | Tissue | ppm 11231(ug/g tissue) |
|---|---|---|---|---|
| R053608 | 2027-05-01 | L33709 | Leaf | 14.69 |
| R053608 | 2027-05-01 | L33709 | Root | 3.97 |
| R053621 | 2028-06-06 | L33709 | Leaf | 22.65 |
| R053621 | 2028-06-06 | L33709 | Root | 0.10 |
| R053643 | 2029-03-09 | L33709 | Leaf | 1.05 |
| R053643 | 2029-03-09 | L33709 | Root | 3.83 |
| R053675 | 2028-03-06 | L33709 | Leaf | 7.13 |
| R053675 | 2028-03-06 | L33709 | Root | 2.23 |
| R053688 | 2028-04-02 | L33709 | Leaf | 56.80 |
| R053688 | 2028-04-02 | L33709 | Root | 9.83 |
| R053690 | 2028-04-02 | L33709 | Leaf | 98.69 |
| R053690 | 2028-04-02 | L33709 | Root | 6.38 |
| R053708 | 2027-01-02 | L33710 | Leaf | 12.79 |
| R053708 | 2027-01-02 | L33710 | Root | 4.94 |
| R053781 | 2028-02-19 | L33710 | Leaf | 8.47 |
| R053781 | 2028-02-19 | L33710 | Root | 4.72 |

TABLE 10-continued

Comparison of Non-Targeted and Plastid Targeted
Leaf vs Root Expression of Cry3Bb Variant v11231
in R₀ Corn Transformation Events

| R0 # | Event # | Construct | Tissue | ppm 11231(ug/g tissue) |
|---|---|---|---|---|
| R053785 | 2027-04-06 | L33710 | Leaf | 21.97 |
| R053785 | 2027-04-06 | L33710 | Root | 7.20 |
| R053799 | 2028-01-16 | L33710 | Leaf | 12.41 |
| R053799 | 2028-01-16 | L33710 | Root | 6.19 |
| R053800 | 2028-01-16 | L33710 | Leaf | 5.69 |
| R053800 | 2028-01-16 | L33710 | Root | 3.32 |
| R053801 | 2028-01-16 | L33710 | Leaf | 16.19 |
| R053801 | 2028-01-16 | L33710 | Root | 7.80 |
| R053824 | 2027-01-11 | L33710 | Leaf | 6.93 |
| R053824 | 2027-01-11 | L33710 | Root | 10.35 |
| R053838 | 2030-08-12 | L33710 | Leaf | 14.32 |
| R053838 | 2030-08-12 | L33710 | Root | 5.64 |
| R053857 | 2030-08-08 | L33710 | Leaf | 12.70 |
| R053857 | 2030-08-08 | L33710 | Root | 3.97 |
| R053858 | 2028-02-32 | L33710 | Leaf | 2.33 |
| R053858 | 2028-02-32 | L33710 | Root | 4.15 |
| R053859 | 2028-02-32 | L33710 | Leaf | 9.39 |
| R053859 | 2028-02-32 | L33710 | Root | 5.76 |
| R053904 | 2027-02-03 | L33709 | Leaf | 226.05 |
| R053904 | 2027-02-03 | L33709 | Root | 1.55 |
| R053923 | 2029-01-08 | L33710 | Leaf | 12.16 |
| R053923 | 2029-01-08 | L33710 | Root | 11.77 |
| R053924 | 2029-01-08 | L33710 | Leaf | 10.74 |
| R053924 | 2029-01-08 | L33710 | Root | 7.94 |
| R053928 | 2029-01-05 | L33710 | Leaf | 14.86 |
| R053928 | 2029-01-05 | L33710 | Root | 3.84 |
| R053929 | 2029-01-05 | L33710 | Leaf | 15.04 |
| R053929 | 2029-01-05 | L33710 | Root | 3.49 |

All but one pMON33709 line (Ro53643) produced between 3 to 15 times more insecticidal protein in the leaves than in the root tissue. The one line that produced less in the leaves also produced less than 1 ppm in the root, whereas the other lines produced up to almost 100 ppm in the leaves. The amount of Cry3Bb variant protein expressed was even more variable in the non-targeted lines derived from pMON33710 transformation events which were determined to be expressing the recombinant protein in both leaf and root tissues. While most of these lines produced more protein in the leaves than in the roots, some also produced more in the roots, but the difference between the amount produced in the roots in those improved root-expressors was less substantial than in the single pMON33709 targeted event. Also, the range of expression levels was less pronounced in the non-targeted events with one exception. Surprisingly, one line (Ro53904) produced substantially more protein in the leaves than was observed in any other line, targeted or non-targeted. This line would be expected to be a candidate for a commercial line directed to protection against *Coleopteran* pests which feed on leaf tissues. Conversely, lines such as Ro53923 would be expected to be optimum candidates for protecting corn plants against root-feeding pests such as corn rootworms.

The data in summary indicates that targeting the Bt Cry3B protein to the plastid or chloroplast improves the accumulation of the protein in leaf tissue but not in root tissue, and improves the overall expression of the protein in leaves in plants transformed with such constructs as compared to the levels of expression observed in root tissues in those same plants.

In view of the above, it will be seen that the several advantages of the invention are achieved and other advantageous results attained. As various changes could be made in the above methods and compositions without departing from the scope of the invention, it is intended that all matter contained in the above description and shown in the accompanying drawings shall be interpreted as illustrative and not in a limiting sense.

In addition, all references referred to in this application are herein incorporated by reference in their entirety.

What is claimed is:

1. An expression cassette comprising the nucleotide sequence as set forth in SEQ ID NO:19 from nucleotide 14 through nucleotide 3020.

2. A cell comprising the expression cassette of claim 1.

3. The cell according to claim 2, wherein said cell is a plant cell or a bacterial cell.

4. The cell according to claim 3, wherein said plant cell is a maize cell.

5. A method of producing a transformed cell, said method comprising introducing into a cell an expression cassette for expression of an insecticidal protein, wherein said expression cassette comprises the nucleotide sequence as set forth in SEQ ID NO:19 from nucleotide 14 through nucleotide 3020, and wherein said cell is a plant cell or a microbial cell.

6. The method of claim 5, wherein said cell is a plant cell.

7. The method of claim 6, wherein said plant cell is a maize cell.

8. A method of producing an insect resistant maize plant, said method comprising introducing into a maize plant cell the expression cassette as set forth in SEQ ID NO:19 for expression of an insecticidal protein, selecting a transformed maize plant cell, and regenerating a maize plant from said transformed maize plant cell, wherein said maize plant comprises said expression cassette.

9. A seed or progeny from a plant produced according to the method of claim 8, wherein said seed or progeny comprises said expression cassette.

10. A plant comprising the expression cassette as set forth in SEQ ID NO:19 from nucleotide 14 through nucleotide 3020.

11. A seed or progeny from the plant of claim 10, wherein said seed or progeny comprises said expression cassette.

12. A plant grown from the seed of claim 11.

13. A method of controlling *Coleopteran* insect infestation in a field of crop plants, said method comprising providing to a *Coleopteran* insect a transgenic plant on which said *Coleopteran* insect feeds, said transgenic plant expressing the insecticidal protein encoded by the polynucleotide sequence as set forth in SEQ ID NO:19 from nucleotide 14 through nucleotide 3020.

14. A method of controlling *Coleopteran* insect infestation of a plant, said method comprising providing to a *Coleopteran* insect a transgenic plant on which said *Coleopteran* insect feeds, said transgenic plant expressing the insecticidal protein encoded by the polynucleotide sequence as set forth in SEQ ID NO:19 from nucleotide 14 through nucleotide 3020.

15. A vector comprising a polynucleotide sequence encoding the peptide as set forth in SEQ ID NO:20.

* * * * *